US009962389B2

(12) United States Patent
Lücking et al.

(10) Patent No.: US 9,962,389 B2
(45) Date of Patent: *May 8, 2018

(54) 4-ARYL-N-PHENYL-1,3,5-TRIAZIN-2-AMINES CONTAINING A SULFOXIMINE GROUP

(71) Applicant: Bayer Intellectual Property GmbH, Monheim (DE)

(72) Inventors: Ulrich Lücking, Berlin (DE); Rolf Bohlmann, Berlin (DE); Arne Scholz, Berlin (DE); Gerhard Siemeister, Berlin (DE); Mark Jean Gnoth, Mettmann (DE); Ulf Bömer, Glienicke (DE); Dirk Kosemund, Berlin (DE); Philip Lienau, Berlin (DE); Gerd Rühter, Hamburg (DE); Carsten Schultz-Fademrecht, Dortmund (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/488,155

(22) Filed: Apr. 14, 2017

(65) Prior Publication Data

US 2017/0217949 A1 Aug. 3, 2017

Related U.S. Application Data

(63) Continuation of application No. 14/122,063, filed as application No. PCT/EP2012/059399 on May 21, 2012, now Pat. No. 9,669,034.

(30) Foreign Application Priority Data

May 24, 2011 (EP) ..................... 11167317
Sep. 9, 2011 (EP) ..................... 11180759
Mar. 5, 2012 (EP) ..................... 12158030

(51) Int. Cl.
| | | |
|---|---|---|
| C07D 251/44 | (2006.01) | |
| C07D 251/42 | (2006.01) | |
| C07D 251/22 | (2006.01) | |
| C07D 251/16 | (2006.01) | |
| C07D 401/12 | (2006.01) | |
| C07D 405/12 | (2006.01) | |
| C07D 413/12 | (2006.01) | |
| C07D 417/12 | (2006.01) | |
| C07C 381/10 | (2006.01) | |
| A61K 31/53 | (2006.01) | |
| A61P 35/00 | (2006.01) | |
| C07D 405/04 | (2006.01) | |
| C07B 59/00 | (2006.01) | |

(52) U.S. Cl.
CPC ............ *A61K 31/53* (2013.01); *C07B 59/002* (2013.01); *C07C 381/10* (2013.01); *C07D 251/16* (2013.01); *C07D 251/22* (2013.01); *C07D 251/42* (2013.01); *C07D 251/44* (2013.01); *C07D 401/12* (2013.01); *C07D 405/04* (2013.01); *C07D 405/12* (2013.01); *C07D 413/12* (2013.01); *C07D 417/12* (2013.01); *C07B 2200/05* (2013.01)

(58) Field of Classification Search
CPC .. C07D 251/42; C07D 403/04; C07D 407/04; A61K 31/53
USPC ......................................... 544/213; 514/245
See application file for complete search history.

(56) References Cited

U.S. PATENT DOCUMENTS

| | | | |
|---|---|---|---|
| 7,291,616 | B2 | 11/2007 | Bhatt et al. |
| 7,338,958 | B2 | 3/2008 | Luecking et al. |
| 7,618,968 | B2 | 11/2009 | Bhatt et al. |
| 7,687,634 | B2 | 3/2010 | Loso et al. |
| 7,825,128 | B2 | 11/2010 | Lücking et al. |
| 1,030,660 | A1 | 12/2011 | Wabnitz et al. |
| 8,084,457 | B2 | 12/2011 | Choidas et al. |
| 8,507,510 | B2 | 8/2013 | Lücking et al. |
| 8,735,412 | B2 | 5/2014 | Lücking et al. |
| 8,916,557 | B2 | 12/2014 | Lücking et al. |
| 9,108,926 | B2 | 8/2015 | Lücking et al. |
| 9,133,171 | B2 | 9/2015 | Lücking et al. |
| 9,226,929 | B2 | 1/2016 | Rühter et al. |
| 9,242,937 | B2 | 1/2016 | Rühter et al. |
| 9,499,492 | B2 | 11/2016 | Lücking et al. |

(Continued)

FOREIGN PATENT DOCUMENTS

| | | |
|---|---|---|
| DE | 2129678 | 6/1971 |
| EP | 1218360 | 5/2008 |

(Continued)

OTHER PUBLICATIONS

Allenmark, S. et al. (1983). "Enantioselective Liquid Chromatographic Retention of a Series of Sulfoxides and N-substituted Sulfoximines on Chiral Stationary Phases," *Acta Chemica Scandinavica B* 37: 325-328.

Bark-Jones, S.J. et al. (2006). "EBV EBNA 2 stimulates CDK9-dependent transcription and RNA polymerase II phosphorylation on serine 5," *Oncogene* 25: 1775-1785.

Barnes, A.C. et al. (1979). "Pharmacologically Active Sulfoximides: 5-Hexyl-7-(S-methylsulfonimidoyl)xanthone-2-carboxylic Acid, a Potent Antiallergic Agent," *Journal of Medicinal Chemistry* 22(4): 418-424.

(Continued)

*Primary Examiner* — Venkataraman Balasubramanian
(74) *Attorney, Agent, or Firm* — Morrison & Foerster LLP

(57) ABSTRACT

The present invention relates to 4-aryl-N-phenyl-1,3,5-triazin-2-amines containing a sulfoximine group of general formula (I) or (Ia) as described and defined herein, and methods for their preparation, their use for the treatment and/or prophylaxis of disorders, in particular of hyperproliferative disorders and/or virally induced infectious diseases and/or of cardiovascular diseases. The invention further relates to intermediate compounds useful in the preparation of said compounds of general formula (I) or (Ia).

15 Claims, No Drawings

(56) References Cited

U.S. PATENT DOCUMENTS

| | | | |
|---|---|---|---|
| 9,669,034 B2* | 6/2017 | Lucking et al. | ..... C07D 413/12 |
| 2004/0209895 A1 | 10/2004 | Luecking et al. | |
| 2007/0191393 A1 | 8/2007 | Lücking et al. | |
| 2009/0023782 A1 | 1/2009 | Babcock | |
| 2010/0093776 A1 | 4/2010 | Beckwith | |
| 2010/0184789 A1 | 7/2010 | Wabnitz et al. | |
| 2011/0028492 A1 | 2/2011 | Barsanti et al. | |
| 2013/0079345 A1 | 3/2013 | Eickhoff et al. | |
| 2015/0259300 A1 | 9/2015 | Lücking et al. | |
| 2015/0274666 A1 | 10/2015 | Lücking et al. | |
| 2015/0274695 A1 | 10/2015 | Lücking et al. | |
| 2015/0291528 A1 | 10/2015 | Lücking et al. | |
| 2015/0291559 A1 | 10/2015 | Lücking et al. | |
| 2016/0143893 A1 | 5/2016 | Kosemund et al. | |

FOREIGN PATENT DOCUMENTS

| | | |
|---|---|---|
| EP | 2527332 | 11/2012 |
| GB | 1307271 | 2/1973 |
| WO | WO-02059110 | 8/2002 |
| WO | WO-02066481 | 8/2002 |
| WO | WO-03037346 | 5/2003 |
| WO | WO-2004009562 | 1/2004 |
| WO | WO-2004072063 | 8/2004 |
| WO | WO-2005037800 | 4/2005 |
| WO | WO-2006064251 | 6/2006 |
| WO | WO-2007023507 | 3/2007 |
| WO | WO-2007071455 | 6/2007 |
| WO | WO-2008012971 | 1/2008 |
| WO | WO-2008025556 | 3/2008 |
| WO | WO-2008028590 | 3/2008 |
| WO | WO-2008060248 | 5/2008 |
| WO | WO-2008079918 | 7/2008 |
| WO | WO-2008079933 | 7/2008 |
| WO | WO-2008109943 | 9/2008 |
| WO | WO-2008129070 | 10/2008 |
| WO | WO-2008129071 | 10/2008 |
| WO | WO-2008129080 | 10/2008 |
| WO | WO-2008132138 | 11/2008 |
| WO | WO-2009029998 | 3/2009 |
| WO | WO-2009032861 | 3/2009 |
| WO | WO-2009118567 | 10/2009 |
| WO | WO-2010009155 | 1/2010 |
| WO | WO-2011012661 | 2/2011 |
| WO | WO-2011046970 | 4/2011 |
| WO | WO-2011116951 | 9/2011 |
| WO | WO-2012117059 | 9/2012 |
| WO | WO-2013037894 | 3/2013 |
| WO | WO-2013037896 | 3/2013 |
| WO | WO-2014060376 | 4/2014 |
| WO | WO-2014076028 | 5/2014 |
| WO | WO-2014076091 | 5/2014 |
| WO | WO-2015001021 | 1/2015 |
| WO | WO-2015136028 | 9/2015 |

OTHER PUBLICATIONS

Bauer, V.J. et al. (Oct. 1966). "The Reactions of Carbamoyl Azides with Sulfur Nucleophiles," *Journal of Organic Chemisty* 31: 3440-3441.

Bennet, J.C., and Plum, F. ed. (1996). *Cecil Textbook of Medicine*, W.B. Saunders Company: Philadelphia, PA, 1:1004-1010.

Berge, S.M. et al. (Jan. 1977). "Pharmaceutical Salts," *Journal of Pharmaceutical Sciences* 66(1): 1-19.

Bolm, C. et al. (1998). "Palladium-Catalyzed Carbon-Nitrogen Bond Formation: A Novel, Catalytic Approach towards N-Arylated Sulfoximines," *Tetrahedron Letters* 39: 5731-5734.

Bolm, C. et al. (2000). "Palladium-Catalyzed N-Arylation of Sulfoximines with Aryl Bromides and Aryl Iodides," *Journal of Organic Chemistry* 65: 169-175.

Bolm, C. et al. (Feb. 2000). "Catalytic Coupling of Aryl Sulfonates with $sp^2$-Hybridized Nitrogen Nucleophiles: Palladium- and Nickel-catalyzed Synthesis of N-Aryl Sulfoximines," *Synthesis* 7: 911-913.

Bolm, C. et al. (2001). "Synthesis of Pseudopeptides with Sulfoximines as Chiral Backbone Modifying Elements," *Chem. Eur. J.* 7(5): 1118-1128.

Bolm, C. et al. (2002). "A Mild Synthetic Procedure for the Preparation of N-Alkylated Sulfoximines," *Synthesis* 7: 879-887.

Cho, G.Y., et al. (2005). "Synthesis and Palladium-Catalyzed Coupling Reaction of Enantiopure p-Bromophenyl Methyl Sulfoximine," *J. Org. Chem.* 70(6): 2346-2349.

Cho, S. et al. (May 1, 2010). "CYCLINg through transcription Posttranslational modification of P-TEFb regulate transcription elongation," *Cell Cycle* 9(9): 1697-1705.

Copeland, R. A. et al. (2006). "Drug-target residence time and its implications for lead optimization," *Nature Reviews Drug Discovery* 5: 730-739.

Craig, D. et al. (1995). " Asymmetric Intramolecular Diels-Alder Reactions of Sulfoximine-activated Trienes," *Tetrahedron* 51(21): 6071-6098.

Cram, D.J. (Dec. 16, 1970). "Stereochemistry of Sulfur Compounds. I. Stereochemical Reactions Cycles Involving an Open Chain Sulfoxide, Sulfimide, and Sulfoximide," *Journal of the American Chemical Society* 92(25): 7369-7384.

De Meijere, A. et al. (2004). "Metal-Catalyzed Cross-Coupling Reactions," *WILEY-VCH Verlag GmbH & Co. KGaA*, Weinheim, pp. 83-91.

Dermer, G.B. (Mar. 1994). "Another Anniversary for the War on Cancer," *Bio/Technology* 12: 320.

Dey, A. et al. (Aug. 1, 2007). "HEXIM1 and the Control of Transcription Elongation from Cancer and Inflammation to AIDS and Cardiac Hypertrophy," Cell Cycle 6(15): 1856-1863.

Freshney et al. (1983). "Culture of Animal Cells" Chapter 1 in *A Manual of Basic Technique*, Alan R. Liss, Inc., New York, NY, pp. 4.

Füger, B. et al. (2009). "Ring-Closing Enyne Metathesis (RCEYM) for the Synthesis of Cyclic Sulfoximines," *Synlett* 10: 1601-1604.

Golub, T.R. et al. (Oct. 15, 1999). "Molecular Classification of Cancer: Class Discovery and Class Prediction by Gene Expression Monitoring," *Science* 285: 531-537.

Hackenberger, C.P.R., et al. (2004). "Synthetic and Spectroscopic Investigation of N-Acylated Sulfoximines," *Chem. Eur. J.* 10: 2942-2952.

He, N. et al. (Mar. 14, 2008). "A La-Related Protein Modulates 7SK snRNP Integrity to Suppress P-TEFb-Dependent Transcriptional Elongation and Tumorigenesis," *Molecular Cell* 29: 588-599.

International Search Report dated Jun. 22, 2012 for PCT Application No. PCT/EP2012/059399, filed on May 21, 2012, 3 pages.

Johnson, C.R. (Nov. 4, 1970). "Preparation and Synthetic Applications of (Dimethylamino)phenyloxosulfonium Methylide," *Journal of the American Chemical Society* 92(22): 6594-6598.

Johnson, C.R. (1978). "Preparation of α-Halo Sulfoximines," *Journal of Organic Chemistry* 43(21): 4136-4140.

Johnson, C.R. et al. (1993). "Alkylation of Sulfoximines and Related Compounds at the Imino Nitrogen under Phase-Transfer Conditions," *Journal of Organic Chemistry* 58(7): 1922-1923.

Jones, M.R. et al. (Apr. 3, 1974). "Stereochemisty of Sulfur Compounds. VII. Course of Substitution at Sulfur Attached to Four Different Ligands," *Journal of the American Chemical Society* 96(7): 2183-2190.

Krystof, V. et al. (2012). "Perspective of Cyclin-dependent kinase 9 (CDK9) as a Drug Target," *Current Pharmaceutical Design* 18: 2883-2890.

Mancheño, O.G. et al. (2007). "Synthesis of N-(1H)-Tetrazole Sulfoximines," *Organic Letters* 9(15): 2951-2954.

Mancheño, O.G. et al. (2010). "Synthesis of Sulfoximines and Sulfilimines with Aryl and Pyrazolylmethyl Substituents," *Adv. Synth. Catal.* 352: 309-316.

Okamura, H. et al. (2004). "Rhodium-Catalyzed Imination of Sulfoxides and Sulfides: Efficient Preparation of N-Unsubstituted Sulfoximines and Sulfilimines," Organic Letters 6(8): 1305-1307.

Polla, M.O. et al. (2004). "Design and synthesis of potent, orally active, inhibitors of carboxypeptidase U (TAFIa)," *Bioorganic & Medicinal Chemistry Letters* 12: 1151-1175.

(56) References Cited

OTHER PUBLICATIONS

Roemer, T. et al. (2013). "Auxiliary factors: a chink in the armor of MRSA resistance to β-lactam antibiotics," *Current Opinion in Microbiology* 16: 538-548.
Sammond, D.M. et al. (2005). "Discovery of a novel and potent series of dianilinopyrimidineurea and urea isostere inhibitors of VEGFR2 tyrosine kinase," Bioorganic & Medicinal Chemistry Letters 15: 3519-3523.
Sauer, D.T. et al. (1972). "Bis(perfluoroalkyl)sulfur Oxyimines and Silver Bis(trifluoromethyl)sulfur Oxyimine," *Inorganic Chemistry* 11(2): 238-242.
Stoss, P. et al. (1978). "Transannulare Acylwanderungen in cyclischen Sulfoximiden," *Chem. Ber.* 111: 1453-1463.
Wang, S. et al. (2008). "Cyclin-dependent kinase 9: a key transcriptional regulator and potential drug target in oncology, virology and cardiology," *Trends in Pharmacological Sciences* 29(6): 302-313.
Wang, S. et al. (2010). "Discovery and Characterization of 2-Anilino-4-(Thiazol-5-yl)Pyrimidine Transcriptional CDK Inhibitors as Anticancer Agents," *Chemistry & Biology* 17: 1111-1121.
Wesierska-Gadek, J. et al. (2011). "The impact of multi-targeted cyclin-dependent kinase inhibition in breast cancer cells: clinical implications," *Expert Opin. Investig. Drugs* 20(12): 1611-1628.
Yang, Z. et al. (Aug. 19, 2005). "Recruitment of P-TEFb for Stimulation of Transcriptional Elongation by the Bromodomain Protein Brd4," Molecular Cell 19: 535-545.
Zhou, M. et al. (Dec. 2004). "Coordination of Transcription Factor Phosphorylation and Histone Methylation by the P-TEFb Kinase during Human Immunodeficiency Virus Type 1 Transcription," *Journal of Virology* 78(24): 13522-13533.
Zhou, Q. et al. (Sep. 2006). "The Yin and Yang of P-TEFb Regulation: Implications for Human Immunodeficiency Virus Gene Expression and Global Control of Cell Growth and Differentiation," *Microbiology and Molecular Biology Reviews* 70(3): 646-659.

\* cited by examiner

4-ARYL-N-PHENYL-1,3,5-TRIAZIN-2-AMINES CONTAINING A SULFOXIMINE GROUP

CROSS REFERENCE TO RELATED APPLICATIONS

This application is a continuation application of U.S. patent application Ser. No. 14/122,063, which adopts the international filing date of May 21, 2012, which is the National Phase application under 35 U.S.C. § 371 of International Application No. PCT/EP2012/059399, filed May 21, 2012, which claims priority benefit to European Application Nos. 12158030.2, filed Mar. 5, 2012, 11180759.0, filed Sep. 9, 2011, and 11167317.4, filed May 24, 2011, the disclosures of each of which are hereby incorporated by reference in their entireties for all purposes.

The present invention relates to 4-aryl-N-phenyl-1,3,5-triazin-2-amines containing a sulfoximine group of general formula (I) or (Ia) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I) or (Ia).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNApolymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 2010, 9, 1697). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol. Cell 2008, 29, 588). The remaining half of P-TEFb exists in an active complex containing the bromodomain protein Brd4 (Yang et al., Mol. Cell 2005, 19, 535). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol. Mol. Biol. Rev. 2006, 70, 646).

Furthermore, the activity of P-TEFb is regulated by posttranslational modifications including phosphorylation/de-phosphorylation, ubiquitination, and acteylation (reviewed in Cho et al., Cell Cycle 2010, 9, 1697).

Deregulated activity of CDK9 kinase activity of the P-TEFb heterodimer is associated with a variety of human pathological settings such as hyper-proliferative diseases (e.g. cancer), virally induced infectious diseases or cardiovascular diseases.

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance. Inhibition of P-TEFb kinase activity was shown to reduce transcriptional activity of RNA polymerase II leading to a decline of short-lived anti-apoptotic proteins, especially Mcl-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol. Sci. 2008, 29, 302).

Many viruses rely on the transcriptional machinery of the host cell for the transcription of their own genome. In case of HIV-1 RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 repliction at kinase inhibitor concentrations that are not cytotoxic to the host cells (reviewed in Wang & Fischer, Trends Pharmacol. Sci. 2008, 29, 302). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene 2006, 25, 1775), and the human T-lymphotropic virus type 1 (HTLV-1), where the transcriptional activator Tax recruits P-TEFb (Zhou et al., J. Virol. 2006, 80, 4781).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 2007, 6, 1856).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDK's (e.g. CDK1/cyclin B, CDK2/cyclin A, CDK2/cyclinE, CDK4/cyclinD, CDK6/cyclinD) and of CDK9 is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are therefore required.

CDK inhibitors in general as well as CDK9 inhibitors are described in a number of different publications:

WO2008129070 and WO2008129071 both describe 2,4 disubstituted aminopyrimidines as CDK inhibitors in general. It is also asserted that some of these compounds may act as selective CDK9 inhibitors (WO2008129070) and as CDK5 inhibitors (WO2008129071), respectively, but no specific CDK9 IC50 (WO2008129070) or CDK5 IC50 (WO200812971) data is presented.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

EP1218360 B1 describes triazin derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

Wang et al. (Chemistry & Biology 2010, 17, 1111-1121) describe 2-anilino-4-(thiazol-5-yl)pyrimidine transcriptional CDK inhibitors, which show anticancer activity in animal models.

WO2004009562 discloses substituted triazine kinase inhibitors. For selected compounds CDK1 and CDK 4 test data, but no CDK9 data is presented.

WO2004072063 describes heteroaryl (pyrimidine, triazine) substituted pyrroles as inhibitors of protein kinases such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to U.S. Pat. No. 7,618, 968B2, U.S. Pat. No. 7,291,616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2008025556 describes carbamoyl sulfoximides having a pyrimidine core, which are useful as kinase inhibitors. No CDK9 data is presented.

WO2002066481 describes pyrimidine derivatives as cyclin dependent kinase inhibitors CDK9 is not mentioned and no CDK9 data is presented.

WO2008109943 concerns phenyl aminopyri(mi)dine compounds and their use as kinase inhibitors, in particular as JAK2 kinase inhibitors. The specific examples focus on compounds having a pyrimidine core.

WO2009032861 describes substituted pyrimidinyl amines as JNK kinase inhibitors. The specific examples focus on compounds having a pyrimidine core.

WO2011046970 concerns amino-pyrimidine compounds as inhibitors of TBKL and/or IKK epsilon. The specific examples focus on compounds having a pyrimidine core.

Despite the fact that various inhibitors of CDK's are known, there remains a need for selective CDK9 inhibitors to be used for the treatment of diseases such as hyperproliferative diseases, viral diseases, and/or diseases of the heart, which offer one or more advantages over the compounds known from prior art, such as: improved activity and/or efficacy,
  beneficial kinase selectivity profile according to the respective therapeutic need,
  improved side effect profile, such as fewer undesired side effects,
  lower intensity of side effects, or reduced (cyto)toxicity,
  improved physicochemical properties, such as solubility in water and body fluids,
  improved pharmacokinetic properties, allowing e.g. for dose reduction or an easier dosing scheme.

A particular object of the invention is to provide CDK9 kinase inhibitors which, compared to the compounds known from prior art, show an increased solubility in water.

A particular object of the invention is to provide CDK9 kinase inhibitors which, compared to the compounds known from prior art, show an increased selectivity for CDK9/Cyclin T1 as compared to CDK2/Cyclin E.

Another object of the invention is to provide CDK9 kinase inhibitors which show an increased potency to inhibit CDK9 activity (demonstrated by a lower IC50 value for CDK9/Cyc T1) compared to the compounds known from prior art.

Another object of the invention is to provide CDK9 kinase inhibitors, which show an improved anti-proliferative activity in one or more of certain tumor cell lines such as for example HeLa or DU145 compared to the compounds known from prior art.

Another object of the invention is to provide CDK9 kinase inhibitors, which show an improved side effect profile such as a reduced carbonic anhydrase-1 and -2 inhibition compared to the compounds known from prior art.

Further, it is also an object of the present invention to provide CDK9 kinase inhibitors, which, compared to the compounds known from prior art, show an increased solubility in water and/or which are highly selective for CDK9/Cyclin T1 as compared to CDK2/Cyclin E, and/or which show an increased potency to inhibit CDK9 activity (demonstrated by a lower IC50 value for CDK9/Cyc T1) and/or which show an improved anti-proliferative activity in one or more of certain tumor cell lines such as HeLa or DU145.

The present invention relates to compounds of general formula (I)

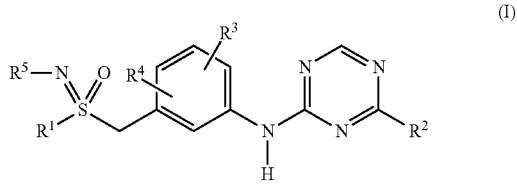

or of general formula (Ia)

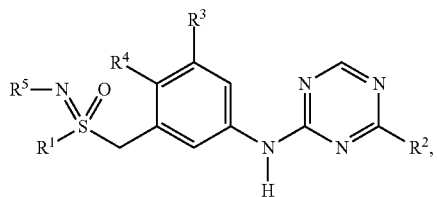

(Ia)

wherein

R$^1$ represents a group selected from C$_1$-C$_6$-alkyl-, C$_3$-C$_7$-cycloalkyl-, heterocyclyl-, phenyl, heteroaryl, phenyl-C$_1$-C$_3$-alkyl- or heteroaryl-C$_1$-C$_3$-alkyl-,
  wherein said group is optionally substituted with one or two or three substituents, identically or differently, selected from the group consisting of hydroxy, cyano, halogen, halo-C$_1$-C$_3$-alkyl-, C$_1$-C$_6$-alkoxy-, C$_1$-C$_3$-fluoroalkoxy-, amino, alkylamino-, dialkylamino-, acetylamino-, N-methyl-N-acetylamino-, cyclic amines;

R$^2$ represents a group selected from

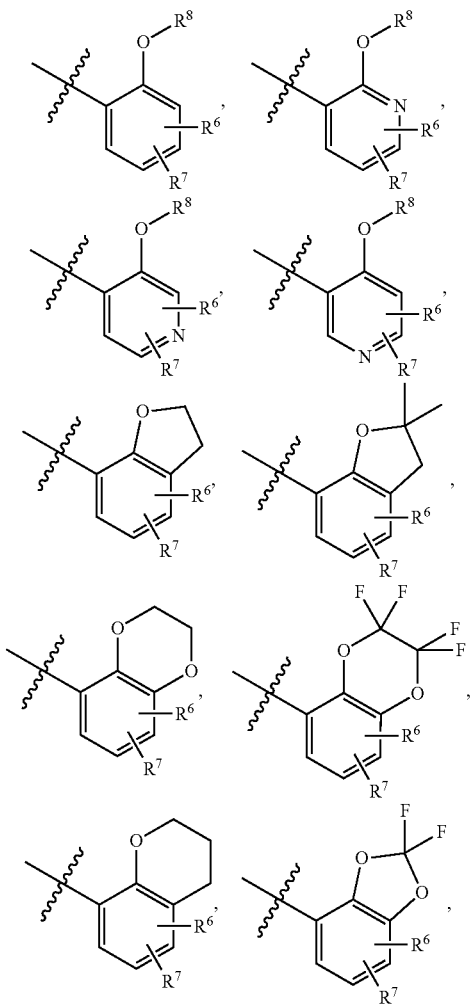

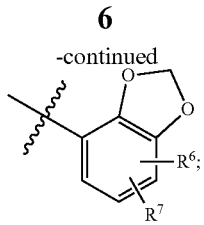

R$^3$, R$^4$ represent, independently from each other, a group selected from a hydrogen atom, fluoro atom, chloro atom, cyano, C$_1$-C$_3$-alkyl-, C$_1$-C$_3$-alkoxy-, halo-C$_1$-C$_3$-alkyl-, C$_1$-C$_3$-fluoroalkoxy-;

R$^5$ represents a group selected from a hydrogen atom, cyano, —C(O)R$^9$, —C(O)OR$^9$, —S(O)$_2$R$^9$, —C(O)NR$^{10}$R$^{11}$, C$_1$-C$_6$-alkyl-, C$_3$-C$_7$-cycloalkyl-, heterocycyl-, phenyl, heteroaryl
  wherein said C$_1$-C$_6$-alkyl, C$_3$-C$_7$-cycloalkyl-, heterocycyl-, phenyl or heteroaryl group is optionally substituted with one, two or three substituents, identically or differently, selected from halogen, hydroxy, cyano, C$_1$-C$_3$-alkyl-, C$_1$-C$_3$-alkoxy-, amino, alkylamino-, dialkylamino-, acetylamino-, N-methyl-N-acetylamino-, cyclic amines, halo-C$_1$-C$_3$-alkyl-, C$_1$-C$_3$-fluoroalkoxy-;

R$^6$, R$^7$ represent, independently from each other, a group selected from a hydrogen atom, fluoro atom, chloro atom, cyano, C$_1$-C$_3$-alkyl-, C$_1$-C$_3$-alkoxy-, halo-C$_1$-C$_3$-alkyl-, C$_1$-C$_3$-fluoroalkoxy-;

R$^8$ represents a group selected from a) a C$_1$-C$_{10}$-alkyl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-, C$_2$-C$_3$-alkenyl-, C$_2$-C$_3$-alkynyl-, C$_3$-C$_7$-cycloalkyl-, heterocycyl-, phenyl, heteroaryl, wherein said C$_3$-C$_7$-cycloalkyl-, heterocycyl-, phenyl or heteroaryl group is optionally substituted with one, two or three substituents, identically or differently, selected from halogen, hydroxy, cyano, C$_1$-C$_3$-alkyl-, C$_1$-C$_3$-alkoxy-, amino, alkylamino-, dialkylamino-, acetylamino-, N-methyl-N-acetylamino-, cyclic amines, halo-C$_1$-C$_3$-alkyl-, C$_1$-C$_3$-fluoroalkoxy-;

b) a C$_3$-C$_7$-cycloalkyl- group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-, C$_2$-C$_3$-alkenyl-, C$_2$-C$_3$-alkynyl-;

c) a heterocyclyl- group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-, C$_2$-C$_3$-alkenyl-, C$_2$-C$_3$-alkynyl-;

d) a phenyl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

e) a heteroaryl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

f) a phenyl-$C_1$-$C_3$-alkyl- group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

g) a heteroaryl-$C_1$-$C_3$-alkyl- group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

$R^9$ represents a group selected from $C_1$-$C_6$-alkyl-, $C_3$-$C_7$-cycloalkyl-, heterocycyl-, phenyl, benzyl or heteroaryl wherein said group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from hydrogen, $C_1$-$C_6$-alkyl-, $C_3$-$C_7$-cycloalkyl-, heterocycyl-, phenyl or heteroaryl wherein said $C_1$-$C_6$-alkyl, $C_3$-$C_7$-cycloalkyl-, heterocycyl-, phenyl or heteroaryl group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

or their salts, solvates or salts of solvates.

Compounds according to the invention are the compounds of the formula (I) or (Ia) or (Ib) and the salts, solvates and solvates of the salts thereof, the compounds of the hereinafter recited formula which are encompassed by formula (I) or (Ia) or (Ib) and the salts, solvates and solvates of the salts thereof, and the compounds which are encompassed by formula (I) or (Ia) or (Ib) and which are mentioned hereinafter as exemplary embodiments and the salts, solvates and solvates of the salts thereof, where the compounds which are encompassed by formula (I) or (Ia) or (Ib) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol. Additionally, basic nitrogen containing groups may be quaternised with such agents as lower alkylhalides such as methyl-, ethyl-, propyl-, and butylchlorides, -bromides and -iodides; dialkylsulfates like dimethyl-, diethyl-, dibutyl- and diamylsulfates, long chain halides such as decyl-, lauryl-, myristyl- and stearylchlorides, -bromides and -iodides, aralkylhalides like benzyl- and phenethylbromides and others.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

For the purposes of the present invention, the substituents have the following meaning, unless otherwise specified:

The term "halogen", "halogen atom" or "halo" represents fluorine, chlorine, bromine and iodine, particularly chlorine or fluorine, preferably fluorine atoms.

The term "alkyl" represents a linear or branched alkyl radical having the number of carbon atoms specifically indicated, e.g. $C_1$-$C_{10}$ one, two, three, four, five, six, seven, eight, nine or ten carbon atoms, e.g. methyl, ethyl, n-propyl, isopropyl, n-butyl, isobutyl, sec-butyl, tert-butyl, pentyl, isopentyl, hexyl, heptyl, octyl, nonyl-, decyl-, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. If the number of carbon atoms is not specifically indicated the term "alkyl" represents a linear or branched alkyl radical having, as a rule, 1 to 9, particularly 1 to 6, preferably 1 to 4 carbon atoms. Particularly, the alkyl group has 1, 2, 3, 4, 5 or 6 carbon atoms ("$C_1$-$C_6$-alkyl"), e.g. methyl, ethyl, n-propyl-, isopropyl, n-butyl, tert-butyl, pentyl, isopentyl, hexyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. Preferably, the alkyl group has 1, 2 or 3 carbon atoms ("$C_1$-$C_3$-alkyl"), methyl, ethyl, n-propyl or isopropyl.

The term "$C_2$-$C_3$-alkenyl" is to be understood as preferably meaning a linear or branched, monovalent hydrocarbon group, which contains one double bond, and which has 2 or 3 carbon atoms ("$C_2$-$C_3$-alkenyl"). Said alkenyl group is, for example, a vinyl, allyl, (E)-2-methylvinyl, (Z)-2-methylvinyl or isopropenyl group.

The term "$C_2$-$C_3$-alkynyl" is to be understood as preferably meaning a linear, monovalent hydrocarbon group which contains one triple bond, and which contains 2 or 3 carbon atoms. Said $C_2$-$C_3$-alkynyl group is, for example, ethynyl, prop-1-ynyl or prop-2-ynyl group.

The term "$C_3$-$C_7$-cycloalkyl" is to be understood as preferably meaning a saturated, monovalent, monocyclic hydrocarbon ring which contains 3, 4, 5, 6 or 7 carbon atoms. Said $C_3$-$C_7$-cycloalkyl group is for example, a monocyclic hydrocarbon ring, e.g. a cyclopropyl, cyclobutyl, cyclopentyl, cyclohexyl or cycloheptyl group. Said cycloalkyl ring can optionally contain one or more double bonds e.g. cycloalkenyl, such as a cyclopropenyl, cyclobutenyl, cyclopentenyl, cyclohexenyl or cycloheptenyl group, wherein the bond between said ring with the rest of the molecule may be to any carbon atom of said ring, be it saturated or unsaturated. Preferably the "$C_3$-$C_7$-cycloalkyl" is a cyclopropyl group.

The term "heterocyclyl" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl" is to be understood as meaning a "4- to 10-membered heterocyclic ring".

The term a "4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen. Said heterocyclic ring is for example, a monocyclic heterocyclic ring such as an oxetanyl, azetidinyl, tetrahydrofuranyl, pyrrolidinyl, 1,3-dioxolanyl, imidazolidinyl, pyrazolidinyl, oxazolidinyl, isoxazolidinyl, 1,4-dioxanyl, pyrrolinyl, tetrahydropyranyl, piperidinyl, morpholinyl, 1,3-dithianyl, thiomorpholinyl, piperazinyl, or chinuclidinyl group. Optionally, said heterocyclclic ring can contain one or more double bonds, e.g. 4H-pyranyl, 2H-pyranyl, 2,5-dihydro-1H-pyrrolyl, 1,3-dioxolyl, 4H-1,3,4-thiadiazinyl, 2,5-dihydrofuranyl, 2,3-dihydrofuranyl, 2,5-dihydrothienyl, 2,3-dihydrothienyl, 4,5-dihydrooxazolyl, 4,5-dihydroisoxazolyl, or 4H-1,4-thiazinyl group, or, it may be benzo fused.

Particularly, the term "heterocyclyl" is to be understood as being a heterocyclic ring which contains 3, 4 or 5 carbon atoms, and 1, 2 or 3 of the above-mentioned heteroatom-containing groups (a "4- to 7-membered heterocyclic ring"), more particularly said ring can contain 4 or 5 carbon atoms, and 1, 2 or 3 of the above-mentioned heteroatom-containing groups (a "5- to 7-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the above-mentioned heteroatom-containing groups, preferably 4 carbon atoms and 2 of the above-mentioned heteroatom-containing groups.

The term "$C_1$-$C_6$-alkoxy-" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentyloxy, iso-pentyloxy, n-hexyloxy group, or an isomer thereof. Particularly, the "$C_1$-$C_6$-alkoxy-" group is a "$C_1$-$C_4$-alkoxy-", a "$C_1$-$C_3$-alkoxy-", a methoxy, ethoxy, or propoxy group, preferably a methoxy, ethoxy or propoxy group.

The term "$C_1$-$C_3$-fluoroalkoxy-" is to be understood as preferably meaning a linear or branched, saturated, monovalent, $C_1$-$C_3$-alkoxy- group, as defined supra, in which one or more of the hydrogen atoms is replaced, identically or differently, by one or more fluoro atoms. Said $C_1$-$C_3$-fluoroalkoxy- group is, for example a 1,1-difluoromethoxy-, a 1,1,1-trifluoromethoxy-, a 2-fluoroethoxy-, a 3-fluoropropoxy-, a 2,2,2-trifluoroethoxy-, a 3,3,3-trifluoropropoxy-particularly a "$C_1$-$C_2$-fluoroalkoxy-" group.

The term "alkylamino-" is to be understood as preferably meaning an alkylamino group with a linear or branched alkyl group as defined supra. ($C_1$-$C_3$)-alkylamino- for example means a monoalkylamino group with 1, 2 oder 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, iso-propylamino-, tert.-butylamino-, n-pentylamino- or n-hexylamino-.

The term "dialkylamino-" is to be understood as preferably meaning an alkylamino group having two linear or branched alkyl groups as defined supra, which are independent from each other. ($C_1$-$C_3$)-dialkylamino- for example represents a dialkylamino group with two alkyl groups each of them having 1 to 3 carbon atoms per alkyl group. The term "dialkylamino-" comprises for example: N,N-Dimethylamino-, N,N-Diethylamino-, N-Ethyl-N-methylamino-, N-Methyl-N-n-propylamino-, N-Isopropyl-N-n-propylamino-, N-t-Butyl-N-methylamino-, N-Ethyl-N-n-pentylamino-und N-n-Hexyl-N-methylamino-.

The term "cyclic amine" is to be understood as preferably meaning a cyclic amine group. Suitable cyclic amines are especially azetidine, pyrrolidine, piperidine, piperazine, 1-methylpiperazine, morpholine, thiomorpholine, which could be optionally substituted by one or two methyl groups.

The term "halo-$C_1$-$C_3$-alkyl-" is to be understood as preferably meaning a linear or branched, saturated, monovalent hydrocarbon group in which the term "$C_1$-$C_3$-alkyl" is defined supra, and in which one or more hydrogen atoms is replaced by a halogen atom, identically or differently, i.e. one halogen atom being independent from another. Particularly, said halogen atom is fluorine. Preferred is fluoro-$C_1$-$C_3$-alkyl such as for example —$CF_3$, —$CHF_2$, —$CH_2F$, —$CF_2CF_3$, or —$CH_2CF_3$. Said halo-$C_1$-$C_3$-alkyl- group is, for example, a halo-$C_1$-$C_2$-alkyl- group, —$CF_3$, —$CHF_2$, —$CH_2F$, —$CF_2CF_3$, or —$CH_2CF_3$, preferably it is —$CF_3$.

The term "phenyl-$C_1$-$C_3$-alkyl-" is to be understood as preferably meaning a phenyl group, in which one of the hydrogen atoms is replaced by a $C_1$-$C_3$-alkyl group, as defined supra, that links the phenyl-$C_1$-$C_3$-alkyl- group to the molecule. Particularly, the "phenyl-$C_1$-$C_3$-alkyl-" is a phenyl-$C_1$-$C_2$-alkyl-, preferably a benzyl- group.

The term "heteroaryl" is to be understood as preferably meaning a monovalent, aromatic, mono- or bicyclic aromatic ring system having 5, 6, 7, 8, 9, 10, 11, 12, 13 or 14 ring atoms (a "5- to 14-membered heteroaryl" group), particularly 5 (a "5-membered heteroaryl") or 6 (a "6-membered heteroaryl") or 9 (a "9-membered heteroaryl") or 10 ring atoms (a "10-membered heteroaryl"), and which contains at least one heteroatom which may be identical or different, said heteroatom being such as oxygen, nitrogen or sulfur, and can be monocyclic, bicyclic, or tricyclic, and in addition in each case can be benzo-condensed. Particularly, heteroaryl is selected from thienyl, furanyl, pyrrolyl, oxazolyl, thiazolyl, imidazolyl, pyrazolyl, isoxazolyl, iso-thiazolyl, oxadiazolyl, triazolyl, thiadiazolyl, tetrazolyl etc., and benzo derivatives thereof, such as, for example, benzo-furanyl, benzothienyl, benzoxazolyl, benzisoxazolyl, benz-imidazolyl, benzotriazolyl, indazolyl, indolyl, isoindolyl, etc.; or pyridyl, pyridazinyl, pyrimidinyl, pyrazinyl, triazi-nyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxali-nyl, naphthyridinyl, pteridinyl, carbazolyl, acridinyl, phenazinyl, phenothiazinyl, phenoxazinyl, xanthenyl, or oxepinyl, 1,4-benzodioxanyl etc. Preferably, heteroaryl is selected from monocyclic heteroaryl, 5-membered het-eroaryl or 6-membered heteroaryl.

The term "5-membered heteroaryl" is understood as preferably meaning a monovalent, aromatic, mono-aromatic ring system having 5 ring atoms and which contains at least one heteroatom which may be identical or different, said heteroatom being such as oxygen, nitrogen or sulfur. Particularly, "5 membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl.

The term "6-membered heteroaryl" is understood as preferably meaning a monovalent, aromatic, mono-aromatic ring system having 6 ring atoms and which contains at least one heteroatom which may be identical or different, said heteroatom being such as oxygen, nitrogen or sulfur. Particularly, "6 membered heteroaryl" is selected from pyridyl, pyridazinyl, pyrimidinyl, pyrazinyl, triazinyl.

The term "heteroaryl-$C_1$-$C_3$-alkyl-" is to be understood as preferably meaning a heteroaryl, a 5-membered heteroaryl or a 6-membered heteroaryl group, each as defined supra, in which one of the hydrogen atoms is replaced by a $C_1$-$C_3$-alkyl group, each as defined supra, that links the heteroaryl-$C_1$-$C_3$-alkyl- group to the molecule. Particularly, the "het-eroaryl-$C_1$-$C_3$-alkyl-" is a heteroaryl-$C_1$-$C_2$-alkyl-, a pyridinyl-$C_1$-$C_3$-alkyl-, a pyridinylmethyl-, a pyridinyl-ethyl-, a pyridinylpropyl-, -a pyrimidinyl-$C_1$-$C_3$-alkyl-, a pyrimidinylmethyl-, a pyrimidinylethyl-, a pyrimidinylpro-pyl-, preferably a pyridinylmethyl- or a pyridinylethyl- or a pyrimidinylethyl- or a pyrimidinylpropyl- group.

The term "$C_1$-$C_{10}$", as used throughout this text, e.g. in the context of the definition of "$C_1$-$C_{10}$-alkyl" is to be understood as meaning an alkyl group having a finite number of carbon atoms of 1 to 10, i.e. 1, 2, 3, 4, 5, 6, 7, 8, 9 or 10 carbon atoms. It is to be understood further that said term "$C_1$-$C_{10}$" is to be interpreted as any sub-range comprised therein, e.g. $C_1$-$C_{10}$, $C_1$-$C_9$, $C_1$-$C_8$, $C_1$-$C_7$, $C_1$-$C_6$ $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, $C_9$-$C_{10}$.

Similarly, as used herein, the term "$C_1$-$C_6$", as used throughout this text, e.g. in the context of the definition of "$C_1$-$C_6$-alkyl", "$C_1$-$C_6$-alkoxy" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$ $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_3$", as used throughout this text, e.g. in the context of the definition of "$C_1$-$C_3$-alkyl", "$C_1$-$C_3$-alkoxy" or "$C_1$-$C_3$-fluoroalkoxy" is to be understood as meaning an alkyl group having a finite number of carbon atoms of 1 to 3, i.e. 1, 2 or 3 carbon atoms. It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$, $C_5$-$C_6$, $C_6$-$C_7$.

A symbol ⌐ at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

Where the plural form of the word compounds, salts, hydrates, solvates and the like, is used herein, this is taken to mean also a single compound, salt, isomer, hydrate, solvate or the like.

The present invention relates to compounds of general formula (I) or (Ia), wherein
$R^1$ represents a group selected from $C_1$-$C_6$-alkyl-, $C_3$-$C_7$-cycloalkyl- or heterocyclyl-;
$R^2$ represents a group selected from

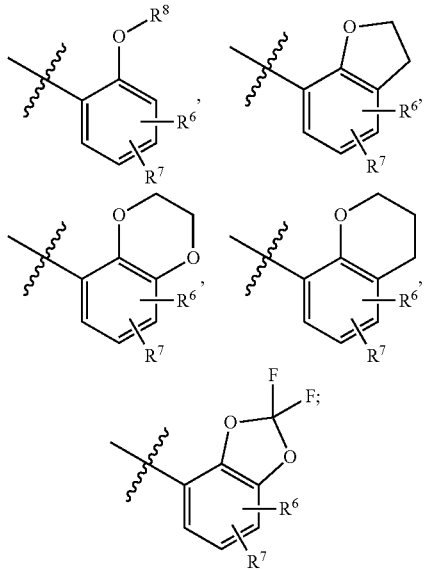

$R^3$, $R^4$ represent, independently from each other, a group selected from a hydrogen atom, fluoro atom, chloro atom or $C_1$-$C_3$-alkyl-;
$R^5$ represents a group selected from a hydrogen atom, cyano, —C(O)$R^9$, —C(O)O$R^9$, —S(O)$_2R^9$, —C(O)N$R^{10}R^{11}$, $C_1$-$C_6$-alkyl-;

$R^6$, $R^7$ represent, independently from each other, a group selected from a hydrogen atom, fluoro atom, chloro atom;
$R^8$ represents a group selected from
  a) a $C_1$-$C_{10}$-alkyl group, which is optionally substituted with one or two or three substituents, selected from the group consisting of halogen, hydroxy, $C_2$-$C_3$-alkenyl-, $C_2$-$C_3$-alkynyl-, $C_3$-$C_7$-cycloalkyl-, heterocycyl-, phenyl, heteroaryl,
    wherein said $C_3$-$C_7$-cycloalkyl-, heterocycyl-, phenyl or heteroaryl group is optionally substituted with one, two or three substituents, identically or differently, selected from halogen, cyano, $C_1$-$C_3$-alkyl-, halo-$C_1$-$C_3$-alkyl-;
  b) a phenyl group;
  c) a phenyl-$C_1$-$C_3$-alkyl- group, which phenyl group is optionally substituted with one or two or three substituents, identically or differently, selected from the group consisting of halogen, cyano, $C_1$-$C_3$-alkyl-, halo-$C_1$-$C_3$-alkyl-;
  d) a heteroaryl-$C_1$-$C_3$-alkyl- group, which heteroaryl group is optionally substituted with one substituent selected from the group consisting of halogen;
$R^9$ represents a $C_1$-$C_6$-alkyl group:
$R^{10}$, $R^{11}$ represent, independently from each other, a group selected from hydrogen or $C_1$-$C_6$-alkyl-;
or their salts, solvates or salts of solvates.

In a preferred embodiment the present invention relates to compounds of general formula (I) or (Ia), wherein
$R^1$ represents a $C_1$-$C_6$-alkyl- or $C_3$-$C_7$-cycloalkyl- group;
$R^2$ represents a group selected from

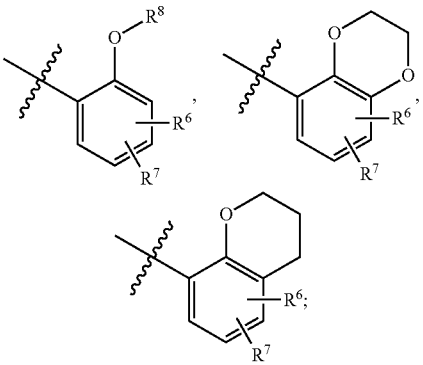

$R^3$, $R^4$ represent, independently from each other, a group selected from a hydrogen atom, fluoro atom, chloro atom, $C_1$-$C_3$-alkyl-;
$R^5$ represents a group selected from a hydrogen atom, cyano, —C(O)$R^9$, —C(O)O$R^9$, —C(O)N$R^{10}R^{11}$;
$R^6$, $R^7$ represent, independently from each other, a hydrogen atom or fluoro atom;
$R^8$ represents a group selected from
  a) a $C_1$-$C_{10}$-alkyl group, which is optionally substituted with one or two substituents, selected from the group consisting of hydroxy, $C_2$-$C_3$-alkenyl-, $C_2$-$C_3$-alkynyl-, $C_3$-$C_7$-cycloalkyl-, phenyl, heteroaryl, wherein said $C_3$-$C_7$-cycloalkyl-, phenyl or heteroaryl group is optionally substituted with one, two or three substituents, identically or differently, selected from halogen, cyano, halo-$C_1$-$C_3$-alkyl-;
  b) a phenyl-$C_1$-$C_3$-alkyl- group, which phenyl group is optionally substituted with one or two or three substituents, identically or differently, selected from the group consisting of halogen, cyano, halo-$C_1$-$C_3$-alkyl-;

c) a heteroaryl-$C_1$-$C_3$-alkyl- group, which heteroaryl group is optionally substituted with one substituent selected from the group consisting of halogen;
$R^9$ represents a $C_1$-$C_6$-alkyl group;
$R^{10}$, $R^{11}$ represent, independently frown each other, a group selected from hydrogen or $C_1$-$C_6$-alkyl-;
or their salts, solvates or salts of solvates.

In another preferred embodiment the present invention relates to compounds of general formula (I) or (Ia), wherein
$R^1$ represents a $C_1$-$C_6$-alkyl- group;
$R^2$ represents a group selected from $R^3$ represents a hydrogen atom;
$R^4$ represents a hydrogen atom;
$R^5$ represents a group selected from a hydrogen atom, cyano group or —C(O)$NR^{10}R^{11}$;
$R^6$, $R^7$ represent, independently from each other, a hydrogen atom or fluoro atom;
$R^8$ represents a group selected from
 a) a $C_1$-$C_{10}$-alkyl group, which is optionally substituted with one substituent selected from the group consisting of $C_2$-$C_3$-alkynyl;
$R^{10}$, $R^{11}$ represent, independently from each other, a hydrogen atom or a $C_1$-$C_6$-alkyl- group;
or their salts, solvates or salts of solvates.

In another preferred embodiment the present invention relates to compounds of general formula (Ib)

(Ib)

wherein
$R^1$ represents a $C_1$-$C_6$-alkyl- group:
$R^3$ represents a hydrogen or fluoro or chloro atom;
$R^4$ represents a hydrogen or fluoro atom;
$R^5$ represents a group selected from a hydrogen atom, cyano. —C(O)$R^9$, —C(O)$OR^9$, —C(O)$NR^{10}R^{11}$;
$R^8$ represents a group selected from
 a) a $C_1$-$C_{10}$-alkyl group, which is optionally substituted with one or two substituents, selected from the group consisting of $C_2$-$C_3$-alkenyl-, $C_2$-$C_3$-alkynyl-, phenyl, heteroaryl, wherein said phenyl or heteroaryl group is optionally substituted with one, two or three substituents, identically or differently, selected from halogen, cyano, halo-$C_1$-$C_3$-alkyl-;
 b) a phenyl group;
 c) a phenyl-$C_1$-$C_3$-alkyl- group, which phenyl group is optionally substituted with one or two or three substituents, identically or differently, selected from the group consisting of halogen, cyano, halo-$C_1$-$C_3$-alkyl-;
 d) a heteroaryl-$C_1$-$C_3$-alkyl- group, which heteroaryl group is optionally substituted with one substituent selected from the group consisting of halogen;
$R^9$ represents a $C_1$-$C_6$-alkyl group;
$R^{10}$, $R^{11}$ represent, independently from each other, a group selected from hydrogen or $C_1$-$C_6$-alkyl-;
or their salts, solvates or salts of solvates.

The present invention relates to compounds of general formula (I) or (Ia), wherein
$R^1$ represents a group selected from $C_1$-$C_6$-alkyl- or heterocyclyl-;
$R^2$ represents a group selected from $R^1$, $R^4$ represent, independently from each other, a group selected from a hydrogen atom, fluoro atom, chloro atom;
$R^5$ represents a group selected from a hydrogen atom, cyano, —C(O)$R^9$, —C(O)$OR^9$, —S(O)$_2R^9$, —C(O)$NR^{10}R^{11}$, $C_1$-$C_6$-alkyl-;
$R^6$, $R^7$ represent, independently from each other, a group selected from a hydrogen atom, fluoro atom, chloro atom;
$R^8$ represents a group selected from
 a) a $C_1$-$C_{10}$-alkyl group, which is optionally substituted with one substituent, selected from the group consisting of $C_3$-$C_7$-cycloalkyl-, heterocycyl-, phenyl, wherein said $C_3$-$C_7$-cycloalkyl-, heterocycyl- or phenyl group is optionally substituted with one, or two substituents, identically or differently, selected from halogen
 b) a phenyl group;
 c) a phenyl-$C_1$-$C_3$-alkyl- group, which is optionally substituted with one or two substituents, identically or differently, selected from the group consisting of halogen;
$R^9$ represents a $C_1$-$C_6$-alkyl group;
$R^{10}$, $R^{11}$ represent, independently from each other, a group selected from hydrogen or $C_1$-$C_6$-alkyl-;
or their salts, solvates or salts of solvates.

The present invention relates to compounds of general formula (I) or (Ia), wherein $R^1$ represents a $C_1$-$C_6$-alkyl- group;
$R^2$ represents a group selected from

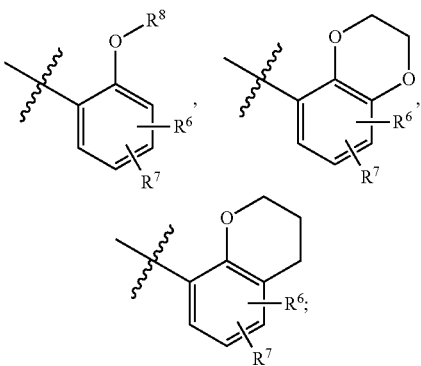

$R^3$, $R^4$ represent, independently from each other, a group selected from a hydrogen atom, fluoro atom, chloro atom:
$R^5$ represents a group selected from a hydrogen atom, cyano, —C(O)$R^9$, —C(O)O$R^9$, —S(O)$_2R^9$, —C(O)N$R^{10}R^{11}$;
$R^6$, $R^7$ represent, independently from each other, a group selected from a hydrogen atom, fluoro atom;
$R^8$ represents a group selected from
   a) a $C_1$-$C_{10}$-alkyl group, which is optionally substituted with one substituent selected from the group consisting of $C_3$-$C_7$-cycloalkyl-, phenyl, wherein said $C_3$-$C_7$-cycloalkyl- or phenyl group is optionally substituted with one halogen atom;
   b) a phenyl-$C_1$-$C_3$-alkyl- group, which is optionally substituted with one halogen atom;
$R^9$ represents a $C_1$-$C_6$-alkyl group;
$R^{10}$, $R^{11}$ represent, independently from each other, a group selected from hydrogen, $C_1$-$C_6$-alkyl-; or their salts, solvates or salts of solvates.

The present invention relates to compounds of general formula (I) or (Ia), wherein
$R^1$ represents a $C_1$-$C_6$-alkyl- group:
$R^2$ represents a group selected from

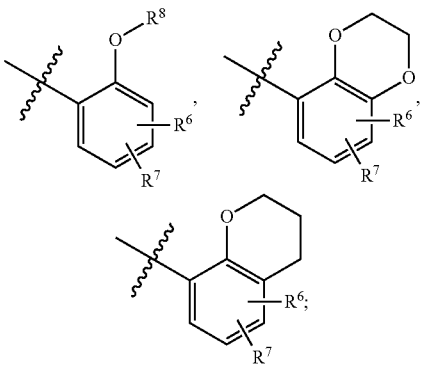

$R^3$, $R^4$ represent, independently from each other, a group selected from a hydrogen atom, fluoro atom, chloro atom;
$R^5$ represents a group selected from a hydrogen atom, cyano, —C(O)$R^9$, —C(O)O$R^9$, —C(O)N$R^{10}R^{11}$;
$R^6$, $R^7$ represent, independently from each other, a group selected from a hydrogen atom, fluoro atom;
$R^8$ represents a group selected from
   a) a $C_1$-$C_{10}$-alkyl group, which is optionally substituted with one phenyl group, wherein said phenyl group is optionally substituted with one halogen atom;
   b) a phenyl-$C_1$-$C_3$-alkyl- group, which is optionally substituted with one halogen atom;
$R^9$ represents a $C_1$-$C_6$-alkyl group:
$R^{10}R^{11}$ represent, independently from each other, a group selected from hydrogen, $C_1$-$C_6$-alkyl-; or their salts, solvates or salts of solvates.

The present invention relates to compounds of general formula (I) or (Ia), wherein
$R^1$ represents a $C_1$-$C_6$-alkyl- group;
$R^2$ represents a group selected from

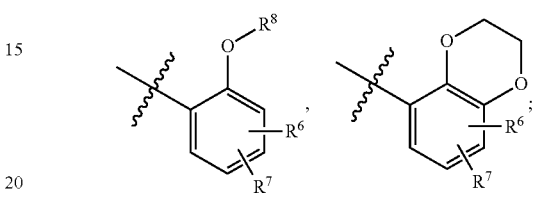

$R^3$, $R^4$ represent a hydrogen atom;
$R^5$ represents a group selected from a hydrogen atom or —C(O)N$R^{10}R^{11}$;
$R^6$, $R^7$ represent, independently from each other, a hydrogen or a fluoro atom;
$R^8$ represents a $C_1$-$C_{10}$-alkyl group;
$R^{10}$, $R^{11}$ represent, independently from each other, a hydrogen atom or $C_1$-$C_6$-alkyl- group; or their salts, solvates or salts of solvates.

The present invention relates to compounds of general formula (I) or (Ia), wherein
$R^1$ represents a $C_1$-$C_6$-alkyl- group;
$R^2$ represents a group selected from

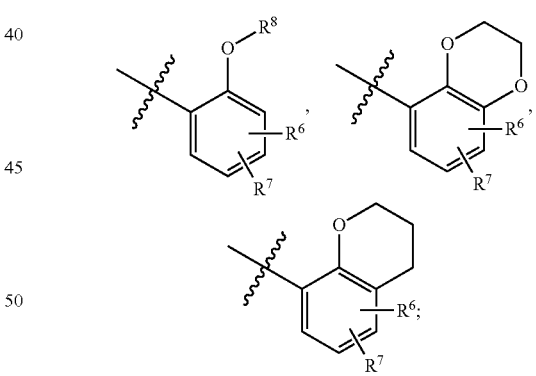

$R^3$, $R^4$ represent a hydrogen atom:
$R^5$ represents a group selected from a hydrogen atom or —C(O)N$R^{10}R^{11}$;
$R^6$, $R^7$ represent, independently from each other, a hydrogen atom or a fluoro atom;
$R^8$ represents a $C_1$-$C_{10}$-alkyl group;
$R^{10}$, $R^{11}$ represent, independently from each other, a group selected from hydrogen, $C_1$-$C_6$-alkyl-;
or their salts, solvates or salts of solvates.

In another embodiment the present invention concerns compounds of general formula (I) or (Ia), wherein R¹ represents $C_1$-$C_6$-alkyl-,
R² represents a group selected from

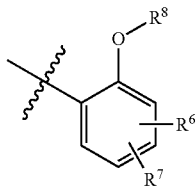

R³, R⁴ represent a hydrogen atom:
R⁵ represents a group selected from a hydrogen atom or —C(O)OR⁹;
R⁶, R⁷ represent, independently from each other, a group selected from a hydrogen atom or a fluoro atom;
R⁸ represents a group selected from
  a) a $C_1$-$C_{10}$-alkyl- group or
  b) a phenyl-$C_1$-$C_3$-alkyl- group;
R⁹ represents a $C_1$-$C_6$-alkyl- group;
or their salts, solvates or salts of solvates.

The present invention relates to compounds of general formula (I) or (Ia), wherein
  R¹ represents a group selected from methyl, ethyl, cyclopropyl, tetrahydro-2H-pyranyl;
  R² represents a group selected from

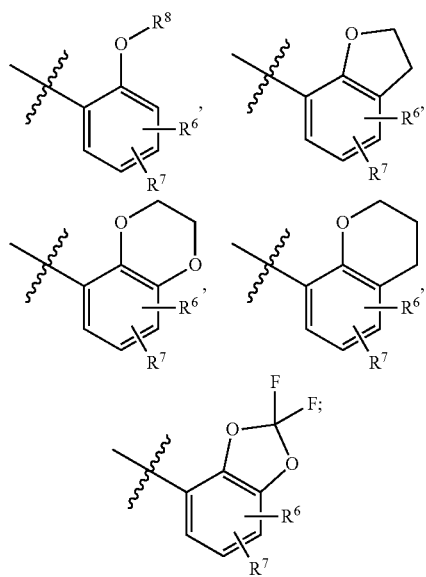

R³, R⁴ represent, independently from each other, a group selected from a hydrogen atom, fluoro atom, chloro atom or methyl;
R⁵ represents a group selected from a hydrogen atom, cyano, —C(O)R⁹, —C(O)OR⁹, —S(O)₂R⁹, —C(O)NR¹⁰R¹¹ or $C_1$-$C_6$-alkyl-;
R⁶, R⁷ represent, independently from each other, a group selected from a hydrogen atom, fluoro atom, chloro atom;
R⁸ represents a group selected from
  a) a methyl ethyl propyl or butyl group, which group is optionally substituted with one or two or three substituents, selected from the group consisting of halogen, hydroxy, ethenyl, propenyl, ethynyl, propynyl, cyclopentyl, cyclohexyl, tetrahydro-2H-pyranyl, phenyl, pyridinyl, thiazolyl, oxazolyl, wherein said phenyl or pyridinyl group is optionally substituted with one, two or three substituents, identically or differently, selected from a fluoro or chloro atom, cyano, methyl, or trifluoromethyl;
  b) a (²H₂)methyl group substituted with a (²H₅)phenyl group;
  c) a phenyl group;
  d) a benzyl group, which phenyl ring is optionally substituted with one or two or three substituents, identically or differently, selected from the group consisting of a fluoro atom, chloro atom, cyano, methyl or trifluoromethyl-;
  e) a pyridin-2-ylmethyl- group, which pyridine is optionally substituted with one fluoro atom;
  f) a pyridin-3-ylmethyl- group, which pyridine is optionally substituted with one fluoro atom;
  g) a pyridin-4-ylmethyl- group, which pyridine is optionally substituted with one fluoro atom;
  h) a thiazolylmethyl- group;
  i) an oxazolylmethyl- group
R⁹ represents a methyl or ethyl group;
R¹⁰, R¹¹ represent, independently from each other, a group selected from hydrogen, methyl;
or their salts, solvates or salts of solvates.

The present invention relates to compounds of general formula (I) or (Ia), wherein
  R¹ represents a group selected from methyl, tetrahydro-2H-pyranyl;
  R² represents a group selected from

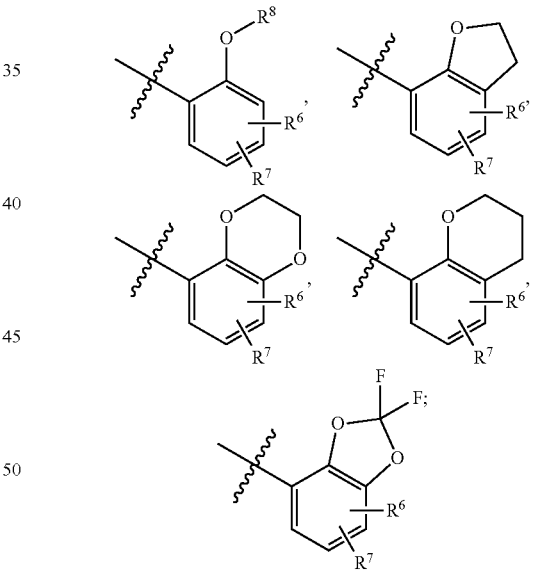

R³, R⁴ represent, independently from each other, a group selected from a hydrogen atom, fluoro atom, chloro atom;
R⁵ represents a group selected from a hydrogen atom, cyano, —C(O)R⁹, —C(O)OR⁹, —S(O)₂R⁹, —C(O)NR¹⁰R¹¹, methyl;
R⁶, R⁷ represent, independently from each other, a group selected from a hydrogen atom, fluoro atom, chloro atom;
R⁸ represents a group selected from
  a) a methyl group, which is optionally substituted with one substituent, selected from the group consisting of cyclohexyl tetrahydro-2H-pyranyl, phenyl, wherein said phenyl group is optionally substituted with one, or two substituents, identically or differently, selected from a fluoro or chloro atom;
b) a ($^2H_2$)methyl group substituted with a ($^2H_5$)phenyl group;
c) an ethyl group, which group is optionally substituted with one substituent selected from the group consisting of tetrahydro-2H-pyranyl, cyclopentyl;
d) a phenyl group;
e) a phenyl-$C_1$-$C_3$-alkyl- group, which is optionally substituted with one or two substituents, identically or differently, selected from a fluoro or chloro atom;

$R^9$ represents a methyl or ethyl group;
$R^{10}$, $R^{11}$ represent, independently from each other, a group selected from hydrogen, methyl;
or their salts, solvates or salts of solvates.

The present invention relates to compounds of general formula (I) or (Ia), wherein
$R^1$ represents a methyl or ethyl or cyclopropyl group;
$R^2$ represents a group selected from

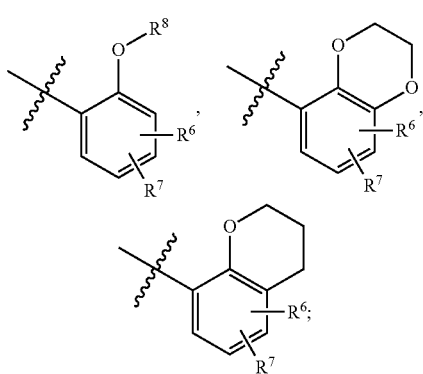

$R^3$, represents a group selected from a hydrogen atom, fluoro atom, chloro atom or methyl;
$R^4$ represents a group selected from a hydrogen atom or fluoro atom
$R^5$ represents a group selected from a hydrogen atom, cyano, —C(O)$R^9$, —C(O)O$R^9$. —C(O)N$R^{10}R^{11}$;
$R^6$, $R^7$ represent, independently from each other, a group selected from a hydrogen atom or fluoro atom;
$R^8$ represents a group selected from
methyl, ethyl, prop-2-en-1-yl, 2-methylprop-2-en-1-yl, 2-(hydroxymethyl)prop-2-en-1-yl, (2Z)-but-2-en-1-yl, prop-2-yn-1-yl, but-2-yn-1-yl, cyclohexylmethyl, benzyl, 3-cyanobenzyl, 3-fluorobenzyl, 3-chlorobenzyl, 4-fluorobenzyl, 4-chlorobenzyl, 3-fluoro-5-(trifluoromethyl)benzyl, 3-chloro-5-fluorobenzyl, pyridin-4-yl, 2-fluoropyridin-4-yl 2,3,5-trifluorobenzyl, 3,4,5-trifluorobenzyl;
$R^9$ represents a methyl or ethyl group;
$R^{10}$, $R^{11}$ represent, independently from each other, a group selected from hydrogen, $C_1$-$C_6$-alkyl-;
or their salts, solvates or salts of solvates.

The present invention relates to compounds of general formula (I) or (Ia), wherein
$R^1$ represents a group selected from methyl;
$R^2$ represents a group selected from

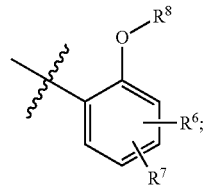

$R^3$ represents a hydrogen atom;
$R^4$ represents a hydrogen atom;
$R^5$ represents a hydrogen atom, a cyano group or —C(O)N$R^{10}R^{11}$;
$R^6$, $R^7$ represent, independently from each other, a hydrogen atom or fluoro atom;
$R^8$ represents a group selected from
a) a methyl group, which is optionally substituted with one substituent selected from the group consisting of ethynyl, propynyl;
b) an ethyl group;
$R^{10}$ represents a hydrogen atom;
$R^{11}$ represents a methyl group;
or their salts, solvates or salts of solvates.

The present invention relates to compounds of general formula (I) or (Ia), wherein
$R^1$ represents a methyl group;
$R^2$ represents a group selected from

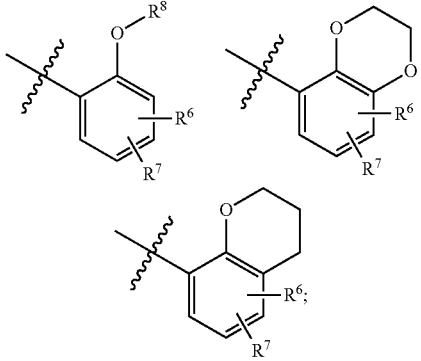

$R^3$, $R^4$ represent, independently from each other, a hydrogen, fluoro or chloro atom;
$R^5$ represents a group selected from a hydrogen atom, cyano, —C(O)$R^9$, —C(O)O$R^9$, —S(O)$_2R^9$, —C(O)N$R^{10}R^{11}$;
$R^6$, $R^7$ represent, independently from each other, a group selected from a hydrogen atom, fluoro atom;
$R^8$ represents a group selected from
a) methyl group, which is optionally substituted with one substituent, selected from the group consisting of cyclohexyl and phenyl, wherein said phenyl group is optionally substituted with one fluoro atom;
b) a benzyl group, which is optionally substituted with one fluoro atom:
$R^9$ represents a methyl or ethyl group;
$R^{10}$, $R^{11}$ represent, independently from each other, a group selected from hydrogen or methyl:
or their salts, solvates or salts of solvates.

The present invention relates to compounds of general formula (I) or (Ia), wherein $R^1$ represents a methyl group;
$R^2$ represents a group selected from

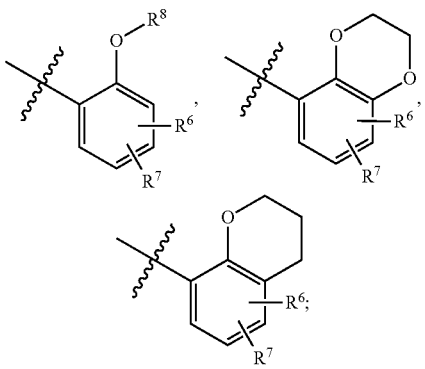

$R^3$, $R^4$ represent, independently from each other, a hydrogen, fluoro or chloro atom;
$R^5$ represents a group selected from a hydrogen atom, cyano, —C(O)$R^9$, —C(O)O$R^9$, —C(O)N$R^{10}R^{11}$;
$R^6$, $R^7$ represent, independently from each other, a group selected from a hydrogen atom, fluoro atom;
$R^8$ represents a group selected from
  a) a methyl group, which is optionally substituted with one phenyl group, wherein said phenyl group is optionally substituted with one fluoro atom;
  b) a benzyl group, which is optionally substituted with one fluoro atom;
$R^9$ represents a methyl or ethyl group;
$R^{10}$, $R^{11}$ represent, independently from each other, a group selected from hydrogen or methyl;
or their salts, solvates or salts of solvates.

The present invention relates to compounds of general formula (I) or (Ia), wherein
$R^1$ represents a methyl group;
$R^2$ represents a group selected from

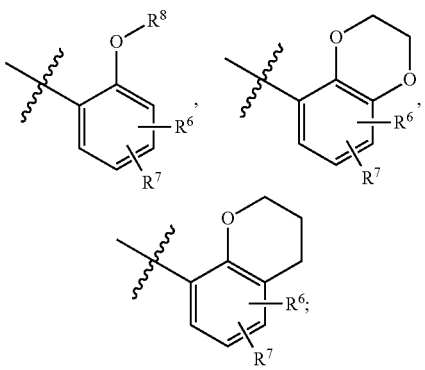

$R^3$, $R^4$ each represent a hydrogen atom;
$R^5$ represents a group selected from a hydrogen atom, —C(O)N$R^{10}R^{11}$;
$R^6$, $R^7$ represent, independently from each other, a hydrogen or a fluoro atom;
$R^8$ represents a methyl group;
$R^{10}$, $R^{11}$ represent, independently from each other, a group selected from hydrogen, methyl;
or their salts, solvates or salts of solvates.

The present invention relates to compounds of general formula (I) or (Ia), wherein
$R^1$ represents a methyl group;
$R^2$ represents a group selected from

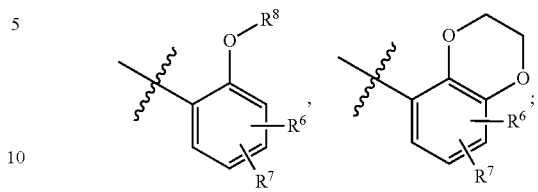

$R^3$, $R^4$ represent a hydrogen atom;
$R^5$ represents a hydrogen atom or a —C(O)N$R^{10}R^{11}$ group;
$R^6$, $R^7$ represent, independently from each other, a hydrogen or a fluoro atom;
$R^8$ represents a methyl group;
$R^{10}$, $R^1$ represent, independently from each other, a hydrogen atom or a methyl group;
or their salts, solvates or salts of solvates.

In another embodiment the present invention concerns compounds of general formula (I) or (Ia), wherein
$R^1$ represents methyl,
$R^2$ represents a group selected from

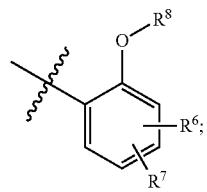

$R^3$, $R^4$ represent a hydrogen atom;
$R^5$ represents a group selected from a hydrogen atom or —C(O)O$R^9$;
$R^6$, $R^7$ represent, independently from each other, a group selected from a hydrogen atom or fluoro atom;
$R^8$ represents a group selected from methyl or benzyl;
$R^9$ represents ethyl;
or their salts, solvates or salts of solvates.

In another embodiment the present invention concerns compounds of general formula (I) or (Ia), wherein
$R^1$ represents methyl;
$R^2$ represents a group selected from

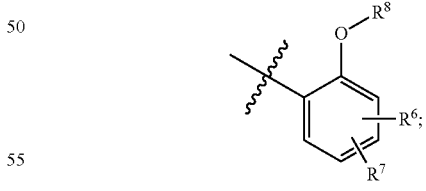

$R^3$ represents a fluoro atom;
$R^4$ represents a hydrogen atom;
$R^5$ represents a group selected from a hydrogen atom or cyano;
$R^6$, $R^7$ represent, independently from each other, a group selected from a hydrogen atom or fluoro atom;
$R^8$ represents a group selected from methyl or benzyl;
or their salts, solvates or salts of solvates.

The present invention relates to compounds of general formula (Ia)

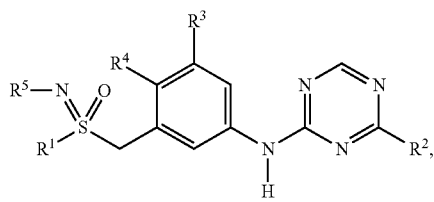

wherein

R$^1$ represents a methyl group;

R$^2$ represents a group selected from 2-methoxyphenyl-, 4-fluoro-2-methoxyphenyl-, 5-fluoro-2-methoxyphenyl-, 2-(benzyloxy)-4-fluorophenyl-, 4,5-difluoro-2-methoxyphenyl-, 4-chloro-2-methoxyphenyl, 2-[(4-fluorobenzyl)oxy]phenyl-, 2-(cyclohexylmethoxy)-4-fluorophenyl-, 4-fluoro-2-[(4-fluorobenzyl)oxy]phenyl-; 2-[(3,4-dichlorobenzyl)oxy]phenyl-, 2-(1-cyclopentylethoxy)-4-fluorophenyl-, 3-chloro-2-methoxyphenyl-, 2-phenoxyphenyl-;

R$^3$ represents a group selected from a hydrogen atom, fluoro atom, chloro atom;

R$^4$ represents a group selected from a hydrogen atom or chloro atom;

R$^5$ represents a group selected from a hydrogen atom, —C(O)R$^9$, —C(O)OR$^9$, methyl;

R$^9$ represents methyl or ethyl;

or their salts, solvates or salts of solvates.

The present invention late to compounds of general formula (Ia)

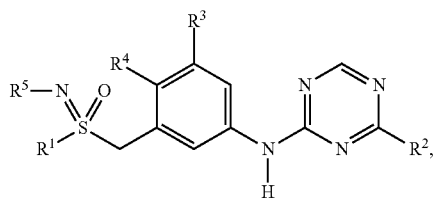

wherein

R$^1$ represents a methyl group;

R$^2$ represents a group selected from 2-methoxyphenyl-, 4-fluoro-2-methoxyphenyl-, 5-fluoro-2-methoxyphenyl-, 2-(benzyloxy)-4-fluorophenyl-, 4,5-difluoro-2-methoxyphenyl-, 4-chloro-2-methoxyphenyl-, 2-[(4-fluorobenzyl)oxy]phenyl-, 2-(cyclohexylmethoxy)-4-fluorophenyl-, 4-fluoro-2-[(4-fluorobenzyl)oxy]phenyl-; 2-[(3,4-dichlorobenzyl)oxy]phenyl-, 2-(1-cyclopentylethoxy)-4-fluorophenyl-;

R$^3$ represents a group selected from a hydrogen atom, fluoro atom, chloro atom;

R$^4$ represents a group selected from a hydrogen atom, chloro atom;

R$^5$ represents a hydrogen atom;

or their salts, solvates or salts of solvates.

The present invention relates to compounds of general formula (Ia)

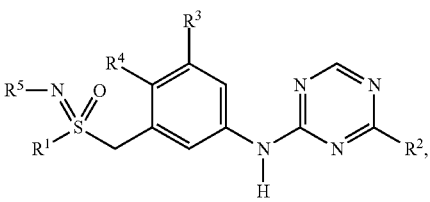

wherein

R$^1$ represents a methyl group;

R$^2$ represents a group selected from 2-methoxyphenyl-, 4-fluoro-2-methoxyphenyl-, 2-(benzyl)oxy-4-fluorophenyl-, 4,5-difluoro-2-methoxyphenyl-, 2-[(4-fluorobenzyl)oxy]phenyl-, 2-(cyclohexylmethoxy)-4-fluorophenyl-, 4-fluoro-2-[(4-fluorobenzyl)oxy]phenyl-;

R$^3$ represents a group selected from a hydrogen atom, fluoro atom, chloro atom;

R$^4$ represents a group selected from a hydrogen atom, chloro atom;

R$^5$ represents a group selected from a hydrogen atom;

or their salts, solvates or salts of solvates.

The present invention relates to compounds of general formula (Ia)

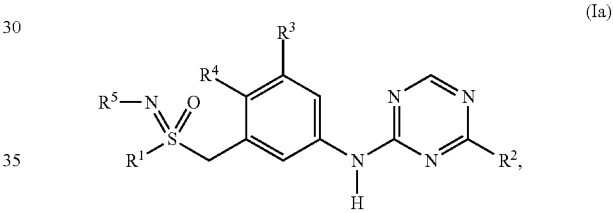

wherein

R$^1$ represents a group selected from methyl;

R$^2$ represents a group selected from 4-fluoro-2-methoxyphenyl-, 2-(benzyloxy)-4-fluorophenyl-, 4,5-difluoro-2-methoxyphenyl-, 2-[(4-fluorobenzyl)oxy]phenyl-, 4-fluoro-2-[(4-fluorobenzyl)oxy]phenyl-;

R$^3$ represents a group selected from a hydrogen atom, fluoro atom, chloro atom;

R$^4$ represents a group selected from a hydrogen atom, chloro atom;

R$^5$ represents a group selected from a hydrogen atom, —C(O)R$^9$, —C(O)OR$^9$;

R$^9$ represents methyl or ethyl:

or their salts, solvates or salts of solvates.

The present invention relates to compounds of general formula (Ia)

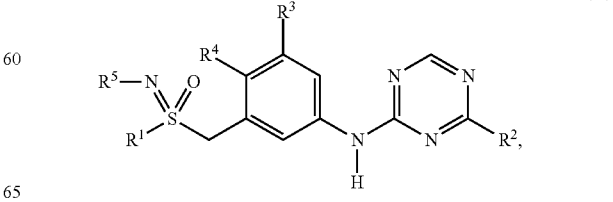

wherein
R¹ represents a group selected from methyl;
R² represents a group selected from 4-fluoro-2-methoxyphenyl-, 5-fluoro-2-methoxyphenyl-, 4,5-difluoro-2-methoxyphenyl-;
R³, R⁴ represent, independently from each other, a hydrogen atom;
R⁵ represents a hydrogen atom;
or their salts, solvates or salts of solvates.

The present invention relates to compounds of general formula (Ia)

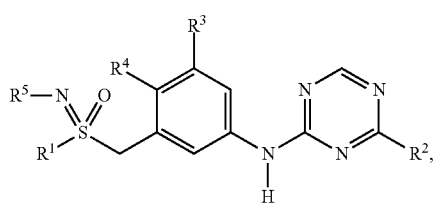

wherein
R¹ represents a group selected from methyl;
R² represents a group selected from 4-fluoro-2-methoxyphenyl-, 4,5-difluoro-2-methoxyphenyl-;
R³, R⁴ represent, independently from each other, a hydrogen atom;
R⁵ represents a hydrogen atom;
or their salts, solvates or salts of solvates.

In another preferred embodiment the present invention relates to compounds of general formula (Ib)

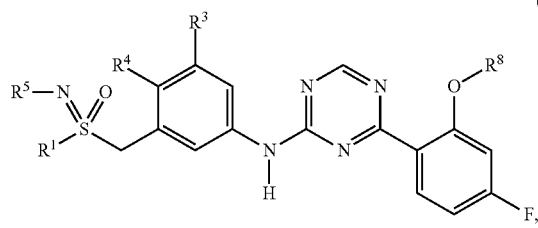

wherein
R¹ represents a methyl group;
R³ represents a group selected from a hydrogen atom or fluoro atom or chloro atom:
R⁴ represents a group selected from a hydrogen atom or fluoro atom;
R⁵ represents a group selected from a hydrogen atom, cyano, —C(O)CH3-C(O)OCH2CH3-; —C(O)NHCH3;
R⁸ represents a group selected from methyl, ethyl, prop-2-en-1-yl, 2-methylprop-2-en-1yl, (2Z)-but-2-en-1-yl, prop-2-yn-1yl, but-2-yn-1yl, 2-(hydroxymethyl)prop-2-en-1-yl, phenyl, benzyl, 3-cyanobenzyl, 3-fluorobenzyl, 3-chlorobenzyl, 4-fluorobenzyl, 4-chlorobenzyl, 3-fluoro-5-(trifluoromethyl)benzyl, 3-chloro-5-fluorobenzyl, pyridin-4-yl, 2-fluoropyridin-4-yl, 2,3,5-trifluorobenzyl, 3,4,5-trifluorobenzyl;
or their salts, solvates or salts of solvates.

In another embodiment the invention relates to compounds of formula (I) or (Ia) or (Ib), in which R¹ represents a C₁-C₃-alkyl-, a C₃-C₅-cycloalkyl- or a heterocyclyl group.

In another embodiment the invention relates to compounds of formula (I) or (Ia) or (Ib), in which R¹ represents a C₁-C₃-alkyl- or a heterocyclyl group.

In another embodiment the invention relates to compounds of formula (I) or (Ia) or (Ib), in which R¹ represents a C₁-C₃-alkyl- group.

In another embodiment the invention relates to compounds of formula (I) or (Ia) or (Ib), in which R¹ represents a methyl group.

In a preferred embodiment the invention relates to compounds of formula (I) or (Ia) or (Ib), in which R¹ represents a methyl group.

In another embodiment the invention relates to compounds of formula (I) or (Ia) or (Ib), in which R¹ represents a C₃-C₅-cycloalkyl- group, preferably a cyclopropyl group.

In another embodiment the invention relates to compounds of formula (I) or (Ia), in which R² represents

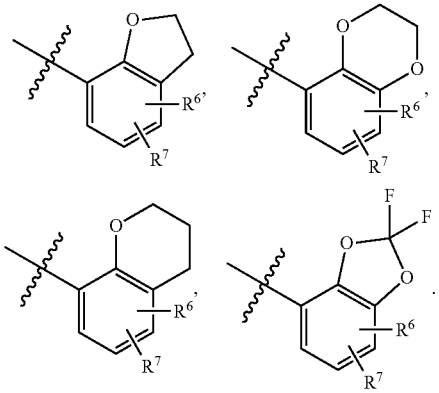

In another embodiment the invention relates to compounds of formula (I) or (Ia), in which R² represents

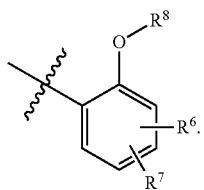

In a preferred embodiment the invention relates to compounds of formula (I) or (Ia), in which R² represents

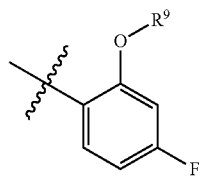

In another preferred embodiment the invention relates to compounds of formula (I) or (Ia), in which R² represents

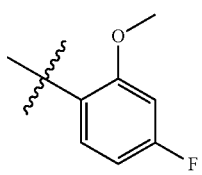 [SMILES: *c1ccc(F)cc1OC]

In another embodiment the invention relates to compounds of formula (I) or (Ia), in which $R^2$ represents a group selected from 2-methoxyphenyl-, 4-fluoro-2-methoxyphenyl-, 5-fluoro-2-methoxyphenyl-, 2-(benzyloxy)-4-fluorophenyl-, 4,5-difluoro-2-methoxyphenyl-, 4-chloro-2-methoxyphenyl-, 2-[(4-fluorobenzyl)oxy]phenyl-, 2-(cyclohexylmethoxy)-4-fluorophenyl-, 4-fluoro-2-[(4-fluorobenzyl)oxy]phenyl-, 2-[(3,4-dichlorobenzyl)oxy]phenyl-, 2-(1-cyclopentylethoxy)-4-fluorophenyl-, 3-chloro-2-methoxyphenyl-, 2-phenoxyphenyl-.

In a preferred embodiment the invention relates to compounds of formula (I) or (Ia), in which $R^2$ represents a group selected from 4-fluoro-2-methoxyphenyl-, 4-fluoro-2-[(4-fluorobenzyl)oxy]phenyl-; 4-fluoro-2-[(2-fluoropyridin-4-yl)methoxy]phenyl-, 2-(but-2-yn-1-yloxy)-4-fluorophenyl-, 4-fluoro-2-(prop-2-yn-1-yloxy)phenyl-.

In another, particularly preferred embodiment the invention relates to compounds of formula (I) or (Ia), in which $R^2$ represents a group selected from 4-fluoro-2-methoxyphenyl-, 4-fluoro-2-[(4-fluorobenzyl)oxy]phenyl-; 4-fluoro-2-[(2-fluoropyridin-4-yl)methoxy]phenyl-, 4-fluoro-2-(prop-2-yn-1-yloxy)phenyl-.

In another, particularly preferred embodiment the invention relates to compounds of formula (I) or (Ia), in which $R^2$ represents a group selected from 4-fluoro-2-methoxyphenyl-.

In another embodiment the invention relates to compounds of formula (I) or (Ia) or (Ib), in which $R^3$ represents a group selected from a hydrogen atom, fluoro atom, chloro atom, cyano, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I) or (Ia) or (Ib), in which $R^3$ represents a hydrogen atom or a fluoro atom or a chloro atom.

In another embodiment the invention relates to compounds of formula (I) or (Ia) or (Ib), in which $R^3$ represents a hydrogen atom or a fluoro atom.

In a preferred embodiment the invention relates to compounds of formula (I) or (Ia) or (Ib), in which $R^3$ represents a hydrogen atom.

In another preferred embodiment the invention relates to compounds of formula (I) or (Ia) or (Ib), in which $R^3$ represents a fluoro atom.

In another embodiment the invention relates to compounds of formula (I) or (Ia), in which $R^3$ represents a fluoro atom and in which $R^3$ is in meta position of the N-phenyl substituent in 2-position of the 1, 3, 5-triazine core.

In another embodiment the invention relates to compounds of formula (I) or (Ia), in which $R^3$ represents a fluoro atom and in which $R^3$ is in meta position of the N-phenyl substituent in 2-position of the 1, 3, 5-triazine core, and in which $R^4$ represents a hydrogen atom.

In another embodiment the invention relates to compounds of formula (I), in which $R^3$ represents a fluoro atom and in which $R^3$ is in para position of the N-phenyl substituent in 2-position of the 1, 3, 5-triazine core.

In another embodiment the invention relates to compounds of formula (I), in which $R^3$ represents a fluoro atom and in which $R^3$ is in para position of the N-phenyl substituent in 2-position of the 1, 3, 5-triazine core, and in which $R^4$ represents a hydrogen atom.

In another embodiment the invention relates to compounds of formula (I) or (Ia) or (Ib), in which $R^4$ represents a group selected from a hydrogen atom, fluoro atom, chloro atom, cyano, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I) or (Ia) or (Ib), in which $R^4$ represents a group selected from a hydrogen, a fluoro or a chloro atom.

In another embodiment the invention relates to compounds of formula (I) or (Ia) or (Ib), in which $R^4$ represents a group selected from a hydrogen atom or fluoro atom.

In another embodiment the invention relates to compounds of formula (I) or (Ia) or (Ib), in which $R^4$ represents a hydrogen atom.

In another embodiment the invention relates to compounds of formula (I) or (Ia) or (Ib), in which $R^4$ represents a chloro atom.

In a preferred embodiment the invention relates to compounds of formula (Ia) or (Ib), in which $R^3$ represents a fluoro atom and $R^4$ represents a hydrogen atom.

In another embodiment the invention relates to compounds of formula (Ia) or (Ib), in which $R^3$ represents a hydrogen atom and $R^4$ represents a fluoro atom.

In another preferred embodiment the invention relates to compounds of formula (Ia) or (Ib), in which $R^3$ represents a hydrogen atom and $R^4$ represents a hydrogen atom.

In another embodiment the invention relates to compounds of formula (I) or (Ia) or (Ib), in which $R^5$ represents a group selected from a hydrogen atom, cyano, —C(O)$R^9$, —C(O)O$R^9$, —S(O)$_2$$R^9$, —C(O)N$R^{10}$$R^{11}$, $C_1$-$C_6$-alkyl-, $C_3$-$C_7$-cycloalkyl-, heterocycyl, phenyl, heteroaryl, wherein said $C_1$-$C_6$-alkyl, $C_3$-$C_7$-cycloalkyl-, heterocycyl, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I) or (Ia) or (Ib), in which $R^5$ represents a group selected from a hydrogen atom, cyano, —C(O)$R^9$, —C(O)O$R^9$, —S(O)$_2$$R^9$, —C(O)N$R^{10}$$R^{11}$, methyl.

In another embodiment the invention relates to compounds of formula (I) or (Ia) or (Ib), in which $R^5$ represents a group selected from cyano, —C(O)$R^9$, —C(O)O$R^9$, —S(O)$_2$$R^9$, —C(O)N$R^{10}$$R^{11}$, methyl.

In another embodiment the invention relates to compounds of formula (I) or (Ia) or (Ib), in which $R^5$ represents a group selected from a hydrogen atom, cyano, —C(O)O$R^9$, C(O)N$R^{10}$$R^{11}$.

In another embodiment the invention relates to compounds of formula (I) or (Ia) or (Ib), in which $R^5$ represents a group selected from cyano, —C(O)O$R^9$, C(O)N$R^{10}$$R^{11}$.

In another embodiment the invention relates to compounds of formula (I) or (Ia) or (Ib), in which $R^5$ represents a group selected from a hydrogen atom, cyano or —C(O)O$R^9$.

In another embodiment the invention relates to compounds of formula (I) or (Ia) or (Ib), in which $R^5$ represents a group selected from cyano or —C(O)O$R^9$.

In a preferred embodiment the invention relates to compounds of formula (I) or (Ia) or (Ib), in which $R^5$ represents a group selected from a hydrogen atom or a cyano group.

In another embodiment the invention relates to compounds of formula (I) or (Ia) or (Ib), in which $R^5$ represents a group selected from cyano, $-S(O)_2R^9$, $-C(O)NR^{10}R^{11}$.

In another embodiment the invention relates to compounds of formula (I) or (Ia) or (Ib), in which $R^5$ represents a group selected from a hydrogen atom or $-C(O)OR^9$.

In another embodiment the invention relates to compounds of formula (I) or (Ia) or (Ib), in which $R^5$ represents a hydrogen atom.

In another embodiment the invention relates to compounds of formula (I) or (Ia) or (Ib), in which R represents $-C(O)OR^9$.

In another embodiment the invention relates to compounds of formula (I) or (Ia) or (Ib), in which $R^5$ represents $-C(O)NR^{10}R^{11}$.

In another embodiment the invention relates to compounds of formula (I) or (Ia) or (Ib), in which $R^5$ represents $-S(O)_2R^9$.

In another preferred embodiment the invention relates to compounds of formula (I) or (Ia) or (Ib), in which $R^5$ represents a cyano group.

In another preferred embodiment the invention relates to compounds of formula (I) or (Ia) or (Ib), in which $R^5$ represents a hydrogen atom.

In another embodiment the invention relates to compounds of formula (I) or (Ia), in which $R^6$ represents a group selected from a hydrogen atom, fluoro atom, chloro atom, cyano, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I) or (Ia), in which $R^6$ represents a group selected from a hydrogen atom or fluoro atom or chloro atom.

In another embodiment the invention relates to compounds of formula (I) or (Ia), in which $R^6$ represents a group selected from a hydrogen atom or fluoro atom.

In another embodiment the invention relates to compounds of formula (I) or (Ia), in which $R^6$ represents a hydrogen atom.

In another preferred embodiment the invention relates to compounds of formula (I) or (Ia), in which $R^6$ is in para position of the phenyl substituent in 4-position of the 1, 3, 5-triazine core and represents a fluoro atom.

In another preferred embodiment the invention relates to compounds of formula (I) or (Ia), in which
$R^6$ is in para position of the phenyl substituent in 4-position of the 1, 3, 5-triazine core and represents a fluoro atom;
$R^7$ represents a hydrogen atom.

In another embodiment the invention relates to compounds of formula (I) or (Ia), in which $R^7$ represents a group selected from a hydrogen atom, fluoro atom, chloro atom, cyano, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I) or (Ia), in which $R^7$ represents a group selected from a hydrogen atom or fluoro or chloro atom.

In another embodiment the invention relates to compounds of formula (I) or (Ia), in which $R^7$ represents a group selected from a hydrogen atom or fluoro atom.

In another embodiment the invention relates to compounds of formula (I) or (Ia), in which $R^7$ represents a fluoro atom.

In another embodiment the invention relates to compounds of formula (I) or (Ia), in which $R^7$ represents a chloro atom.

In another embodiment the invention relates to compounds of formula (I) or (Ia), in which $R^7$ is a hydrogen atom.

In another embodiment the invention relates to compounds of formula (I) or (Ia), in which $R^6$ is in para position of the phenyl substituent in 4-position of the 1, 3, 5-triazine core and $R^6$ represents a fluoro atom and in which $R^7$ represents a group selected from a hydrogen atom, fluoro atom, chloro atom, $C_1$-$C_2$-alkyl-, $C_1$-$C_2$-alkoxy-$C_1$-$C_2$-alkyl-, $C_1$-$C_2$-fluoroalkoxy-.

In another embodiment the invention relates to compounds of formula (I) or (Ia), in which $R^6$ is in para position of the phenyl substituent in 4-position of the 1, 3, 5-triazine core and $R^6$ represents a fluoro atom and in which $R^7$ represents a group selected from a hydrogen atom or fluoro atom.

In another embodiment the invention relates to compounds of formula (I) or (Ia), in which $R^6$ is in para position of the phenyl substituent in 4-position of the 1, 3, 5-triazine core and $R^6$ represents a fluoro atom and in which $R^7$ represents a hydrogen atom.

In a preferred embodiment the invention relates to compounds of formula (I) or (Ia), in which $R^6$ is in para position of the phenyl substituent in 4-position of the 1, 3, 5-triazine core and $R^6$ represents a fluoro atom and in which $R^7$ represents a hydrogen atom.

In another embodiment the invention relates to compounds of formula (I) or (Ia) or (Ib), in which $R^8$ represents a $C_1$-$C_2$-alkyl group, which is optionally substituted with one substituent, selected from the group consisting of $C_3$-$C_7$-cycloalkyl-, heterocycyl-, phenyl, wherein said $C_3$-$C_7$-cycloalkyl-, heterocycyl- or phenyl group is optionally substituted with one, or two substituents, identically or differently, selected from halogen.

In another embodiment the invention relates to compounds of formula (I) or (Ia) or (Ib), in which $R^8$ represents a methyl group, which is optionally substituted with one substituent selected from the group consisting of phenyl, wherein said phenyl group is optionally substituted with one or two substituents, identically or differently, selected from a fluoro or chloro atom.

In another embodiment the invention relates to compounds of formula (I) or (Ia) or (Ib), in which $R^8$ represents a methyl group, which is optionally substituted with one substituent selected from the group consisting of heteroaryl, wherein said heteroaryl group is optionally substituted with one or two substituents, identically or differently, selected from a fluoro or chloro atom.

In a preferred embodiment the invention relates to compounds of formula (I) or (Ia) or (Ib), in which $R^8$ represents a methyl group.

In another embodiment the invention relates to compounds of formula (I) or (Ia) or (Ib), in which $R^8$ represents a group selected from $-CH_2-CH_2CF_3$, $-CH_2CH_2CF_2CF_3$.

In another embodiment the invention relates to compounds of formula (I) or (Ia) or (Ib), in which $R^8$ represents a methyl or a $(^2H_3)$methyl group.

In another embodiment the invention relates to compounds of formula (I) or (Ia) or (Ib), in which $R^8$ represents a phenyl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I) or (Ia) or (Ib), in which $R^8$ represents a heteroaryl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I) or (Ia) or (Ib), in which $R^8$ represents a phenyl-$C_1$-$C_3$-alkyl- group, which is optionally substituted with one or two or three substituents, identically or differently, selected from the group consisting of fluoro atom, chloro atom, cyano, methyl-, trifluoromethyl-.

In another embodiment the invention relates to compounds of formula (I) or (Ia) or (Ib), in which $R^8$ represents a phenyl-$C_1$-$C_3$-alkyl- group, which is optionally substituted with one or two substituents, identically or differently, selected from the group consisting of halogen.

In another embodiment the invention relates to compounds of formula (I) or (Ia) or (Ib), in which $R^8$ represents a benzyl group, which is optionally substituted with one or two or three substituents, identically or differently, selected from the group consisting of fluoro atom, chloro atom, cyano, methyl-, trifluoromethyl-.

In another embodiment the invention relates to compounds of formula (I) or (Ia) or (Ib), in which $R^8$ represents a benzyl group, which is optionally substituted with one or two substituents, identically or differently, selected from the group consisting of a fluoro or chloro atom.

In another embodiment the invention relates to compounds of formula (I) or (Ia) or (Ib), in which $R^8$ represents a benzyl group, which is optionally substituted with one fluoro atom.

In another embodiment the invention relates to compounds of formula (I) or (Ia) or (Ib), in which $R^8$ represents a heteroaryl-$C_1$-$C_2$-alkyl-, which is optionally substituted with one or two or three substituents, identically or differently, selected from the group consisting of halogen, halo-$C_1$-$C_2$-alkyl- and $C_1$-$C_2$-alkoxy-.

In another embodiment the invention relates to compounds of formula (I) or (Ia) or (Ib), in which $R^8$ represents a pyridyl-$C_1$-$C_2$-alkyl- group, wherein said pyridyl is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I) or (Ia) or (Ib), in which $R^8$ represents a pyridyl-$C_1$-$C_2$-alkyl- group, wherein said pyridyl is optionally substituted with one or two or three substituents, identically or differently, selected from the group consisting of halogen, halo-$C_1$-$C_2$-alkyl- and $C_1$-$C_2$-alkoxy-.

In another embodiment the invention relates to compounds of formula (I) or (Ia) or (Ib), in which $R^8$ represents a oxazolyl-$C_1$-$C_2$-alkyl- or thiazolyl-$C_1$-$C_2$-alkyl- group, wherein said oxazolyl or thiazolyl group is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I) or (Ia) or (Ib), in which $R^8$ represents a oxazolyl-$C_1$-$C_2$-alkyl- or thiazolyl-$C_1$-$C_2$-alkyl- group, wherein said oxazolyl or thiazolyl group is optionally substituted with one or two or three substituents, identically or differently, selected from the group consisting of halogen, halo-$C_1$-$C_2$-alkyl-, $C_1$-$C_2$-alkoxy-.

In another embodiment the invention relates to compounds of formula (I) or (Ia) or (Ib), in which $R^8$ represents a group selected from methyl, ethyl, prop-2-en-1-yl-, 2-methylprop-2-en-1yl-, 2-(hydroxymethyl)prop-2-en-1-yl-, (2Z)-but-2-en-1-yl-, prop-2-yn-1yl-, but-2-yn-1yl-, cyclohexylmethyl-, benzyl-, 3-cyanobenzyl-, 4-cyanobenzyl-, 3-fluorobenzyl-, 3-chlorobenzyl-, 4-fluorobenzyl-, 4-chlorobenzyl-, 3-fluoro-5-(trifluoromethyl)benzyl-, 3-chloro-5-fluorobenzyl-, pyridin-4-yl-, 2-fluoropyridin-4-yl-, 2,3,5-trifluorobenzyl-, 3,4,5-trifluorobenzyl-.

In a preferred embodiment the invention relates to compounds of formula (I) or (Ia) or (Ib), in which $R^8$ represents a group selected from methyl, ethyl, prop-2-en-1-yl-, 2-methylprop-2-en-1yl-, 2-(hydroxymethyl)prop-2-en-1-yl-, (2Z)-but-2-en-1-yl-, prop-2-yn-1 yl-, but-2-yn-1yl-, phenyl, 3-cyanobenzyl-, 3-fluorobenzyl-, 3-chlorobenzyl-, 4-fluorobenzyl-, 4-chlorobenzyl-, 3-fluoro-5-(trifluoromethyl)benzyl-, 3-chloro-5-fluorobenzyl-, pyridin-4-yl-, 2-fluoropyridin-4-yl-, 2,3,5-trifluorobenzyl-, 3,4,5-trifluorobenzyl-.

In another embodiment the invention relates to compounds of formula (I) or (Ia) or (Ib), in which $R^8$ represents a group selected from $C_1$-$C_3$-alkyl or benzyl.

In another embodiment the invention relates to compounds of formula (I) or (Ia) or (Ib), in which $R^8$ represents a group selected from methyl or benzyl.

In a preferred embodiment the invention relates to compounds of formula (I) or (Ia) or (Ib), in which $R^8$ represents methyl.

In another embodiment the invention relates to compounds of formula (I) or (Ia) or (Ib), in which $R^8$ represents benzyl.

In another embodiment the invention relates to compounds of formula (I) or (Ia) or (Ib), in which $R^9$ represents a $C_1$-$C_6$-alkyl- group.

In another embodiment the invention relates to compounds of formula (I) or (Ia) or (Ib), in which $R^{10}$ represents a group selected from a hydrogen atom or $C_1$-$C_6$-alkyl-.

In another embodiment the invention relates to compounds of formula (I) or (Ia) or (Ib), in which $R^{10}$ represents a hydrogen atom.

In another embodiment the invention relates to compounds of formula (I) or (Ia) or (Ib), in which $R^{11}$ represents a group selected from a hydrogen atom or $C_1$-$C_6$-alkyl-.

In another embodiment the invention relates to compounds of formula (I) or (Ia) or (Ib), in which $R^{11}$ represents methyl.

It is to be understood that the present invention relates to any sub-combination within any embodiment of the present invention of compounds of formula (I) or (Ia) or (Ib), supra.

More particularly still, the present invention covers compounds of formula (I) or (Ia) or (Ib) which are disclosed in the Example section of this text, infra.

Very specially preferred are combinations of two or more of the abovementioned preferred ranges.

In particular, further preferred subjects of the present invention are the compounds selected from:
(rac)-Ethyl [(3-{[4-(4-fluoro-2-methoxyphenyl)-1,3,5-triazin-2-yl]amino}benzyl)(methyl)oxido-$\lambda^6$-sulfanylidene]carbamate, (rac)-4-(4-Fluoro-2-methoxyphenyl)-N-{3-[(S-methylsulfonimidoyl)methyl]phenyl}-1, 3,5-triazin-2-amine, 4-(4-Fluoro-2-methoxyphenyl)-N-{3-[(S-methylsulfonimidoyl)methyl]phenyl}-1,3,5-triazin-2-amine; enantiomer 1, 4-(4-Fluoro-2-methoxyphenyl)-N-{3-[(S-methylsulfonimidoyl)methyl]phenyl}-1,3,5-triazin-2-amine; enantiomer 2, (rac)-Ethyl {[3-({4-[2-(benzyloxy)-4-fluorophenyl]-1,3,5-triazin-2-yl]amino}benzyl(methyl)oxido-$\lambda^6$-sulfanylidene}carbamate, (rac)-4-[2-(Benzyloxy)-4-fluorophenyl]-N-{3-[(S-methylsulfonimidoyl)methyl]phenyl}-1,3,5-triazin-2-amine, 4-[2-(Benzyloxy)-4-fluorophenyl]-N-{3-[(S-methylsulfonimidoyl)methyl]phenyl}-1,3,5-triazin-2-amine; enantiomer 1, 4-[2-(Benzyloxy)-4-fluorophenyl]-N-{3-[(S-methylsulfonimidoyl)methyl]phenyl}-1,3,5-triazin-2-amine; enantiomer 2, (rac)-Ethyl [(3-{[4-(4,5-difluoro-2-methoxyphenyl)-1,3,5-triazin-2-yl]amino}benzyl)(methyl)oxido-$\lambda^6$-sulfanylidene]carbamate, (rac)-4-(4,5-Difluoro-2-methoxyphenyl)-N-{3-[(S-methylsulfonimidoyl)methyl]phenyl}-1,3,5-triazin-2-amine, (rac)-Ethyl [(3-{[4-(4-chloro-2-methoxyphenyl)-1,3,5-triazin-2-yl]amino}benzyl)(methyl)oxido-$\lambda^6$-sulfanylidene]carbamate.

(rac) 4-(4-Chloro-2-methoxyphenyl)-N-{3-[(S-methylsulfonimidoyl)methyl]phenyl}-1,3,5-triazin-2-amine, 4-(4-Chloro-2-methoxyphenyl)-N-{3-[(S-methylsulfonimidoyl)methyl]phenyl}-1,3,5-triazin-2-amine; enantiomer 1, 4-(4-Chloro-2-methoxyphenyl)-N-{3-[(S-methylsulfonimidoyl)methyl]phenyl}-1,3,5-triazin-2-amine; enantiomer 2, (rac)-1-[(3-{[4-(4-Fluoro-2-methoxyphenyl)-1,3,5-triazin-2-yl]amino}benzyl)(methyl)oxido-$\lambda$6-sulfanylidene]-3-methylurea, 1-[(3-{[4-(4-Fluoro-2-methoxyphenyl)-1,3,5-triazin-2-yl]amino}benzyl)(methyl)oxido-$\lambda$6-sulfanylidene]-3-methylurea; enantiomer 1, 1-[(3-{[4-(4-Fluoro-2-methoxyphenyl)-1,3,5-triazin-2-yl]amino}benzyl)(methyl)oxido-$\lambda$6-sulfanylidene]-3-methylurea; enantiomer 2

(rac)-Ethyl [(3-{[4-(2,2-difluoro-1,3-benzodioxol-4-yl)-1,3,5-triazin-2-yl]amino}benzyl)(methyl)oxido-$\lambda^6$-sulfanylidene]carbamate, (rac)-4-(2,2-Difluoro-1,3-benzodioxol-4-yl)-N-{3-[(S-methylsulfonimidoyl)methyl]phenyl}-1,3,5-triazin-2-amine, (rac)-Ethyl [(3-{[4-(5-fluoro-2-methoxyphenyl)-1,3,5-triazin-2-yl]amino}benzyl)(methyl)oxido-$\lambda^6$-sulfanylidene]carbamate, (rac)-4-(5-Fluoro-2-methoxyphenyl)-N-{3-[(S-methylsulfonimidoyl)methyl]phenyl}-1,3,5-triazin-2-amine, 4-(5-Fluoro-2-methoxyphenyl)-N-{3-[(S-methylsulfonimidoyl)methyl]phenyl}-1,3,5-triazin-2-amine; enantiomer 1, 4-(5-Fluoro-2-methoxyphenyl)-N-{3-[(S-methylsulfonimidoyl)methyl]phenyl}-1,3,5-triazin-2-amine; enantiomer 2, (rac)-N-[(3-{[4-(4-fluoro-2-methoxyphenyl)-1,3,5-triazin-2-yl]amino}benzyl)(methyl)oxido-$\lambda^6$-sulfanylidene]acetamide, (rac)-Ethyl [(3-{[4-(2-methoxyphenyl)-1,3,5-triazin-2-yl]amino}benzyl)(methyl)oxido-$\lambda^6$-sulfanylidene]carbamate, (rac)-4-(2-Methoxyphenyl)-N-{3-[(S-methylsulfonimidoyl)methyl]phenyl}-1,3,5-triazin-2-amine, 4-(2-Methoxyphenyl)-N-{3-[(S-methylsulfonimidoyl)methyl]phenyl}-1,3,5-triazin-2-amine; enantiomer 1, 4-(2-Methoxyphenyl)-N-{3-[(S-methylsulfonimidoyl)methyl]phenyl}-1,3,5-triazin-2-amine; enantiomer 2, (rac)-Ethyl [(3-{[4-(3,4-dihydro-2H-chromen-8-yl)-1,3,5-triazin-2-yl]amino}benzyl)(methy)oxido-$\lambda^6$-sulfanylidene]carbamate, (rac)-4-(3,4-Dihydro-2H-chromen-8-yl)-N-{3-[(S-methylsulfonimidoyl)methyl]phenyl}-1,3-[(S-methylsulfonimidoyl)methyl]phenyl}-1,3,5-triazin-2-amine, 4-(3,4-Dihydro-2H-chromen-8-yl)-N-{3-[(S-methylsulfonimidoyl)methyl]phenyl}-1,3,5-triazin-2-amine; enantiomer 1, 4-(3,4-Dihydro-2H-chromen-8-yl)-N-{3-[(S-methylsulfonimidoyl)methyl]phenyl}-1,3,5-triazin-2-amine; enantiomer 2, (rac)-Ethyl [(3-{[4-(2,3-dihydro-1-benzofuran-7-yl)-1,3,5-triazin-2-yl]amino}benzyl)(methyl)oxido-$\lambda^6$-sulfanylidene]carbamate.

(rac)-4-(2,3-Dihydro-1-benzofuran-7-yl)-N-{3-[(S-methylsulfonimidoyl)methyl]phenyl}-1,3,5-triazin-2-amine, 4-(2,3-Dihydro-1-benzofuran-7-yl)-N-{3-[(S-methylsulfonimidoyl)methyl]phenyl}-1,3,5-triazin-2-amine; enantiomer 1, 4-(2,3-Dihydro-1-benzofuran-7-yl)-N-{3-[(S-methylsulfonimidoyl)methyl]phenyl}-1,3,5-triazin-2-amine; enantiomer 2, (rac)-Ethyl [(3-{[4-(2,3-dihydro-1,4-benzodioxin-5-yl)-1,3,5-triazin-2-yl]amino}benzyl)(methyl)oxido-$\lambda^6$-sulfanylidene]carbamate, (rac)-4-(2,3-Dihydro-1,4-benzodioxin-5-yl)-N-{3-[(S-methylsulfonimidoyl)methyl]phenyl}-1,3,5-triazin-2-amine, 4-(2,3-Dihydro-1,4-benzodioxin-5-yl)-N-{3-[(S-methylsulfonimidoyl)methyl]phenyl}-1,3,5-triazin-2-amine; enantiomer 1, 4-(2,3-Dihydro-1,4-benzodioxin-5-yl)-N-{3-[(S-methylsulfonimidoyl)methyl]phenyl}-1,3,5-triazin-2-amine; enantiomer 2, (rac)-N-{3-[(N,S-Dimethylsulfonimidoyl)methyl]phenyl}-4-(4-fluoro-2-methoxyphenyl)-1,3,5-triazin-2-amine, (rac)-Ethyl [{3-[(4-{2-[(4-fluorobenzyl)oxy]phenyl}-1,3,5-triazin-2-yl)amino]benzyl}(methyl)oxido-$\lambda^6$-sulfanylidene]carbamate.

(rac)-4-{2-[(4-Fluorobenzyl)oxy]phenyl}-N-{3-[(S-methylsulfonimidoyl)methyl]phenyl}-1,3,5-triazin-2-amine, (rac)-N-[(3-{[4-(4-Fluoro-2-methoxyphenyl)-1,3,5-triazin-2-yl]amino)}benzyl)(methyl)oxido-$\lambda^6$-sulfanylidene]methanesulfonamide, (rac)-Ethyl [(3-{[4-(3-chloro-2-methoxyphenyl)-1,3,5-triazin-2-yl]amino}benzyl)(methyl)oxido-$\lambda^6$-sulfanylidene]carbamate.

(rac)-Ethyl {[3-({4-[5-fluoro-2-(tetrahydro-2H-pyran-4-ylmethoxy)phenyl]-1,3,5-triazin-2-yl}amino)benzyl](methyl)oxido-$\lambda^6$-sulfanylidene}carbamate, (rac)-Ethyl [methyl(oxido)(3-{[4-(2-phenoxyphenyl)-1,3,5-triazin-2-yl]amino}benzyl)-$\lambda^6$-sulfanylidene]carbamate.

(rac)-[(3-{[4-(4-fluoro-2-methoxyphenyl)-1,3,5-triazin-2-yl]amino}benzyl)(methyl)oxido-$\lambda^6$-sulfanylidene]cyanamide,

[(3-{[4-(4-fluoro-2-methoxyphenyl)-1,3,5-triazin-2-yl]amino}benzyl)(methyl)oxido-$\lambda^6$-sulfanylidene]cyanamide; enantiomer 1,

[(3-{[4-(4-fluoro-2-methoxyphenyl)-1,3,5-triazin-2-yl]amino}benzyl)(methyl)oxido-$\lambda^6$-sulfanylidene]cyanamide; enantiomer 2, (rac)-Ethyl [(3-fluoro-5-{[4-(4-fluoro-2-methoxyphenyl)-1,3,5-triazin-2-yl]amino}benzyl)(methyl)oxido-$\lambda^6$-sulfanylidene]carbamate, (rac)-4-(4-Fluoro-2-methoxyphenyl)-N-{3-fluoro-5-[(S-methylsulfonimidoyl)methyl]phenyl}-1,3,5-triazin-2-amine, 4-(4-Fluoro-2-methoxyphenyl)-N-{3-fluoro-5-[(S-methylsulfonimidoyl)methyl]phenyl}-1,3,5-triazin-2-amine, enantiomer 1, 4-(4-Fluoro-2-methoxyphenyl)-N-{3-fluoro-5-[(S-methylsulfonimidoyl)methyl]phenyl}-1,3,5-triazin-2-amine, enantiomer 2, (rac)-4-[2-(cyclohexylmethoxy)-4-fluorophenyl]-N-{3-[(S-methylsulfonimidoyl)methyl]phenyl}-1,3,5-triazin-2-amine, (rac)-4-{4-Fluoro-2-[(4-fluorobenzyl)oxy]phenyl}-N-{3-[(S-methylsulfonimidoyl)methyl]phenyl}-1,3,5-triazin-2-amine, (rac)-4-{4-Fluoro-2-[2-(tetrahydro-2H-pyran-4-yl)ethoxy]phenyl}-N-{3-[(S-methylsulfonimidoyl)-methyl]phenyl}-1,3,5-triazin-2-amine, (rac)-4-(4-Fluoro-2-methoxyphenyl)-N-(3-{[S-(tetrahydro-2H-pyran-4-yl)sulfonimidoyl]methyl}-phenyl)-1,3,5-triazin-2-amine, (rac)-N-{4-Chloro-3-[(S-methylsulfonimidoyl)methyl]phenyl}-4-(4-fluoro-2-methoxyphenyl)-1,3,5-triazin-2-amine, (rac)-Ethyl [3-[(4-{2-[(3,4-dichlorobenzyl)oxy]phenyl-1,3,5-triazin-2-yl)amino]benzyl}methyl)-oxido-$\lambda^6$-sulfanylidene]carbamate, (rac)-4-{2-[(3,4-Dichlorobenzyl)oxy]phenyl}-N-{3-[(S-methylsulfonimidoyl)methyl]phenyl}-1,3,5-triazin-2-amine, (rac)-4-(4-Fluoro-2-{[($^2$H$_5$)phenyl($^2$H$_2$)methyl]oxy}phenyl)-N-{3-[(S-methylsulfonimidoyl)methyl]-phenyl}-1,3,5-triazin-2-amine, 4-[2-(1-cyclopentylethoxy)-4-fluorophenyl]-N-{3-[(S-methylsulfonimidoyl)methyl]phenyl}-1,3,5-triazin-2-amine, (rac)-N-{3-Chloro-5-[(S-methylsulfonimidoyl)methyl]phenyl}-4-(4-fluoro-2-methoxyphenyl)-1,3,5-triazin-2-amine, (rac)-4-[4-Fluoro-2-(3,3,3-trifluoropropoxy)phenyl]-N-{3-[(S-methylsulfonimidoyl)methyl]phenyl}-1,3,5-triazin-2-amine, (rac)-4-[4-Fluoro-2-(pyridin-3-ylmethoxy)phenyl]-N-{3-[(S-methylsulfonimidoyl)methyl]phenyl}-1,3,5-triazin-2-amine, (rac)-4-[4-Fluoro-2-(pyridin-2-ylmethoxy)phenyl]-N-{3-[(S-methylsulfonimidoyl)methyl]phenyl}-1,3,5-triazin-2-amine, (rac)-4-[4-Fluoro-2-(pyridin-4-ylmethoxy)phenyl]-N-{3-[(S-methylsulfonimidoyl)methyl]phenyl}-1,3,5-triazin-2-amine, 4-{4-Fluoro-2-[1-(4-fluorophenyl)ethoxy]phenyl}-N-{3-[(S-methylsulfonimidoyl)methyl]phenyl}-1,3,5-triazin-2-amine, mixture of 4 stereoisomers, (rac)-[(3-Fluoro-5-{[4-(4-fluoro-2-methoxyphenyl)-1,3,5-triazin-2-yl]amino}benzyl)methyl-$\lambda$6-sulfanylidene]cyanamide,

[(3-Fluoro-5-{[4-(4-fluoro-2-methoxyphenyl)-1,3,5-triazin-2-yl]amino}benzyl)(methyl)-$\lambda$6-sulfanylidene]cyanamide; enantiomer 1,

[(3-Fluoro-5-{[4-(4-fluoro-2-methoxyphenyl)-1,3,5-triazin-2-yl]amino}benzyl)(methyl-$\lambda$6-sulfanylidene]cyanamide; enantiomer 2, (rac)-4-[2-(But-2-yn-1-yloxy)-4-fluorophenyl]-N-{3-[(S-methylsulfonimidoyl)methyl]phenyl}-1,3,5-triazin-2-amine, 4-[2-(But-2-yn-1-yloxy)-4-fluorophenyl]-N-{3-[(S-methylsulfonimidoyl)methyl]phenyl}-1,3,5-triazin-2-amine; enantiomer 1, 4-[2-(But-2-yn-1-yloxy)-4-fluorophenyl]-N-{3-[(S-methylsulfonimidoyl)methyl]phenyl}-1,3,5-triazin-2-amine; enantiomer 2, (rac)-4-[2-(2-Cyclopropylethoxy)-4-fluorophenyl]-N-{3-[(S-methylsulfonimidoyl)methyl]phenyl}-1,3,5-triazin-2-amine, (rac)-4-[4-Fluoro-2-(prop-2-yn-1-yloxy)phenyl]-N-{3-[(S-methylsulfonimidoyl)methyl]phenyl}-1,3,5-triazin-2-amine, 4-[4-Fluoro-2-(prop-2-yn-1-yloxy)phenyl]-N-{3-[(S-methylsulfonimidoyl)methyl]phenyl}-1,3,5-triazin-2-amine; enantiomer 1, 4-[4-Fluoro-2-(prop-2-yn-1-yloxy)phenyl]-N-{3-[(S-methylsulfonimidoyl)methyl]phenyl}-1,3,5-triazin-2-amine; enantiomer 2, (rac)-4-{2-[(3,4-Difluorobenzyl)oxy]-4-fluorophenyl}-N-{3-[(S-methylsulfonimidoyl)methyl]phenyl}-1,3,5-triazin-2-amine, (rac)-4-[4-Fluoro-2-(1,3-thiazol-5-ylmethoxy)phenyl]-N-{3-[(S-methylsulfonimidoyl)methyl]phenyl}-1,3,5-triazin-2-amine, (rac)-4-{4-Fluoro-2-[(2-fluoropyridin-4-yl)methoxy]phenyl}-N-{3-[(S-methylsulfonimidoyl)methyl]-phenyl}-1,3,5-triazin-2-amine, 4-{4-Fluoro-2-[(2-fluoropyridin-4-yl)methoxy]phenyl}-N-{3-[(S-methylsulfonimidoyl)methyl]phenyl}-1,3,5-triazin-2-amine; enantiomer 1, 4-{4-Fluoro-2-[(2-fluoropyridin-4-yl)methoxy]phenyl}-N-{3-[(S-methylsulfonimidoyl)methyl]phenyl}-1,3,5-triazin-2-amine; enantiomer 2, (rac)-4-[4-Fluoro-2-(prop-2-en-1-yloxy)phenyl]-N-{3-[(S-methylsulfonimidoyl)methyl]phenyl}-1,3,5-triazin-2-amine, (rac)-4-(4-Fluoro-2-{[4-(trifluoromethyl)benzyl]oxy}phenyl)-N-{3-[(S-methylsulfonimidoyl)methyl]phenyl}-1,3,5-triazin-2-amine, (rac)-4-{2-[(4-Chlorobenzyl)oxy]-4-fluorophenyl}-N-{3-[(S-methylsulfonimidoyl)methyl]phenyl}-1,3,5-triazin-2-amine, (rac)-4-(2-Ethoxy-4-fluorophenyl)-N-{3-[(S-methylsulfonimidoyl)methyl]phenyl}-1,3,5-triazin-2-amine, (rac)-4-(4-Fluoro-2-{[3-fluoro-5-(trifluoromethyl)benzyl]oxy}phenyl)-N-{3-[(S-methylsulfonimidoyl)-methyl]phenyl}-1,3,5-triazin-2-amine, (rac)-4-{4-Fluoro-2-[(3-fluorobenzyl)oxy]phenyl}-N-{3-[(S-methylsulfonimidoyl)methyl]phenyl}-1,3,5-triazin-2-amine, (rac)-4-(4-Fluoro-2-propoxyphenyl)-N-{3-[(S-methylsulfonimidoyl)methyl]phenyl}-1,3,5-triazin-2-amine, (rac)-4-{2-[(3-Chlorobenzyl)oxy]-4-fluorophenyl}-N-{3-[(S-methylsulfonimidoyl)methyl]phenyl}-1,3,5-triazin-2-amine, (rac)-4-[4-Fluoro-2-(1,2-oxazol-3-ylmethoxy)phenyl]-N-{3-[(S-methylsulfonimidoyl)methyl]phenyl}-1,3,5-triazin-2-amine, (rac)-4-{2-[(3-Chloro-5-fluorobenzyl)oxy]-4-fluorophenyl}-N-{3-[(S-methylsulfonimidoyl)methyl]-phenyl}-1,3,5-triazin-2-amine, (rac)-4-[2-(2,2-Difluoroethoxy)-4-fluorophenyl]-N-{3-[(S-methylsulfonimidoyl)methyl]phenyl}-1,3,5-triazin-2-amine, (rac)-4-{4-Fluoro-2-[(4-fluoro-3-methylbenzyl)oxy]phe-nyl}-N-{3-[(S-methylsulfonimidoyl)methyl]-phenyl}-1,3,5-triazin-2-amine,
(rac)-4-{2-[(3-Chloro-4-fluorobenzyl)oxy]-4-fluorophe-nyl}-N-{3-[(S-methylsulfonimidoyl)methyl]-phenyl}-1,3,5-triazin-2-amine,
(rac)-3-({5-Fluoro-2-[4-({3-[(S-methylsulfonimidoyl)methyl]phenyl}amino)-1,3,5-triazin-2-yl]-phenoxy}methyl)benzonitrile,
(rac)-4-{4-Fluoro-2-[(2-methylprop-2-en-1-yl)oxy]phe-nyl}-N-{3-[(S-methylsulfonimidoyl)methyl]-phenyl}-1,3,5-triazin-2-amine,
(rac)-4-[4-Fluoro-2-(4,4,4-trifluorobutoxy)phenyl]-N-{3-[(S-methylsulfonimidoyl)methyl]phenyl}-1,3,5-triazin-2-amine,
(rac)-4-{4-Fluoro-2-[(2,3,5-trifluorobenzyl)oxy]phenyl}-N-{3-[(S-methylsulfonimidoyl)methyl]-phenyl}-1,3,5-tri-azin-2-amine,
(rac)-4-{2-[(2Z)-But-2-en-1-yloxy]-4-fluorophenyl}-N-{3-[(S-methylsulfonimidoyl)methyl]phenyl}-1,3,5-triazin-2-amine,
(rac)-4-{4-Fluoro-2-[(2,4,5-trifluorobenzyl)oxy]phenyl}-N-{3-[(S-methylsulfonimidoyl)methyl]-phenyl}-1,3,5-tri-azin-2-amine,
(rac)-4-{4-Fluoro-2-[(3,4,5-trifluorobenzyl)oxy]phenyl}-N-{3-[(S-methylsulfonimidoyl)methyl]-phenyl}-1,3,5-tri-azin-2-amine,
(rac)-[(2,3-Difluoro-5-{[4-(4-fluoro-2-methoxyphenyl)-1,3,5-triazin-2-yl]amino}benzyl)methyl)oxido-$\lambda^6$-sulfa-nylidene]cyanamide,
(rac)-N-{3,4-Difluoro-5-[(S-methylsulfonimidoyl)methyl]phenyl}-4-(4-fluoro-2-methoxyphenyl)-1,3,5-triazin-2-amine,
(rac)-[Ethyl(3-{[4-(4-fluoro-2-methoxyphenyl)-1,3,5-tri-azin-2-yl]amino}benzyl)oxido-$\lambda^6$-sulfanylidene]cyana-mide,
(rac)-N-{3-[(S-ethylsulfonimidoyl)methyl]phenyl}-4-(4-fluoro-2-methoxyphenyl)-1,3,5-triazin-2-amine;
N-{3-[(S-ethylsulfonimidoyl)methyl]phenyl}-4-(4-fluoro-2-methoxyphenyl)-1,3,5-triazin-2-amine; enantiomer 1,
N-{3-[(S-ethylsulfonimidoyl)methyl]phenyl}-4-(4-fluoro-2-methoxyphenyl)-1,3,5-triazin-2-amine; enantiomer 2,
(rac)-[(3-{[4-(4-Fluoro-2-methoxyphenyl)-1,3,5-triazin-2-yl]amino}-5-methylbenzyl)(methyl)oxido-$\lambda^6$-sulfa-nylidene]cyanamide,
(rac)-2-({5-Fluoro-2-[4-({3-[(S-methylsulfonimidoyl)methyl]phenyl}amino)-1,3,5-triazin-2-yl]phenoxy}methyl)prop-2-en-1-ol,
(rac)-[Cyclopropyl(3-{[4-(4-fluoro-2-methoxyphenyl)-1,3,5-triazin-2-yl]amino}benzyl)oxido-?6-sulfanylidene]cy-anamide,
or their salts, solvates or salts of solvates.

The above-mentioned definitions of radicals which have been detailed in general terms or in preferred ranges also apply to the end products of the formula (I) or (Ia) or (Ib) and, analogously, to the starting materials or intermediates required in each case for the preparation.
Scheme 1:
The invention furthermore relates to a process for the preparation of the compounds of formula (I) or (Ia) or (Ib) according to the invention, in which N-unprotected sulfoxi-mines of formula (6) are reacted to give N-functionalized sulfoximines of formula (I) or (Ia) or (Ib).

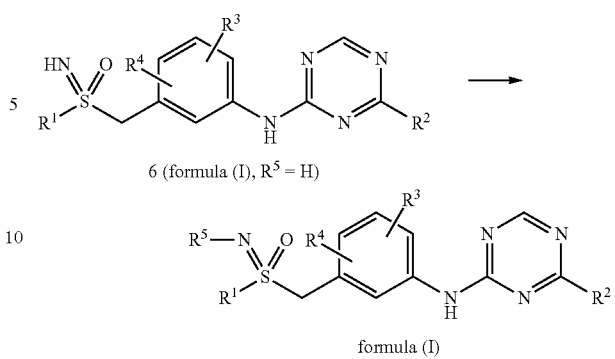

6 (formula (I), $R^5$ = H)

formula (I)

The present invention therefore relates to a method for the preparation of the compounds of formula (I) or (Ia) or (Ib), in which $R^5$ is not a hydrogen atom, according to the invention, in which method the nitrogen of the sulfoximine group of a compound of formula (6)

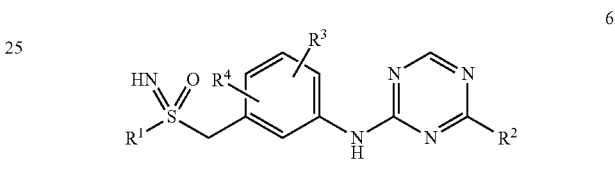

6 in which $R^1$, $R^2$, $R^3$ and $R^4$ are as defined for the compound of general formula (I) or (Ia) or (Ib) according to the invention, is functionalized according to methods known in the art,
thus providing a compound of general formula (I) or (Ia) or (Ib) according to the invention, in which $R^5$ is not hydrogen, and
the resulting compounds are optionally, if appropriate, reacted with the corresponding (i) solvents and/or (ii) bases or acids to the solvates, salts and/or solvates of the salts thereof.

There are multiple methods for the preparation of N-func-tionalized sulfoximines by functionalization of the nitrogen of the sulfoximine group:
Alkylation: see for example: a) U. Lücking et al, US 2007/0232632; b) C. R. Johnson, J. Org. Chem. 1993, 58, 1922; c) C. Bolm et al, Synthesis 2009, 10, 1601.
Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.
Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C. Bolm et al, J. Org. Chem. 2005, 70, 2346; e) U. Lücking et al, WO2007/71455.
Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.
Reaction with sulfonylchlorides: see for example: a) D. J. Cram et al, J. Am. Chem. Soc. 1970, 92, 7369; b) C. R. Johnson et al. J. Org. Chem. 1978, 43, 4136; c) A. C. Barnes. J. Med. Chem. 1979, 22, 418; d) D. Craig et al, Tet. 1995, 51, 6071; e) U. Lücking et al, US2007/191393.

Reaction with chloroformiates: see for example: a) P. B. Kirby et al, DE2129678; b) D. J. Cram et al. J. Am. Chem. Soc. 1974, 96, 2183; c) P. Stoss et al, Chem. Ber. 1978, 111, 1453; d) U. Lücking et al, WO2005/37800.

N-unprotected sulfoximines of formula (6) can be prepared by deprotection of N-protected sulfoximines of formula (5). Preferred it the use of sodium ethanolate in ethanol at 60° C. (see for example: U. Lücking et al, WO2005/37800).

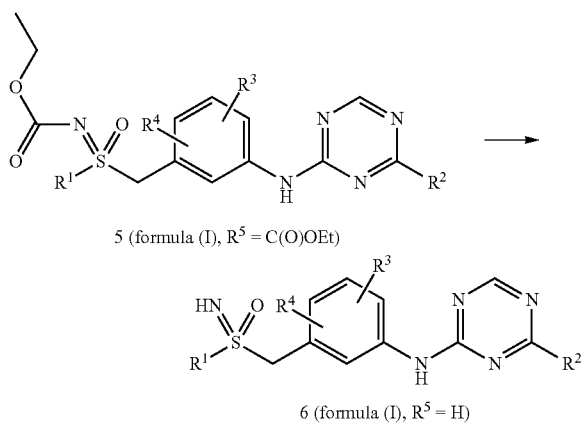

5 (formula (I), $R^5$ = C(O)OEt)

6 (formula (I), $R^5$ = H)

The invention therefore furthermore relates to a method for the preparation of the compounds of formula (I) or (Ia) or (Ib) according to the present invention, in which $R^5$ is a hydrogen atom (identical to the N-unprotected sulfoximines of formula (6) shown above), according to the invention, in which method the —C(O)O-Ethyl group of an N-protected compound of formula (5)

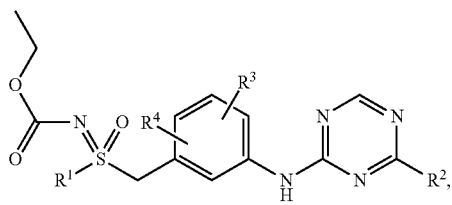

in which $R^1$, $R^2$, $R^3$ and $R^4$ are as defined for the compound of general formula (I) or (Ia) or (Ib), is deprotected according to methods known in the art.

thus providing a compound of general formula (I) or (Ia) or (Ib) according to the invention, in which $R^5$ is a hydrogen atom, and the resulting compounds (the N-unprotected sulfoximines of formula (6) shown above) are optionally, if appropriate, reacted with the corresponding (i) solvents and/or (ii) bases or acids to the solvates, salts and/or solvates of the salts thereof.

The invention furthermore relates to a method for the preparation of the compounds of formula (I) or (Ia) or (Ib) according to the present invention, in which $R^5$ is —C(O)O-Ethyl (identical to the N-protected sulfoximines of formula (5) shown above), in which method an intermediate compound of formula (3),

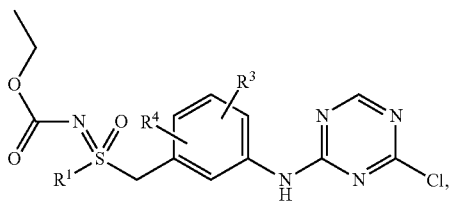

in which $R^1$, $R^3$ and $R^4$ are as defined for the compound of general formula (I) or (Ia) or (Ib), is reacted with a compound of formula (4)

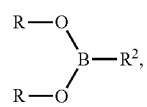

in which $R^2$ is as defined for the compound of general formula (I) or (Ia) or (Ib), and R represent, independently from each other, a hydrogen atom, or a $C_1$-$C_{10}$-alkyl group or, alternatively, both R together form a R—R group, which is —C(CH$_3$)$_2$—C(CH$_3$)$_2$—, thus providing a compound of general formula (I) or (Ia) or (Ib) according to the invention, in which $R^5$ is —C(O)O-Ethyl, and the resulting compounds (see N-protected sulfoximines of formula (5) shown above) are optionally, if appropriate, reacted with the corresponding (i) solvents and/or (ii) bases or acids to the solvates, salts and/or solvates of the salts thereof.

Compounds of general formula (4) can be prepared analogously to known processes (review: D. G. Hall, Boronic Acids, 2005 WILEY-VCH Verlag GmbH & Co. KGaA, Weinheim, ISBN 3-527-30991-8 and references cited herein). Further, a wide variety of compounds of general formula (4) are commercially available.

The coupling reaction of compounds of formula (3) with compounds of formula (4) is catalyzed by Pd catalysts, e.g. by Pd(0) catalysts or by Pd(II) catalysts. Examples for Pd(0) catalysts are tetrakis(triphenylphosphine)palladium(0) [Pd(PPh$_3$)$_4$] or tris(dibenzylideneacetone)di-palladium(0) [Pd$_2$(dba)$_3$], examples for Pd(II) catalysts dichlorobis(triphenylphosphine)-palladium(II) [Pd(PPh$_3$)$_2$Cl$_2$], palladium(II) acetate and triphenylphosphine or [1,1'-bis(diphenylphosphino)ferrocene]palladium dichloride [Pd(dppf)Cl$_2$] (review: D. G. Hall Boronic Acids, 2005 WILEY-VCH Verlag GmbH & Co. KGaA, Weinheim, ISBN 3-527-30991-8 and references cited therein).

This reaction is preferably carried out in aprotic or protic solvents, preferably in a mixture of aprotic and protic solvents, more preferably in solvents like, for example, 1,2-dimethoxyethane, dioxane, dimethlyformamid, tetrahydrofuran, or isopropanol with water (review: D. G. Hall, Boronic Acids, 2005 WILEY-VCH Verlag GmbH & Co. KGaA, Weinheim, ISBN 3-527-30991-8 and references cited therein).

Preferably the reaction is carried out in the presence of a suitable base, such as for example aqueous potassium carbonate, aqueous sodium bicarbonate or aqueous potassium phosphate (review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature (=20° C.) to the boiling point of the solvent. Further on, the reaction can be performed at temperatures above the boiling point using pressure tubes and a microwave oven. (review: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

Compounds of general formula (3) can be obtained as follows:

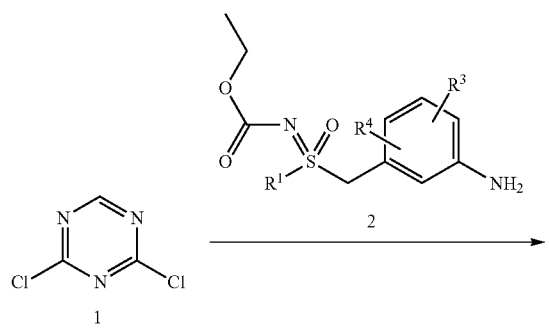

2,4-dichloro-1,3,5-triazine (1), which is known [CAS-Registry Number: 2831-66-5] or can be prepared analogously to known processes, is reacted with suitable anilines of formula (2) to give the corresponding 4-chloro-N-phenyl-1,3,5-triazin-2-amines of formula (3).

This reaction can be carried out with one equivalent of the aniline of formula (2) in an inert solvent like, for example, 1,2-dimethoxyethane, dioxane, dimethlyformamid, tetrahydrofuran, or an alcohol like, for example, isopropanol, or mixtures of such solvents. Preferably, the reaction is carried out at a temperature below 0° C. in such a way that the reaction mixture is kept homogenous. Preferred conditions use an additional base like for example triethylamine or N,N-diisopropylethylamine. The reaction is preferably completed after 1 to 6 hours.

Anilines of formula (2) can be prepared by the following processes:

Reaction of suitable benzylchlorides or -bromides of formula (7) with suitable thiols of formula (8) under basic conditions yields the corresponding thioethers of formula (9) (see for example: Sammond et al, Bioorg. Med. Chem. Lett. 2005, 15, 3519).

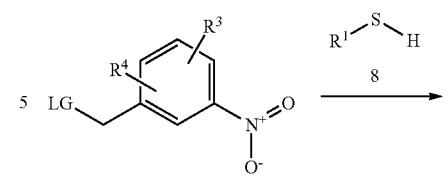

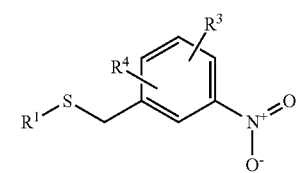

LG = Cl, Br

Oxidation of thioethers of formula (9) gives the corresponding sulfoxides of formula (10). The oxidation can be performed analogously to known processes (see for example: (a) M. H. Ali et al, Synthesis 1997, 764; (b) M. C. Carreno, Chem. Rev. 1995, 95, 1717; (c) 1. Patel et al. Org. Proc. Res. Dev. 2002, 6, 225; (d) N. Khiar et al, Chem. Rev. 2003, 103, 3651). Preferred is the herein described use of periodic acid und iron(III)chloride.

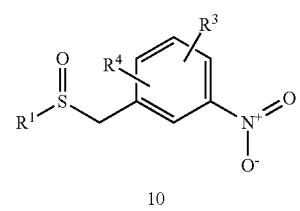

Rhodium-catalyzed imination of the sulfoxides of formula (10) followed by deprotection gives the corresponding N-unprotected sulfoximines of formula (11) (see for example: Bolm et al, Org. Lett. 2004, 6, 1305).

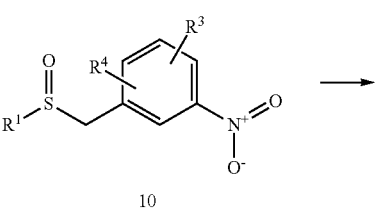

-continued

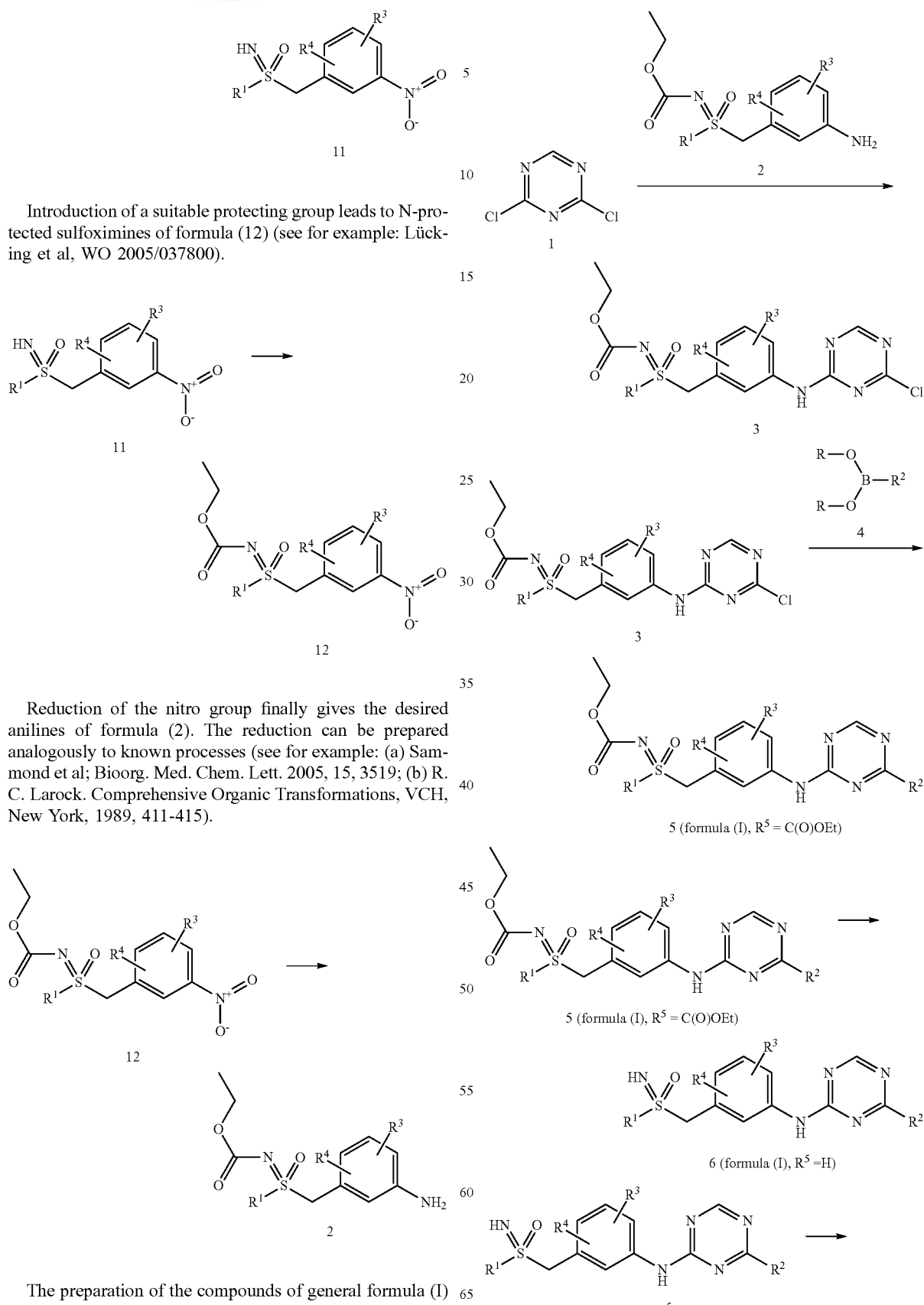

Introduction of a suitable protecting group leads to N-protected sulfoximines of formula (12) (see for example: Lücking et al, WO 2005/037800).

Reduction of the nitro group finally gives the desired anilines of formula (2). The reduction can be prepared analogously to known processes (see for example: (a) Sammond et al; Bioorg. Med. Chem. Lett. 2005, 15, 3519; (b) R. C. Larock. Comprehensive Organic Transformations, VCH, New York, 1989, 411-415).

The preparation of the compounds of general formula (I) or (Ia) or (Ib) according to the invention can be illustrated by the following synthesis scheme (Scheme 1):

-continued

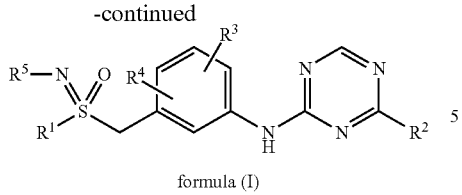

formula (I)

Compounds of general formula (Ia), (Ib), (2a), (3a), (5a), (6a) can be prepared analogously.

Scheme 2:

The invention furthermore relates to a method for the preparation of the compounds of formula (I) or (Ia) or (Ib) according to the present invention, in which $R^5$ is a hydrogen atom (identical to the N-unprotected sulfoximines of formula (6) shown above), in which method a compound of formula (15)

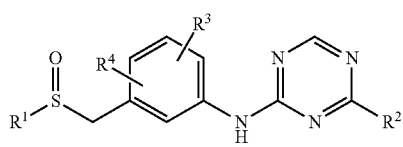

15 in which $R^1$, $R^2$, $R^3$ and $R^4$ are as defined for the compound of formula (I) or (Ia) or (Ib) according to the present invention, is reacted with sodium azide in the presence of an acid thus providing a compound of general formula (I) or (Ia) or (Ib) according to the invention, in which $R^5$ is a hydrogen atom, and, the resulting compounds (the N-unprotected sulfoximines of formula (6) shown above) are optionally, if appropriate, reacted with the corresponding (i) solvents and/or (ii) bases or acids to the solvates, salts and/or solvates of the salts thereof.

This reaction is preferably carried out in the presence of sulfuric acid or polyphosphoric acid. It is preferably carried out in trichloromethane in the presence of sulfuric acid and at temperatures ranging from 40° C. to 50° C., preferably from 43° C. to 47° C. most preferred at about 45° C. This reaction is preferably completed after 12 hours to 120 hours of reaction time (see for example: a) H. R. Bentley et al, J. Chem. Soc. 1952, 1572; b) C. R. Johnson et al, J. Am. Chem. Soc. 1970, 92, 6594; c) Satzinger et al, Angew. Chem. 1971, 83, 83).

In another embodiment of the present invention the method of the present invention is performed with sodium azide in polyphosphoric acid at temperatures ranging from 40° C. to 70° C., preferably from 55° C. to 65° C., most preferred at about 60° C. (see for example: a) M. D. Sindkhedkar et al, WO 2007/023507). The preparation of compounds of general formula (15) is described below in context of the description of synthesis Scheme 2. Compounds of general formula (Ia) or (Ib) can be prepared analogously.

Scheme 3

The invention furthermore relates to a method for the preparation of the compounds of formula (I) or (Ia) or (Ib) according to the present invention, in which $R^5$ is a cyano group (identical to the N-cyanosulfoximines of formula (20)),

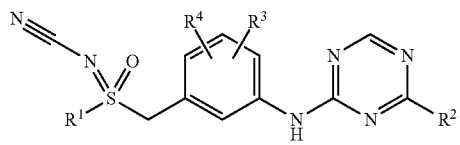

20 in which method a compound of formula (19)

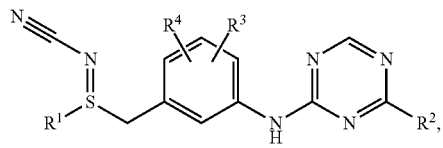

19 in which $R^1$, $R^2$, $R^3$ and $R^4$ are as defined for the compound of formula (I) or (Ia) or (Ib) according to the present invention, is oxidized according to methods known in the art, thus providing a compound of general formula (I) or (Ia) or (Ib) according to the invention, in which $R^5$ is a cyano group, and the resulting compounds (the N-cyanosulfoximines of formula (20) as shown above) are optionally, if appropriate, reacted with the corresponding (i) solvents and/or (ii) bases or acids to the solvates, salts and/or solvates of the salts thereof.

There are multiple methods for the oxidation of N-cyanosulfilimines of formula (19) to N-cyanosulfoximines of formula (20):

a) C. Bolm et al, Org. Lett. 2007, 9, 3809
b) J. E. G. Kemp et al, Tet. Lett. 1979, 39, 3785
c) M. R. Loso et al, US patent publication US2007/0203191.

The preparation of compounds of general formula (19) is described below in context of the description of synthesis Scheme 3. Compounds of general formula (Ia) or (Ib) can be prepared analogously.

The invention furthermore relates to a method for the preparation of the compounds of formula (I) or (Ia) or (Ib), in which $R^5$ is a hydrogen atom (identical to the sulfoximines of formula (6)),

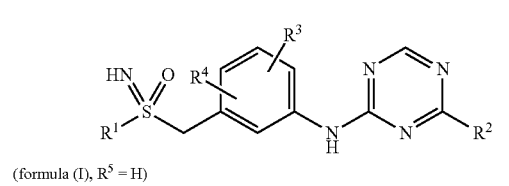

6

(formula (I), $R^5$ = H)

in which method the N-cyano group of the compound of formula (20)

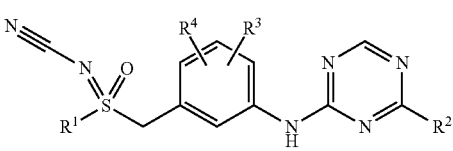

20 in which $R^1$, $R^2$, $R^3$ and $R^4$ are as defined for the compound of formula (I) or (Ia) or (Ib), is converted upon treatment with TFAA to the corresponding N-trifluoroacetylsulfoximine, which N-trifluoroacetylsulfoximine is converted by methanolysis into the compound of general formula (I) or (Ia) or (Ib) according to the invention, in which $R^5$ is a hydrogen group, and the resulting compounds (compounds of general formula (6)) are optionally, if appropriate, reacted with the corresponding (i) solvents and/or (ii) bases or acids to the solvates, salts and/or solvates of the salts thereof.

The preparation of compounds of general formula (6) from compounds of general formula (20) is described in more detail below in context of the description of synthesis Scheme 3.

Scheme 4:

The invention furthermore relates to a method for the preparation of the compounds of formula (I) or (Ia) or (Ib) according to the present invention, in which $R^5$ is a hydrogen atom (identical to the N-unprotected sulfoximines of formula (6) shown above), in which method a compound of formula (22)

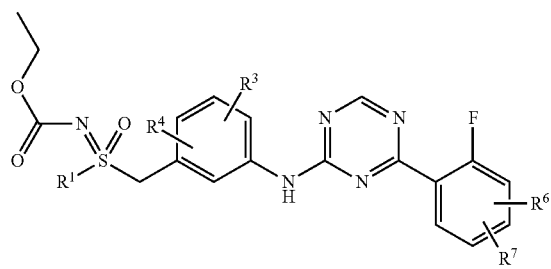

(22)

in which $R^1$, $R^3$, $R^4$, $R^6$ and $R^7$ are as defined for the compound of general formula (I) or (Ia) or (Ib) according to the invention, is solubilized in an alcohol $R^8$—OH, in which $R^8$ is as defined for the compounds of general formula (I) or (Ia) or (Ib) according to the invention and is reacted with at least two equivalents of alkali hydride, thus providing a compound of general formula (I) or (Ia) or (Ib) according to the invention, in which $R^5$ is a hydrogen atom, and the resulting compounds (the N-unprotected sulfoximines of formula (6)) are optionally, if appropriate, reacted with the corresponding (i) solvents and/or (ii) bases or acids to the solvates, salts and/or solvates of the salts thereof.

The reaction can be performed with potassium hydride or sodium hydride. Preferably, it is performed with sodium hydride. The reaction is performed at temperatures ranging from 40° C. to the boiling point of the alcohol $R^8$—OH, preferably at 50° C. to 70° C. The reaction is preferably completed after 10 to 100 hours of reaction time.

The preparation of compounds of general formula (22) is described below in context of the description of synthesis Scheme 4. Compounds of general formula (Ia) and (Ib) can be prepared analogously.

In another embodiment the present invention concerns intermediate compounds of general formula (3)

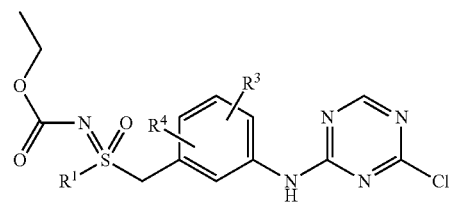

(3)

or of general formula (3a)

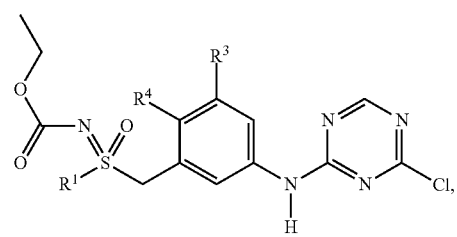

(3a)

wherein $R^1$, $R^3$ and $R^4$ are as defined for the compound of general formula (I) or (Ia) or (Ib) according to the invention.

In another embodiment the present invention concerns compounds of general formula (5)

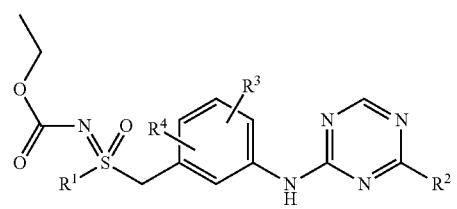

(5)

or of general formula (5a)

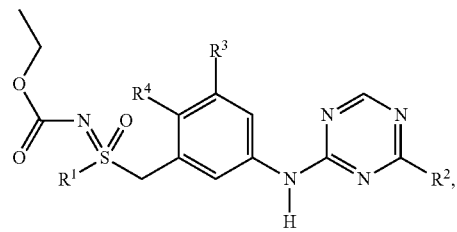

(5a)

wherein $R^1$, $R^2$, $R^3$ and $R^4$ are as defined for the compound of general formula (I) or (Ia) or (Ib) according to the invention.

In another embodiment the present invention concerns compounds of general formula (2)

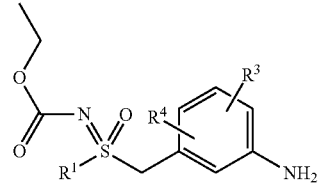

2 or of general formula (2a)

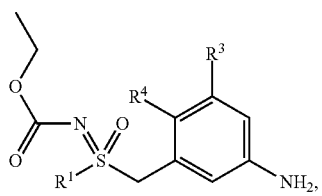

2a wherein
$R^1$, $R^3$ and $R^4$ are as defined for the compound of general formula (I) or (Ia) or (Ib) according to the invention.

In another embodiment the present invention concerns compounds of general formula (11)

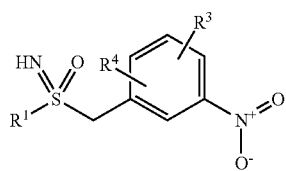

11 or of general formula (11a)

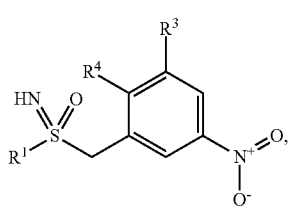

11a wherein
$R^1$, $R^3$ and $R^4$ are as defined for the compound of general formula (I) or (Ia) or (Ib) according to the invention.

In another embodiment the present invention concerns compounds of general formula (12)

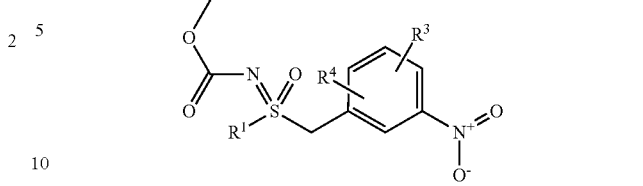

12 or of general formula (12a)

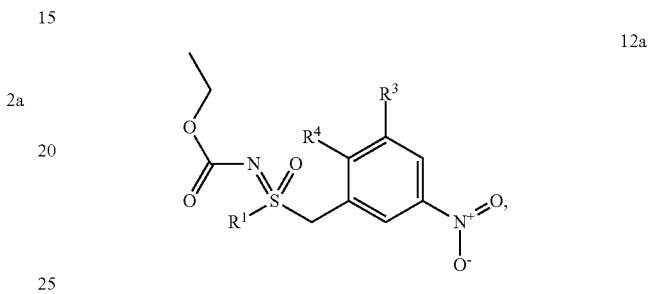

12a wherein
$R^1$, $R^3$ and $R^4$ are as defined for the compound of general formula (I) or (Ia) or (Ib) according to the invention.

In another embodiment the present invention concerns compounds of general formula (20)

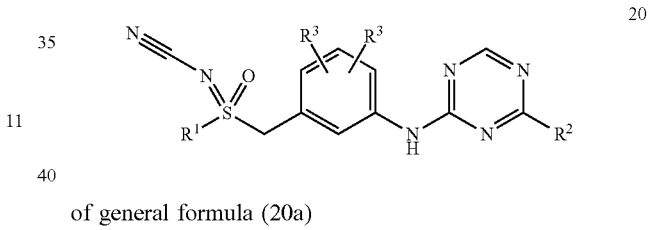

20 of general formula (20a)

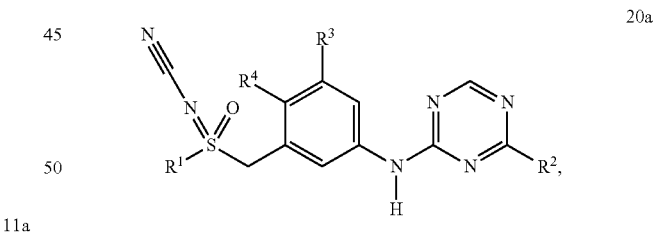

20a wherein
$R^1$, $R^2$, $R^3$ and $R^4$ are as defined for the compound of general formula (I) or (Ia) or (Ib) according to the invention.

The compounds according to the invention show a valuable pharmacological and pharmacokinetic spectrum of action which could not have been predicted.

They are therefore suitable for use as medicaments for the treatment and/or prophylaxis of disorders in humans and animals.

Within the scope of the present invention, the term "treatment" includes prophylaxis.

The pharmaceutical activity of the compounds according to the invention can be explained by their action as inhibitors of CDK9. Thus, the compounds according to the general formula (I) or (Ia) or (Ib) as well as pharmaceutically acceptable salts thereof are used as inhibitors for CDK9.

Furthermore, the compounds according to the invention show a particularly high potency (demonstrated by a low $IC_{50}$ value in the CDK9/CycT1 assay) for inhibiting CDK9 activity.

In context of the present invention, the $IC_{50}$ value with respect to CDK9 can be determined by the methods described in the method section below. Preferably, it is determined according to Method 1. ("CDK9/CycT1 kinase assay") described in the Materials and Method section below.

Surprisingly it turned out that the compounds according to the general formula (I) or (Ia) or (Ib) as well as pharmaceutically acceptable salts thereof selectively inhibit CDK9 in comparison to other cyclin-dependent protein kinases, preferably in comparison to CDK2. Thus, the compounds according to the general formula (I) or (Ia) or (Ib) as well as pharmaceutically acceptable salts thereof are preferably used as selective inhibitors for CDK9.

Compounds of the present invention according to general formula (I) or (Ia) or (Ib) show a significantly stronger CDK9 than CDK2 inhibition. Preferred compounds of the present invention show a CDK2 $IC_{50}$/CDK9 $IC_{50}$ ratio of more than 40, preferably of more than 55 and even more preferably of more than 70. The CDK9 $IC_{50}$ is determined according to Method 1, the CDK2 $IC_{50}$ according to Method 2, both described in more detail in the Materials and Method section below.

In context of the present invention, the $IC_{50}$ value with respect to CDK2 can be determined by the methods described in the method section below. Preferably, it is determined according to Method 2. ("CDK2/CycE kinase assay") described in the Materials and Method section below.

Further, compounds of the present invention according to formula (I) or (Ia) or (Ib) mediate a surprisingly strong anti-proliferative activity in tumor cell lines such as HeLa and/or DU145. In context of the present invention, the $IC_{50}$ values of the compounds with respect to these cell lines is preferably determined according to Method 3. ("Proliferation Assay") described in the Materials and Method section below.

Further, preferred compounds of the present invention according to formula (I) or (Ia) or (Ib) surprisingly show an increased solubility in water at pH 6.5 compared to the compounds described in the prior art.

In context of the present invention the solubility in water at pH 6.5 is preferably determined according to Method 4. ("Equilibrium Shake Flask Solubility Assay") described in the Materials and Method section below.

Further, compounds of the present invention according to formula (I) or (Ia) or (Ib) show no significant inhibition of carbonic anhydrase-1 or -2 (IC50 values of more than 10 μM) and therefore show an improved side effect profile as compared to those CDK inhibitors described in the prior art containing a sulfonamide group, which inhibit carbonic anhydrase-1 or -2. In context of the present invention, the carbonic anhydrase-1 and -2 inhibition is preferably determined according to Method 5. ("Carbonic anhydrase Assay") described in the Materials and Method section below.

A further subject matter of the present invention is the use of the compounds of general formula (I) or (Ia) or (Ib) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit the activity or expression of CDK9. Therefore, the compounds of formula (I) or (Ia) or (Ib) are expected to be valuable as therapeutic agents.

Accordingly, in another embodiment, the present invention provides a method of treating disorders relating to or mediated by CDK9 activity in a patient in need of such treatment, comprising administering to the patient an effective amount of a compound of formula (I) or (Ia) or (Ib) as defined above. In certain embodiments, the disorders relating to CDK9 activity are hyper-proliferative disorders, virally induced infectious diseases and/or of cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity such as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways.

The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ. Canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypothalamic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers. Anal gland adenocarcinomas, mast cell tumors.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer. Mast cell tumors.

Head-and-neck cancers include, but are not limited to laryngeal, hypopharyngeal, nasopharyngeal, oropharyngeal cancer, lip and oral cavity cancer, and squamous cell cancer. Oral melanoma.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Malignant histiocytosis, fibrosarcoma, hemangiosarcoma, hemangiopericytoma, leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders. i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group consisting of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the Flaviviridae is selected from HCV, West nile or Yellow Fever.

The compounds according to general formula (I) or (Ia) or (Ib) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation. Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage. Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) or (Ia) or (Ib) according to the invention for the treatment and/or prophylaxis of disorders, in particular of the disorders mentioned above.

A further subject matter of the present invention are the compounds according to the invention for use in a method for the treatment and/or prophylaxis of the disorders mentioned above.

A further subject matter of the present invention is the use of the compounds according to the invention in the manufacture of a medicament for the treatment and/or prophylaxis of disorders, in particular the disorders mentioned above.

A further subject matter of the present invention is a method for the treatment and/or prophylaxis of disorders, in particular the disorders mentioned above, using an effective amount of the compounds according to the invention.

Another aspect of the present invention relates to pharmaceutical combinations comprising a compound of general formula (I) or (Ia) or (Ib) according to the invention in combination with at least one or more further active ingredients.

As used herein the term "pharmaceutical combination" refers to a combination of at least one compound of general formula (I) or (Ia) or (Ib) according to the invention as active ingredient together with at least one other active ingredient with or without further ingredients, carrier, diluents and/or solvents.

Another aspect of the present invention relates to pharmaceutical compositions comprising a compound of general formula (I) or (Ia) or (Ib) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Compounds of formula (I) or (Ia) or (Ib) may be administered as the sole pharmaceutical agent or in combination with one or more additional therapeutic agents where the combination causes no unacceptable adverse effects. This pharmaceutical combination includes administration of a single pharmaceutical dosage formulation which contains a compound of formula (I) or (Ia) or (Ib) and one or more additional therapeutic agents, as well as administration of the compound of formula (I) or (Ia) or (Ib) and each additional therapeutic agent in its own separate pharmaceutical dosage formulation. For example, a compound of formula (I) or (Ia) or (Ib) and a therapeutic agent may be administered to the patient together in a single oral dosage composition such as a tablet or capsule, or each agent may be administered in separate dosage formulations.

Where separate dosage formulations are used, the compound of formula (I) or (Ia) or (Ib) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and episteride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptotheccin, 10-hydroxycamptothccin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; Merial melanoma vaccine Biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, aflibercept, telatinib, brivanib alaninate, vatalanib, pazopanib, and ranibizumab; Palladia EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus:

c-Met inhibitors;

PI3K and AKT inhibitors;

CDK inhibitors such as roscovitine and flavopiridol;

Spindle assembly checkpoints inhibitors and targeted anti-mitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors (such as e.g. RDEA 119) and Raf inhibitors such as sorafenib;

Farnesyl transferase inhibitors such as, e.g., tipifarnib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors; Palladia, masitinib Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydro-chloride, granisetron, Zindol, and AB-1001;

Integrin inhibitors including alpha5-beta1 integrin inhibitors such as, e.g., E7820, JSM 6425, voloximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, aminoglutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

The compounds of the present invention may also be employed in cancer treatment in conjunction with radiation therapy and/or surgical intervention.

In a further embodiment of the present invention the compounds of the present invention may be used in fixed or separate combination with one or more other active ingredients such as:

131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diflitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, nmasoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumnab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans.
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Furthermore, the compounds of formula (I) or (Ia) or (Ib) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneouly, perneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds of the invention of general formula (I) or (Ia) and/or the pharmaceutical composition of the present invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological assays one or more times. When tested more than once, data are reported as either average values or as median values, wherein
- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro pharmacological and physico-chemical properties of the compounds can be determined according to the following assays and methods.

1. CDK9/CycT1 Kinase Assay:

CDK9/CycT1-inhibitory activity of compounds of the present invention was quantified employing the CDK9/CycT1 TR-FRET assay as described in the following paragraphs:

Recombinant full-length His-tagged human CDK9 and CycT1, expressed in insect cells and purified by Ni-NTA affinity chromatography, were purchased from Invitrogen (Cat. No PV4131). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 µg/mL. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values were calculated by a 4 parameter fit.

2. CDK2/CycE Kinase Assay:

CDK2/CycE -inhibitory activity of compounds of the present invention was quantified employing the CDK2/CycE TR-FRET assay as described in the following paragraphs:

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI Peptide Technologies (Berlin. Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.25 µM=>final conc. in the 5 µl assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/mL. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values were calculated by a 4 parameter fit.

3. Proliferation Assay:

Cultivated tumour cells (NCI-H460, human non-small cell lung carcinoma cells, ATCC HTB-177; DU145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumour cells, ATCC CCL-2; Caco-2 human colorectal carcinoma, ATCC HTB-37; B16F10 mouse melanoma cells, ATCC CRL-6475) were plated at a density of 5000 cells/well (DU145, HeLa-MaTu-ADR), 3000 cells/well (NCI-H460, HeLa-MaTu, HeLa), 1500 cells/well (Caco-2), or 1000 cells/well (B16F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µL), to which the test substances were added in various concentrations (0 µM, as well as in the range of 0.001-10 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µL/measuring point of an 11% glutaric aldehyde solution for 15 minutes at room temperature. After three washing cycles of the fixed cells with water, the plates were dried at room temperature. The cells were stained by adding 100 µL/measuring point of a 0.1% crystal violet solution (pH 3.0). After three washing cycles of the stained cells with water, the plates were dried at room temperature. The dye was dissolved by adding 100 µL/measuring point of a 10% acetic acid solution. The absorbance was determined by photometry at a wavelength of 595 nm. The change of cell number, in percent, was calculated by normalization of the measured values to the absorbance values of the zero-point plate (=0%) and the absorbance of the untreated (0 µM) cells (=100%). The IC50 values were determined by means of a 4 parameter fit.

4. Equilibrium Shake Flask Solubility Assay:

The thermodynamic solubility of compounds in water was determined by an equilibrium shake flask method (see for example: E. H. Kerns, L. Di: Drug-like Properties: Concepts. Structure Design and Methods, 276-286. Burlington, Mass., Academic Press, 2008). A saturated solution of the drug was prepared and the solution was mixed for 24 h to ensure that equilibrium was reached. The solution was centrifuged to remove the insoluble fraction and the concentration of the compound in solution was determined using a standard calibration curve.

To prepare the sample, 2 mg solid compound was weighed in a 4 mL glass vial. 1 mL phosphate buffer pH 6.5 was added. The suspension was stirred for 24 hrs at room temperature. The solution was centrifuged afterwards. To prepare the sample for the standard calibration, 2 mg solid sample was dissolved in 30 mL acetonitrile. After sonification the solution was diluted with water to 50 mL. Sample and standards were quantified by HPLC with UV-detection. For each sample two injection volumes (5 and 50 µl) in triplicates were made. Three injection volumes (5 µl, 10 µl and 20 µl) were made for the standard.

Chromatographic Conditions:
HPLC column: Xterra MS Cl8 2.5 µm 4.6×30 mm
Injection volume: Sample: 3×5 µl and 3×50 µl
   Standard: 5 µl, 10 µl, 20 µl
Flow: 1.5 mL/min
Mobile phase: acidic gradient:
   A: Water/0.01% TFA
   B: Acetonitrile/0.01% TFA
   0 min→95% A 5% B
   0-3 min→35% A 65% B, linear gradient
   3-5 min→35% A 65% B, isocratic
   5-6 min→95% A 5% B, isocratic
UV detector: wavelength near the absorption maximum (between 200 and 400 nm)

The areas of sample- and standard injections as well as the calculation of the solubility value (in mg/l) were determined by using HPLC software (Waters Empower 2 FR).

5. Carbonic Anhydrase Assay

The principle of the assay is based on the hydrolysis of 4-nitrophenyl acetate by carbonic anhydrases (Pocker & Stone, Biochemistry, 1967, 6, 668), with subsequent photometric determination of the dye product 4-nitrophenolate at 400 nm by means of a 96-channel spectral photometer.

2 microL of the test compounds, dissolved in DMSO (100-fold final concentration), in a concentration range of 0.03-10 micromol/L (final), was pipetted as quadruplicates into the wells of a 96-hole microtiter plate. Wells that contained the solvent without test compounds were used as reference values (1. Wells without carbonic anhydrase for correction of the non-enzymatic hydrolysis of the substrate, and 2. Wells with carbonic anhydrase for determining the activity of the non-inhibited enzyme).

188 microL of assay buffer (10 millimol/L of Tris/HCl, pH 7.4, 80 millimol/L of NaCl), with or without 3 units/well of carbonic anhydrase-1 [=human carbonic anhydrase-1 (Sigma, #C4396)] in order to determine carbonic anhydrase-1 inhibition or 3 units/well of carbonic anhydrase-2 [=human carbonic anhydrase-2 (Sigma, #C6165)] for measuring carbonic anhydrase-2 inhibition, was pipetted into the wells of the microtiter plate. The enzymatic reaction was started by the addition of 10 microL of the substrate solution (1 millimol/L of 4-nitrophenyl acetate (Fluka #4602), dissolved in anhydrous acetonitrile (final substrate concentration: 50 micromol/L). The plate was incubated at room temperature for 15 minutes. Absorption was measured by photometry at a wavelength of 400 nm. The enzyme inhibition was calculated after the measured values were normalized to the absorption of the reactions in the wells without enzyme (=100% inhibition) and to the absorption of reactions in the wells with non-inhibited enzyme (=0% inhibition). IC50 values were determined by means of a 4 parameter fit.

PREPARATIVE EXAMPLES

Syntheses of Compounds

The syntheses of the inventive disubstituted triazines according to the present invention is preferably carried out according to one of the general synthetic sequences, shown in schemes 1, 2, 3 or 4 below:

Scheme 1:

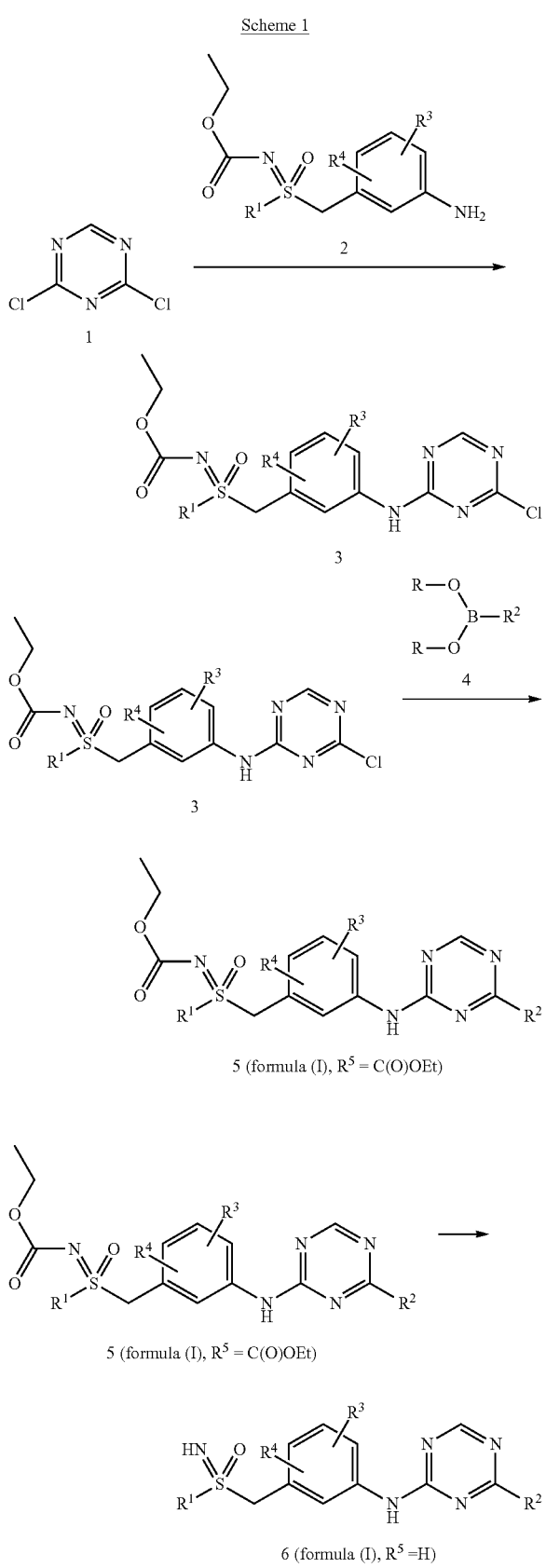

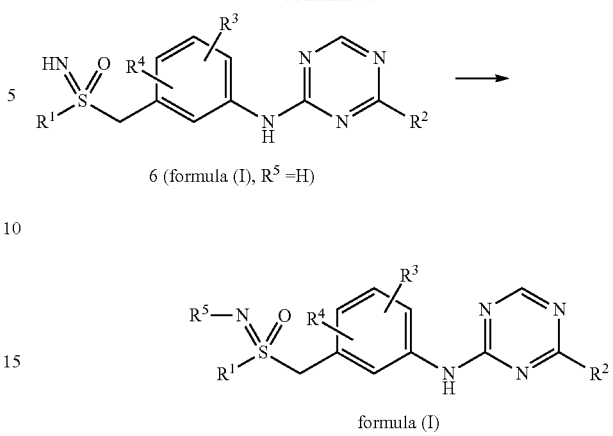

In the first step 2,4-dichloro-1,3,5-triazine (1) is reacted with suitable anilines (2) to give the corresponding 4-chloro-N-phenyl-1,3,5-triazin-2-amines (3). The reaction is carried out with one equivalent of the aniline (2) in an inert solvent like DMF, THF, DME, dioxane or an alcohol like isopropanol, or mixtures of such solvents. Preferably, the reaction is carried out at a temperature below 0° C. in such a way that the reaction mixture is kept homogenous. Preferred conditions use an additional base like triethylamine or N,N-diisopropylethylamine.

In the second step the intermediate 4-chloro-N-phenyl-1,3,5-triazin-2-amine (3) is reacted with a boronic acid derivative $R^2$—$B(OR)_2$ (4) to give compounds of formula (5). The boronic acid derivative (4) may be a boronic acid (R═—H) or an ester of the boronic acid, e.g. its isopropyl ester (R═—CH(CH$_3$)$_2$), preferably an ester derived from pinacol in which the boronic acid intermediate forms a 2-aryl-4,4,5,5-tetramethyl-1,3,2-dioxaborolane (R—R═—C(CH$_3$)$_2$—C(CH$_3$)$_2$—).

The coupling reaction is catalyzed by Pd catalysts, e.g. by Pd(0) catalysts like tetrakis(triphenylphosphine)palladium(0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride [Pd(dppf)Cl2].

The reaction is preferably carried out in a mixture of a solvent like 1,2-dimethoxyethane, dioxane, DMF, DME, THF or isopropanol with water and in the presence of a base like aqueous potassium carbonate, aqueous sodium bicarbonate or potassium phosphate.

Deprotection of compounds of formula (5) gives the corresponding N-unprotected sulfoximines of formula (6). The deprotection is preferably carried out with sodium ethanolate in ethanol at 60° C.

N-unprotected sulfoximines of formula (6) may be reacted to to give N-functionalized derivatives of formula (I).

Scheme 2

Another synthesis route to N-unprotected sulfoximines of formula (6) is shown in Scheme 2.

Scheme 2

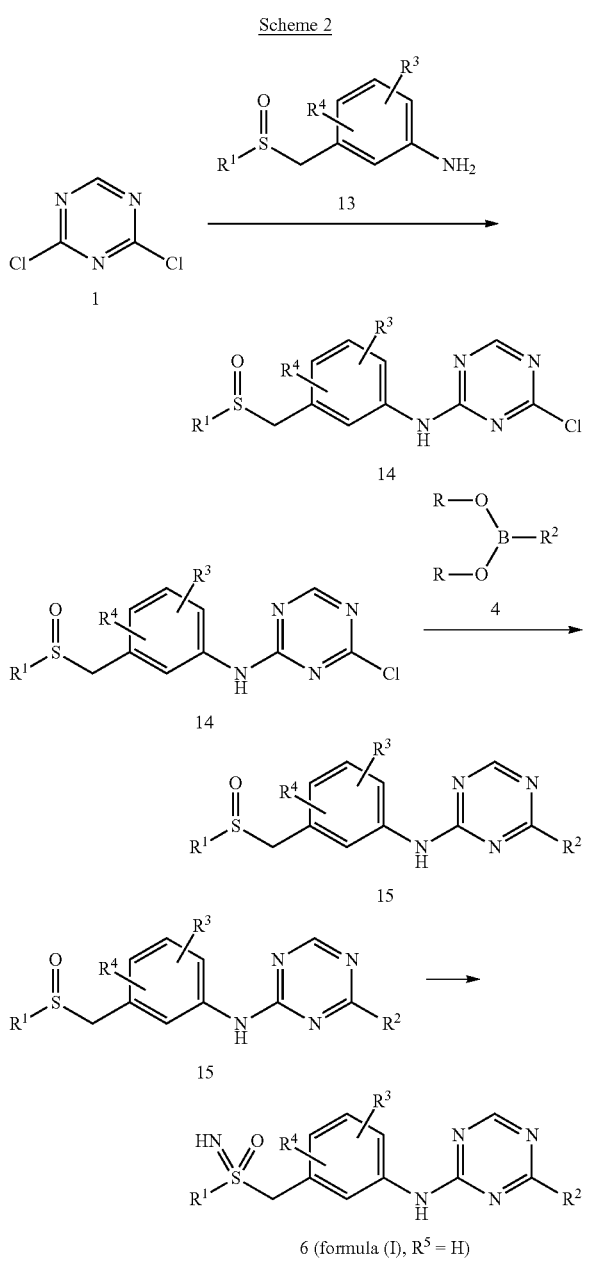

6 (formula (I), R⁵ = H)

In the first step 2,4-dichloro-1,3,5-triazine (1) is reacted with suitable anilines of formula (13) to give the corresponding 4-chloro-N-phenyl-1,3,5-triazin-2-amines of formula (14). The reaction is carried out with one equivalent of the aniline (13) in an inert solvent like DMF, THF, DME, dioxane or an alcohol like isopropanol, or mixtures of such solvents. Preferably, the reaction is carried out at a temperature below 0° C. in such a way that the reaction mixture is kept homogenous. Preferred conditions use an additional base like triethylamine or N,N-diisopropylethylamine.

In the second step the intermediate 4-chloro-N-phenyl-1,3,5-triazin-2-amine of formula (14) is reacted with a boronic acid derivative R²—B(OR)₂ (4) to give compounds of formula (15). The boronic acid derivative (4) may be a boronic acid (R=—H) or an ester of the boronic acid, e.g. its isopropyl ester (R=—CH(CH₃)₂), preferably an ester derived from pinacol in which the boronic acid intermediate forms a 2-aryl-4,4,5,5-tetramethyl-1,3,2-dioxaborolane (R—R=—C(CH₃)₂—C(CH₃)₂—).

The coupling reaction is catalyzed by Pd catalysts, e.g. by Pd(0) catalysts like tetrakis(triphenylphosphine)palladium (0) [Pd(PPh₃)₄], tris(dibenzylideneacetone)di-palladium(0) [Pd₂(dba)₃], or by Pd(II) catalysts like dichlorobis(triphenylphosphine)-palladium(II) [Pd(PPh₃)₂Cl₂], palladium(II) acetate and triphenylphosphine or by [1,1'-bis(diphenylphosphino)ferrocene]palladium dichloride [Pd(dppf)Cl₂].

The reaction is preferably carried out in a mixture of a solvent like 1,2-dimethoxyethane, dioxane, DMF, DME, THF, or isopropanol with water and in the presence of a base like aqueous potassium carbonate, aqueous sodium bicarbonate or potassium phosphate.

Finally, the compound of formula (15) is reacted with sodium azide in trichloromethane and sulfuric acid at 45° C. to give the N-unprotected sulfoximine of formula (6) (see for example: a) H. R. Bentley et al, J. Chem. Soc. 1952, 1572; b) C. R. Johnson et al, J. Am. Chem. Soc. 1970, 92, 6594; c) Satzinger et al, Angew. Chem. 1971, 83, 83).

Scheme 3

Another synthesis route to N-cyanosulfoximines of formula (20), which can also be converted to unprotected sulfoximines of formula (6), is shown in Scheme 3.

Scheme 3

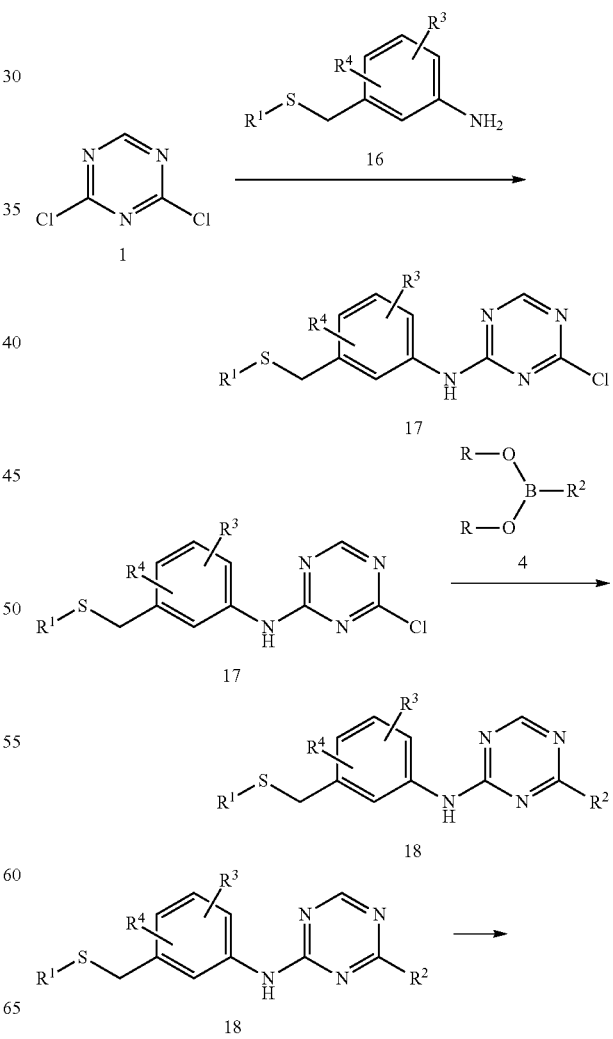

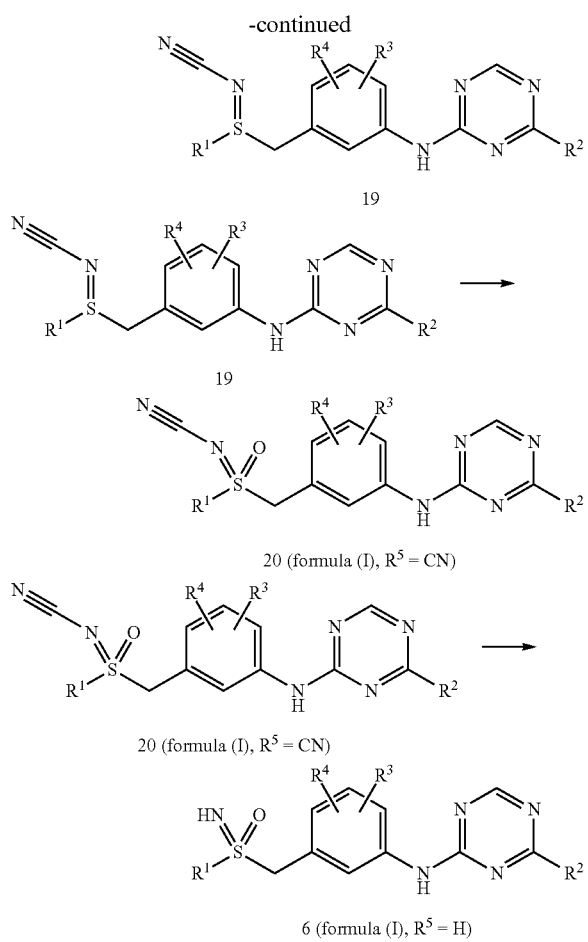

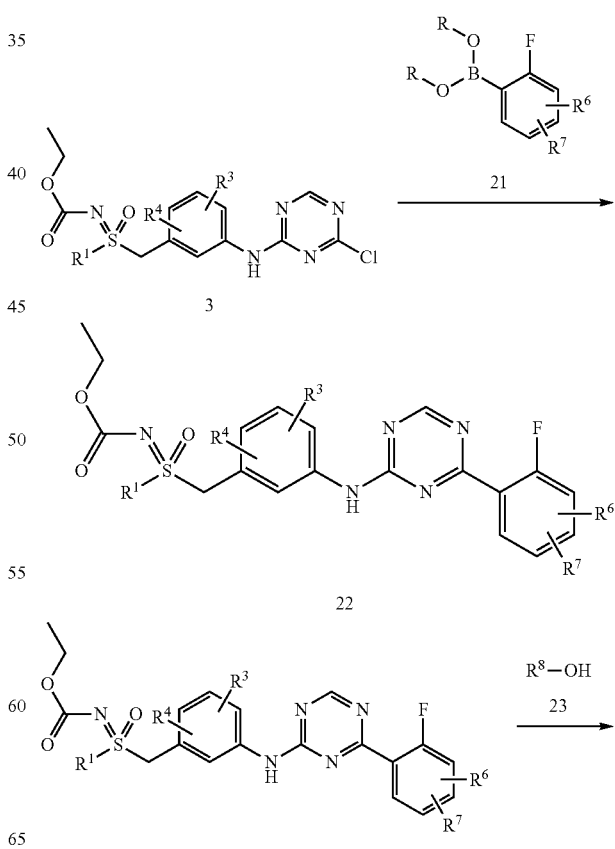

like aqueous potassium carbonate, aqueous sodium bicarbonate or potassium phosphate.

In the next step, the sulfide of formula (18) is reacted with cyanogen amine as a nitrogen source to give the corresponding N-cyanosulfilimine of formula (19). Preferably, the reaction is carried out using NBS and potassium tert-butoxide in methanol at room temperature (see for example: a) C. Bolm et al, Org. Lett. 2007, 9, 3809). Even more preferred is the use of iodobenzenediacetate in DCM at room temperature (see for example: a) J. M. Babcock, US 2009/0023782).

Finally, N-cyanosulfilimine of formula (19) is oxidized to the corresponding N-cyanosulfoximine of formula (20). The reaction is preferably carried out using mCPBA and potassium carbonate in ethanol at room temperature (see for example: a) C. Bolm et al, Org. Lett. 2007, 9, 3809). Even more preferred is the use of potassium permanganate in acetone at 50° C. (see for example: a) C. Bolm et al, Adv. Synth. Catal. 2010, 352, 309).

The N-cyano group of compound (20) is cleaved upon treatment with TFAA affording the corresponding N-trifluoroacetylsulfoximine which is converted into the NH-free sulfoximine of formula (6) by methanolysis of the trifluoroacetyl moiety (see for example: C. Bolm et al, Org. Lett. 2007, 9(19), 3809).

Scheme 4:

Another synthesis route to N-unprotected sulfoximines of formula (6) is shown in Scheme 4.

In the first step 2,4-dichloro-1,3,5-triazine (1) is reacted with suitable anilines of formula (16) to give the corresponding 4-chloro-N-phenyl-1,3,5-triazin-2-amines of formula (17). The reaction is carried out with one equivalent of the aniline of formula (2) in an inert solvent like DMF, THF, DME, dioxane or an alcohol like isopropanol, or mixtures of such solvents. Preferably, the reaction is carried out at a temperature below 0° C. in such a way that the reaction mixture is kept homogenous. Preferred conditions use an additional base like triethylamine or N,N-diisopropylethylamine.

In the second step the intermediate 4-chloro-N-phenyl-1,3,5-triazin-2-amine of formula (17) is reacted with a boronic acid derivative $R^2$—$B(OR)_2$ (4) to give compounds of formula (18). The boronic acid derivative (4) may be a boronic acid (R=—H) or an ester of the boronic acid, e.g. its isopropyl ester (R=—CH(CH$_3$)$_2$), preferably an ester derived from pinacol in which the boronic acid intermediate forms a 2-aryl-4,4,5,5-tetramethyl-1,3,2-dioxaborolane (R—R=—C(CH3)2-C(CH3)2-).

The coupling reaction is catalyzed by Pd catalysts, e.g. by Pd(0) catalysts like tetrakis(triphenylphosphine)palladium (0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride [Pd(dppf)Cl$_2$].

The reaction is preferably carried out in a mixture of a solvent like 1,2-dimethoxyethane, dioxane, DMF, DME, THF, or isopropanol with water and in the presence of a base

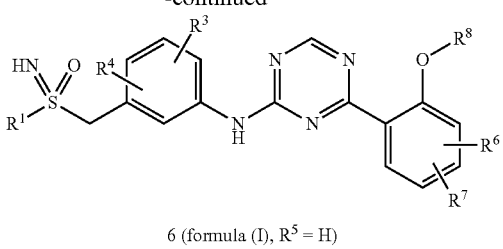

6 (formula (I), R⁵ = H)

In the first step the intermediate 4-chloro-N-phenyl-1,3,5-triazin-2-amine (3) is reacted with a suitable ortho-fluorine boronic acid derivative of formula (21) to give a compound of formula (22). The boronic acid derivative of formula (21) may be a boronic acid (R═—H) or an ester of the boronic acid, e.g. its isopropyl ester (R═—CH(CH₃)₂), or an ester derived from pinacol in which the boronic acid intermediate forms a 2-aryl-4,4,5,5-tetramethyl-1,3,2-dioxaborolane (R—R═—C(CH₃)₂—C(CH₃)₂—).

The coupling reaction is catalyzed by Pd catalysts, e.g. by Pd(O) catalysts like tetrakis(triphenylphosphine)palladium (0) [Pd(PPh₃)₄], tris(dibenzylideneacetone)di-palladium(0) [Pd₂(dba)₃], or by Pd(II) catalysts like dichlorobis(triphenylphosphine)-palladium(II) [Pd(PPh₃)₂Cl₂], palladium(II) acetate and triphenylphosphine or by [1,1'-bis(diphenylphosphino)ferrocene]palladium dichloride [Pd(dppf)Cl₂].

The reaction is preferably carried out in a mixture of a solvent like 1,2-dimethoxyethane, dioxane, DMF, DME, THF, or isopropanol with water and in the presence of a base like aqueous potassium carbonate, aqueous sodium bicarbonate or potassium phosphate.

In the second step the ortho-flourine of the substituent in 4-position of the compound of formula (22) is replaced by a suitable alkoxy group. —OR⁸. The reaction is preferably carried out by adding at least two equivalents of sodium hydride to a solution of compound (22) in alkohol (23) to give the desired N-unprotected sulfoximines of formula (6). The reactions are run at a temperature of 60° C. or in the temperature range between 50° C. and 70° C.

Preparation of Compounds:

Abbreviations Used in the Description of the Chemistry and in the Examples that Follow are:

CDCl₃ (deuterated chloroform); cHex (cyclohexane); DCM (dichloromethane); DIPEA (di-iso-propylethylamine); DME (1,2-dimethoxyethane), DMF (dimethylformamide); DMSO (dimethyl sulfoxide); eq (equivalent); ES (electrospray); EtOAc (ethyl acetate); EtOH (ethanol); iPrOH (isopropanol); mCPBA (meta-chloroperoxybenzoic acid), MeOH (methanol); MS (mass spectrometry); NBS (N-bromosuccinimide), NMR (nuclear magnetic resonance); Pd(dppf)Cl₂ ([1,1'-bis(diphenylphosphino)ferrocene]dichloro palladium(II) complex with dichloromethane); iPrOH (isopropanol); RT (room temperature); sat. aq. (saturated aqueous); SiO₂ (silica gel); TFA (trifluoroacetic acid); TFAA (trifluoroacetic anhydride), THF (tetrahydrofuran).

The IUPAC names of the examples were generated using the program ACD/Name batch version 12.01 from ACD LABS.

Example 1

(rac)-Ethyl [(3-{[4-(4-fluoro-2-methoxyphenyl)-1,3,5-triazin-2-yl]amino}benzyl)(methyl)oxido-λ⁶-sulfanylidene]carbamate

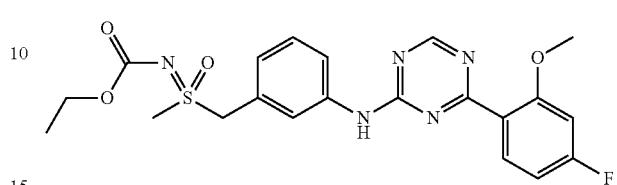

Preparation of Intermediate 1.1

1-[(Methylsulfanyl)methyl]-3-nitrobenzene

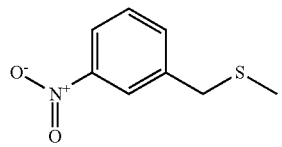

Sodium methanethiolate (13.5 g; 192 mmol) was added in two portions to a stirred solution of 1-(chloromethyl)-3-nitrobenzene (30.0 g; 175 mmol; Aldrich) in ethanol (360 mL) at −15° C. The cold bath was removed and the batch was stirred at room temperature for 3 hours. The batch was diluted with brine and extracted with ethyl acetate (2×). The combined organic phases were washed with water, dried (sodium sulfate), filtered and concentrated to give the desired product (32.2 g) that was used without further purification.

¹H NMR (400 MHz, CDC₃, 300K) δ=8.18 (m, 1H), 8.11 (m, 1H), 7.66 (m, 1H), 7.50 (m, 1H), 3.75 (s, 2H), 2.01 (s, 3H).

Preparation of Intermediate 1.2

(rac)-1-[(Methylsulfinyl)methyl]-3-nitrobenzene

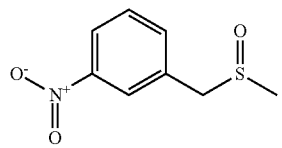

Iron(III)chloride (0.55 g; 3.4 mmol) was added to a solution of 1-[(methylsulfanyl)methyl]-3-nitrobenzene (21.6 g; 117.9 mmol) in acetonitrile (280 mL) and the batch was stirred at room temperature for 10 minutes. Periodic acid (28.8 g; 126.1 mmol) was added under stirring in one portion and the temperature was kept below 30° C. by cooling. The batch was stirred at room temperature for 90 minutes before it was added to a stirred solution of sodium thiosulfate pentahydrate (163 g; 660 mmol) in ice water (1500 mL). The batch was saturated with solid sodium chloride and extracted with THF (2×). The combined organic phases were washed with brine, dried (sodium sulfate), filtered and concentrated. The residue was purified by chromatography (DCM/ethanol 95:5) to give the desired product (16.6 g; 83.1 mmol).

$^1$H NMR (400 MHz, CDCl$_3$, 300K) δ=8.21 (m, 1H), 8.17 (m, 1H), 7.67 (m, 1H), 7.58 (m, 1H), 4.10 (d, 1H), 3.97 (d, 1H), 2.53 (s, 3H).

Preparation of Intermediate 1.3

(rac)-2,2,2-Trifluoro-N-[methyl(3-nitrobenzyl) oxido-λ$^6$-sulfanylidene]acetamide

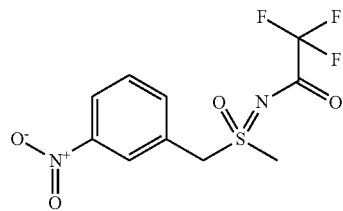 [SMILES: CS(=O)(Cc1cccc([N+](=O)[O-])c1)=NC(=O)C(F)(F)F]

To a suspension of (rac)-1-[(methylsulfinyl)methyl]-3-nitrobenzene (16.6 g; 83.1 mmol), trifluoroacetamide (18.8 g; 166.1 mmol), magnesium oxide (13.4 g; 332.3 mmol) and rhodium(II)-acetate dimer (1.7 g; 8.3 mmol) in DCM (2290 mL) was added iodobenzene diacetate (40.1 g; 124.6 mmol) at room temperature. The batch was stirred for 16 hours at room temperature, filtered and concentrated. The residue was purified by chromatography (DCM/ethanol 97:3) to give the desired product (25.6 g; 82.4 mmol).

$^1$H NMR (400 MHz, CDCl$_3$, 300K) δ=8.36 (m, 1H), 8.31 (m, 1H), 7.80 (m, 1H), 7.69 (m, 1H), 4.91 (d, 1H), 4.79 (d, 1H), 3.28 (s, 3H).

Preparation of Intermediate 1.4

(rac)-1-[(S-Methylsulfonimidoyl)methyl]-3-nitrobenzene

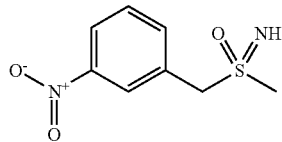

Potassium carbonate (56.9 g; 411.8 mmol) was added to a solution of (rac)-2,2,2-trifluoro-N-[methyl(3-nitrobenzyl) oxido-λ$^6$-sulfanylidene]acetamide (25.6 g; 82.4 mmol) in methanol (1768 mL) at room temperature. The batch was stirred for 1 hour at room temperature before it was diluted with ethyl acetate and brine. After extraction with ethyl acetate (2×) the combined organic phases were dried (sodium sulfate), filtered and concentrated to give the desired product (13.9 g; 65.1 mmol).

$^1$H NMR (400 MHz, CDCl$_3$, 300K) δ=8.29 (m, 2H), 7.79 (m, 1H), 7.63 (m, 1H), 4.47 (d, 1H), 4.34 (d, 1H), 2.99 (s, 3H), 2.66 (br, 1H).

Preparation of Intermediate 1.5

(rac)-Ethyl [methyl(3-nitrobenzyl)oxido-λ$^6$-sulfanylidene]carbamate

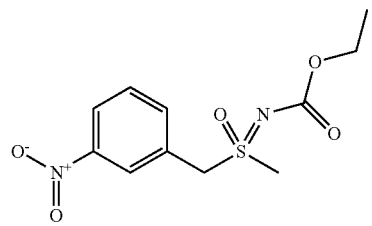 [SMILES: CCOC(=O)N=S(C)(=O)Cc1cccc([N+](=O)[O-])c1]

Ethyl chlorocarbonate (8.1 mL; 84.6 mmol) was added dropwise to a stirred solution of (rac)-1-[(S-methylsulfonimidoyl)methyl]-3-nitrobenzene (13.9 g; 65.1 mmol) in pyridine (615 mL) at 0° C. The batch was slowly warmed to room temperature. After 24 hours the batch was concentrated and the residue was dissolved in ethyl acetate and washed with brine. The organic phase was filtered using a Whatman filter and concentrated to give the desired product (19.7 g) that was used without further purification.

$^1$H NMR (400 MHz, d$_6$-CDCl$_3$, 300K) δ=8.30 (m, 2H), 7.81 (m, 1H), 7.64 (m, 1H), 4.88 (d, 1H), 4.79 (d, 1H), 4.18 (q, 2H), 3.07 (s, 3H), 1.31 (tr, 3H).

Preparation of Intermediate 1.6

(rac)-Ethyl [(3-aminobenzyl)(methyl)oxido-λ$^6$-sulfanylidene]carbamate

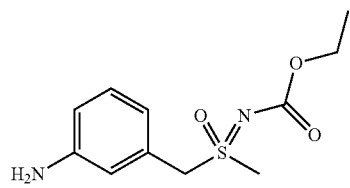

Titanium(III)chloride solution (about 15% in about 10% hydrochloric acid, 118 mL; Merck Schuchardt OHG) was added to a stirred solution of (rac)-ethyl [methyl(3-nitrobenzyl)oxido-λ$^6$-sulfanylidene]carbamate (5.0 g; 17.5 mmol) in THF (220 mL) at room temperature. The batch was stirred for 18 hours. By adding 2N sodium hydroxide solution the pH value of the reaction mixture, that was cooled with an ice bath, was raised to 8. The batch was saturated with solid sodium chloride and extracted with ethyl acetate (3×). The combined organic phases were washed with brine, dried (sodium sulfate), filtered and concentrated to give the desired product (4.2 g) that was used without further purification.

$^1$H NMR (400 MHz, d$_6$-DMSO, 300K) δ=7.00 (m, 1H), 6.53 (m, 3H), 5.18 (br, 2H), 4.62 (s, 2H), 3.95 (m, 2H), 3.08 (s, 3H), 1.13 (tr, 3H).

Preparation of Intermediate 1.7

(rac)-Ethyl [{3-[(4-chloro-1,3,5-triazin-2-yl)amino]benzyl}(methyl)oxido-$\lambda^6$-sulfanylidene]-carbamate

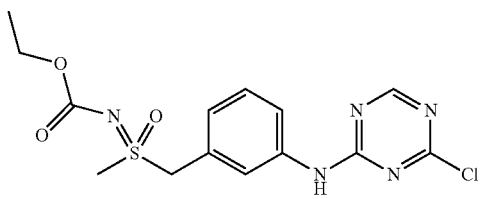 [SMILES: CCOC(=O)N=S(C)(=O)Cc1cccc(Nc2ncnc(Cl)n2)c1]

DIPEA (3.1 mL; 17.8 mmol) was added to a stirred solution of 2,4-dichloro-1,3,5-triazine (1.34 g; 8.9 mmol) in THF/i-PrOH (1:1; 18 mL) at −40° C. Then a solution of (rac)-ethyl [(3-aminobenzyl)(methyl)oxido-$\lambda^6$-sulfanylidene]carbamate (2.29 g; 8.9 mmol) in THF/i-PrOH (1:1; 9 mL) was added at this temperature. Under stirring the temperature of the reaction mixture was slowly raised over 3 hours to 0° C. The batch was concentrated to give the crude product (4.9 g) that was used without further purification.

| System: | Waters Acquity UPLC-MS: Binary Solvent Manager, Sample Manager/Organizer, Column Manager, PDA, ELSD, SQD 3001 |
|---|---|
| Column: | Acquity UPLC BEH C18 1.7 50 × 2.1 mm |
| Solvent: | A1 = H₂O + 0.1% HCOOH |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 µl |
| Detection: | DAD scan range 210-400 nm -> Peaktable ELSD |
| Method: | MS ESI+, ESI− Switch |
| | A1 + B1 = C:\MassLynx\Mass_160_1000.flp |
| Retention: | 0.88 min |
| MS(ES+): | m/z = 370 [M + H] |

Preparation of End Product:

A batch with crude (rac)-ethyl [{3-[(4-chloro-1,3,5-triazin-2-yl)amino]benzyl}(methyl)oxido-$\lambda^6$-sulfanylidene]carbamate (400 mg), (4-fluoro-2-methoxyphenyl)boronic acid (276 mg; 1.62 mmol; Aldrich) and tetrakis(triphenylphosphine)palladium(0) (187 mg; 0.16 mmol) in 1,2-dimethoxyethane (5.0 mL) and 2M solution of potassium carbonate (1.1 mL) was degassed using argon. The batch was stirred under argon for 80 minutes at 100° C. After cooling the batch was diluted with ethyl acetate and washed with brine. The organic phase was filtered using a Whatman filter and concentrated. The residue was purified by chromatography (DCM/ethanol 95:5) to give the desired product (178 mg; 0.39 mmol).

¹H NMR (400 MHz, CDCl₃, 300K) δ=8.82 (s, 1H), 7.94 (m, 1H), 7.84 (s, 1H), 7.74 (br, 1H), 7.53 (s, 1H), 7.42 (m, 1H), 7.16 (m, 1H), 6.77 (m, 2H), 4.74 (m, 2H), 4.17 (q, 2H), 3.93 (s, 3H), 3.00 (s, 3H), 1.30 (tr, 3H).

Example 2

(rac)-4-(4-Fluoro-2-methoxyphenyl)-N-{3-[(S-methylsulfonimidoyl)methyl]phenyl}-1,3,5-triazin-2-amine

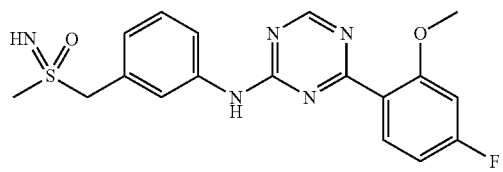 [SMILES: COc1cc(F)ccc1-c1ncnc(Nc2cccc(CS(C)(=N)=O)c2)n1]

A freshly prepared 1.5M solution of sodium ethanolate in ethanol (2.9 mL; 4.35 mmol) was added under argon to a solution of (rac)-ethyl [(3-{[4-(4-fluoro-2-methoxyphenyl)-1,3,5-triazin-2-yl]amino}-benzyl)(methyl)oxido-$\lambda^6$-sulfanylidene]carbamate (500 mg; 1.09 mmol) in ethanol (18.5 mL). The batch was stirred at 60° C. for 2 hours. Further 1.5M solution of sodium ethanolate in ethanol (2.9 mL; 4.35 mmol) was added and the batch was stirred for additional 5 hours at 60° C. After cooling the batch was diluted with brine and extracted with ethyl acetate (3×). The combined organic phases were filtered using a Whatman filter and concentrated. The residue was purified by chromatography (DCM/ethanol 9:1) to give the desired product (378 mg; 0.98 mmol).

¹H NMR (400 MHz, CDCl₃, 300K) δ=8.80 (s, 1H), 7.95 (m, 1H), 7.77 (m, 2H), 7.55 (s, 1H), 7.40 (m, 1H), 7.15 (m, 1H), 6.75 (m, 2H), 4.39 (d, 1H), 4.26 (d, 1H), 3.92 (s, 3H), 2.96 (s, 3H), 2.71 (s, 1H).

Alternative preparation of Example 2 ((rac)-4-(4-Fluoro-2-methoxyphenyl)-N-{3-[(S-methyl-sulfonimidoyl)methyl]phenyl}-1,3,5-triazin-2-amine)

Preparation of Intermediate 2.1

(rac)-4-Chloro-N-{3-[(methylsulfinyl)methyl]phenyl}-1,3,5-triazin-2-amine

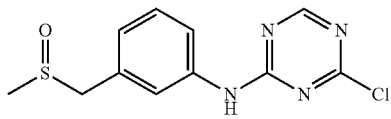 [SMILES: CS(=O)Cc1cccc(Nc2ncnc(Cl)n2)c1]

Intermediate 2.1 was prepared under similar conditions as described in the preparation of Intermediate 1.7 using (rac)-3-[(methylsulfinyl)methyl]aniline (UkrOrgSynthesis Ltd.).

| System: | Waters Acquity UPLC-MS: Binary Solvent Manager, Sample Manager/Organizer, Column Manager, PDA, ELSD, SQD 3001 |
|---|---|
| Column: | Acquity UPLC BEH C18 1.7 50 × 2.1 mm |
| Solvent: | A2 = H₂O + 0.2% NH₃ |
| | B1 = Acetonitrile |
| Gradient: | 0-1.6 min 1-99% B, 1.6-2.0 min 99% B |
| Flow: | 0.8 mL/min |
| Temperature: | 60° C. |
| Injektion: | 2.0 µl |
| Detection: | DAD scan range 210-400 nm -> Peaktable ELSD |

| | |
|---|---|
| Method: | MS ESI+, ESI− Switch<br>A2 + B1 = C:\ MassLynx\NH3_Mass_100_1000.olp |
| System: | Waters Acquity UPLC-MS: Binary Solvent Manager, Sample Manager/Organizer, Column Manager, PDA, ELSD, SQD 3001 |
| Retention | 1.13 min |
| MS(ES−): | m/z = 283 [M + H] |

Preparation of Intermediate 2.2

(rac)-4-(4-Fluoro-2-methoxyphenyl)-N-{3-[(methyl-sulfinyl)methyl]phenyl}-1,3,5-triazin-2-amine

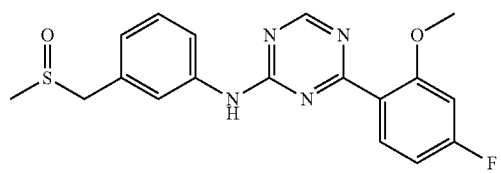 [SMILES: COc1cc(F)ccc1-c1ncnc(Nc2cccc(CS(C)=O)c2)n1]

Intermediate 2.2 was prepared under similar conditions as described in the preparation of Example 42 using crude (rac)-4-chloro-N-{3-[(methylsulfinyl)methyl]phenyl}-1,3,5-triazin-2-amine and (4-fluoro-2-methoxyphenyl)boronic acid (Aldrich Chemical Company Inc). The batch was purified by column chromatography (DCM/EtOH 95:5) to give the desired product.

$^1$H NMR (400 MHz, CDCl$_3$, 300K) δ=8.82 (s, 1H), 7.95 (br, 1H), 7.74 (br, 1H), 7.65 (s, 1H), 7.40 (m, 2H), 7.05 (m, 1H), 6.77 (m, 2H), 4.07 (d, 1H), 3.95 (m, 4H), 2.49 (s, 3H).
Preparation of End Product Concentrated sulfuric acid (2.5 mL) was added dropwise to a stirred batch of sodium azide (0.61 g; 9.4 mmol) and ((rac)-4-(4-fluoro-2-methoxyphenyl)-N-{3-[(methylsulfi-nyl)methyl]phenyl}-1,3,5-triazin-2-amine (1.75 g; 4.7 mmol) in trichloromethane (8.0 mL) at 0° C. The batch was stirred for 18 hours at 45° C. While cooling in an ice bath the batch was cautiously diluted with ice water. The batch was further diluted with saturated sodium chloride solution and THF before solid sodium bicarbonate was added under stirring to neutralize the acid. The batch was extracted with THF (3×). The combined organic phases were washed with saturated sodium chloride solution, dried (Na$_2$SO$_4$), filtered and concentrated to give the desired product (1.79 g; 4.6 mmol).

$^1$H NMR (400 MHz, CDCl$_3$, 300K) δ=8.80 (s, 1H), 7.95 (m, 1H), 7.77 (m, 2H), 7.55 (s, 1H), 7.40 (m, 1H), 7.15 (m, 1H), 6.75 (m, 2H), 4.39 (d, 1H), 4.26 (d, 1H), 3.92 (s, 3H), 2.96 (s, 3H), 2.71 (s, 1H).

Example 3 and 4

(−)-4-(4-Fluoro-2-methoxyphenyl)-N-{3-[(S-methyl-sulfonimidoyl)methyl]phenyl}-1,3,5-triazin-2-amine (enantiomer 1) and (+)-4-(4-fluoro-2-methoxyphe-nyl)-N-{3-[(S-methylsulfonimidoyl)-methyl]phe-nyl}-1,3,5-triazin-2-amine (enantiomer 2)

(rac)-4-(4-Fluoro-2-methoxyphenyl)-N-{3-[(S-methyl-sulfonimidoyl)methyl]phenyl}-1,3,5-triazin-2-amine (see example 2 was separated into the enantiomers by preparative HPLC.

| | |
|---|---|
| System: | Dionex: Pump P 580, Gilson: Liquid Handler 215, Knauer: UV-Detektor K-2501 |
| Column: | Chiralpak IC 5 μm 250 × 20 mm |
| Solvent: | Hexane/Ethanol 60:40 + 0.1% Diethylamine |
| Flow: | 40 mL/min |
| Solution: | 2600 mg/44 mL EtOH/DMSO 2:1 |
| Injektion: | 55 × 0.8 mL |
| Temperature: | RT |
| Detection: | UV 254 nm |

| | Retention time in min | purity in % | Optical rotation index |
|---|---|---|---|
| Example 3 Enantiomer 1 | 13.4-15.6 | 98.3 | −5.2° +/− 0.31° (c = 1.0000 g/100 mL CHCl$_3$) 20° C. or 17.9° +/− 0.48° (c = 1.0000 g/100 mL DMSO) 20° C. |
| Example 4 Enantiomer 2 | 15.6-17.8 | 95.5 | 2.3° +/− 0.06° (c = 1.0000 g/100 mL CHCl$_3$) 20° C. or −14.0° +/− 0.40° (c = 1.0000 g/100 mL DMSO) 20° C. |

Enantiomer 1: $^1$H NMR (400 MHz, CDCl$_3$, 300K) δ=8.80 (s, 1H), 7.95 (m, 1H), 7.77 (m, 2H), 7.55 (s, 1H), 7.40 (m, 1H), 7.15 (m, 1H), 6.75 (m, 2H), 4.39 (d, 1H), 4.26 (d, 1H), 3.92 (s, 3H), 2.96 (s, 3H), 2.71 (s, 1H).

Enantiomer 2: $^1$H NMR (400 MHz, CDCl$_3$, 300K) δ=8.80 (s, 1H), 7.95 (m, 1H), 7.77 (m, 2H), 7.55 (s, 1H), 7.40 (m, 1H), 7.15 (m, 1H), 6.75 (m, 2H), 4.39 (d, 1H), 4.26 (d, 1H), 3.92 (s, 3H), 2.96 (s, 3H), 2.71 (s, 1H).

Due to its negative optical rotation index in chloroform Enantiomer 1 is also referred to as (−)-4-(4-Fluoro-2-methoxyphenyl)-N-{3-[(S-methylsulfonimidoyl)methyl]phenyl}-1,3,5-triazin-2-amine. Enantiomer 2 is also referred to as (+)-4-(4-Fluoro-2-methoxyphenyl)-N-{3-[(S-methyl-sulfonimidoyl)-methyl]phenyl}-1,3,5-triazin-2-amine.

Example 5

(rac)-Ethyl {[3-({4-[2-(benzyloxy)-4-fluorophenyl]-1,3,5-triazin-2-yl}amino)benzyl](methyl)oxido-λ$^6$-sulfanylidene}carbamate

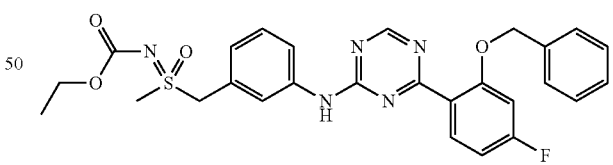

Example 5 was prepared under similar conditions as described in the preparation of Example 1 using crude (rac)-ethyl[{3-[(4-chloro-1,3,5-triazin-2-yl)amino]benzyl}(methyl)oxido-λ$^6$-sulfanylidene]carbamate and [2-(benzy-loxy)-4-fluorophenyl]boronic acid (ABCR GmbH & Co. KG). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |

-continued

| | | |
|---|---|---|
| Gradient: | B = Acetonitrile 0-1 min 1% B, 1-8 min 1-99% B, 8-10 min 99% B | |
| Flow: | 50 mL/min | |
| Temperature: | RT | |
| Solution: | Max. 250 mg/max. 2.5 mL DMSO o. DMF | |
| Injektion: | 1 × 2.5 mL | |
| Detection: | DAD scan range 210-400 nm MS ESI+, ESI−, scan range 160-1000 m/z | |

$^1$H NMR (400 MHz, CDCl$_3$, 300K) δ=8.82 (s, 1H), 7.94 (m, 1H), 7.82 (s, 1H), 7.65 (m, 1H), 7.44 (m, 3H), 7.31 (m, 4H), 7.12 (m, 1H), 6.80 (m, 2H), 5.20 (s, 2H), 4.66 (s, 2H), 4.16 (q, 2H), 2.96 (s, 3H), 1.30 (tr, 3H).

Example 6

(rac)-4-[2-(Benzyloxy)-4-fluorophenyl]-N-{3-[(S-methylsulfonimidoyl)methyl]phenyl}-1,3,5-triazin-2-amine

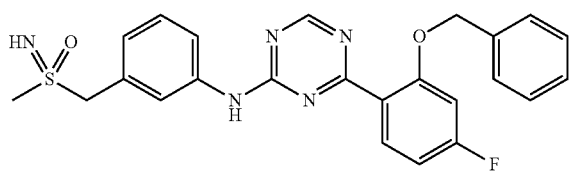 [SMILES: CS(=N)(=O)Cc1cccc(Nc2ncnc(-c3ccc(F)cc3OCc3ccccc3)n2)c1]

Example 6 was prepared under similar conditions as described in the preparation of Example 2 using (rac)-ethyl {[3-({4-[2-(benzyloxy)-4-fluorophenyl]-1,3,5-triazin-2-yl}amino)benzyl](methyl)oxido-λ$^6$-sulfanylidene}carbamate. The batch was purified by column chromatography (DCM/EtOH 95:5).

$^1$H NMR (400 MHz, CDCl$_3$, 300K) δ=8.82 (s, 1H), 7.95 (m, 1H), 7.70 (m, 2H), 7.50 (s, 1H), 7.44 (m, 2H), 7.32 (m, 4H), 7.12 (m, 1H), 6.79 (m, 2H), 5.20 (s, 2H), 4.33 (d, 1H), 4.21 (d, 1H), 2.92 (s, 3H), 2.69 (s, 1H).

Example 7 and 8

(−)-4-[2-(Benzyloxy)-4-fluorophenyl]-N-{3-[(S-methylsulfonimidoyl)methyl]phenyl}-1,3,5-triazin-2-amine (enantiomer 1) and (+)-4-[2-(benzyloxy)-4-fluorophenyl]-N-{3-[(S-methylsulfonimidoyl)-methyl]phenyl}-1,3,5-triazin-2-amine (enantiomer 2)

(rac)-4-[2-(Benzyloxy)-4-fluorophenyl]-N-{3-[(S-methylsulfonimidoyl)methyl]phenyl}-1,3,5-triazin-2-amine was separated into the enantiomers by preparative HPLC.

| | |
|---|---|
| System: | Dionex: Pump P 580, Gilson: Liquid Handler 215, Knauer: UV-Detektor K-2501 |
| Column: | Chiralpak IC 5 μm 250 × 30 mm |
| Solvent: | Hexane/Ethanol 50:50 + 0.1% Diethylamine |
| Flow: | 30 mL/min |
| Solution: | 52 mg/1.5 mL EtOH/MeOH 1:1 |
| Injektion: | 2 × 0.75 mL |
| Temperature: | RT |
| Detection: | UV 254 nm |

| | Retention time in min | purity in % | Optical rotation index |
|---|---|---|---|
| Example 7 Enantiomer 1 | 12.0-13.5 | >99.9 | −7.1° +/− 0.11° (c = 1.0000 g/100 mL CHCl$_3$) 20° C. |
| Example 8 Enantiomer 2 | 13.5-15.3 | 98.2 | 3.5° +/− 0.08° (c = 1.0000 g/100 mL CHCl$_3$) 20° C. |

Enantiomer 1: $^1$H NMR (400 MHz, CDCl$_3$, 300K) δ=8.82 (s, 1H), 7.95 (m, 1H), 7.70 (m, 2H), 7.50 (s, 1H), 7.44 (m, 2H), 7.32 (m, 4H), 7.12 (m, 1H), 6.79 (m, 2H), 5.20 (s, 2H), 4.33 (d, 1H), 4.21 (d, 1H), 2.92 (s, 3H), 2.69 (s, 1H).
Enantiomer 2: $^1$H NMR (400 MHz, CDCl$_3$, 300K) δ=8.82 (s, 1H), 7.95 (m, 1H), 7.70 (m, 2H), 7.50 (s, 1H), 7.44 (m, 2H), 7.32 (m, 4H), 7.12 (m, 1H), 6.79 (m, 2H), 5.20 (s, 2H), 4.33 (d, 1H), 4.21 (d, 1H), 2.92 (s, 3H), 2.69 (s, 1H).

Example 9

(rac)-Ethyl [(3-{[4-(4,5-difluoro-2-methoxyphenyl)-1,3,5-triazin-2-yl]amino}benzyl)(methyl)oxido-λ$^6$-sulfanylidene]carbamate

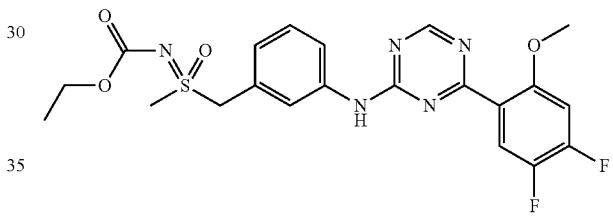

Example 9 was prepared under similar conditions as described in the preparation of Example 1 using crude (rac)-ethyl [{3-[(4-chloro-1,3,5-triazin-2-yl)amino]benzyl}(methyl)oxido-λ$^6$-sulfanylidene]carbamate and (4,5-difluoro-2-methoxyphenyl)boronic acid (Aldrich). The batch was purified by column chromatography (DCM/EtOH 95:5).

$^1$H NMR (400 MHz, CDCl$_3$, 300K) δ=8.82 (s, 1H), 7.82 (m, 3H), 7.46 (m, 2H), 7.18 (m, 1H), 6.87 (m, 1H), 4.74 (m, 2H), 4.17 (q, 2H), 3.92 (s, 3H), 3.01 (s, 3H), 1.31 (tr, 3H).

Example 10

(rac)-4-(4,5-Difluoro-2-methoxyphenyl)-N-{3-[(S-methylsulfonimidoyl)methyl]phenyl}-1,3,5-triazin-2-amine

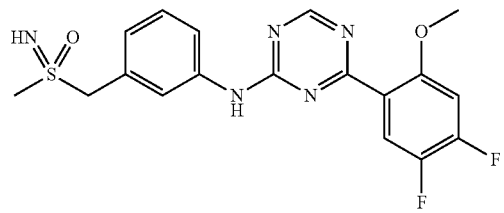

Example 10 was prepared under similar conditions as described in the preparation of Example 2 using (rac)-ethyl

[(3-{[4-(4,5-difluoro-2-methoxyphenyl)-1,3,5-triazin-2-yl]amino}benzyl)(methyl)oxido-λ⁶-sulfanylidene]carbamate. The batch was purified by preparative HPLC.

| | |
|---|---|
| System: | Waters Autopurificationsystem: Pump 254, Sample Manager 2767, CFO, DAD 2996, ELSD 2424, SQD 3001 |
| Column: | XBrigde C18 5 μm 100 × 30 mm |
| Solvent: | A = H₂O + 0.2% NH₃ |
| | B = Acetonitrile |
| Gradient: | 0-1 min 15% B, 1-8 min 15-60% B |
| Flow: | 50 mL/min |
| Solution: | 48 mg/2 mL DMSO |
| Injektion: | 2 × 1 mL |
| Temperature: | RT |
| Detection: | DAD scan range 210-400 nm |
| | MS ESI+, scan range 160-1000 m/z |
| | ELSD |
| Retention | 7.57-8.00 min |

$^1$H NMR (400 MHz, CDCl₃, 300K) δ=8.81 (s, 1H), 7.78 (m, 3H), 7.54 (s, 1H), 7.42 (m, 1H), 7.17 (m, 1H), 6.86 (m, 1H), 4.40 (d, 1H), 4.27 (d, 1H), 3.91 (s, 3H), 2.96 (s, 3H), 2.72 (s, 1H).

Example 11

(rac)-Ethyl [(3-{[4-(4-chloro-2-methoxyphenyl)-1,3,5-triazin-2-yl]amino}benzyl)(methyl)oxido-λ⁶-sulfanylidene]carbamate Example 11 was prepared under similar conditions as described in the preparation of Example 1 using crude (rac)-ethyl [{3-[(4-chloro-1,3,5-triazin-2-yl)amino]benzyl}(methyl)oxido-λ⁶-sulfanylidene]-carbamate and (4-chloro-2-methoxyphenyl)boronic acid (ABCR GmbH & Co. KG). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl₃, 300K) δ=8.82 (s, 1H), 7.85 (m, 2H), 7.75 (br, 1H), 7.57 (m, 1H), 7.42 (m, 1H), 7.17 (m, 1H), 7.04 (m, 2H), 4.73 (m, 1H), 4.16 (q, 2H), 3.93 (s, 3H), 2.99 (s, 3H), 1.30 (tr, 3H).

Example 12

(rac)-4-(4-Chloro-2-methoxy phenyl)-N-{3-[(S-methylsulfonimidoyl)methyl]phenyl}-1,3,5-triazin-2-amine

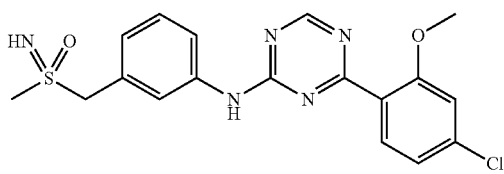 [SMILES: COc1cc(Cl)ccc1-c1ncnc(Nc2cccc(CS(C)(=N)=O)c2)n1]

Example 12 was prepared under similar conditions as described in the preparation of Example 2 using (rac)-ethyl [(3-{[4-(4-chloro-2-methoxyphenyl)-1,3,5-triazin-2-yl]amino}benzyl)(methyl)oxido-λ⁶-sulfanylidene]carbamate. The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl₃, 300K) δ=8.80 (s, 1H), 7.80 (m, 4H), 7.39 (m, 1H), 7.15 (m, 1H), 7.03 (m, 2H), 4.39 (d, 1H), 4.26 (d, 1H), 3.92 (s, 3H), 2.96 (s, 3H), 2.39 (br, 1H).

Example 13 and 14

Enantiomers of 4-(4-Chloro-2-methoxyphenyl)-N-{3-[(S-methylsulfonimidoyl)methyl]phenyl}-1,3,5-triazin-2-amine (rac)-4-(4-Chloro-2-methoxyphenyl)-N-{3-[(S-methylsulfonimidoyl)methyl]phenyl}-1,3,5-triazin-2-amine was separated into the enantiomers by preparative HPLC.

| | |
|---|---|
| System: | Agilent: Prep 1200, 2 × Prep Pump, DLA, MWD, Prep FC |
| Column: | Chiralpak IC 5 μm 250 × 20 mm |
| Solvent: | Ethanol/Methanol 65:35 + 0.1% DEA |
| Flow: | 12 mL/min |
| Solution: | 34 mg/1.5 mL MeOH/DMSO 2:1 |
| Injektion: | 5 × 0.3 mL |
| Temperature: | RT |
| Detection: | MWD 254 nm |

| | Retention time in min | purity in % |
|---|---|---|
| Example 13 Enantiomer 1 | 7.8-8.4 | >99.9 |
| Example 14 Enantiomer 2 | 8.4-9.4 | >95% |

Enantiomer 1: $^1$H NMR (400 MHz, CDCl₃, 300K) δ=8.80 (s, 1H), 7.80 (m, 4H), 7.39 (m, 1H), 7.15 (m, 1H), 7.03 (m, 2H), 4.39 (d, 1H), 4.26 (d, 1H), 3.92 (s, 3H), 2.96 (s, 3H), 2.39 (br, 1H).

Enantiomer 2: $^1$H NMR (400 MHz, CDCl$_3$, 300K) δ=8.80 (s, 1H), 7.80 (m, 4H), 7.39 (m, 1H), 7.15 (m, 1H), 7.03 (m, 2H), 4.39 (d, 1H), 4.26 (d, 1H), 3.92 (s, 3H), 2.96 (s, 3H), 2.39 (br, 1H).

Example 15

(rac)-1-[(3-{[4-(4-Fluoro-2-methoxyphenyl)-1,3,5-triazin-2-yl]amino}benzyl)(methyl)oxido-λ$^6$-sulfanylidene]-3-methylurea

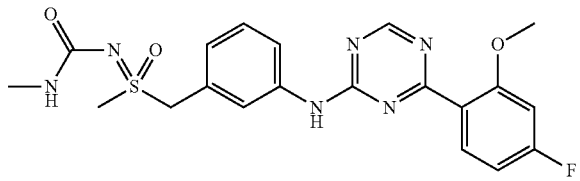 [SMILES: CNC(=O)N=S(C)(=O)Cc1cccc(Nc2ncnc(-c3ccc(F)cc3OC)n2)c1]

Isocyanatomethane (7.6 µl; 0.13 mmol) was added to a solution of (rac)-4-(4-fluoro-2-methoxyphenyl)-N-{3-[(S-methylsulfonimidoyl)methyl]phenyl}-1,3,5-triazin-2-amine (50 mg; 0.13 mmol) in DMF (2.0 ml) and triethylamine (18.0 µl; 0.13 mmol) at room temperature. The batch was stirred for 5 hours before further isocyanatomethane (3.8 µl; 0.07 mmol) was added. After 72 hours the batch was diluted with sodium bicarbonate and extracted with ethyl acetate (2×). The combined organic phases were filtered using a Whatman filter and concentrated. The residue was purified by preparative HPLC to give the desired product (34 mg; 0.08 mmol)

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.81 (s, 1H), 7.80 (m, 4H), 7.41 (m, 1H), 7.17 (m, 1H), 6.78 (m, 2H), 5.04 (br, 1H), 4.83 (d, 1H), 4.64 (d, 1H), 3.94 (s, 3H), 3.00 (s, 3H), 2.78 (d, 3H).

Example 16 and 17

(−)-1-[(3-{[4-(4-Fluoro-2-methoxyphenyl)-1,3,5-triazin-2-yl]amino}benzyl)(methyl)oxido-λ$^6$-sulfanylidene]-3-methylurea (enantiomer 1) and (+)-1-[(3-{[4-(4-Fluoro-2-methoxyphenyl)-1,3,5-triazin-2-yl]amino}benzyl)(methyl)oxido-λ$^6$-sulfanylidene]-3-methylurea (enantiomer 2)

(rac)-1-[(3-{[4-(4-Fluoro-2-methoxyphenyl)-1,3,5-triazin-2-yl]amino}benzyl)(methyl)oxido-λ$^6$-sulfanylidene]-3-methylurea was separated into the enantiomers by preparative HPLC.

| System: | Dionex: Pump P 580, Gilson: Liquid Handler 215, Knauer: UV-Detektor K-2501 |
|---|---|
| Column: | Chiralpak IA 5 µm 250 × 30 mm |
| Solvent: | Ethanol/Methanol 50:50 |
| Flow: | 30 mL/min |
| Temperature: | RT |
| Solution: | 26 mg/1.5 mL EtOH/MeOH 1:1 |
| Injektion: | 1 × 1.5 mL |
| Detection: | UV 254 nm |

| | Retention time in min | purity in % | Optical rotation index |
|---|---|---|---|
| Example 16 Enantiomer 1 | 27.5-35.5 | 98.9 | −25.1° +/− 0.19° (c = 1.0000 g/100 mL CHCl$_3$) 20° C. |
| Example 17 Enantiomer 2 | 37.0-50.3 | 99.2 | 18.7° +/− 0.10° (c = 1.0000 g/100 mL CHCl$_3$) 20° C. |

Enantiomer 1: $^1$H NMR (400 MHz, CDCl$_3$, 300K) δ=8.81 (s, 1H), 7.80 (m, 4H), 7.41 (m, 1H), 7.17 (m, 1H), 6.78 (m, 2H), 5.04 (br, 1H), 4.83 (d, 1H), 4.64 (d, 1H), 3.94 (s, 3H), 3.00 (s, 3H), 2.78 (d, 3H).

Enantiomer 2: $^1$H NMR (400 MHz, CDCl$_3$, 300K) δ=8.81 (s, 1H), 7.80 (m, 4H), 7.41 (m, 1H), 7.17 (m, 1H), 6.78 (m, 2H), 5.04 (br, 1H), 4.83 (d, 1H), 4.64 (d, 1H), 3.94 (s, 3H), 3.00 (s, 3H), 2.78 (d, 3H).

Example 18

(rac)-Ethyl [(3-{[4-(2,2-difluoro-1,3-benzodioxol-4-yl)-1,3,5-triazin-2-yl]amino}benzyl)(methyl)-oxido-λ$^6$-sulfanylidene]carbamate

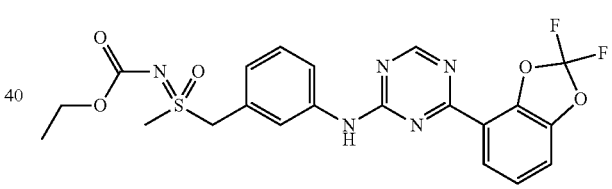

Example 18 was prepared under similar conditions as described in the preparation of Example 1 using crude (rac)-ethyl [{3-[(4-chloro-1,3,5-triazin-2-yl)amino]benzyl}(methyl)oxido-λ$^6$-sulfanylidene]carbamate and (2,2-difluoro-1,3-benzodioxol-4-yl)boronic acid (Combi Blocks Inc.). The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.86 (s, 1H), 8.12 (m, 1H), 7.82 (m, 1H), 7.48 (m, 3H), 7.24 (m, 3H), 4.76 (m, 2H), 4.17 (q, 2H), 3.02 (s, 3H), 1.31 (tr, 3H).

Example 19

(rac)-4-(2,2-Difluoro-1,3-benzodioxol-4-yl)-N-{3-[(S-methylsulfonimidoyl)methyl]phenyl}-1,3,5-triazin-2-amine

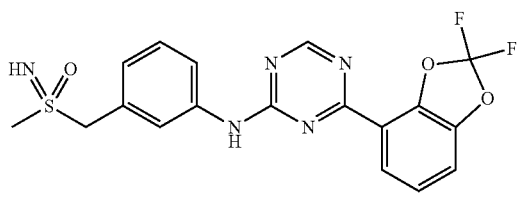 [SMILES: CS(=N)(=O)Cc1cccc(Nc2ncnc(-c3cccc4c3OC(F)(F)O4)n2)c1]

Example 19 was prepared under similar conditions as described in the preparation of Example 2 using (rac)-ethyl [(3-{[4-(2,2-difluoro-1,3-benzodioxol-4-yl)-1,3,5-triazin-2-yl]amino}benzyl)(methyl)oxido-$\lambda^6$-sulfanylidene]carbamate. The batch was purified by column chromatography (DCM/EtOH 95:5).

$^1$H NMR (400 MHz, CDCl$_3$, 300K) δ=8.84 (s, 1H), 8.13 (m, 1H), 7.87 (m, 2H), 7.52 (br, 1H), 7.45 (m, 1H), 7.22 (m, 3H), 4.44 (d, 1H), 4.29 (d, 1H), 2.97 (s, 3H), 2.70 (s, 1H).

Example 20

(rac)-Ethyl [(3-{[4-(5-fluoro-2-methoxyphenyl)-1,3,5-triazin-2-yl]amino}benzyl)(methyl)oxido-$\lambda^6$-sulfanylidene]carbamate

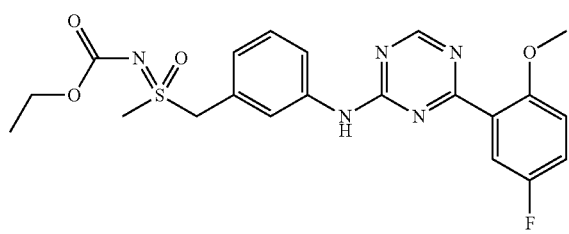 [SMILES: CCOC(=O)N=S(C)(=O)Cc1cccc(Nc2ncnc(-c3cc(F)ccc3OC)n2)c1]

Example 20 was prepared under similar conditions as described in the preparation of Example 1 using crude (rac)-ethyl [{3-[(4-chloro-1,3,5-triazin-2-yl)amino]benzyl}(methyl)oxido-$\lambda^6$-sulfanylidene]carbamate and (5-fluoro-2-methoxyphenyl)boronic acid (Aldrich Chemical Company Inc.). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI−, scan range 160-1000 m/z |

$^1$H NMR (400 MHz, CDCl$_3$, 300K) δ=8.84 (s, 1H), 7.84 (m, 1H), 7.73 (br, 1H), 7.60 (m, 1H), 7.51 (s, 1H), 7.43 (m, 1H), 7.19 (m, 2H), 7.00 (m, 1H), 4.74 (m, 2H), 4.18 (q, 2H), 3.91 (s, 3H), 3.00 (s, 3H), 1.30 (tr, 3H).

Example 21

(rac)-4-(5-Fluoro-2-methoxyphenyl)-N-{3-[(S-methylsulfonimidoyl)methyl]phenyl}-1,3,5-triazin-2-amine

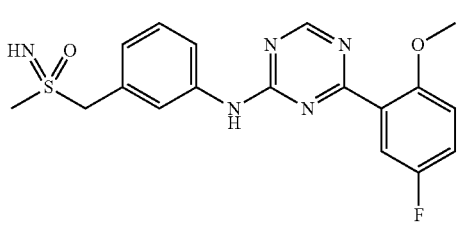

Example 21 was prepared under similar conditions as described in the preparation of Example 2 using (rac)-ethyl [(3-{[4-(5-fluoro-2-methoxyphenyl)-1,3,5-triazin-2-yl]amino}benzyl)(methyl)oxido-$\lambda^6$-sulfanylidene]carbamate. The batch was purified by column chromatography (DCM/EtOH 95:5).

$^1$H NMR (400 MHz, CDCl$_3$, 300K) δ=8.84 (s, 1H), 7.73 (m, 2H), 7.63 (m, 1H), 7.43 (m, 2H), 7.19 (m, 2H), 7.02 (m, 1H), 4.38 (d, 1H), 4.28 (d, 1H), 3.91 (s, 3H), 2.95 (s, 3H), 2.70 (br, 1H).

Example 22 and 23

Enantiomers of 4-(5-fluoro-2-methoxyphenyl)-N-{3-[(S-methylsulfonimidoyl)methyl]phenyl}-1,3,5-triazin-2-amine (rac)-4-(5-Fluoro-2-methoxyphenyl)-N-{3-[(S-methylsulfonimidoyl)methyl]phenyl}-1,3,5-triazin-2-amine was separated into the enantiomers by preparative HPLC:

| | |
|---|---|
| System: | Agilent: Prep 1200, 2 × Prep Pump, DLA, MWD, Prep FC |
| Column: | Chiralcel OJ-H 5 μm 250 × 20 mm |
| Solvent: | Ethanol/ethanol 50:50 + 0.1% DEA |
| Flow: | 16 mL/min |
| Temperature: | RT |
| Solution: | 57 mg/0.6 mL EtOH/MeOH 1:1 |
| Injektion: | 2 × 0.3 mL |
| Detection: | MWD 254 nm |

| | Retention time in min | purity in % |
|---|---|---|
| Example 22<br>Enantiomer 1 | 6.1-7.2 | >99% |
| Example 23<br>Enantiomer 2 | 8.6-10.2 | >99% |

Enantiomer 1: $^1$H NMR (400 MHz, CDCl$_3$, 300K) δ=8.84 (s, 1H), 7.73 (m, 2H), 7.63 (m, 1H), 7.43 (m, 2H), 7.19 (m, 2H), 7.02 (m, 1H), 4.38 (d, 1H), 4.28 (d, 1H), 3.91 (s, 3H), 2.95 (s, 3H), 2.70 (br, 1H).

Enantiomer 2: $^1$H NMR (400 MHz, CDCl$_3$, 300K) δ=8.84 (s, 1H), 7.73 (m, 2H), 7.63 (m, 1H), 7.43 (m, 2H), 7.19 (m, 2H), 7.02 (m, 1H), 4.38 (d, 1H), 4.28 (d, 1H), 3.91 (s, 3H), 2.95 (s, 3H), 2.70 (br, 1H).

Example 24

(rac)-N-[(3-{[4-(4-fluoro-2-methoxyphenyl)-1,3,5-triazin-2-yl]amino}benzyl)(methyl)oxido-λ⁶-sulfanylidene]acetamide

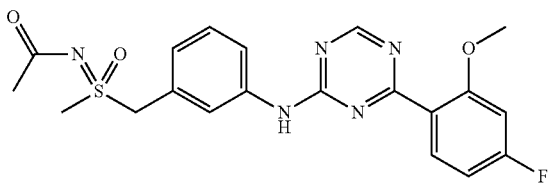 [SMILES: COc1cc(F)ccc1-c1ncnc(Nc2cccc(CS(C)(=O)=NC(C)=O)c2)n1]

Acetyl chloride (10.1 μl; 0.14 mmol) was added to a solution of (rac)-4-(4-fluoro-2-methoxyphenyl)-N-{3-[(S-methylsulfonimidoyl)methyl]phenyl}-1,3,5-triazin-2-amine (50 mg; 0.13 mmol) in DCM (1.5 ml) and triethylamine (45.0 μl; 0.32 mmol) at 0° C. The ice bath was removed and the batch was stirred for 23 hours before further acetyl chloride (4.0 μl; 0.06 mmol) was added. After 24 hours additional acetyl chloride (5.0 μl; 0.07 mmol) was added and the batch was stirred for 3 hours before it was diluted with water and extracted with ethyl acetate (2×). The combined organic phases were filtered using a Whatman filter and concentrated. The residue was purified by preparative HPLC to give the desired product (35 mg; 0.08 mmol).

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H₂O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI−, scan range 160-1000 m/z |

$^1$H NMR (400 MHz, CDCl₃, 300K) δ=8.82 (s, 1H), 7.95 (m, 1H), 7.78 (m, 2H), 7.56 (m, 1H), 7.42 (m, 1H), 7.16 (m, 1H), 6.79 (m, 2H), 4.78 (d, 1H), 4.65 (d, 1H), 3.94 (s, 3H), 3.03 (s, 3H), 2.12 (s, 3H).

Example 25

(rac)-Ethyl [(3-{[4-(2-methoxyphenyl)-1,3,5-triazin-2-yl]amino}benzyl)(methyl)oxido-λ⁶-sulfanylidene]carbamate

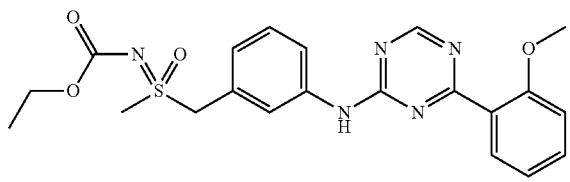 [SMILES: CCOC(=O)N=S(C)(=O)Cc1cccc(Nc2ncnc(-c3ccccc3OC)n2)c1]

Example 25 was prepared under similar conditions as described in the preparation of Example 1 using crude (rac)-ethyl [{3-[(4-chloro-1,3,5-triazin-2-yl)amino]benzyl} (methyl)oxido-λ⁶-sulfanylidene]carbamate and (2-methoxyphenyl)boronic acid (Aldrich Chemical Company Inc.). The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H₂O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI−, scan range 160-1000 m/z |

$^1$H NMR (400 MHz, CDCl₃, 300K) δ=8.82 (s, 1H), 7.85 (m, 2H), 7.71 (m, 1H), 7.56 (s, 1H), 7.48 (m, 1H), 7.42 (m, 1H), 7.17 (m, 1H), 7.07 (m, 2H), 4.73 (s, 2H), 4.17 (q, 2H), 3.93 (s, 3H), 2.98 (s, 3H), 1.30 (tr, 3H).

Example 26

(rac)-4-(2-Methoxyphenyl)-N-{3-[(S-methylsulfonimidoyl)methyl]phenyl}-1,3,5-triazin-2-amine

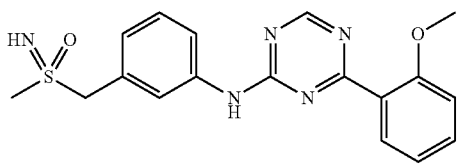

Example 26 was prepared under similar conditions as described in the preparation of Example 2 using (rac)-ethyl [(3-{[4-(2-methoxyphenyl)-1,3,5-triazin-2-yl]amino}benzyl)(methyl)oxido-λ⁶-sulfanylidene]-carbamate. After aqueous work up no further purification was necessary.

$^1$H NMR (400 MHz, CDCl₃, 300K) δ=8.83 (s, 1H), 7.86 (m, 1H), 7.75 (m, 2H), 7.54 (s, 1H), 7.49 (m, 1H), 7.41 (m, 1H), 7.16 (m, 1H), 7.05 (m, 2H), 4.38 (d, 1H), 4.26 (d, 1H), 3.93 (s, 3H), 2.94 (s, 3H), 2.70 (s, 1H).

Example 27 and 28

Enantiomers of 4-(2-Methoxyphenyl)-N-{3-[(S-methylsulfonimidoyl)methyl]phenyl}-1,3,5-triazin-2-amine(rac)-4-(2-Methoxyphenyl)-N-{3-[(S-methylsulfonimidoyl)methyl]phenyl}-1,3,5-triazin-2-amine was separated into the enantiomers by preparative HPLC:

| System: | Agilent: Prep 1200, 2 × Prep Pump, DLA, MWD, Prep FC |
|---|---|
| Column: | Chiralcel OJ-H 5 μm 250 × 20 mm |
| Solvent: | Ethanol/methanol 50:50 + 0.1% DEA |
| Flow: | 16 mL/min |
| Temperature: | RT |
| Solution: | 59 mg/0.6 mL EtOH |
| Injektion: | 2 × 0.3 mL |
| Detection: | MWD 254 nm |

-continued

|  | Retention time in min | purity in % |
|---|---|---|
| Example 27 Enantiomer 1 | 11.7-12.2 | >99% |
| Example 28 Enantiomer 2 | 7.5-7.9 | >99% |

Enantiomer 1: $^1$H NMR (400 MHz, CDCl$_3$, 300K) δ=8.83 (s, 1H), 7.86 (m, 1H), 7.75 (m, 2H), 7.54 (s, 1H), 7.49 (m, 1H), 7.41 (m, 1H), 7.16 (m, 1H), 7.05 (m, 2H), 4.38 (d, 1H), 4.26 (d, 1H), 3.93 (s, 3H), 2.94 (s, 3H), 2.70 (s, 1H).

Enantiomer 2: $^1$H NMR (400 MHz, CDCl$_3$, 300K) δ=8.83 (s, 1H), 7.86 (m, 1H), 7.75 (m, 2H), 7.54 (s, 1H), 7.49 (m, 1H), 7.41 (m, 1H), 7.16 (m, 1H), 7.05 (m, 2H), 4.38 (d, 1H), 4.26 (d, 1H), 3.93 (s, 3H), 2.94 (s, 3H), 2.70 (s, 1H).

Example 29

(rac)-Ethyl [(3-{[4-(3,4-dihydro-2H-chromen-8-yl)-1,3,5-triazin-2-yl]amino}benzyl)(methyl)oxido-λ$^6$-sulfanylidene]carbamate

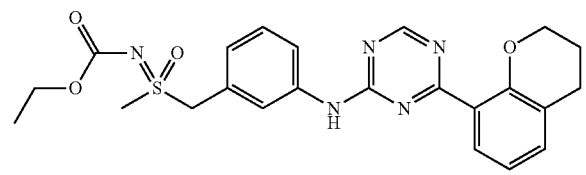 [SMILES: CCOC(=O)N=S(C)(=O)Cc1cccc(Nc2ncnc(-c3cccc4c3OCCC4)n2)c1]

Example 29 was prepared under similar conditions as described in the preparation of Example 1 using crude (rac)-ethyl [{3-[(4-chloro-1,3,5-triazin-2-yl)amino]benzyl}(methyl)oxido-λ$^6$-sulfanylidene]carbamate and 3,4-dihydro-2H-chromen-8-ylboronic acid (Parkway Scientific LLC). The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI−, scan range 160-1000 m/z |

$^1$H NMR (400 MHz, CDCl$_3$, 300K) δ=8.84 (s, 1H), 7.85 (m, 1H), 7.74 (br, 1H), 7.65 (m, 1H), 7.42 (m, 2H), 7.19 (m, 2H), 6.94 (m, 1H), 4.73 (s, 2H), 4.30 (tr, 2H), 4.17 (q, 2H), 2.98 (s, 3H), 2.89 (tr, 2H), 2.10 (m, 2H), 1.31 (tr, 3H).

Example 30

(rac)-4-(3,4-Dihydro-2H-chromen-8-yl)-N-{3-[(S-methylsulfonimidoyl)methyl]phenyl}-1,3,5-triazin-2-amine

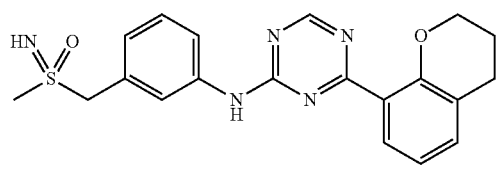 [SMILES: CS(=N)(=O)Cc1cccc(Nc2ncnc(-c3cccc4c3OCCC4)n2)c1]

Example 30 was prepared under similar conditions as described in the preparation of Example 2 using (rac)-ethyl [(3-{[4-(3,4-dihydro-2H-chromen-8-yl)-1,3,5-triazin-2-yl]amino}benzyl)(methyl)oxido-λ$^6$-sulfanylidene]carbamate. After aqueous work up no further purification was necessary.

$^1$H NMR (400 MHz, CDCl$_3$, 300K) δ=8.83 (s, 1H), 7.74 (m, 3H), 7.49 (br, 1H), 7.40 (m, 1H), 7.17 (m, 2H), 6.94 (m, 1H), 4.30 (m, 4H), 2.94 (s, 3H), 2.88 (tr, 2H), 2.69 (s, 1H), 2.10 (m, 2H).

Example 31 and 32

Enantiomers of 4-(3,4-dihydro-2H-chromen-8-yl)-N-{3-[(S-methylsulfonimidoyl)methyl]phenyl}-1,3,5-triazin-2-amine(rac)-4-(3,4-Dihydro-2H-chromen-8-yl)-N-{3-[(S-methylsulfonimidoyl)methyl]phenyl}-1,3,5-triazin-2-amine was separated into the enantiomers by preparative HPLC.

| System: | Agilent: Prep 1200, 2 × Prep Pump, DLA, MWD, Prep FC |
|---|---|
| Column: | Chiralcel OJ-H 5 μm 250 × 20 mm |
| Solvent: | Ethanol/methanol 50:50 + 0.1% DEA |
| Flow: | 16 mL/min |
| Temperature: | RT |
| Solution: | 46 mg/0.6 mL MeOH |
| Injektion: | 2 × 0.3 mL |
| Detection: | MWD 254 nm |

|  | Retention time in min | purity in % |
|---|---|---|
| Example 31 Enantiomer 1 | 7.0-8.1 | >99% |
| Example 32 Enantiomer 2 | 10.0-11.3 | >99% |

Enantiomer 1: $^1$H NMR (400 MHz, CDCl$_3$, 300K) δ=8.83 (s, 1H), 7.74 (m, 3H), 7.49 (br, 1H), 7.40 (m, 1H), 7.17 (m, 2H), 6.94 (m, 1H), 4.30 (m, 4H), 2.94 (s, 3H), 2.88 (tr, 2H), 2.69 (s, 1H), 2.10 (m, 2H).

Enantiomer 2: $^1$H NMR (400 MHz, CDCl$_3$, 300K) δ=8.83 (s, 1H), 7.74 (m, 3H), 7.49 (br, 1H), 7.40 (m, 1H), 7.17 (m, 2H), 6.94 (m, 1H), 4.30 (m, 4H), 2.94 (s, 3H), 2.88 (tr, 2H), 2.69 (s, 1H), 2.10 (m, 2H).

Example 33

(rac)-Ethyl [(3-{[4-(2,3-dihydro-1-benzofuran-7-yl)-1,3,5-triazin-2-yl]amino}benzyl)(methyl)oxido-λ⁶-sulfanylidene]carbamate

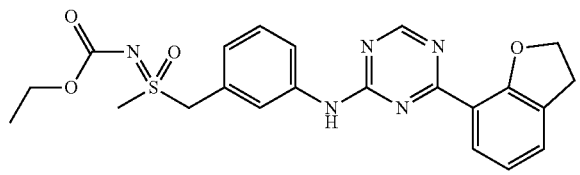 [SMILES: CCOC(=O)N=S(C)(=O)Cc1cccc(Nc2ncnc(-c3cccc4c3OCC4)n2)c1]

Example 33 was prepared under similar conditions as described in the preparation of Example 1 using crude (rac)-ethyl [{3-[(4-chloro-1,3,5-triazin-2-yl)amino]benzyl}(methyl)oxido-λ⁶-sulfanylidene]carbamate and (2,3-dihydro-1-benzofuran-7-yl)boronic acid (ChemBridge Corporation). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 µm 100 × 30 mm |
| Solvent: | A = H₂O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI−, scan range 160-1000 m/z |

¹H NMR (400 MHz, CDCl₃, 300K) δ=8.85 (s, 1H), 8.10 (m, 1H), 7.96 (s, 1H), 7.75 (m, 1H), 7.42 (m, 3H), 7.18 (m, 1H), 6.98 (m, 1H), 4.80 (tr, 2H), 4.76 (s, 2H), 4.17 (q, 2H), 3.29 (tr, 2H), 3.01 (s, 3H), 1.31 (tr, 3H).

Example 34

(rac)-4-(2,3-Dihydro-1-benzofuran-7-yl)-N-{3-[(S-methylsulfonimidoyl)methyl]phenyl}-1,3,5-triazin-2-amine

Example 34 was prepared under similar conditions as described in the preparation of Example 2 using (rac)-ethyl [(3-{[4-(2,3-dihydro-1-benzofuran-7-yl)-1,3,5-triazin-2-yl]amino}benzyl)(methyl)oxido-λ⁶-sulfanylidene]carbamate. After aqueous work up no further purification was necessary.

¹H NMR (400 MHz, CDCl₃, 300K) δ=8.85 (s, 1H), 8.11 (m, 1H), 7.87 (s, 1H), 7.76 (br, 1H), 7.44 (m, 2H), 7.39 (m, 1H), 7.17 (m, 1H), 6.98 (m, 1H), 4.81 (tr, 2H), 4.40 (d, 1H), 4.30 (d, 1H), 3.29 (tr, 2H), 2.95 (s, 3H), 2.72 (s, 1H).

Example 35 and 36

Enantiomers of 4-(2,3-dihydro-1-benzofuran-7-yl)-N-{3-[(S-methylsulfonimidoyl)methyl]phenyl}-1,3,5-triazin-2-amine (rac)-4-(2,3-Dihydro-1-benzofuran-7-yl)-N-{3-[(S-methylsulfonimidoyl)methyl]phenyl}-1,3,5-triazin-2-amine was separated into the enantiomers by preparative HPLC.

| | |
|---|---|
| System: | Agilent: Prep 1200, 2 × Prep Pump, DLA, MWD, Prep FC |
| Column: | Chiralpak IA 5 µm 250 × 20 mm |
| Solvent: | Ethanol/methanol 50:50 + 0.1% DEA |
| Flow: | 15 mL/min |
| Temperature: | RT |
| Solution: | 74 mg/0.9 mL DMSO |
| Injektion: | 3 × 0.3 mL |
| Detection: | MWD 254 nm |

| | Retention time in min | purity in % |
|---|---|---|
| Example 35 Enantiomer 1 | 9.1-10.5 | >97% |
| Example 36 Enantiomer 2 | 10.8-15.8 | >95% |

Enantiomer 1: ¹H NMR (400 MHz, CDCl₃, 300K) δ=8.85 (s, 1H), 8.11 (m, 1H), 7.87 (s, 1H), 7.76 (br, 1H), 7.44 (m, 2H), 7.39 (m, 1H), 7.17 (m, 1H), 6.98 (m, 1H), 4.81 (tr, 2H), 4.40 (d, 1H), 4.30 (d, 1H), 3.29 (tr, 2H), 2.95 (s, 3H), 2.72 (s, 1H).

Enantiomer 2: ¹H NMR (400 MHz, CDCl₃, 300K) δ=8.85 (s, 1H), 8.11 (m, 1H), 7.87 (s, 1H), 7.76 (br, 1H), 7.44 (m, 2H), 7.39 (m, 1H), 7.17 (m, 1H), 6.98 (m, 1H), 4.81 (tr, 2H), 4.40 (d, 1H), 4.30 (d, 1H), 3.29 (tr, 2H), 2.95 (s, 3H), 2.72 (s, 1H).

Example 37

(rac)-Ethyl [(3-{[4-(2,3-dihydro-1,4-benzodioxin-5-yl)-1,3,5-triazin-2-yl]amino}benzyl)(methyl)-oxido-λ⁶-sulfanylidene]carbamate

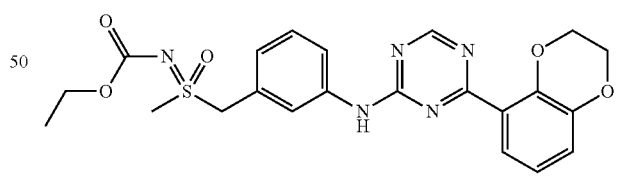

Example 37 was prepared under similar conditions as described in the preparation of Example 1 using crude (rac)-ethyl [{3-[(4-chloro-1,3,5-triazin-2-yl)amino]benzyl}(methyl)oxido-λ⁶-sulfanylidene]carbamate and 2,3-dihydro-1,4-benzodioxin-5-ylboronic acid (Combi Blocks Inc.). The batch was purified by column chromatography (DCM/EtOH 95:5).

¹H NMR (400 MHz, CDCl₃, 300K) δ=8.85 (s, 1H), 7.87 (s, 1H), 7.71 (m, 1H), 7.48 (m, 2H), 7.42 (m, 1H), 7.17 (m, 1H), 7.04 (m, 1H), 6.95 (m, 1H), 4.74 (m, 2H), 4.37 (m, 4H), 4.17 (q, 2H), 3.00 (s, 3H), 1.31 (tr, 3H).

Example 38

(rac)-4-(2,3-Dihydro-1,4-benzodioxin-5-yl)-N-{3-[(S-methylsulfonimidoyl)methyl]phenyl}-1,3,5-triazin-2-amine

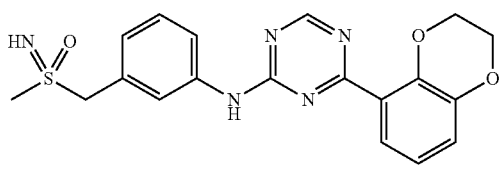 [SMILES: CS(=N)(=O)Cc1cccc(Nc2ncnc(-c3cccc4c3OCCO4)n2)c1]

Example 38 was prepared under similar conditions as described in the preparation of Example 2 using (rac)-ethyl [(3-{[4-(2,3-dihydro-1,4-benzodioxin-5-yl)-1,3,5-triazin-2-yl]amino}benzyl)(methyl)oxido-$\lambda^6$-sulfanylidene]carbamate. After aqueous work up no further purification was necessary.

$^1$H NMR (400 MHz, CDCl$_3$, 300K) δ=8.84 (s, 1H), 7.75 (m, 2H), 7.56 (s, 1H), 7.49 (m, 1H), 7.40 (m, 1H), 7.15 (m, 1H), 7.04 (m, 1H), 6.94 (m, 1H), 4.38 (m, 5H), 4.26 (d, 1H), 2.95 (s, 3H), 2.72 (s, 1H).

Example 39 and 40

Enantiomers of 4-(2,3-dihydro-1,4-benzodioxin-5-yl)-N-{3-[(S-methylsulfonimidoyl)methyl]-phenyl}-1,3,5-triazin-2-amine(rac)-4-(2,3-Dihydro-1,4-benzodioxin-5-yl)-N-{3-[(S-methylsulfonimidoyl)methyl]phenyl}-1,3,5-triazin-2-amine was separated into the enantiomers by preparative HPLC.

| System: | Agilent: Prep 1200, 2 × Prep Pump, DLA, MWD, Prep FC |
|---|---|
| Column: | Chiralcel OJ-H 5 μm 250 × 20 mm |
| Solvent: | Ethanol/methanol 50:50 + 0.1% DEA |
| Flow: | 16 mL/min |
| Temperature: | RT |
| Solution: | 140 mg/1.5 mL MeOH |
| Injektion: | 5 × 0.3 mL |
| Detection: | MWD 254 nm |

| | Retention time in min | purity in % |
|---|---|---|
| Example 39 Enantiomer 1 | 7.5-9.0 | >99% |
| Example 40 Enantiomer 2 | 9.4-11.3 | >98% |

Enantiomer 1: $^1$H NMR (400 MHz, CDC$_3$, 300K) δ=8.84 (s, 1H), 7.75 (m, 2H), 7.56 (s, 1H), 7.49 (m, 1H), 7.40 (m, 1H), 7.15 (m, 1H), 7.04 (m, 1H), 6.94 (m, 1H), 4.38 (m, 5H), 4.26 (d, 1H), 2.95 (s, 3H), 2.72 (s, 1H).

Enantiomer 2: $^1$H NMR (400 MHz, CDCl$_3$, 300K) δ=8.84 (s, 1H), 7.75 (m, 2H), 7.56 (s, 1H), 7.49 (m, 1H), 7.40 (m, 1H), 7.15 (m, 1H), 7.04 (m, 1H), 6.94 (m, 1H), 4.38 (m, 5H), 4.26 (d, 1H), 2.95 (s, 3H), 2.72 (s, 1H).

Example 41

(rac)-N-{3-[(N,S-Dimethylsulfonimidoyl)methyl]phenyl}-4-(4-fluoro-2-methoxyphenyl)-1,3,5-triazin-2-amine

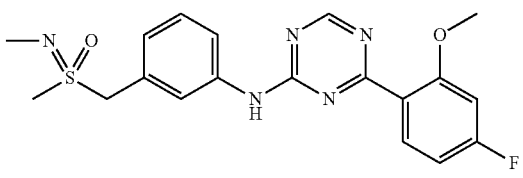 [SMILES: CN=S(C)(=O)Cc1cccc(Nc2ncnc(-c3ccc(F)cc3OC)n2)c1]

Formaldehyde (17.9 μl; 0.65 mmol) was added to a solution of (rac)-4-(4-fluoro-2-methoxyphenyl)-N-{3-[(S-methylsulfonimidoyl)methyl]phenyl}-1,3,5-triazin-2-amine (50 mg; 0.13 mmol) in formic acid (1.0 ml) at room temperature. The batch was stirred at 80° C. for 24 hours. After cooling the batch was diluted with aqueous sodium bicarbonate solution and extracted with ethyl acetate (2×). The combined organic phases were filtered using a Whatman filter and concentrated. The residue was purified by preparative HPLC to give the desired product (5 mg; 0.01 mmol).

| System: | Waters Autopurificationsystem: Pump 254, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.2% NH$_3$<br>B = MeOH |
| Gradient: | 0-1 min 15% B, 1-8 min 15-60% B, 8-8.1 min 60-100% B, 8.1-10 min 100% B |
| Flow: | 50 mL/min |
| Temperature: | RT |
| Solution: | 59 mg/4.5 mL DMSO |
| Injektion: | 9 × 0.5 mL |
| Detection: | DAD scan range 210-400 nm<br>MS ESI+, ESI−, scan range 160-1000 m/z<br>ELSD |
| Retention: | 5.6-5.8 min |

$^1$H NMR (400 MHz, CDCl$_3$, 300K) δ=8.81 (s, 1H), 7.94 (m, 1H), 7.71 (m, 2H), 7.58 (m, 1H), 7.40 (m, 1H), 7.13 (m, 1H), 6.75 (m, 2H), 4.33 (s, 2H), 3.93 (s, 3H), 2.86 (s, 3H), 2.74 (s, 3H).

Example 42

(rac)-Ethyl [{3-[(4-{2-[(4-fluorobenzyl)oxy]phenyl}-1,3,5-triazin-2-yl)amino]benzyl}(methyl)oxido-$\lambda^6$-sulfanylidene]carbamate

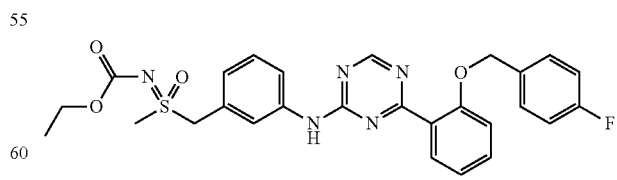

A batch with crude (rac)-ethyl [{3-[(4-chloro-1,3,5-triazin-2-yl)amino]benzyl}(methyl)oxido-$\lambda^6$-sulfanylidene]carbamate (400 mg), {2-[(4-fluorobenzyl)oxy]phenyl}boronic acid (266 mg; 1.08 mmol; Aldrich Chemical Company Inc.) and [1,1'-bis(diphenylphosphino)ferrocene]

palladium dichloride (132 mg; 0.16 mmol) in 1,2-dimethoxyethane (2.5 mL) and 2M solution of potassium carbonate (1.1 mL) was degassed using argon. The batch was stirred under argon for 90 minutes at 100° C. After cooling the batch was diluted with DCM. The organic phase was filtered using a Whatman filter and concentrated. The residue was purified by chromatography (DCM/ethanol 95:5) to give the desired product (134 mg; 0.25 mmol).

$^1$H NMR (400 MHz, CDCl$_3$, 300K) δ=8.84 (s, 1H), 7.86 (m, 2H), 7.62 (m, 1H), 7.42 (m, 5H), 7.12 (m, 3H), 7.09 (m, 2H), 5.16 (s, 2H), 4.67 (s, 2H), 4.16 (q, 2H), 2.95 (s, 3H), 1.30 (tr, 3H).

Example 43

(rac)-4-{2-[(4-Fluorobenzyl)oxy]phenyl}-N-{3-[(S-methylsulfonimidoyl)methyl]phenyl}-1,3,5-triazin-2-amine

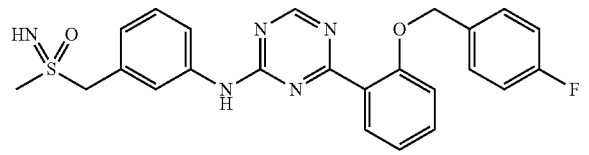 [SMILES: CS(=N)(=O)Cc1cccc(Nc2ncnc(-c3ccccc3OCc3ccc(F)cc3)n2)c1]

Example 43 was prepared under similar conditions as described in the preparation of Example 2 using (rac)-ethyl [{3-[(4-{2-[(4-fluorobenzyl)oxy]phenyl}-1,3,5-triazin-2-yl)amino]benzyl}(methyl)oxido-λ$^6$-sulfanylidene]carbamate. After aqueous work up no further purification was necessary.

$^1$H NMR (400 MHz, CDCl$_3$, 300K) δ=8.83 (s, 1H), 7.87 (m, 1H), 7.76 (s, 1H), 7.68 (m, 1H), 7.42 (m, 5H), 7.04 (m, 5H), 5.16 (s, 2H), 4.34 (d, 1H), 4.22 (d, 1H), 2.92 (s, 3H), 2.70 (s, 1H).

Example 44

(rac)-N-[(3-{[4-(4-Fluoro-2-methoxyphenyl)-1,3,5-triazin-2-yl]amino}benzyl)(methyl)oxido-λ$^6$-sulfanylidene]methanesulfonamide

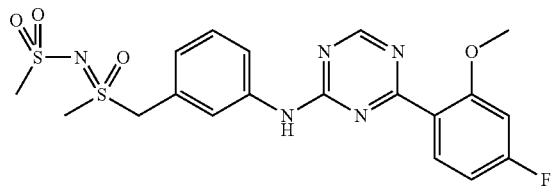 [SMILES: COc1cc(F)ccc1-c1ncnc(Nc2cccc(CS(C)(=O)=NS(C)(=O)=O)c2)n1]

Methanesulfonyl chloride (12.0 µl; 0.16 mmol) was added to a solution of (rac)-4-(4-fluoro-2-methoxyphenyl)-N-{3-[(S-methylsulfonimidoyl)methyl]phenyl}-1,3,5-triazin-2-amine (50.0 mg; 0.13 mmol), triethylamine (21.6 µl; 0.16 mmol) and 4-dimethylaminopyridine (1.6 mg; 0.01 mmol) in DCM (2.0 ml) at room temperature. The batch was stirred for 23 hours before additional methanesulfonyl chloride (8.0 µl; 0.10 mmol) was added. After 23 hours additional methanesulfonyl chloride (8.0 µl; 0.10 mmol) was added. After 24 hours additional methanesulfonyl chloride (12.0 µl; 0.16 mmol) was added. Finally, after 48 hours additional methanesulfonyl chloride (20.0 µl; 0.26 mmol) was added and the batch was stirred for 2 additional hours. The batch was diluted with aqueous water and extracted with DCM (2×). The combined organic phases were filtered using a Whatman filter and concentrated. The residue was purified by preparative HPLC to give the desired product (21 mg; 0.05 mmol).

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.82 (s, 1H), 7.94 (m, 1H), 7.82 (m, 3H), 7.43 (m, 1H), 7.21 (m, 1H), 6.76 (m, 2H), 4.74 (s, 2H), 3.92 (s, 3H), 3.14 (s, 3H), 3.06 (s, 3H).

Example 45

(rac)-Ethyl [(3-{[4-(3-chloro-2-methoxyphenyl)-1,3,5-triazin-2-yl]amino}benzyl)(methyl)oxido-λ$^6$-sulfanylidene]carbamate

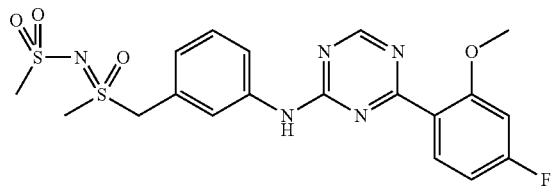 [SMILES: COc1cc(F)ccc1-c1ncnc(Nc2cccc(CS(C)(=O)=NS(C)(=O)=O)c2)n1]

Example 45 was prepared under similar conditions as described in the preparation of Example 42 using crude (rac)-ethyl [{3-[(4-chloro-1,3,5-triazin-2-yl)amino]benzyl}(methyl)oxido-λ$^6$-sulfanylidene]carbamate and (3-chloro-2-methoxyphenyl)boronic acid (Aalen Chemical Co., Ltd.). The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.85 (s, 1H), 7.97 (s, 1H), 7.81 (m, 1H), 7.58 (m, 3H), 7.43 (m, 1H), 7.18 (m, 2H), 4.75 (m, 2H), 4.17 (q, 2H), 3.87 (s, 3H), 3.02 (s, 3H), 1.30 (tr, 3H).

Example 46

(rac)-Ethyl {[3-({4-[5-fluoro-2-(tetrahydro-2H-pyran-4-ylmethoxy)phenyl]-1,3,5-triazin-2-yl}-amino)benzyl](methyl)oxido-$\lambda^6$-sulfanylidene}carbamate

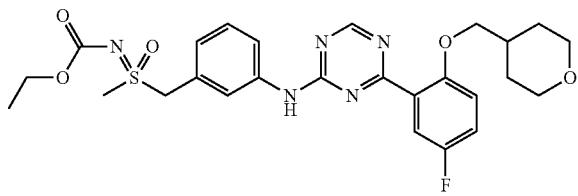 [SMILES: CCOC(=O)N=S(C)(=O)Cc1cccc(Nc2ncnc(-c3cc(F)ccc3OCC3CCOCC3)n2)c1]

Example 46 was prepared under similar conditions as described in the preparation of Example 42 using crude (rac)-ethyl [{3-[(4-chloro-1,3,5-triazin-2-yl)amino]benzyl}(methyl)oxido-$\lambda^6$-sulfanylidene]-carbamate and [5-fluoro-2-(tetrahydro-2H-pyran-4-ylmethoxy)phenyl]boronic acid (FCH Group Company). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI−, scan range 160-1000 m/z |

$^1$H NMR (400 MHz, CDCl$_3$, 300K) δ=8.83 (s, 1H), 7.89 (br, 1H), 7.70 (m, 3H), 7.43 (m, 1H), 7.15 (m, 2H), 6.93 (m, 1H), 4.74 (m, 2H), 4.18 (q, 2H), 3.96 (m, 4H), 3.41 (m, 2H), 3.01 (s, 3H), 2.02 (br, 1H), 1.64 (m, 4H), 1.31 (tr, 3H).

Example 47

(rac)-Ethyl [methyl(oxido)(3-{[4-(2-phenoxyphenyl)-1,3,5-triazin-2-yl]amino}benzyl)-$\lambda^6$-sulfanylidene]carbamate

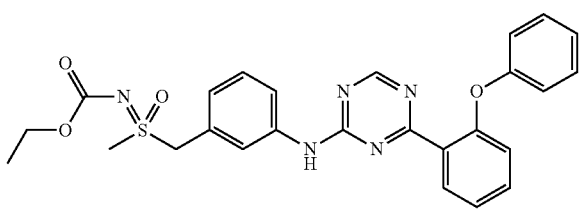 [SMILES: CCOC(=O)N=S(C)(=O)Cc1cccc(Nc2ncnc(-c3ccccc3Oc3ccccc3)n2)c1]

Example 47 was prepared under similar conditions as described in the preparation of Example 42 using crude (rac)-ethyl [{3-[(4-chloro-1,3,5-triazin-2-yl)amino]benzyl}(methyl)oxido-$\lambda^6$-sulfanylidene]-carbamate and (2-phenoxyphenyl)boronic acid (ABCR GmbH & CO. KG). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI−, scan range 160-1000 m/z |

$^1$H NMR (400 MHz, d$_6$-DMSO, 300K) δ=10.35 (s, 1H), 8.72 (s, 1H), 7.89 (m, 2H), 7.65 (br, 1H), 7.52 (m, 1H), 7.26 (m, 4H), 7.03 (m, 3H), 6.89 (m, 2H), 4.78 (s, 2H), 3.93 (q, 2H), 3.12 (s, 3H), 1.09 (tr, 3H).

Example 48

(rac)-[(3-({[4-(4-Fluoro-2-methoxyphenyl)-1,3,5-triazin-2-yl]amino}benzyl)(methyl)oxido-$\lambda^6$-sulfanylidene]cyanamide

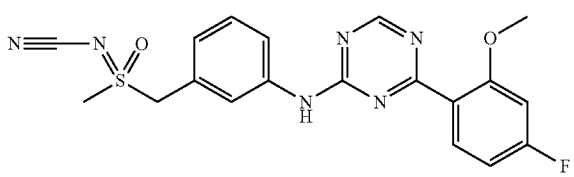

Preparation of Intermediate 48.1

4-Chloro-N-{3-[(methylsulfanyl)methyl]phenyl}-1,3,5-triazin-2-amine

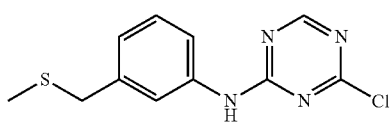 [SMILES: CSCc1cccc(Nc2ncnc(Cl)n2)c1]

Intermediate 48.1 was prepared under similar conditions as described in the preparation of Intermediate 1.7 using 3-[(methylsulfanyl)methyl]aniline (UkrOrgSynthesis Ltd.).

| | |
|---|---|
| System: | Waters Acquity UPLC-MS: Binary Solvent Manager, Sample Manager/Organizer, Column Manager, PDA, ELSD, SQD 3001 |
| Column: | Acquity UPLC BEH C18 1.7 50 × 2.1 mm |
| Solvent: | A2 = H$_2$O + 0.2% NH$_3$<br>B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 μl |
| Detection: | DAD scan range 210-400 nm -> Peaktable ELSD |
| Method: | MS ESI+, ESI− Switch<br>A2 + B1 =<br>C:\MassLynx\Mass_160_1000_BasicReport.flp |

| | |
|---|---|
| System: | Waters Acquity UPLC-MS: Binary Solvent Manager, Sample Manager/Organizer, Column Manager, PDA, ELSD, SQD 3001 |
| Retention | 1.13 min |
| MS(ES−): | m/z = 268 [M + H] |

Preparation of Intermediate 48.2

4-(4-Fluoro-2-melhoxyphenyl)-N-{3-[(methylsulfanyl)methyl]phenyl}-1,3,5-triazin-2-amine

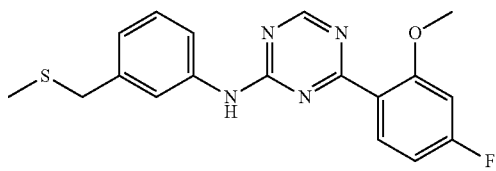 [SMILES: COc1cc(F)ccc1-c1ncnc(Nc2cccc(CSC)c2)n1]

Intermediate 48.2 was prepared under similar conditions as described in the preparation of Example 1 using crude 4-chloro-N-{3-[(methylsulfanyl)methyl]phenyl}-1,3,5-triazin-2-amine and (4-fluoro-2-methoxyphenyl)boronic acid (Aldrich Chemical Company Inc). The batch was purified by column chromatography (DCM/EtOH 95:5) to give the desired product.

$^1$H NMR (400 MHz, CDCl$_3$, 300K) δ=8.80 (s, 1H), 7.97 (br, 1H), 7.83 (m, 2H), 7.50 (s, 1H), 7.31 (m, 1H), 7.07 (m, 1H), 6.77 (m, 2H), 3.93 (s, 3H), 3.69 (s, 2H), 2.02 (s, 3H).

Preparation of Intermediate 48.3

(rac)-[(3 {[4-(4-fluoro-2-methoxyphenyl)-1,3,5-triazin-2-yl]amino}benzyl)(methyl)-λ$^6$-sulfanylidene]cyanamide

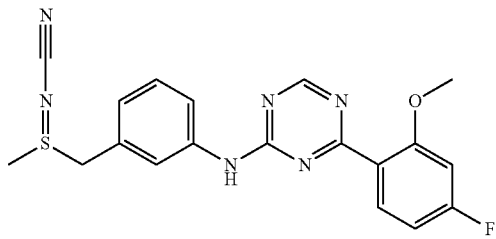 [SMILES: COc1cc(F)ccc1-c1ncnc(Nc2cccc(CS(C)=NC#N)c2)n1]

2-Bromo-1H-isoindole-1,3(2H)-dione (150 mg; 0.84 mmol) was added to a solution of 4-(4-fluoro-2-methoxyphenyl)-N-{3-[(methylsulfanyl)methyl]phenyl}-1,3,5-triazin-2-amine (200 mg; 0.56 mmol), cyanamide (31 mg; 0.73 mmol) and potassium 2-methylpropan-2-olate (76 mg; 0.67 mmol) in methanol (3.0 ml) at room temperature. The batch was stirred for 2 hours before it was diluted with aqueous sodium thiosulfate solution and extracted with DCM (2×). The combined organic phases were filtered using a Whatman filter and concentrated. The residue was purified by preparative HPLC to give the desired product.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI−, scan range 160-1000 m/z |

$^1$H NMR (400 MHz, CDCl$_3$, 300K) δ=8.82 (s, 1H), 7.94 (m, 2H), 7.76 (m, 2H), 7.40 (m, 1H), 7.08 (m, 1H), 6.77 (m, 2H), 4.41 (d, 1H), 4.20 (d, 1H), 3.92 (s, 3H), 2.74 (s, 3H).

Preparation of End Product:

Potassium carbonate (84 mg; 0.61 mmol) and 3-chlorobenzenecarboperoxoic acid (75 mg; 0.30 mmol) were added to a stirred solution of (rac)-[(3-{[4-(4-fluoro-2-methoxyphenyl)-1,3,5-triazin-2-yl]amino}benzyl)(methyl)-λ$^6$-sulfanylidene]cyanamide (80 mg; 0.20 mmol) in ethanol (2.0 ml) at 0° C. The ice bath was removed and the batch was slowly warmed to room temperature. The batch was stirred for 22 hours at room temperature. The batch was diluted with aqueous sodium chloride solution and extracted with ethyl acetate (2×) and DCM (1×). The combined organic phases were filtered using a Whatman filter and concentrated. The residue was purified by preparative HPLC to give the desired product (10 mg; 0.03 mmol).

| | |
|---|---|
| System: | Dionex: Pump P 580, Gilson: Liquid Handler 215, Knauer: UV-Detektor K-2501 |
| Column: | Chiralpak IA 5 μm 250 × 30 mm |
| Solvent: | Methanol + 0.1% diethylamine |
| Flow: | 40 mL/min |
| Temperature: | RT |
| Solution: | 55 mg/2 mL DMSO/MeOH 1:1 |
| Injektion: | 4 × 0.5 mL |
| Detection: | UV 280 nm |
| Retention: | 8.0-10.3 min |

$^1$H NMR (400 MHz, CDCl$_3$, 300K) δ=8.84 (s, 1H), 7.93 (m, 2H), 7.76 (m, 1H), 7.48 (m, 2H), 7.19 (m, 1H), 6.79 (m, 2H), 4.63 (m, 2H), 3.94 (s, 3H), 3.04 (s, 3H).

Example 49 and 50

Enantiomers of [(3-{[4-(4-fluoro-2-methoxyphenyl)-1,3,5-triazin-2-yl]amino}benzyl)(methyl)oxido-λ$^6$-sulfanylidene]cyanamide (rac)-[(3-{[4-(4-fluoro-2-methoxyphenyl)-1,3,5-triazin-2-yl]amino}benzyl)(methyl)oxido-λ$^6$-sulfanylidene]cyanamide was separated into the enantiomers by preparative HPLC:

| | |
|---|---|
| System: | Dionex: Pump P 580, Gilson: Liquid Handler 215, Knauer: UV-Detektor K-2501 |
| Column: | Chiralpak IA 5 μm 250 × 20 mm |
| Solvent: | Ethanol 100 (v/v) |
| Flow: | 20 mL/min |
| Temperature: | RT |
| Solution: | 48 mg/1.2 mL DCM/MeOH 1:1 |
| Injektion: | 2 × 0.6 mL |
| Detection: | UV 254 nm |

-continued

| | Retention time in min | purity in % |
|---|---|---|
| Example 49 Enantiomer 1 | 5.9 | >99 |
| Example 50 Enantiomer 2 | 9.5 | >99 |

Enantiomer 1: $^1$H NMR (400 MHz, CDCl$_3$, 300K) δ=8.84 (s, 1H), 7.93 (m, 2H), 7.76 (m, 1H), 7.48 (m, 2H), 7.19 (m, 1H), 6.79 (m, 2H), 4.63 (m, 2H), 3.94 (s, 3H), 3.04 (s, 3H).

Enantiomer 2: $^1$H NMR (400 MHz, CDCl$_1$, 300K) δ=8.84 (s, 1H), 7.93 (m, 2H), 7.76 (m, 1H), 7.48 (m, 2H), 7.19 (m, 1H), 6.79 (m, 2H), 4.63 (m, 2H), 3.94 (s, 3H), 3.04 (s, 3H).

Example 51

(rac)-Ethyl [(3-fluoro-5-{[4-(4-fluoro-2-methoxyphenyl)-1,3,5-triazin-2-yl]amino}benzyl)(methyl)-oxido-λ$^6$-sulfanylidene]carbamate

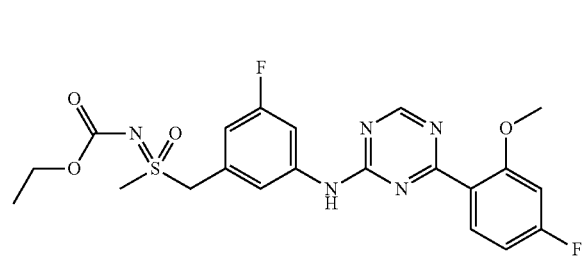 [SMILES: CCOC(=O)N=S(C)(=O)Cc1cc(F)cc(Nc2ncnc(-c3ccc(F)cc3OC)n2)c1]

Preparation of Intermediate 51.1

1-Fluoro-3-[(methylsulfanyl)methyl]-5-nitrobenzene

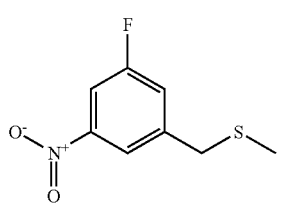

Intermediate 51.1 was prepared under similar conditions as described in the preparation of Intermediate 1.1 using 1-(chloromethyl)-3-fluoro-5-nitrobenzene (Hansa Fine Chemicals GmbH).

$^1$H NMR (400 MHz, CDCl$_3$, 300K) δ=8.00 (m, 1H), 7.82 (m, 1H), 7.44 (m, 1H), 3.74 (s, 2H), 2.03 (s, 3H).

Preparation of Intermediate 51.2

(rac)-1-Fluoro-3-[(methylsulfinyl)methyl]-5-nitrobenzene

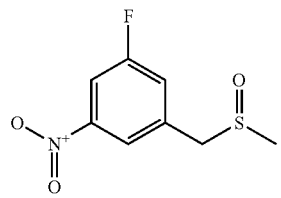

Intermediate 51.2 was prepared under similar conditions as described in the preparation of Intermediate 1.2 using 1-fluoro-3-[(methylsulfanyl)methyl]-5-nitrobenzene.

$^1$H NMR (400 MHz, d$_6$-DMSO, 300K) δ=8.06 (m, 2H), 7.63 (m, 1H), 4.32 (d, 1H), 4.08 (d, 1H), 2.45 (s, 3H).

Preparation of Intermediate 51.3

(rac)-2,2,2-trifluoro-N-[(3-fluoro-5-nitrobenzyl)(methyl)oxido-λ$^6$-sulfanylidene]acetamide

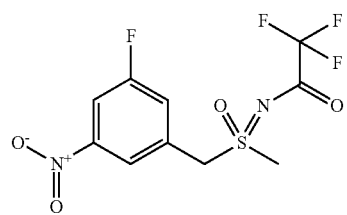 [SMILES: CS(=O)(Cc1cc(F)cc([N+](=O)[O-])c1)=NC(=O)C(F)(F)F]

Intermediate 51.3 was prepared under similar conditions as described in the preparation of Intermediate 1.3 using (rac)-1-fluoro-3-[(methylsulfinyl)methyl]-5-nitrobenzene.

$^1$H NMR (400 MHz, CDC$_3$, 300K) δ=8.13 (m, 1H) 8.07 (m, 1H), 7.56 (m, 1H), 4.92 (d, 1H), 4.76 (d, 1H), 3.33 (s, 3H).

Preparation of Intermediate 51.4

(rac)-1-Fluoro-3-[(S-methylsulfonimidoyl)methyl]-5-nitrobenzene

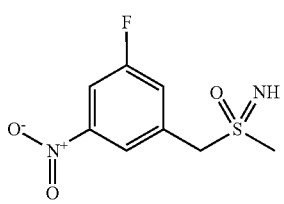

Intermediate 51.4 was prepared under similar conditions as described in the preparation of Intermediate 1.4 using (rac)-2,2,2-trifluoro-N-[(3-fluoro-5-nitrobenzyl)(methyl) oxido-λ$^6$-sulfanylidene]acetamide.

¹H NMR (400 MHz, CDCl₃, 300K) δ=8.19 (m, 1H), 8.08 (m, 1H), 7.76 (m, 1H), 4.60 (d, 1H), 4.49 (d, 1H), 3.85 (s, 1H), 2.79 (s, 3H).

Preparation of Intermediate 51.5

(rac)-Ethyl [(3-fluoro-5-nitrobenzyl)(methyl)oxido-λ⁶-sulfanylidene]carbamate

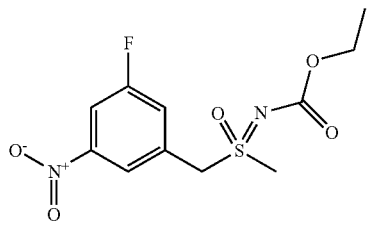 [SMILES: CCOC(=O)N=S(C)(=O)Cc1cc(F)cc([N+](=O)[O-])c1]

Intermediate 51.5 was prepared under similar conditions as described in the preparation of Intermediate 1.5 using (rac)-1-fluoro-3-[(S-methylsulfonimidoyl)methyl]-5-nitrobenzene.
¹H NMR (400 MHz, CDCl₃, 300K) δ=8.11 (m, 1H), 8.02 (m, 1H), 7.57 (m, 1H), 4.90 (d, 1H), 4.759 (d, 1H), 4.18 (q, 2H), 3.12 (s, 3H), 1.31 (tr, 3H).

Preparation of Intermediate 51.6

(rac)-Ethyl [(3-amino-5-fluorobenzyl)(methyl)oxido-λ⁶-sulfanylidene]carbamate

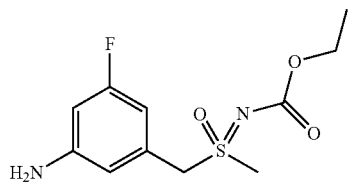 [SMILES: CCOC(=O)N=S(C)(=O)Cc1cc(N)cc(F)c1]

Intermediate 51.6 was prepared under similar conditions as described in the preparation of Intermediate 1.6 using (rac)-ethyl [(3-fluoro-5-nitrobenzyl)(methyl)oxido-λ⁶-sulfanylidene]carbamate.
¹H NMR (400 MHz, CDCl₃, 300K) δ=6.49 (m, 3H), 4.58 (m, 2H), 4.17 (q, 2H), 3.91 (s, 2H), 3.00 (s, 3H), 1.31 (tr, 3H).

Preparation of Intermediate 51.7

(rac)-Ethyl [{3-[(4-chloro-1,3,5-triazin-2-yl)amino]-5-fluorobenzyl}(methyl)oxido-λ⁶-sulfanylidene]carbamate

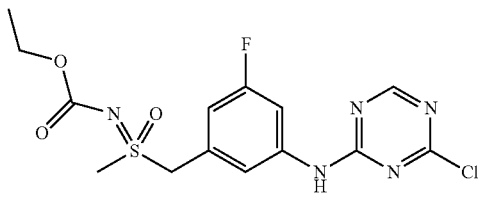 [SMILES: CCOC(=O)N=S(C)(=O)Cc1cc(F)cc(Nc2ncnc(Cl)n2)c1]

Intermediate 51.7 was prepared under similar conditions as described in the preparation of Intermediate 1.7 using (rac)-ethyl [(3-amino-5-fluorobenzyl)(methyl)oxido-λ⁶-sulfanylidene]carbamate.

| System: | Waters Acquity UPLC-MS: Binary Solvent Manager, Sample Manager/Organizer, Column Manager, PDA, ELSD, SQD 3001 |
|---|---|
| Column: | Acquity UPLC BEH C18 1.7 50 × 2.1 mm |
| Solvent: | A1 = H₂O + 0.1% HCOOH<br>B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 µl |
| Detection: | DAD scan range 210-400 nm -> Peaktable<br>ELSD |
| Method: | MS ESI+, ESI– Switch<br>A1 + B1 = C:\ MassLynx\NH3__Mass__100__1000.olp |
| Retention: | 0.94 min |
| MS(ES+): | m/z = 388 [M + H] |

Preparation of End Product:

Example 51 was prepared under similar conditions as described in the preparation of Example 42 using crude (rac)-ethyl [3-[(4-chloro-1,3,5-triazin-2-yl)amino]-5-fluorobenzyl; (methyl)oxido-λ⁶-sulfanylidene]carbamate and (4-fluoro-2-methoxyphenyl)boronic acid (Aldrich Chemical Company Inc). The batch was purified by preparative HPLC.

| System: | Waters Autopurificationsystem: Pump 254, Sample Manager 2767, CFO, DAD 2996, ELSD 2424, SQD 3001 |
|---|---|
| Column: | XBrigde C18 5 µm 100 × 30 mm |
| Solvent: | A = H2O + 0.1% HCOOH<br>B = Acetonitril |
| Gradient: | 0-1 min 30% B, 1-8 min 30-70% B |
| Flow: | 50 mL/min |
| Temperature: | RT |
| Solution: | 664 mg/7 mL acetone |
| Injektion: | 7 × 1 mL |
| Detection: | DAD scan range 210-400 nm<br>MS ESI+, ESI–, scan range 160-1000 m/z<br>ELSD |
| Retention: | 1.12 min |

¹H NMR (400 MHz, d₆-DMSO, 300K) δ=10.65 (s, 1H), 8.86 (s, 1H), 8.32 (br, 1H), 8.00 (br, 1H), 7.48 (br, 1H), 7.12 (m, 1H), 6.98 (m, 1H), 6.92 (m, 1H), 4.87 (m, 2H), 3.98 (m, 2H), 3.92 (s, 3H), 3.22 (s, 3H), 1.15 (tr, 3H).

Example 52

(rac)-4-(4-Fluoro-2-methoxyphenyl)-N-{3-fluoro-5-[(S-methylsulfonimidoyl)methyl]phenyl}-1,3,5-triazin-2-amine

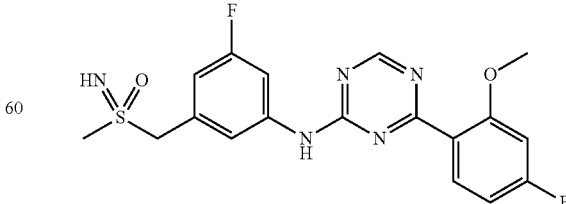

Example 52 was prepared under similar conditions as described in the preparation of Example 2 using (rac)-ethyl

[(3-fluoro-5-{[4-(4-fluoro-2-methoxyphenyl)-1,3,5-triazin-2-yl]amino}benzyl)(methyl)oxido-λ⁶-sulfanylidene]carbamate.

¹H NMR (400 MHz, CDCl₃, 300K) δ=8.79 (s, 1H), 8.10 (br, 2H), 7.92 (br, 1H), 7.20 (br, 1H), 6.85 (m, 1H), 6.76 (m, 2H), 4.36 (d, 1H), 4.22 (s, 1H), 3.95 (s, 3H), 3.01 (s, 3H).

Example 53 and 54

Enantiomers of 4-(4-Fluoro-2-methoxyphenyl)-N-{3-fluoro-5-[(S-methylsulfonimidoyl)methyl]-phenyl}-1,3,5-triazin-2-amine (rac)-4-(4-Fluoro-2-methoxyphenyl)-N-{3-fluoro-5-[(S-methylsulfonimidoyl)methyl]phenyl}-1,3,5-triazin-2-amine was separated into the enantiomers by preparative HPLC:

| System: | Dionex: Pump P 580, Gilson: Liquid Handler 215, Knauer: UV-Detektor K-2501 |
| --- | --- |
| Column: | Chiralpak IC 5 μm 250 × 30 mm |
| Solvent: | Hexane/ethanol 70:30 (v/v) |
| Flow: | 40 mL/min |
| Temperature: | RT |
| Solution: | 1860 mg/10.8 mL THF/DMSO 9:1 |
| Injection: | 36 × 0.3 mL |
| Detection: | UV 280 nm |

| | Retention time in min | purity in % |
| --- | --- | --- |
| Example 53 Enantiomer 1 | 13.7-15.4 | 99.8 |
| Example 54 Enantiomer 2 | 15.4-17.2 | 95.4 |

Enantiomer 1: ¹H NMR (400 MHz, CDCl₃, 300K) δ=8.79 (s, 1H), 8.10 (br, 2H), 7.92 (br, 1H), 7.20 (br, 1H), 6.85 (m, 1H), 6.76 (m, 2H), 4.36 (d, 1H), 4.22 (s, 1H), 3.95 (s, 3H), 3.01 (s, 3H).

Enantiomer 2: ¹H NMR (400 MHz, CDCl₃, 300K) δ=8.79 (s, 1H), 8.10 (br, 2H), 7.92 (br, 1H), 7.20 (br, 1H), 6.85 (m, 1H), 6.76 (m, 2H), 4.36 (d, 1H), 4.22 (s, 1H), 3.95 (s, 3H), 3.01 (s, 3H).

Example 55

(rac)-4-[2-(Cyclohexylmethoxy)-4-fluorophenyl]-N-{3-[(S-methylsulfonimidoyl)methyl]phenyl}-1,3,5-triazin-2-amine

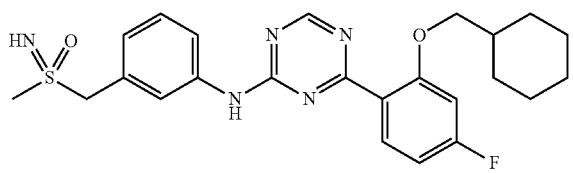 [SMILES: CS(=N)(=O)Cc1cccc(Nc2ncnc(-c3ccc(F)cc3OCC3CCCCC3)n2)c1]

Preparation of Intermediate 55.1

(rac)-Ethyl [(3-{[4-(2,4-difluorophenyl)-1,3,5-triazin-2-yl]amino}benzyl)(methyl)oxido-λ⁶-sulfanylidene]carbamate

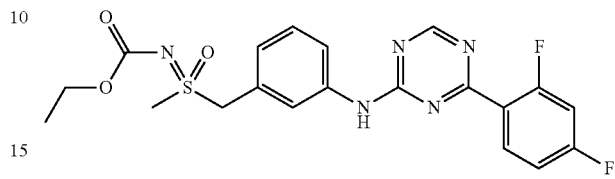

Intermediate 55.1 was prepared under similar conditions as described in the preparation of Example 42 using crude (rac)-ethyl [{3-[(4-chloro-1,3,5-triazin-2-yl)amino]-5-fluorobenzyl}(methyl)oxido-λ⁶-sulfanylidene]carbamate and (2,4-difluorophenyl)boronic acid (Aldrich Chemical Company Inc.). The batch was purified by column chromatography (DCM/EtOH 95:5).

¹H NMR (400 MHz, CDCl₃, 300K) δ=8.82 (s, 1H), 8.31 (m, 1H), 8.05 (br, 1H), 7.61 (m, 1H), 7.45 (m, 2H), 7.21 (m, 1H), 7.00 (m, 2H), 4.76 (dd, 2H), 4.17 (q, 2H), 3.02 (s, 3H), 1.31 (tr, 3H).

Preparation of End Product:

Sodium hydride (60%; 3.2 mg; 0.08 mmol) was added under stirring to a solution of (rac)-ethyl [(3-{[4-(2,4-difluorophenyl)-1,3,5-triazin-2-yl]amino}benzyl)(methyl) oxido-λ⁶-sulfanylidene]carbamate (30.0 mg; 0.07 mmol) in cyclohexylmethanol (0.5 ml) at room temperature. The batch was stirred under argon at 50° C. for 2 hours before additional sodium hydride (60%; 2.7 mg; 0.07 mmol) was added. After 20 hours additional sodium hydride (60%; 2.7 mg; 0.07 mmol) was added and the batch was stirred for further 5 hours. After cooling, the batch was diluted with ethyl acetate and diluted sodium chloride solution. The organic phase was filtered using a Whatman filter and concentrated. The desired product (10 mg; 0.02 mmol) was isolated by preparative HPLC.

| System: | Waters Autopurificationsystem: Pump 2545, Sample Manager 2767, CFO, DAD 2996, ELSD 2424, SQD 3001 |
| --- | --- |
| Column: | XBrigde C18 5 μm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

¹H NMR (400 MHz, CDCl₃, 300K) δ=8.83 (s, 1H), 7.88 (m, 1H), 7.84 (br, 1H), 7.72 (br, 1H), 7.44 (m, 1H), 7.36 (s, 1H), 7.19 (m, 1H), 6.77 (m, 2H), 4.43 (d, 1H), 4.28 (d, 1H), 3.85 (d, 2H), 2.98 (s, 3H), 2.73 (br, 1H), 1.78 (m, 6H), 1.15 (m, 5H).

Example 56

(rac)-4-{4-Fluoro-2-[(4-fluorobenzyl)oxy]phenyl}-N-{3-[(S-methylsulfonimidoyl)methyl]phenyl}-1,3,5-triazin-2-amine

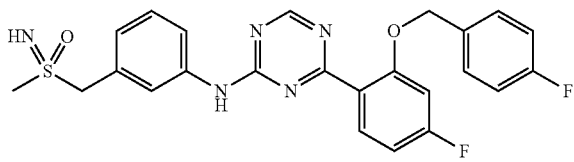

Example 56. was prepared under similar conditions as described in the preparation of Example 55 using (rac)-ethyl [(3-{[4-(2,4-difluorophenyl)-1,3,5-triazin-2-yl]amino}benzyl)(methyl)oxido-$\lambda^6$-sulfanylidene]carbamate and (4-fluorophenyl)methanol.

| System: | Waters Autopurificationsystem: Pump 254, Sample Manager 2767, CFO, DAD 2996, ELSD 2424, SQD 3001 |
|---|---|
| Column: | XBrigde C18 5 µm 100 × 30 mm |
| Solvent: | A = H₂O + 0.1% HCOOH |
| | B = Methanol |
| Gradient: | 0-1 min 50% B, 1-8 min 50-90% B, 8-8.1 min 90-100% B, 8.1-10 min 100% B |
| Flow: | 50 mL/min |
| Temperature: | RT |
| Solution: | 620 mg/4.5 mL DMSO |
| Injektion: | 9 × 0.5 mL |
| Detection: | DAD scan range 210-400 nm |
| | MS ESI+, ESI–, scan range 160-1000 m/z |
| | ELSD |
| Retention: | 5.0-5.6 min |

¹H NMR (400 MHz, CDCl₃, 300K) δ=8.81 (s, 1H), 7.95 (m, 1H), 7.75 (br, 1H), 7.68 (m, 1H), 7.38 (m, 4H), 7.13 (m, 1H), 7.01 (m, 2H), 6.80 (m, 2H), 5.15 (s, 2H), 4.36 (d, 1H), 4.22 (d, 1H), 2.93 (s, 3H), 2.68 (br, 1H).

Example 56.a and 56.b

Enantiomers of 4-{4-fluoro-2-[(4-fluorobenzyl)oxy]phenyl}-N-{3-[(S-methylsulfonimidoyl)methyl-phenyl}-1,3,5-triazin-2-amine(rac)-4-{4-Fluoro-2-[(4-fluorobenzyl)oxy]phenyl}-N-{3-[(S-methylsulfonimidoyl)methyl]phenyl}-1,3,5-triazin-2-amine was separated into the enantiomers by preparative HPLC:

| System: | Dionex: Pump P 580, Gilson: Liquid Handler 215, Knauer: UV-Detektor K-2501 |
|---|---|
| Column: | Chiralpak IA 5 µm 250 × 30 mm |
| Solvent: | Ethanol/methanol 50:50 (v/v) |
| Flow: | 30 mL/min |
| Temperature: | RT |
| Solution: | 190 mg/3 mL EtOH/MeOH |
| Injektion: | 2 × 1.5 mL |
| Detection: | UV 280 nm |

| | Retention time in min | purity in % |
|---|---|---|
| Example 56.a Enantiomer 1 | 17.2-23.5 | >99.9 |
| Example 56.b Enantiomer 2 | 35.8-52.5 | 99.3 |

Enantiomer 1: ¹H NMR (400 MHz, CDCl₃, 300K) δ=8.81 (s, 1H), 7.95 (m, 1H), 7.75 (br, 1H), 7.68 (m, 1H), 7.38 (m, 4H), 7.13 (m, 1H), 7.01 (m, 2H), 6.80 (m, 2H), 5.15 (s, 2H), 4.36 (d, 1H), 4.22 (d, 1H), 2.93 (s, 3H), 2.68 (br, 1H).

Enantiomer 2: ¹H NMR (400 MHz, CDCl₃, 300K) δ=8.81 (s, 1H), 7.95 (m, 1H), 7.75 (br, 1H), 7.68 (m, 1H), 7.38 (m, 4H), 7.13 (m, 1H), 7.01 (m, 2H), 6.80 (m, 2H), 5.15 (s, 2H), 4.36 (d, 1H), 4.22 (d, 1H), 2.93 (s, 3H), 2.68 (br, 1H).

Example 57

(rac)-4-{4-Fluoro-2-[2-(tetrahydro-2H-pyran-4-yl)ethoxy]phenyl}-N-{3-[(S-methylsulfonimidoyl)methyl]phenyl}-1,3,5-triazin-2-amine

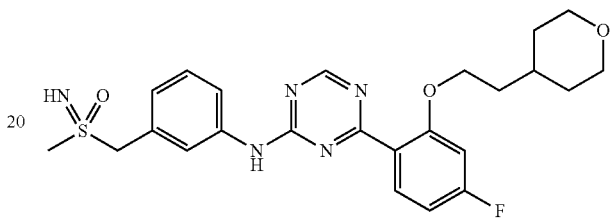

Example 57. was prepared under similar conditions as described in the preparation of Example 55 using (rac)-ethyl [(3-{[4-(2,4-difluorophenyl)-1,3,5-triazin-2-yl]amino}benzyl)(methyl)oxido-$\lambda^6$-sulfanylidene]carbamate and 2-(tetrahydro-2H-pyran-4-yl)ethanol.

| System: | Waters Autopurificationsystem: Pump 254, Sample Manager 2767, CFO, DAD 2996, ELSD 2424, SQD 3001 |
|---|---|
| Column: | XBrigde C18 5 µm 100 × 30 mm |
| Solvent: | A = H₂O 0.1% HCOOH |
| | B = Methanol |
| Gradient: | 0-1 min 50% B, 1-8 min 50-90% B, 8-8.1 min 90-100% B, 8.1-10 min 100% B |
| Flow: | 50 mL/min |
| Temperature: | RT |
| Solution: | 603 mg/4.5 mL DMSO |
| Injektion: | 9 × 0.5 mL |
| Detection: | DAD scan range 210-400 nm |
| | MS ESI+, ESI–, scan range 160-1000 m/z |
| | ELSD |
| Retention: | 3.8-4.2 min |

¹H NMR (400 MHz, CDCl₃, 300K) δ=8.80 (s, 1H), 7.78 (m, 3H), 7.49 (s, 1H), 7.42 (m, 1H), 7.16 (m, 1H), 6.76 (m, 2H), 4.39 (d, 1H), 4.26 (d, 1H), 4.10 (tr, 2H), 3.91 (m, 2H), 3.32 (m, 2H), 2.95 (s, 3H), 2.71 (br, 1H), 1.75 (m, 3H), 1.33 (m, 4H).

Example 58

(rac)-4-(4-Fluoro-2-methoxyphenyl)-N-(3-{[S-(tetrahydro-2H-pyran-4-yl)sulfonimidoyl]methyl}-phenyl)-1,3,5-triazin-2-amine

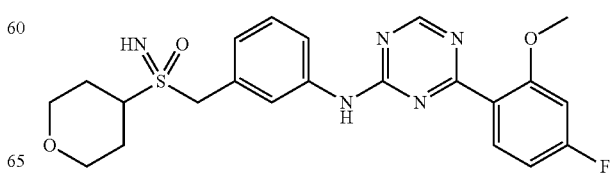

Preparation of Intermediate 58.1

(rac)-4-Chloro-N-{3-[(tetrahydro-2H-pyran-4-yl-sulfinyl)methyl]phenyl}-1,3,5-triazin-2-amine

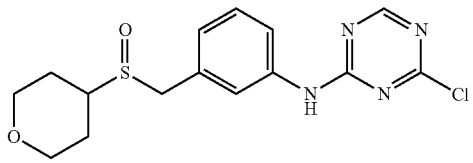 [SMILES: O=S(Cc1cccc(Nc2ncnc(Cl)n2)c1)C1CCOCC1]

Intermediate 58.1 was prepared under similar conditions as described in the preparation of Intermediate 1.7 using (rac)-3-[(tetrahydro-2H-pyran-4-ylsulfinyl)methyl]aniline (UkrOrgSynthesis Ltd.).

| System: | Waters Acquity UPLC-MS: Binary Solvent Manager, Sample Manager/Organizer, Column Manager, PDA, ELSD, SQD 3001 |
|---|---|
| Column: | Acquity UPLC BEH C18 1.7 50 × 2.1 mm |
| Solvent: | A2 = H$_2$O + 0.2% NH$_3$ |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 µl |
| Detection: | DAD scan range 210-400 nm -> Peaktable ELSD |
| Method: | MS ESI+, ESI- Switch |
| | A2 + B1 = C:\ MassLynx\NH3_Mass_100_1000.olp |
| Retention | 0.81 min |
| MS(ES-): | m/z = 351 [M − H] |

Preparation of Intermediate 58.2

(rac)-4-(4-Fluoro-2-methoxyphenyl)-N-{3-[(tetrahydro-2H-pyran-4-ylsulfinyl)methyl]phenyl}-1,3,5-triazin-2-amine

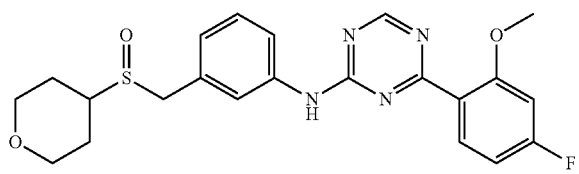 [SMILES: COc1cc(F)ccc1-c1ncnc(Nc2cccc(CS(=O)C3CCOCC3)c2)n1]

Intermediate 58.2 was prepared under similar conditions as described in the preparation of Example 42 using crude (rac)-4-chloro-N-{3-[(tetrahydro-2H-pyran-4-ylsulfinyl)methyl]phenyl}-1,3,5-triazin-2-amine and (4-fluoro-2-methoxyphenyl)boronic acid (Aldrich Chemical Company Inc). The batch was purified by column chromatography (DCM/EtOH 95:5) to give the desired product.

$^1$H NMR (400 MHz, CDCl$_3$, 300K) δ=8.81 (s, 1H), 7.96 (m, 1H), 7.70 (m, 2H), 7.40 (m, 2H), 7.06 (m, 1H), 6.78 (m, 2H), 4.03 (m, 7H), 3.39 (m, 2H), 2.73 (m, 1H), 1.83 (m, 4H).
Preparation and End Product
Example 58 was prepared under similar conditions as described in the alternative preparation of Example 2 using (rac)-4-(4-fluoro-2-methoxyphenyl)-N-{3-[(tetrahydro-2H-pyran-4-ylsulfinyl)methyl]phenyl}-1,3,5-triazin-2-amine, sodium azide, sulfuric acid and trichloromethane.

| System: | Waters Autopurificationsystem: Pump 254, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% Vol. HCOOH (99%) |
| | B = Acetonitrile |
| Gradient: | 0-1 min 10% B, 1-8 min 10-45% B |
| Flow: | 50 mL/min |
| Temperature: | RT |
| Solution: | 200 mg/2 mL DMSO |
| Injektion: | 2 × 1 mL |
| Detection: | DAD scan range 210-400 nm |
| | MS ESI+, ESI-, scan range 160-1000 m/z |
| | ELSD |
| Retention: | 6.5-6.9 min |

$^1$H NMR (400 MHz, CDCl$_3$, 300K) δ=8.81 (s, 1H), 7.97 (br, 1H), 7.76 (m, 2H), 7.53 (s, 1H), 7.41 (m, 1H), 7.16 (m, 1H), 6.77 (m, 2H), 4.31 (d, 1H), 4.09 (m, 3H), 3.93 (s, 3H), 3.36 (m, 2H), 3.15 (m, 1H), 2.61 (s, 1H), 2.01 (m, 4H).

Example 59

(rac)-N-{4-Chloro-3-[(S-methylsulfonimidoyl)methyl]phenyl}-4-(4-fluoro-2-methoxyphenyl)-1,3,5-triazin-2-amine

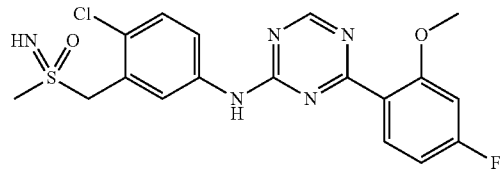 [SMILES: COc1cc(F)ccc1-c1ncnc(Nc2ccc(Cl)c(CS(C)(=N)=O)c2)n1]

Preparation of Intermediate 59.1

(rac)-4-Chloro-N-{4-chloro-3-[(methylsulfinyl)methyl]phenyl}-1,3,5-triazin-2-amine

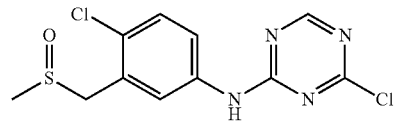 [SMILES: CS(=O)Cc1cc(Nc2ncnc(Cl)n2)ccc1Cl]

Intermediate 59.1 was prepared under similar conditions as described in the preparation of intermediate 1.7 using (rac)-4-chloro-3-[(methylsulfinyl)methyl]aniline (UkrOrgSynthesis Ltd.).

| System: | Waters Acquity UPLC-MS: Binary Solvent Manager, Sample Manager/Organizer, Column Manager, PDA, ELSD, SQD 3001 |
|---|---|
| Column: | Acquity UPLC BEH C18 1.7 50 × 2.1 mm |
| Solvent: | A2 = H$_2$O + 0.2% NH$_3$ |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 µl |
| Detection: | DAD scan range 210-400 nm -> Peaktable ELSD |
| Method: | MS ESI+, ESI- Switch |
| | A2 + B1 = C:\ MassLynx\NH3_Mass_100_1000.olp |

| | |
|---|---|
| System: | Waters Acquity UPLC-MS: Binary Solvent Manager, Sample Manager/Organizer, Column Manager, PDA, ELSD, SQD 3001 |
| Retention | 0.85 min |
| MS(ES−): | m/z = 317 [M + H] |

Preparation of Intermediate 59.2

(rac)-N-{4-Chloro-3-[(methylsulfinyl)methyl]phenyl}-4-(4-fluoro-2-methoxyphenyl)-1,3,5-triazin-2-amine

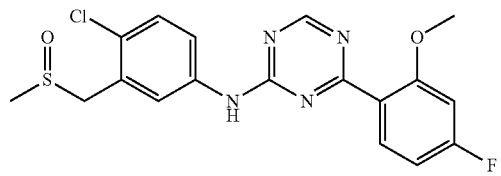 [SMILES: COc1cc(F)ccc1-c1ncnc(Nc2ccc(Cl)c(CS(C)=O)c2)n1]

Intermediate 59.2 was prepared under similar conditions as described in the preparation of Example 42 using crude (rac)-4-chloro-N-{4-chloro-3-[(methylsulfinyl)methyl]phenyl}-1,3,5-triazin-2-anine and (4-fluoro-2-methoxyphenyl) boronic acid (Aldrich Chemical Company Inc). The batch was purified by column chromatography (DCM/EtOH 95:5) to give the desired product.

$^1$H NMR (400 MHz, CDCl$_3$, 300K) δ=8.80 (s, 1H), 7.85 (m, 3H), 7.64 (m, 1H), 7.39 (m, 1H), 6.76 (m, 2H), 4.19 (d, 1H), 4.13 (d, 1H), 3.93 (s, 3H), 2.57 (s, 3H).

Preparation of End Product

Example 59 was prepared under similar conditions as described in the alternative preparation of Example 2 using ((rac)-N-{4-chloro-3-[(methylsulfinyl)methyl]phenyl}-4-(4-fluoro-2-methoxyphenyl)-1,3,5-triazin-2-amine, sodium azide, sulfuric acid and trichloromethane.

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H$_2$O + 0.2% Vol. NH$_3$ (32%) B = Acetonitrile |
| Gradient: | 0-1 min 15% B, 1-8 min 15-60% B |
| Flow: | 50 mL/min |
| Temperature: | RT |
| Solution: | 55 mg/1 mL DMSO/MeOH 1:1 |
| Injektion: | 1 × 1 mL |
| Detection: | DAD scan range 210-400 nm MS ESI+, ESI−, scan range 160-1000 m/z ELSD |
| Retention: | 6.2-6.5 min |

$^1$H NMR (400 MHz, CDCl$_3$, 300K) δ=8.80 (s, 1H), 7.87 (m, 3H), 7.57 (s, 1H), 7.42 (m, 1H), 6.78 (m, 2H), 4.60 (d, 1H), 4.51 (d, 1H), 3.93 (s, 3H), 2.97 (s, 3H), 2.84 (s, 1H).

Example 59.a and 59.b

Enantiomers of N-{4-Chloro-3-[(S-methylsulfonimidoyl)methyl]phenyl}-4-(4-fluoro-2-methoxyphenyl)-1,3,5-triazin-2-amine(rac)-N-{4-Chloro-3-[(S-methylsulfonimidoyl)methyl]phenyl}-4-(4-fluoro-2-mcthoxyphenyl)-1,3,5-triazin-2-amine was separated into the enantiomers by preparative HPLC:

| | |
|---|---|
| System: | Dionex: Pump P 580, Gilson: Liquid Handler 215, Knauer: UV-Detektor K-2501 |
| Column: | Chiralpak IA 5 μm 250 × 20 mm |
| Solvent: | Methanol 100 (v/v) |
| Flow: | 20 mL/min |
| Temperature: | RT |
| Solution: | 14 mg/1 mL DCM/MeOH 1:1 |
| Injektion: | 2 × 0.5 mL |
| Detection: | UV 280 nm |

| | Retention time in min | purity in % |
|---|---|---|
| Example 59.a Enantiomer 1 | 5.3 | 98.7 |
| Example 59.b Enantiomer 2 | 7.3 | 96.8 |

Enantiomer 1: $^1$H NMR (400 MHz, CDCl$_3$, 300K) δ=8.80 (s, 1H), 7.87 (m, 3H), 7.57 (s, 1H), 7.42 (m, 1H), 6.78 (m, 2H), 4.60 (d, 1H), 4.51 (d, 1H), 3.93 (s, 3H), 2.97 (s, 3H), 2.84 (s, 1H).

Enantiomer 2: $^1$H NMR (400 MHz, CDCl$_3$, 300K) δ=8.80 (s, 1H), 7.87 (m, 3H), 7.57 (s, 1H), 7.42 (m, 1H), 6.78 (m, 2H), 4.60 (d, 1H), 4.51 (d, 1H), 3.93 (s, 3H), 2.97 (s, 3H), 2.84 (s, 1H).

Example 60

(rac)-Ethyl [{3-[(4-{2-[(3,4-dichlorobenzyl)oxy]phenyl}-1,3,5-triazin-2-yl)amino]benzyl}(methyl)-oxido-λ$^6$-sulfanylidene]carbamate

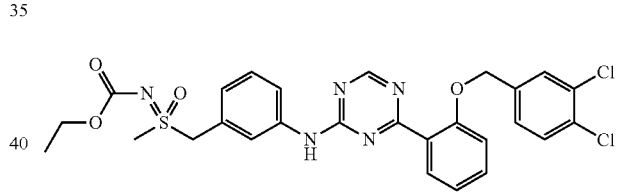

Example 60 was prepared under similar conditions as described in the preparation of Example 42 using crude (rac)-ethyl [{3-[(4-chloro-1,3,5-triazin-2-yl)amino]benzyl}(methyl)oxido-λ$^6$-sulfanylidene]carbamate and {2-[(3,4-dichlorobenzyl)oxy]phenyl}boronic acid (Combi Blocks Inc.). The batch was purified by preparative HPLC.

| | |
|---|---|
| System: | Agilent: Prep 1200, 2 × Prep Pump, DLA, MWD, ELSD, Prep FC |
| Column: | XBrigde C18 5 μm 100 × 30 mm |
| Solvent: | A = H$_2$O + 0.2% NH$_3$ B = Acetonitrile |
| Gradient: | 0-17.5 min 40-80% B; 17.5-20 min 80-100% B |
| Flow: | 38 mL/min |
| Temperature: | RT |
| Solution: | 120 mg/1.6 mL DMSO/ACN 1:1 |
| Injektion: | 2 × 0.8 mL |
| Detection: | MWD 210 nm |
| Retention: | 12.2-13.3 min |

$^1$H NMR (400 MHz, CDCl$_3$, 300K) δ=8.87 (s, 1H), 7.91 (m, 1H), 7.85 (s, 1H), 7.66 (m, 2H), 7.46 (m, 2H), 7.38 (m, 2H), 7.22 (m, 1H), 7.15 (m, 2H), 7.06 (m, 2H), 5.15 (s, 2H), 4.70 (s, 2H), 4.16 (q, 2H), 2.97 (s, 3H), 1.30 (tr, 3H).

Example 61

(rac)-4-{2-[(3,4-Dichlorobenzyl)oxy]phenyl}-N-{3-[(S-methylsulfonimidoyl)methyl]phenyl}-1,3,5-triazin-2-amine

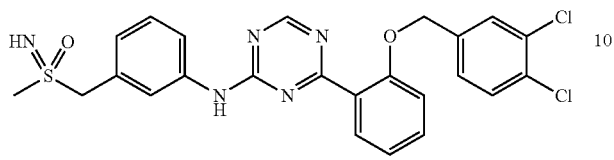

Example 61 was prepared under similar conditions as described in the preparation of Example 2 using (rac)-ethyl [{3-[(4-{2-[(3,4-dichlorobenzyl)oxy]phenyl}-1,3,5-triazin-2-yl)amino]benzyl}(methyl)oxido-λ⁶-sulfanylidene]carbamate. After aqueous work up no further purification was necessary.

¹H NMR (400 MHz, CDCl₃, 300K) δ=8.87 (s, 1H), 7.93 (m, 1H), 7.78 (s, 1H), 7.70 (m, 2H), 7.48 (m, 1H), 7.36 (m, 3H), 7.24 (m, 1H), 7.14 (m, 2H), 7.06 (m, 1H), 5.15 (s, 2H), 4.37 (d, 1H), 4.25 (d, 1H), 2.93 (s, 3H), 2.68 (s, 1H).

Example 62

(rac)-4-(4-Fluoro-2-{[(²H₂)phenyl(²H₂)methyl]oxy}phenyl)-N-{3-[(S-methylsulfonimidoyl)methyl]-phenyl}-1,3,5-triazin-2-amine

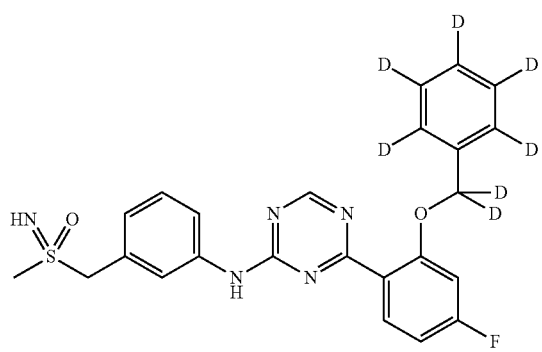 [SMILES: [2H]c1c([2H])c([2H])c(C([2H])([2H])Oc2cc(F)ccc2-c2ncnc(Nc3cccc(CS(C)(=N)=O)c3)n2)c([2H])c1[2H]]

Example 62 was prepared under similar conditions as described in the preparation of Example 55 using (rac)-ethyl [(3-{[4-(2,4-difluorophenyl)-1,3,5-triazin-2-yl]amino}benzyl)(methyl)oxido-λ⁶-sulfanylidene]carbamate and (²H₅)phenyl(²H₂)methanol (Aldrich Chemical Company Inc). The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

¹H NMR (400 MHz, CDCl₃, 300K) δ=8.81 (s, 1H), 7.94 (m, 1H), 7.68 (m, 3H), 7.32 (br, 1H), 7.11 (m, 1H), 6.79 (m, 2H), 4.33 (d, 1H), 4.21 (d, 1H), 2.92 (s, 3H).

Example 63

4-[2-(1-Cyclopentylethoxy)-4-fluorophenyl]-N-{3-[(S-methylsulfonimidoyl)methyl]phenyl}-1,3,5-triazin-2-amine, mixture of all 4 stereoisomers

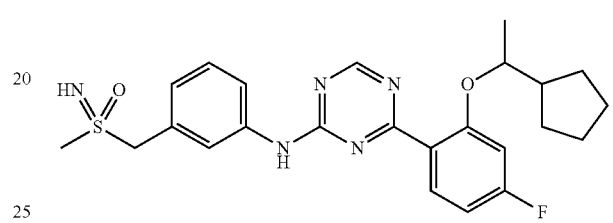

Example 63. was prepared under similar conditions as described in the preparation of Example 55 using (rac)-ethyl [(3-{[4-(2,4-difluorophenyl)-1,3,5-triazin-2-yl]amino}benzyl)(methyl)oxido-λ⁶-sulfanylidene]carbamate and (rac)-1-cyclopentylethanol (ChemSampCo, Inc.).

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

¹H NMR (400 MHz, CDCl₃, 300K) δ=8.78 (s, 1H), 7.76 (m, 3H), 7.54 (s, 1H), 7.40 (m, 1H), 7.15 (m, 1H), 6.72 (m, 2H), 4.39 (d, 1H), 4.24 (m, 2H), 2.95 (s, 3H), 2.70 (br, 1H), 2.09 (m, 1H), 1.47 (m, 11H).

Example 64

(rac)-N-{3-Chloro-5-[(S-methylsulfonimidoyl)methyl]phenyl}-4-(4-fluoro-2-methoxyphenyl)-1,3,5-triazin-2-amine

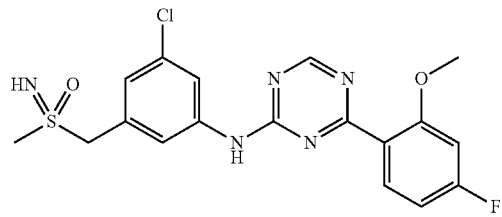 [SMILES: COc1cc(F)ccc1-c1ncnc(Nc2cc(Cl)cc(CS(C)(=N)=O)c2)n1]

Preparation of Intermediate 64.1

1-Chloro-3-[(methylsulfanyl)methyl]-5-nitrobenzene

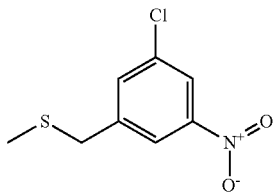

A suspension of 3-bromomethyl-1-chloro-5-nitrobenzene (10.0 g) in ethanol (200 mL) at −20° C. was treated with sodium methanethiolate (3.3 g) in 3 portions, during 3 hours the temperature was increased from −20° C. to room temperature. Then brine was added, extracted with ethyl acetate (3×), the combined organic phases were washed with water to neutrality, dried with sodium sulfate, filtered and concentrated. The title compound (8.6 g) was thus obtained and used without further purification.

Preparation of Intermediate 64.2

1-Chloro-3-[(methylsulfinyl)methyl]-5-nitrobenzene

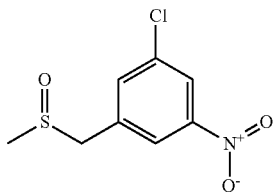

To a solution of 1-chloro-3-[(methylsulfanyl)methyl]-5-nitrobenzene (4.3 g) in methanol (340 mL) water (18.7 mL) and sodium period at (4.4 g) was added and stirred for 24 hours at room temperature. Then the reaction mixture was concentrated under reduced pressure to 30% of the volume, diluted with water, extracted with ethyl acetate (3×), washed with disodium sulfurothioate and brine, dried with sodium sulfate, filtered and concentrated. The title compound (4.5 g) was thus obtained and used without further purification.

$^1$H-NMR (600 MHz, CDCl$_3$): δ=8.23 (t, 1H), 8.08 (t, 1H), 7.67 (t, 1H), 4.07 (d, 1H), 3.92 (d, 1H), 2.57 (s, 3H).

Preparation of Intermediate 64.3

3-Chloro-5-[(methylsulfinyl)methyl]aniline

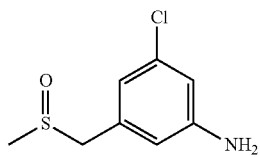

A solution of 1-chloro-3-[(methylsulfinyl)methyl]-5-nitrobenzene (4.4 g) in methanol (40 mL) and water (11.6 mL) was treated with ammoniumchloride (5.1 g), cooled to 0° C., treated with portions of zinc powder (6.2 g) and stirred for 5 hours at room temperature. The reaction mixture was filtered over cellite, washed with THF/ethyl acetate, washed with brine, dried with sodium sulfate and condensed to dryness.

Crystallization of the crude product (4.9 g) from diethyl ether furnished the pure title compound (3.4 g). $^1$H-NMR (600 MHz, CDCl$_3$): δ=6.63 (m, 2H), 6.49 (m, 1H), 3.90 (d, 1H), 3.80 (m, 3H), 2.48 (s, 3H).

Preparation of Intermediate 64.4

4-Chloro-N-{3-chloro-5-[(methylsulfinyl)methyl]phenyl}-1,3,5-triazin-2-amine

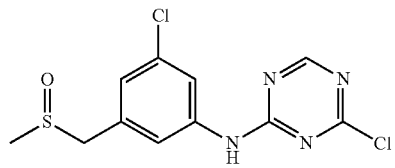 [SMILES: CS(=O)Cc1cc(Cl)cc(Nc2ncnc(Cl)n2)c1]

A solution of 2,4-dichloro-triazine (250 mg) in THF (2.2 mL) and 2-propanol (2.2 mL) at −40° C. was treated with N,N-diisopropylethylamine (0.55 mL) and 3-chloro-5-[(methylsulfinyl)methyl]aniline (322.6 mg) an then stirred and gradually warmed from −40° C. to 0° C. for 3 hours. The reaction mixture was then concentrated in vacuo to give the crude title compound (934 mg) which was used without further purification.

Preparation of Intermediate 64.5

N-{3-Chloro-5-[(methylsulfinyl)methyl]phenyl}-4-(4-fluoro-2-methoxyphenyl)-1,3,5-triazin-2-amine

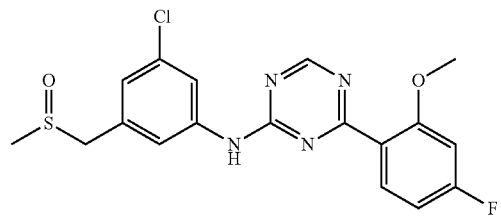 [SMILES: COc1cc(F)ccc1-c1ncnc(Nc2cc(Cl)cc(CS(C)=O)c2)n1]

A solution of 4-chloro-N-{3-chloro-5-[(methylsulfinyl)methyl]phenyl}-1,3,5-triazin-2-amine (934 mg) in 1,2-dimethoxyethane (5.2 mL) and a 2 M solution of sodium carbonate (1.6 mL) is treated with 4-fluoro-2-methoxyphenylboronic acid (269 mg) and Pd(dppf)Cl$_2$ (129 mg) and then heated for 3 hours at 100° C. The reaction mixture was then allowed to cool to room temperature, taken up in ethyl acetate (100 mL) and water (50 mL), washed with saturated brine, dried over sodium sulfate, and condensed in vacuo to give the crude product that was purified by flash column chromatography on SiO$_2$ with DCM/acetone (5%-60%) to give analytically pure product (340 mg).

$^1$H-NMR (500 MHz, CDCl$_3$): δ=8.83 (s, 1H), 8.18 (br. s, 1H), 7.99 (br. s, 1H), 7.33 (br. s, 1H), 7.64 (s, 1H), 7.02 (s, 1H), 6.78 (m, 2H), 3.96 (m, 5H), 2.53 (s, 3H).

Preparation of End Product:

To a solution of N-{3-chloro-5-[(methylsulfinyl)methyl]phenyl}-4-(4-fluoro-2-methoxyphenyl)-1,3,5-triazin-2-amine (75 mg) in chloroform (0.8 mL) sodiumazide (48.4 mg) was added and treated at 0° C. dropwise with conc. sulfuric acid (0.35 mL) and stirred for 48 hours in a sealed tube. Then the reaction mixture was poured into ice water, alkalized with sodium bicarbonate, extracted with ethyl acetate/THF (9:1), washed, dried over sodium sulfate and evaporated to dryness.

The crude product was purified by flash column chromatography on $SiO_2$ with DCM/ethanol (0%-5%) to give the desired product (42 mg).

$^1$H-NMR (600 MHz, CDCl3): δ=8.81 (s, 1H), 7.99 (m, 3H), 7.41 (br, 1H), 7.10 (m, 1H), 6.76 (m, 2H), 4.35 (d, 1H), 4.20 (d, 1H), 3.94 (s, 3H), 3.01 (s, 3H).

Example 65

(rac)-4-[4-Fluoro-2-(3,3,3-trifluoropropoxy)phenyl]-N-{3-[(S-methylsulfonimidoyl)methyl]phenyl}-1,3,5-triazin-2-amine

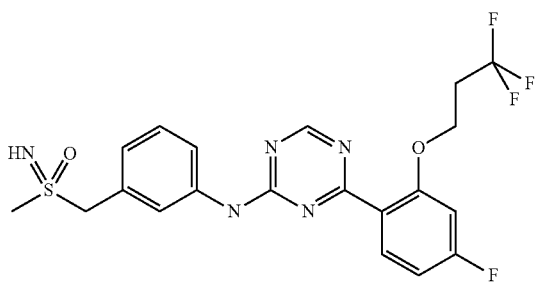 [SMILES: CS(=N)(=O)Cc1cccc(Nc2ncnc(-c3ccc(F)cc3OCCC(F)(F)F)n2)c1]

Sodium hydride (60%; 26.8 mg; 0.67 mmol) was added under stirring to a solution of (rac)-ethyl[(3-{[4-(2,4-difluorophenyl)-1,3,5-triazin-2-yl]amino}benzyl)(methyl)oxido-λ$^6$-sulfanylidene]carbamate (75.0 mg; 0.17 mmol) in 3,3,3-trifluoropropan-1-ol (0.5 ml; ABCR GmbH & CO. KG) at room temperature. The batch was stirred under argon at 70° C. for 19 hours. After UPLC MS check, additional sodium hydride (60%; 13.4 mg; 0.34 mmol) was added and the batch was stirred for additional 22 hours at 70° C. After cooling, the batch was diluted with ethyl acetate and saturated aqueous sodium chloride solution. The organic phase was filtered using a Whatman filter and concentrated. The desired product (12 mg; 0.03 mmol) was isolated by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 µm 100 × 30 mm |
| Solvent: | A = $H_2O$ + 0.1% Vol. HCOOH (99%) |
| | B = methanol |
| Gradient: | 0-1 min 20% B, 1-8 min 20-90% B |
| Flow: | 50 mL/min |
| Temperature: | RT |
| Solution: | 59 mg/2 mL DMSO/MeOH 1:1 |
| Injektion: | 1 × 2 mL |
| Detection: | DAD scan range 210-400 nm |
| | MS ESI+, ESI−, scan range 160-1000 m/z |
| Retention: | 6.5-6.9 min |

$^1$H NMR (400 MHz, $CDCl_3$, 300K) δ=8.78 (s, 1H), 7.88 (m, 1H), 7.71 (m, 3H), 7.39 (m, 1H), 7.15 (m, 1H), 6.82 (m, 1H), 6.73 (m, 1H), 4.39 (d, 1H), 4.25 (m, 3H), 2.96 (s, 3H), 2.60 (m, 3H).

Example 66

(rac)-4-[4-Fluoro-2-(pyridin-3-ylmethoxy)phenyl]-N-{3-[(S-methylsulfonimidoyl)methyl]phenyl}-1,3,5-triazin-2-amine

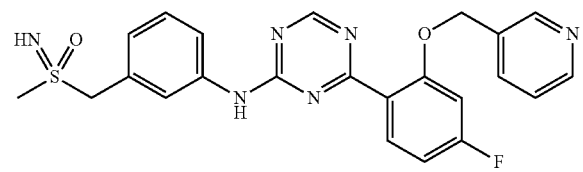 [SMILES: CS(=N)(=O)Cc1cccc(Nc2ncnc(-c3ccc(F)cc3OCc3cccnc3)n2)c1]

Example 66 was prepared under similar conditions as described in the preparation of Example 65 using (rac)-ethyl [(3-{[4-(2,4-difluorophenyl)-1,3,5-triazin-2-yl]amino}benzyl)(methyl)oxido-λ$^6$-sulfanylidene]carbamate and pyridin-3-ylmethanol (Aldrich Chemical Company Inc.). The desired product was isolated by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 µm 100 × 30 mm |
| Solvent: | A = $H_2O$ + 0.2% Vol. $NH_3$ (32%) |
| | B = Methanol |
| Gradient: | 0-1 min 30% B, 1-8 min 30-70% B |
| Flow: | 50 mL/min |
| Temperature: | RT |
| Solution: | 233 mg/2.3 mL DMSO/MeOH 1:1 |
| Injektion: | 3 × 0.75 mL |
| Detection: | DAD scan range 210-400 nm |
| | MS ESI+, ESI−, scan range 160-1000 m/z |
| | ELSD |
| Retention: | 6.3-6.7 min |

$^1$H NMR (400 MHz, $CDCl_3$, 300K) δ=8.82 (s, 1H), 8.76 (br, 1H), 8.55 (m, 1H), 7.98 (m, 1H), 7.77 (m, 2H), 7.69 (m, 1H), 7.39 (m, 2H), 7.28 (m, 1H), 7.14 (m, 1H), 6.82 (m, 2H), 5.20 (s, 2H), 4.37 (d, 1H), 4.23 (d, 1H), 2.94 (s, 3H), 2.70 (br, 1H).

Example 67

(rac)-4-[4-Fluoro-2-(pyridin-2-ylmethoxy)phenyl]-N-{3-[(S-methylsulfonimidoyl)methyl]phenyl}-1,3,5-triazin-2-amine

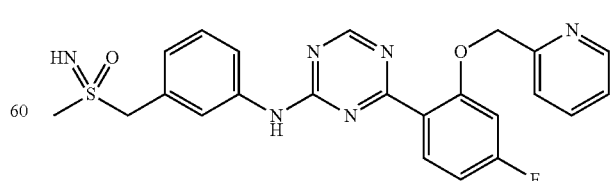

Example 67. was prepared under similar conditions as described in the preparation of Example 65 using (rac)-ethyl [(3-{[4-(2,4-difluorophenyl)-1,3,5-triazin-2-yl]

amino}benzyl)(methyl)oxido-λ⁶-sulfanylidene]carbamate and pyridin-2-ylmethanol (Aldrich Chemical Company Inc.). The desired product was isolated by preparative HPLC.

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H$_2$O + 0.2% Vol. NH$_3$ (32%) |
| | B = Methanol |
| Gradient: | 0-1 min 30% B, 1-8 min 30-70% B |
| Flow: | 50 mL/min |
| Temperature: | RT |
| Solution: | 139 mg/1.5 mL DMSO/MeOH 1:1 |
| Injektion: | 2 × 0.75 mL |
| Detection: | DAD scan range 210-400 nm |
| | MS ESI+, ESI−, scan range 160-1000 m/z |
| | ELSD |
| Retention: | 6.7-7.0 min |

$^1$H NMR (400 MHz, CDCl$_3$, 300K) δ=8.85 (s, 1H), 8.59 (m, 1H), 8.00 (m, 1H), 7.75 (m, 2H), 7.63 (m, 2H), 7.51 (br, 1H), 7.36 (m, 1H), 7.21 (m, 1H), 7.13 (m, 1H), 6.81 (m, 2H), 5.32 (s, 2H), 4.37 (d, 1H), 4.23 (d, 1H), 2.95 (s, 3H), 2.68 (s, 1H).

Example 68

(rac)-4-[4-Fluoro-2-(pyridin-4-ylmethoxy)phenyl]-N-{3-[(S-methylsulfonimidoyl)methyl]phenyl}-1,3,5-triazin-2-amine

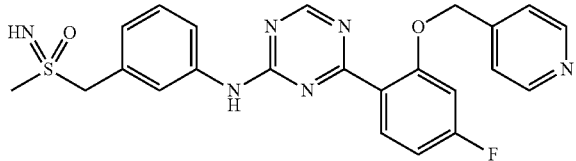 [SMILES: CS(=N)(=O)Cc1cccc(Nc2ncnc(-c3ccc(F)cc3OCc3ccncc3)n2)c1]

Example 68. was prepared under similar conditions as described in the preparation of Example 65 using (rac)-ethyl [(3-{[4-(2,4-difluorophenyl)-1,3,5-triazin-2-yl]amino}benzyl)(methyl)oxido-λ⁶-sulfanylidene]carbamate and pyridin-4-ylmethanol (Aldrich Chemical Company Inc.). The desired product was isolated by preparative HPLC.

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H$_2$O + 0.2% Vol. NH$_3$ (32%) |
| | B = Methanol |
| Gradient: | 0-1 min 30% B, 1-8 min 30-70% B |
| Flow: | 50 mL/min |
| Temperature: | RT |
| Solution: | 123 mg/1.5 mL DMSO/MeOH 1:1 |
| Injektion: | 2 × 0.75 mL |
| Detection: | DAD scan range 210-400 nm |
| | MS ESI+, ESI−, scan range 160-1000 m/z |
| | ELSD |
| Retention: | 6.5-6.8 min |

$^1$H NMR (400 MHz, CDCl$_3$, 300K) δ=8.85 (s, 1H), 8.57 (br, 2H), 8.01 (m, 1H), 7.77 (br, 1H), 7.70 (br, 1H), 7.36 (m, 4H), 7.13 (m, 1H), 6.85 (m, 1H), 6.75 (m, 1H), 5.20 (s, 2H), 4.37 (d, 1H), 4.22 (d, 1H), 2.94 (s, 3H), 2.70 (br, 1H).

Example 69

4-{4-Fluoro-2-[1-(4-fluorophenyl)ethoxy]phenyl}-N-{3-[(S-methylsulfonimidoyl)methyl]phenyl}-1,3,5-triazin-2-amine, mixture of 4 stereoisomers

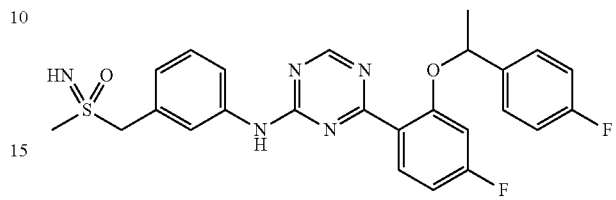

Example 69 was prepared under similar conditions as described in the preparation of Example 65 using (rac)-ethyl [(3-{[4-(2,4-difluorophenyl)-1,3,5-triazin-2-yl]amino}benzyl)(methyl)oxido-λ⁶-sulfanylidene]carbamate and (rac)-1-(4-fluorophenyl)ethanol (Aldrich Chemical Company Inc.). The desired product was isolated by preparative HPLC.

| | |
|---|---|
| System: | Waters Autopurificationsystem: Pump 254, Sample Manager 2767, CFO, DAD 2996, ELSD 2424, SQD 3001 |
| Column: | XBrigde C18 5 μm 100 × 30 mm |
| Solvent: | A = H$_2$O + 0.2% NH$_3$ |
| | B = Acetonitrile |
| Gradient: | 0-1 min 30% B, 1-8 min 30-70% B, 8-8.1 min 70-100% B, 8.1-10 min 100% B |
| Flow: | 50 mL/min |
| Temperature: | RT |
| Solution: | 187 mg/4 mL DMSO |
| Injektion: | 4 × 1 mL |
| Detection: | DAD scan range 210-400 nm |
| | MS ESI+, ESI−, scan range 160-1000 m/z |
| | ELSD |
| Retention: | 5.8-6.2 min |

$^1$H NMR (400 MHz, CDCl$_3$, 300K) δ=8.83 (s, 1H), 7.78 (m, 3H), 7.48 (br, 1H), 7.34 (m, 3H), 7.15 (m, 1H), 6.99 (m, 2H), 6.73 (m, 1H), 6.58 (m, 1H), 5.32 (q, 1H), 4.38 (d, 1H), 4.25 (d, 1H), 2.95 (s, 3H), 1.59 (d, 3H).

Example 70

(rac)-[(3-Fluoro-5-{[4-(4-fluoro-2-methoxyphenyl)-1,3,5-triazin-2-yl]amino}benzyl)(methyl)oxido-λ⁶-sulfanylidene]cyanamide

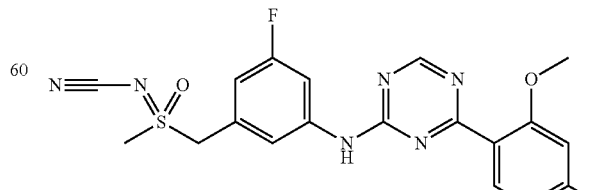

Preparation of Intermediate 70.1

3-Fluoro-5-[(methylsulfanyl)methyl]aniline

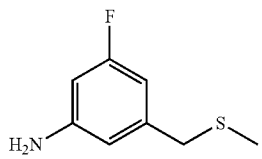

Intermediate 70.1 was prepared under similar conditions as described in the preparation of Intermediate 1.6 using 1-fluoro-3-[(methylsulfanyl)methyl]-5-nitrobenzene.

$^1$H NMR (400 MHz, CDCl$_3$, 300K) δ=6.42 (m, 2H), 6.26 (m, 1H), 3.74 (br, 2H), 3.55 (s, 2H), 2.01 (s, 3H).

Preparation of Intermediate 70.2

4-Chloro-N-{3-fluoro-5-[(methylsulfanyl)methyl]phenyl}-1,3,5-triazin-2-amine

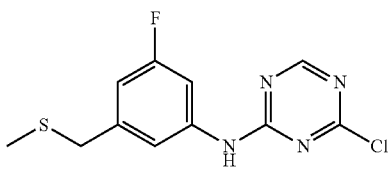 [SMILES: CSCc1cc(F)cc(Nc2ncnc(Cl)n2)c1]

Intermediate 70.2 was prepared under similar conditions as described in the preparation of Intermediate 1.7 using 3-fluoro-5-[(methylsulfanyl)methyl]aniline.

| | |
|---|---|
| System: | Waters Acquity UPLC-MS: Binary Solvent Manager, Sample Manager/Organizer, Column Manager, PDA, ELSD, SQD 3001 |
| Column: | Acquity UPLC BEH C18 1.7 50 × 2.1 mm |
| Solvent: | A2 = H$_2$O + 0.2% NH$_3$ |
| | B1 = Acetonitrile |
| Gradient: | 0-1.6 min 1-99% B, 1.6-2.0 min 99% B |
| Flow: | 0.8 mL/min |
| Temperature: | 60° C. |
| Injektion: | 2.0 μl |
| Detection: | DAD scan range 210-400 nm -> Peaktable ELSD |
| Method: | MS ESI+, ESI− Switch |
| | A2 + B1 = C:\MassLynx\Mass_100_1000_BasicReport.flp |
| Retention | 1.20 min |
| MS (ES−): | m/z = 285 [M + H] |

Preparation of Intermediate 70.3

4-(4-Fluoro-2-methoxyphenyl)-N-{3-fluoro-5-[(methylsulfanyl)methyl]phenyl}-1,3,5-triazin-2-amine

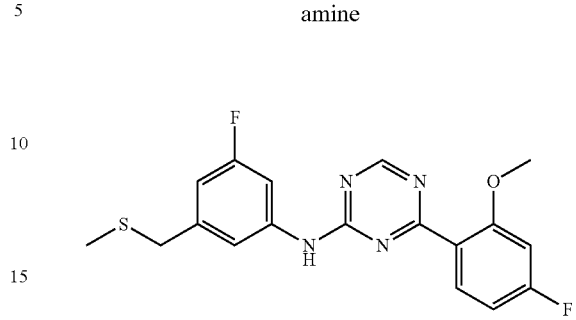

Intermediate 70.3 was prepared under similar conditions as described in the preparation of Example 42 using crude 4-chloro-N-{3-fluoro-5-[(methylsulfanyl)methyl]phenyl}-1,3,5-triazin-2-amine and (4-fluoro-2-methoxyphenyl)boronic acid (Aldrich Chemical Company Inc). The batch was purified by chromatography (hexane/ethyl acetate 6:4) and finally recrystallized from ethyl acetate to give the desired product.

$^1$H NMR (400 MHz, d$_6$-DMSO, 300K) δ=10.47 (s, 1H), 8.81 (s, 1H), 7.95 (br, 2H), 7.38 (br, 1H), 7.09 (m, 1H), 6.89 (m, 1H), 6.81 (m, 1H), 3.87 (s, 3H), 3.64 (s, 2H), 1.94 (s, 3H).

Preparation of Intermediate 70.4

(rac)-[(3-Fluoro-5-{[4-(4-fluoro-2-methoxyphenyl)-1,3,5-triazin-2-yl]amino}benzyl)(methyl-λ$^4$-sulfanylidene]cyanamide

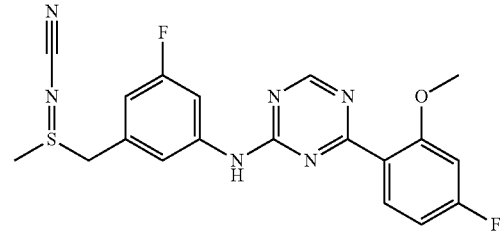 [SMILES: COc1cc(F)ccc1-c1ncnc(Nc2cc(F)cc(CS(C)=NC#N)c2)n1]

A mixture of 4-(4-fluoro-2-methoxyphenyl)-N-{3-fluoro-5-[(methylsulfanyl)methyl]phenyl}-1,3,5-triazin-2-amine (500 mg; 1.33 mmol), cyanamide (112 mg; 2.67 mmol) and bis(acetyloxy)(phenyl)-λ$^3$-iodane (473 mg; 1.47 mmol) in DCM (7.5 ml) was stirred at a temperature between 0-5° C. for 3 hours. The batch was concentrated and the residue was purified by chromatography (DCM/EtOH 92:8) to give the desired product (494 mg; 1.19 mmol).

$^1$H NMR (400 MHz, CDCl$_3$, 300K) δ=8.84 (s, 1H), 8.06 (br, 2H), 7.79 (s, 1H), 7.24 (m, 1H), 6.80 (m, 3H), 4.40 (d, 1H), 4.15 (d, 1H), 3.98 (s, 3H), 2.80 (s, 3H).

Preparation of End Product:

At room temperature sodium metaperiodate (380 mg; 1.774 mmol) was dissolved in water (4.5 ml). DCM (6.0 ml) and ruthenium(III)chloride (2 mg; 0.009 mmol) were added under stirring. A suspension of (rac)-[(3-fluoro-5-{[4-(4-fluoro-2-methoxyphenyl)-1,3,5-triazin-2-yl]amino}benzyl)(methyl-λ$^4$-sulfanylidene]cyanamide (490 mg; 1.183 mmol)

in DCM (8.0 ml) was added dropwise and the batch was stirred at room temperature. After 18 hours additional ruthenium(III)chloride (2 mg; 0.009 mmol) was added and the batch was stirred for 5 hours. Finally, further ruthenium(III) chloride (2 mg; 0.009 mmol) was added and the batch was stirred over night. The batch was filtered and the fitrate was extracted with DCM (3×). The combined organic phases were filtered using a Whatman filter and concentrated. The residue was purified by chromatography (DCM/EtOH 9:1) to give the desired product (146 mg; 0.340 mmol).

$^1$H NMR (400 MHz, d$_6$-DMSO, 300K) δ=10.66 (s, 1H), 8.83 (s, 1H), 8.27 (br, 1H), 7.93 (br, 1H), 7.47 (br, 1H), 7.09 (m, 1H), 6.97 (m, 1H), 6.89 (m, 1H), 4.99 (m, 2H), 3.87 (s, 3H), 3.38 (s, 3H).

Example 71 and 72

Enantiomers of (rac)-[(3-fluoro-5-{[4-(4-fluoro-2-methoxyphenyl)-1,3,5-triazin-2-yl]amino}benzyl)(methyl)oxido-λ$^6$-sulfanylidene]cyanamide (rac)-[(3-Fluoro-5-{[4-(4-fluoro-2-methoxyphenyl)-1,3,5-triazin-2-yl]amino}benzyl)(methyl)oxido-λ$^6$-sulfanylidene]cyanamide was separated into the enantiomers by preparative HPLC.

| System: | Dionex: Pump P 580, Gilson: Liquid Handler 215, Knauer: UV-Detektor K-2501 |
|---|---|
| Column: | Chiralpak IA 5 μm 250 × 30 mm |
| Solvent: | Ethanol/methanol 50:50 (v/v) |
| Flow: | 30 mL/min |
| Temperature: | RT |
| Solution: | 143 mg/3.3 mL EtOH/MeOH/DMSO 1.5:1.5:0.3 |
| Injektion: | 3 × 1.1 mL |
| Detection: | UV 254 nm |

| | Retention time in min | purity in % |
|---|---|---|
| Example 71 Enantiomer 1 | 11.8-15.2 | >99.9 |
| Example 72 Enantiomer 2 | 15.2-25.1 | 96.9 |

Enantiomer 1: $^1$H NMR (400 MHz, d$_6$-DMSO, 300K) δ=10.66 (s, 1H), 8.83 (s, 1H), 8.27 (br, 1H), 7.93 (br, 1H), 7.47 (br, 1H), 7.09 (m, 1H), 6.97 (m, 1H), 6.89 (m, 1H), 4.99 (m, 2H), 3.87 (s, 3H), 3.38 (s, 3H).

Enantiomer 2: $^1$H NMR (400 MHz, d$_6$-DMSO, 300K) δ=10.66 (s, 1H), 8.83 (s, 1H), 8.27 (br, 1H), 7.93 (br, 1H), 7.47 (br, 1H), 7.09 (m, 1H), 6.97 (m, 1H), 6.89 (m, 1H), 4.99 (m, 2H), 3.87 (s, 3H), 3.38 (s, 3H).

Example 73

(rac)-4-[2-(But-2-yn-1-yloxy)-4-fluorophenyl]-N-{3-[(S-methylsulfonimidoyl)methyl]phenyl}-1,3,5-triazin-2-amine

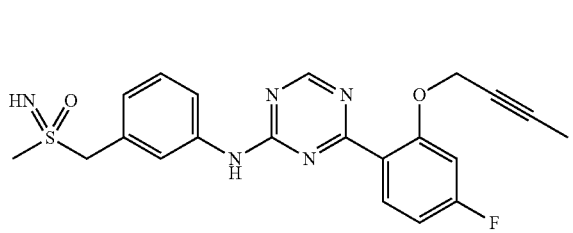 [SMILES: CC#CCOc1cc(F)ccc1-c1ncnc(Nc2cccc(CS(C)(=N)=O)c2)n1]

Example 73 was prepared under similar conditions as described in the preparation of Example 65 using (rac)-ethyl [(3-{[4-(2,4-difluorophenyl)-1,3,5-triazin-2-yl]amino}benzyl)(methyl)oxido-λ$^6$-sulfanylidene]carbamate and but-2-yn-1-ol (Aldrich Chemical Company Inc.). The compound was purified by chromatography (DCM/EtOH 97:3).

$^1$H NMR (400 MHz, CDCl$_3$, 300K) δ=8.79 (s, 1H), 7.96 (m, 1H), 7.80 (m, 2H), 7.60 (m, 1H), 7.41 (m, 1H), 7.15 (m, 1H), 6.96 (m, 1H), 6.80 (m, 1H), 4.79 (d, 2H), 4.42 (d, 1H), 4.29 (d, 1H), 2.95 (s, 3H), 2.72 (br, 1H), 1.85 (tr, 3H).

Example 74 and 75

Enantiomers of 4-[2-(but-2-yn-1-yloxy)-4-fluorophenyl]-N-{3-[(S-methylsulfonimidoyl)methyl]phenyl}-1,3,5-triazin-2-amine (rac)-4-[2-(But-2-yn-1-yloxy)-4-fluorophenyl]-N-{3-[(S-methylsulfonimidoyl)methyl]phenyl}-1,3,5-triazin-2-amine was separated into the enantiomers by preparative HPLC.

| System: | Dionex: Pump P 580, Gilson: Liquid Handler 215, Knauer: UV-Detektor K-2501 |
|---|---|
| Column: | Chiralpak IC 5 μm 250 × 30 mm |
| Solvent: | Hexan/ethanol 70:30 (v/v) |
| Flow: | 40 mL/min |
| Temperature: | RT |
| Solution: | 360 mg/6 mL EtOH/MeOH/DCM |
| Injektion: | 5 × 1.2 mL |
| Detection: | UV 280 nm |

| | Retention time in min | purity in % |
|---|---|---|
| Example 74 Enantiomer 1 | 20.4-23.8 | 99.9 |
| Example 75 Enantiomer 2 | 24.1-28.1 | 98.9 |

Enantiomer 1: $^1$H NMR (400 MHz, CDCl$_3$, 300K) δ=8.79 (s, 1H), 7.96 (m, 1H), 7.80 (m, 2H), 7.60 (m, 1H), 7.41 (m, 1H), 7.15 (m, 1H), 6.96 (m, 1H), 6.80 (m, 1H), 4.79 (d, 2H), 4.42 (d, 1H), 4.29 (d, 1H), 2.95 (s, 3H), 2.72 (br, 1H), 1.85 (tr, 3H).

Enantiomer 2: $^1$H NMR (400 MHz, CDCl$_3$, 300K) δ=8.79 (s, 1H), 7.96 (m, 1H), 7.80 (m, 2H), 7.60 (m, 1H), 7.41 (m, 1H), 7.15 (m, 1H), 6.96 (m, 1H), 6.80 (m, 1H), 4.79 (d, 2H), 4.42 (d, 1H), 4.29 (d, 1H), 2.95 (s, 3H), 2.72 (br, 1H), 1.85 (tr, 3H).

Example 76

(rac)-4-[2-(2-Cyclopropylethoxy)-4-fluorophenyl]-N-{3-[(S-methylsulfonimidoyl)methyl]phenyl}-1,3,5-triazin-2-amine

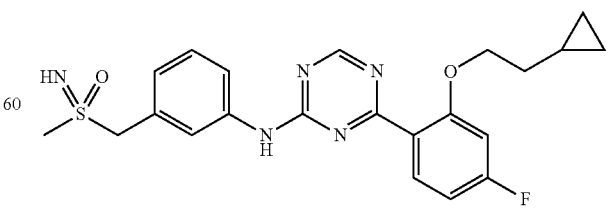

Example 76. was prepared under similar conditions as described in the preparation of Example 65 using (rac)-ethyl

[(3-{[4-(2,4-difluorophenyl)-1,3,5-triazin-2-yl]amino}benzyl)(methyl)oxido-λ⁶-sulfanylidene]carbamate and 2-cyclopropylethanol (ABCR GmbH & CO. KG). The desired product was isolated by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 μm 100 × 30 mm |
| Solvent: | A = H₂O + 0.2% NH₃ |
|  | B = Acetonitrile |
| Gradient: | 0-8 min 30-70% B |
| Flow: | 50 mL/min |
| Temperature: | RT |
| Solution: | 87 mg/2 mL DMSO |
| Injektion: | 4 × 0.5 mL |
| Detection: | DAD scan range 210-400 nm |
|  | MS ESI+, ESI-, scan range 160-1000 m/z |
|  | ELSD |
| Retention: | 5.1-5.4 min |

¹H NMR (400 MHz, CDCl₃, 300K) δ=8.79 (s, 1H), 7.85 (m, 1H), 7.73 (m, 2H), 7.50 (br, 1H), 7.40 (m, 1H), 7.16 (m, 1H), 6.75 (m, 2H), 4.39 (d, 1H), 4.25 (d, 1H), 4.11 (tr, 2H), 2.95 (s, 3H), 2.71 (s, 1H), 1.67 (m, 2H), 0.79 (m, 1H), 0.43 (m, 2H), 0.07 (m, 2H).

Example 77

(rac)-4-[4-Fluoro-2-(prop-2-yn-1-yloxy)phenyl]-N-{3-[(S-methylsulfonimidoyl)methyl]phenyl}-1,3,5-triazin-2-amine

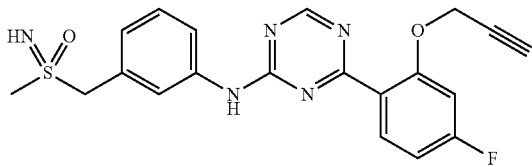 [SMILES: C#CCOc1cc(F)ccc1-c1ncnc(Nc2cccc(CS(C)(=N)=O)c2)n1]

Example 77. was prepared under similar conditions as described in the preparation of Example 65 using (rac)-ethyl [(3-{[4-(2,4-difluorophenyl)-1,3,5-triazin-2-yl]amino}benzyl)(methyl)oxido-λ⁶-sulfanylidene]carbamate and prop-2-yn-1-ol (Aldrich Chemical Company Inc.). The compound was purified by chromatography (DCM/EtOH 97:3).

¹H NMR (400 MHz, CDCl₃, 300K) δ=8.80 (s, 1H), 7.98 (m, 1H), 7.76 (m, 2H), 7.62 (br, 1H), 7.42 (m, 1H), 7.15 (m, 1H), 6.93 (m, 1H), 6.64 (m, 1H), 4.82 (d, 2H), 4.42 (d, 1H), 4.28 (d, 1H), 2.96 (s, 3H), 2.72 (s, 1H), 2.60 (br, 1H).

Example 78 and 79

Enantiomers of 4-[4-fluoro-2-(prop-2-yn-1-yloxy)phenyl]-N-{3-[(S-methylsulfonimidoyl)methyl]phenyl}-1,3,5-triazin-2-amine (rac)-4-[4-Fluoro-2-(prop-2-yn-1-yloxy)phenyl]-N-{3-[(S-methylsulfonimidoyl)methyl]phenyl}-1,3,5-triazin-2-amine was separated into the enantiomers by preparative HPLC.

| System: | Dionex: Pump P 580, Gilson: Liquid Handler 215, Knauer: UV-Detektor K-2501 |
|---|---|
| Column: | Chiralpak IC 5 μm 250 × 30 mm |
| Solvent: | Hexane/ethanol 70:30 (v/v) |
| Flow: | 40 mL/min |
| Temperature: | RT |
| Solution: | 228 mg/3 mL EtOH/MeOH |
| Injektion: | 3 × 1.0 mL |
| Detection: | UV 280 nm |

|  | Retention time in min | purity in % |
|---|---|---|
| Example 78 Enantiomer 1 | 19.1-22.9 | 98.7 |
| Example 79 Enantiomer 2 | 22.9-27.8 | 98.7 |

Enantiomer 1: ¹H NMR (400 MHz, CDCl₃, 300K) δ=8.80 (s, 1H), 7.98 (m, 1H), 7.76 (m, 2H), 7.62 (br, 1H), 7.42 (m, 1H), 7.15 (m, 1H), 6.93 (m, 1H), 6.64 (m, 1H), 4.82 (d, 2H), 4.42 (d, 1H), 4.28 (d, 1H), 2.96 (s, 3H), 2.72 (s, 1H), 2.60 (br, 1H).

Enantiomer 2: ¹H NMR (400 MHz, CDCl₃, 300K) δ=8.80 (s, 1H), 7.98 (m, 1H), 7.76 (m, 2H), 7.62 (br, 1H), 7.42 (m, 1H), 7.15 (m, 1H), 6.93 (m, 1H), 6.64 (m, 1H), 4.82 (d, 2H), 4.42 (d, 1H), 4.28 (d, 1H), 2.96 (s, 3H), 2.72 (s, 1H), 2.60 (br, 1H).

Example 80

(rac)-4-{2-[(3,4-Difluorobenzyl)oxy]-4-fluorophenyl}-N-{3-[(S-methylsulfonimidoyl)methyl]-phenyl}-1,3,5-triazin-2-amine

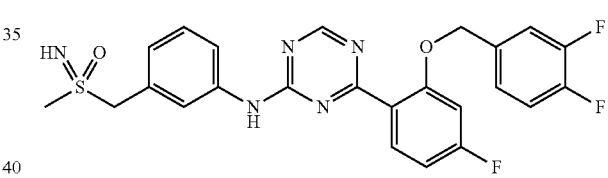

Example 80 was prepared under similar conditions as described in the preparation of Example 65 using (rac)-ethyl [(3-{[4-(2,4-difluorophenyl)-1,3,5-triazin-2-yl]amino}benzyl)(methyl)oxido-λ⁶-sulfanylidene]carbamate and (3,4-difluorophenyl)methanol (ABCR GmbH & CO. KG). The desired product was isolated by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 μm 100 × 30 mm |
| Solvent: | A = H₂O + 0.1% Vol. HCOOH (99%) |
|  | B = Acetonitrile |
| Gradient: | 0-8 min 15-60% B |
| Flow: | 50 mL/min |
| Temperature: | RT |
| Solution: | 238 mg/3.9 mL DMSO/MeOH 1:1 |
| Injektion: | 3 × 1.3 mL |
| Detection: | DAD scan range 210-400 nm |
|  | MS ESI+, ESI-, scan range 160-1000 m/z |
|  | ELSD |
| Retention: | 8.0-8.5 min |

¹H NMR (400 MHz, CDCl₃, 300K) δ=8.80 (s, 1H), 7.96 (m, 1H), 7.69 (m, 3H), 7.33 (m, 2H), 7.09 (m, 3H), 6.83 (m, 2H), 5.25 (s, 2H), 4.37 (d, 1H), 4.23 (d, 1H), 2.95 (s, 3H), 2.70 (br, 1H).

Example 81

(rac)-4-[4-Fluoro-2-(1,3-thiazol-5-ylmethoxy)phenyl]-N-{3-[(S-methylsulfonimidoyl)methyl]-phenyl}-1,3,5-triazin-2-amine

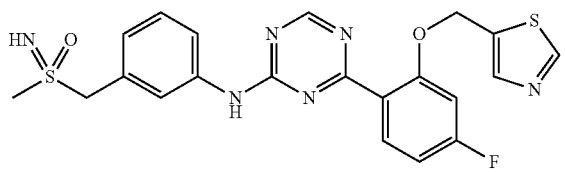 [SMILES: CS(=N)(=O)Cc1cccc(Nc2ncnc(-c3ccc(F)cc3OCc3cncs3)n2)c1]

Example 81 was prepared under similar conditions as described in the preparation of Example 65 using (rac)-ethyl [(3-{[4-(2,4-difluorophenyl)-1,3,5-triazin-2-yl]amino}benzyl)(methyl)oxido-λ⁶-sulfanylidene]carbamate and 1,3-thiazol-5-ylmethanol (ABCR GmbH & CO. KG). The desired product was isolated by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 µm 100 × 30 mm |
| Solvent: | A = H₂O + 0.1% HCOOH |
| | B = Acetonitrile |
| Gradient: | 0-8 min 15-60% B |
| Flow: | 50 mL/min |
| Temperature: | RT |
| Solution: | 579 mg/3.5 mL DMSO |
| Injektion: | 7 × 0.5 mL |
| Detection: | DAD scan range 210-400 nm |
| | MS ESI+, ESI−, scan range 160-1000 m/z |
| | ELSD |
| Retention: | 5.0-5.2 min |

¹H NMR (400 MHz, CDCl₃, 300K) δ=8.79 (m, 2H), 7.96 (m, 1H), 7.88 (m, 1H), 7.74 (br, 1H), 7.68 (m, 1H), 7.51 (br, 1H), 7.37 (m, 1H), 7.14 (m, 1H), 6.86 (m, 2H), 5.37 (s, 2H), 4.38 (d, 1H), 4.23 (d, 1H), 2.95 (s, 3H).

Example 82

(rac)-4-{4-Fluoro-2-[(2-fluoropyridin-4-yl)methoxy]phenyl}-N-{3-[(S-methylsulfonimidoyl)-methyl]phenyl}-1,3,5-triazin-2-amine

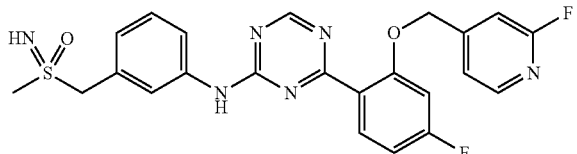

Example 82 was prepared under similar conditions as described in the preparation of Example 65 using (rac)-ethyl [(3-{[4-(2,4-difluorophenyl)-1,3,5-triazin-2-yl]amino}benzyl)(methyl)oxido-λ⁶-sulfanylidene]carbamate and (2-fluoropyridin-4-yl)methanol (Activate Scientific GmbH). The desired product was isolated by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 µm 100 × 30 mm |
| Solvent: | A = H₂O + 0.1% HCOOH |
| | B = Acetonitrile |
| Gradient: | 0-8 min 15-60% B |
| Flow: | 50 mL/min |
| Temperature: | RT |
| Solution: | 312 mg/3 mL DMSO |
| Injektion: | 6 × 0.5 mL |
| Detection: | DAD scan range 210-400 nm |
| | MS ESI+, ESI−, scan range 160-1000 m/z |
| | ELSD |
| Retention: | 5.7-6.0 min |

¹H NMR (400 MHz, CDCl₃, 300K) δ=8.85 (s, 1H), 8.17 (m, 1H), 8.04 (m, 1H), 7.76 (br, 1H), 7.70 (m, 1H), 7.61 (br, 1H), 7.36 (br, 1H), 7.22 (m, 2H), 7.13 (m, 1H), 6.86 (m, 1H), 6.74 (m, 1H), 5.20 (s, 2H), 4.37 (d, 1H), 4.24 (d, 1H), 2.95 (s, 3H), 2.73 (br, 1H).

Example 83 and 84

Enantiomers of 4-{4-fluoro-2-[(2-fluoropyridin-4-yl)methoxy]phenyl}-N-{3-[(S-methylsulfonimidoyl)methyl]phenyl}-1,3,5-triazin-2-amine (rac)-4-{4-Fluoro-2-[(2-fluoropyridin-4-yl)methoxy]phenyl}-N-{3-[(S-methylsulfonimidoyl)methyl]-phenyl}-1,3,5-triazin-2-amine was separated into the enantiomers by preparative HPLC.

| System: | Dionex: Pump P 580, Gilson: Liquid Handler 215, Knauer: UV-Detektor K-2501 |
|---|---|
| Column: | Chiralpak IA 5 µm 250 × 30 mm |
| Solvent: | Ethanol 100% |
| Flow: | 25 mL/min |
| Temperature: | RT |
| Solution: | 67 mg/4 mL EtOH/MeOH |
| Injektion: | 1 × 4.0 mL |
| Detection: | UV 254 nm |

| | Retention time in min | purity in % |
|---|---|---|
| Example 83 Enantiomer 1 | 19.0-31.0 | 99.7 |
| Example 84 Enantiomer 2 | 42.0-65.0 | 99.1 |

Enantiomer 1: ¹H NMR (400 MHz, CDCl₃, 300K) δ=8.85 (s, 1H), 8.17 (m, 1H), 8.04 (m, 1H), 7.76 (br, 1H), 7.70 (m, 1H), 7.61 (br, 1H), 7.36 (br, 1H), 7.22 (m, 2H), 7.13 (m, 1H), 6.86 (m, 1H), 6.74 (m, 1H), 5.20 (s, 2H), 4.37 (d, 1H), 4.24 (d, 1H), 2.95 (s, 3H), 2.73 (br, 1H).

Enantiomer 2: ¹H NMR (400 MHz, CDCl₃, 300K) δ=8.85 (s, 1H), 8.17 (m, 1H), 8.04 (m, 1H), 7.76 (br, 1H), 7.70 (m, 1H), 7.61 (br, 1H), 7.36 (br, 1H), 7.22 (m, 2H), 7.13 (m, 1H), 6.86 (m, 1H), 6.74 (m, 1H), 5.20 (s, 2H), 4.37 (d, 1H), 4.24 (d, 1H), 2.95 (s, 3H), 2.73 (br, 1H).

Example 85

(rac)-4-[4-Fluoro-2-(prop-2-en-1-yloxy)phenyl]-N-{3-[(S-methylsulfonimidoyl)methyl]phenyl}-1,3,5-triazin-2-amine

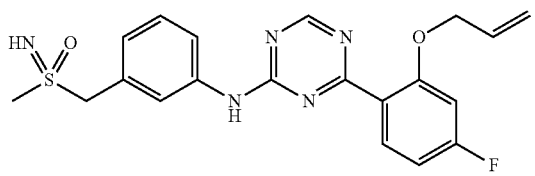 [SMILES: C=CCOc1cc(F)ccc1-c1ncnc(Nc2cccc(CS(C)(=N)=O)c2)n1]

Example 85 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and prop-2-en-1-ol (Aldrich Chemical Company Inc.). The desired product was isolated by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 μm 100 × 30 mm |
| Solvent: | A = H₂O + 0.1% HCOOH |
|  | B = Acetonitrile |
| Gradient: | 0-8 min 30-70% B |
| Flow: | 50 mL/min |
| Temperature: | RT |
| Solution: | 50 mg/2.5 mL DMSO |
| Injektion: | 5 × 0.5 mL |
| Detection: | DAD scan range 210-400 nm |
|  | MS ESI+, ESI−, scan range 160-1000 m/z |
|  | ELSD |
| Retention: | 3.2-3.4 min |

$^1$H NMR (400 MHz, CDCl₃, 300K) δ=8.81 (s, 1H), 7.92 (m, 1H), 7.75 (m, 2H), 7.49 (s, 1H), 7.40 (m, 1H), 7.16 (m, 1H), 6.76 (m, 2H), 6.03 (m, 1H), 5.46 (m, 1H), 5.28 (m, 1H), 4.85 (m, 2H), 4.39 (d, 1H), 4.26 (d, 1H), 2.94 (s, 3H), 2.70 (br, 1H).

Example 86

(rac)-4-(4-Fluoro-2-{[4-(trifluoromethyl)benzyl]oxy}phenyl)-N-{3-[(S-methylsulfonimidoyl)methyl]phenyl}-1,3,5-triazin-2-amine

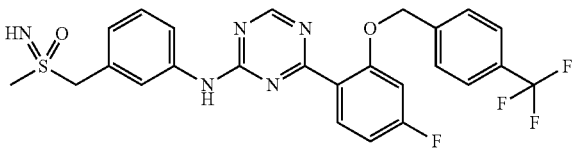

Example 86 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and [4-(trifluoromethyl)phenyl]methanol (ABCR GmbH & CO. KG). The desired product was isolated by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 μm 100 × 30 mm |
| Solvent: | A = H₂O + 0.2% NH₃ |
|  | B = Acetonitrile |
| Gradient: | 0-8 min 30-70% B |
| Flow: | 50 mL/min |
| Temperature: | RT |
| Solution: | 389 mg/4.5 mL DMSO |
| Injektion: | 9 × 0.5 mL |
| Detection: | DAD scan range 210-400 nm |
|  | MS ESI+, ESI−, scan range 160-1000 m/z |
|  | ELSD |
| Retention: | 6.2-6.6 min |

$^1$H NMR (400 MHz, CDCl₃, 300K) δ=8.82 (s, 1H), 7.99 (m, 1H), 7.90 (br, 1H), 7.60 (m, 5H), 7.45 (m, 1H), 7.34 (m, 1H), 7.13 (m, 1H), 6.81 (m, 2H), 5.22 (s, 2H), 4.36 (d, 1H), 4.23 (d, 1H), 2.94 (s, 3H), 2.73 (br, 1H).

Example 87

(rac)-4-{2-[(4-Chlorobenzyl)oxy]-4-fluorophenyl}-N-{3-[(S-methylsulfonimidoyl)methyl]phenyl}-1,3,5-triazin-2-amine

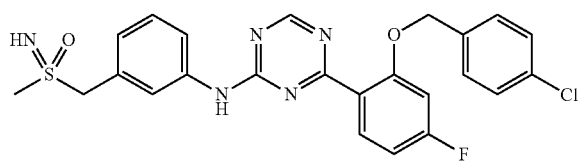 [SMILES: CS(=N)(=O)Cc1cccc(Nc2ncnc(-c3ccc(F)cc3OCc3ccc(Cl)cc3)n2)c1]

Example 87 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and (4-chlorophenyl)methanol (Aldrich Chemical Company Inc). The desired product was isolated by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H₂O + 0.1% HCOOH |
|  | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
|  | MS ESI+, ESI−, scan range 160-1000 m/z |

$^1$H NMR (400 MHz, CDCl₃, 300K) δ=8.94 (s, 1H), 7.99 (m, 1H), 7.75 (m, 2H), 7.34 (m, 6H), 7.16 (m, 1H), 6.82 (m, 2H), 5.18 (s, 2H), 4.39 (d, 1H), 4.25 (d, 1H), 2.96 (s, 3H), 2.70 (br, 1H).

Example 88

(rac)-4-(2-Ethoxy-4-fluorophenyl)-N-{3-[(S-methyl-sulfonimidoyl)methyl]phenyl}-1,3,5-triazin-2-amine

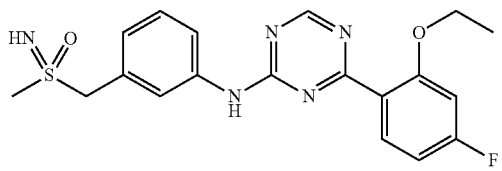 [SMILES: CCOc1cc(F)ccc1-c1ncnc(Nc2cccc(CS(C)(=N)=O)c2)n1]

Example 88 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and ethanol. The desired product was isolated by preparative HPLC.

| | |
|---|---|
| System: | Waters Autopurificationsystem: Pump 254, Sample Manager 2767, CFO, DAD 2996, ELSD 2424, SQD 3100 |
| Column: | XBrigde C18 5 µm 100 × 30 mm |
| Solvent: | A = H₂O + 0.2% NH₃ |
| | B = Acetonitrile |
| Gradient: | 0-8 min 15-60% B |
| Flow: | 50 mL/min |
| Temperature: | RT |
| Solution: | 129 mg/3 mL DMSO |
| Injektion: | 6 × 0.5 mL |
| Detection: | DAD scan range 210-400 nm |
| | MS ESI+, ESI−, scan range 160-1000 m/z |
| | ELSD |
| Retention: | 5.8-6.2 min |

$^1$H NMR (400 MHz, CDCl₃, 300K) δ=8.83 (s, 1H), 7.81 (m, 3H), 7.53 (s, 1H), 7.43 (m, 1H), 7.18 (m, 1H), 6.78 (m, 2H), 4.41 (d, 1H), 4.28 (d, 1H), 4.16 (q, 2H), 2.97 (s, 3H), 2.73 (s, 1H), 1.44 (tr, 3H).

Example 89

(rac)-4-(4-Fluoro-2-{[3-fluoro-5-(trifluoromethyl)benzyl]oxy}phenyl)-N-{3-[(S-methylsulfonimidoyl)methyl]phenyl}-1,3,5-triazin-2-amine

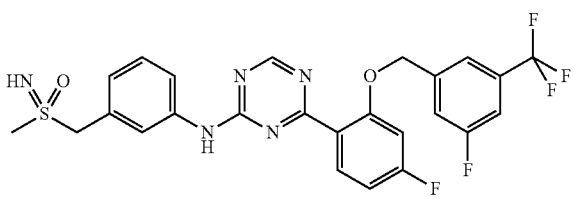 [SMILES: CS(=N)(=O)Cc1cccc(Nc2ncnc(-c3ccc(F)cc3OCc3cc(F)cc(C(F)(F)F)c3)n2)c1]

Example 89 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and [3-fluoro-5-(trifluoromethyl)phenyl]methanol (ABCR GmbH & CO. KG). The desired product was isolated by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 µm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl₃, 300K) δ=8.84 (s, 1H), 8.04 (s, 1H), 7.77 (br, 1H), 7.67 (m, 2H), 7.42 (m, 3H), 7.26 (m, 1H), 7.15 (m, 1H), 6.83 (m, 2H), 5.21 (s, 2H), 4.38 (d, 1H), 4.25 (d, 1H), 2.95 (s, 3H).

Example 90

(rac)-4-{4-Fluoro-2-[(3-fluorobenzyl)oxy]phenyl}-N-{3-[(S-methylsulfonimidoyl)methyl]phenyl}-1,3,5-triazin-2-amine

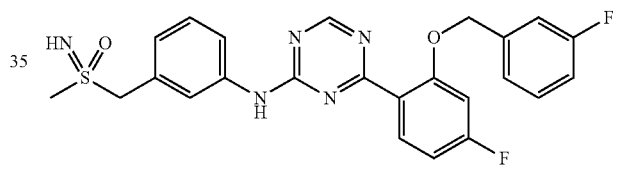

Example 90 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and (3-fluorophenyl)methanol (ABCR GmbH & CO. KG). The desired product was isolated by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 µm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl₃, 300K) δ=8.86 (s, 1H), 8.02 (m, 1H), 7.75 (m, 2H), 7.54 (s, 1H), 7.35 (m, 3H), 7.18 (m, 2H), 7.01 (m, 1H), 6.82 (m, 2H), 5.21 (s, 2H), 4.39 (d, 1H), 4.26 (d, 1H), 2.96 (s, 3H).

Example 91

(rac)-4-(4-Fluoro-2-propoxyphenyl)-N-{3-[(S-methylsulfonimidoyl)methyl]phenyl}-1,3,5-triazin-2-amine

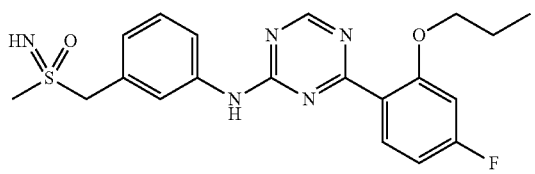

Example 91 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and propan-1-ol. The desired product was isolated by preparative HPLC.

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H$_2$O + 0.2% NH$_3$ |
| | B = Acetonitrile |
| Gradient: | 0-8 min 30-70% B |
| Flow: | 50 mL/min |
| Temperature: | RT |
| Solution: | 126 mg/4 mL DMSO |
| Injektion: | 8 × 0.5 mL |
| Detection: | DAD scan range 210-400 nm |
| | MS ESI+, ESI−, scan range 160-1000 m/z |
| | ELSD |
| Retention: | 6.6-6.9 min |

$^1$H NMR (400 MHz, CDCl$_3$, 300K) δ=8.80 (s, 1H), 7.85 (m, 1H), 7.75 (m, 2H), 7.42 (m, 2H), 7.16 (m, 1H), 8.74 (m, 2H), 4.39 (d, 1H), 4.26 (d, 1H), 4.01 (tr, 2H), 2.95 (s, 3H), 2.70 (s, 1H), 1.81 (m, 2H), 1.00 (tr, 3H).

Example 92

(rac)-4-{2-[(3-Chlorobenzyl)oxy]-4-fluorophenyl}-N-{3-[(S-methylsulfonimidoyl)methyl]phenyl}-1,3,5-triazin-2-amine

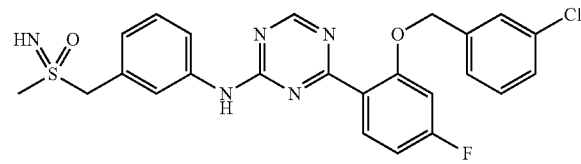 [SMILES: CS(=N)(=O)Cc1cccc(Nc2ncnc(-c3ccc(F)cc3OCc3cccc(Cl)c3)n2)c1]

Example 92 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and (3-chlorophenyl)methanol (ABCR GmbH & CO. KG). The desired product was isolated by preparative HPLC.

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H$_2$O + 0.2% NH$_3$ |
| | B = Acetonitrile |
| Gradient: | 0-8 min 30-70% B |
| Flow: | 50 mL/min |
| Temperature: | RT |
| Solution: | 233 mg/3 mL DMSO |
| Injektion: | 6 × 0.5 mL |
| Detection: | DAD scan range 210-400 nm |
| | MS ESI+, ESI−, scan range 160-1000 m/z |
| | ELSD |
| Retention: | 5.9-6.2 min |

$^1$H NMR (400 MHz, CDCl$_3$, 300K) δ=8.84 (s, 1H), 8.00 (m, 1H), 7.68 (m, 3H), 7.53 (s, 1H), 7.35 (m, 1H), 7.26 (m, 3H), 7.14 (m, 1H), 6.81 (m, 2H), 5.16 (s, 2H), 4.36 (d, 1H), 4.23 (d, 1H), 2.94 (s, 3H), 2.70 (br, 1H).

Example 93

(rac)-4-[4-Fluoro-2-(1,2-oxazol-3-ylmethoxy)phenyl]-N-{3-[(S-methylsulfonimidoyl)methyl]-phenyl}-1,3,5-triazin-2-amine

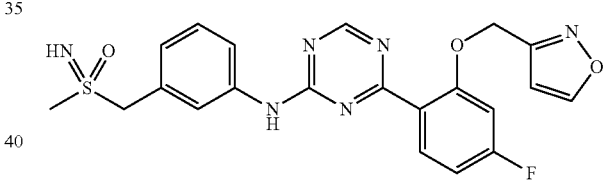

Example 93 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and 1,2-oxazol-3-ylmethanol (UkrOrgSynthesis Ltd.). The desired product was isolated by preparative HPLC.

| | |
|---|---|
| System: | Agilent: Prep 1200, 2xPrep Pump, DLA, MWD, Prep FC, |
| Column: | XBrigde C18 5 μm 100 × 30 mm |
| Solvent: | A = H$_2$O + 0.1% TFA |
| | B = Methanol |
| Gradient: | 0-17.5 min 25-55% B, 17.5-20 min 55-100% B |
| Flow: | 38 mL/min |
| Temperature: | RT |
| Solution: | 29 mg/0.8 mL DMSO |
| Injektion: | 1 × 0.8 mL |
| Detection: | UV 210 nm |
| Retention: | 8.3-10.2 min |

$^1$H NMR (400 MHz, d$_6$-DMSO, 300K) δ=10.41 (s, 1H), 8.80 (m, 2H), 7.80 (m, 3H), 7.37 (m, 1H), 7.18 (m, 2H), 6.94 (m, 1H), 6.55 (br, 1H), 5.33 (s, 2H), 4.99 (m, 2H), 3.37 (s, 3H).

Example 94

(rac)-4-{2-[(3-Chloro-5-fluorobenzyl)oxy]-4-fluoro-phenyl}-N-{3-[(S-methylsulfonimidoyl)methyl]-phenyl}-1,3,5-triazin-2-amine

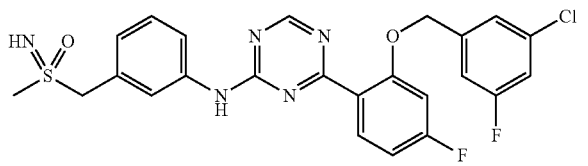

Example 94 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and (3-chloro-5-fluorophenyl)methanol (Apollo Scientific Ltd.). The desired product was isolated by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 µm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.85 (s, 1H), 8.03 (m, 1H), 7.77 (s, 1H), 7.69 (m, 1H), 7.46 (m, 1H), 7.37 (m, 2H), 7.16 (m, 2H), 7.01 (m, 1H), 6.85 (m, 1H), 6.76 (m, 1H), 5.14 (s, 2H), 4.38 (d, 1H), 4.24 (d, 1H), 2.95 (s, 3H).

Example 95

(rac)-4-[2-(2,2-Difluoroethoxy)-4-fluorophenyl]-N-{3-[(S-methylsulfonimidoyl)methyl]phenyl}-1,3,5-triazin-2-amine

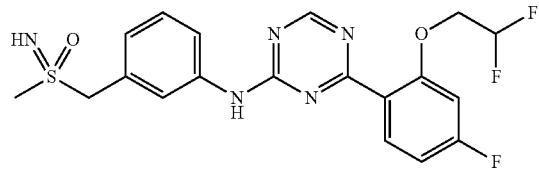 [SMILES: CS(=N)(=O)Cc1cccc(Nc2ncnc(-c3ccc(F)cc3OCC(F)F)n2)c1]

Example 95 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and 2,2-difluoroethanol (ABCR GmbH & CO. KG). The desired product was isolated by preparative HPLC.

| | |
|---|---|
| System: | Waters Autopurificationsystem: Pump 254, Sample Manager 2767, CFO, DAD 2996, ELSD 2424, SQD 3100 |
| Column: | XBrigde C18 5 µm 100 × 30 mm |
| Solvent: | A = H$_2$O + 0.2% NH$_3$ |
| | B = Acetonitrile |
| Gradient: | 0-8 min 15-50% B |
| Flow: | 50 mL/min |
| Temperature: | RT |
| Solution: | 68 mg/3 mL DMSO/MeOH 1:1 |
| Injektion: | 3 × 1 mL |
| Detection: | DAD scan range 210-400 nm |
| | MS ESI+, ESI−, scan range 160-1000 m/z |
| | ELSD |
| Retention: | 6.18-6.54 min |

$^1$H NMR (400 MHz, CDCl$_3$, 300K) δ8.80 (s, 1H), 7.95 (m, 1H), 7.77 (br, 1H), 7.69 (m, 1H), 7.43 (m, 1H), 7.34 (br, 1H), 7.18 (m, 1H), 6.88 (m, 1H), 6.76 (m, 1H), 6.05 (m, 1H), 4.40 (d, 1H), 4.27 (m, 3H), 2.95 (s, 3H), 2.68 (s, 1H).

Example 96

(rac)-4-{4-Fluoro-2-[(4-fluoro-3-methylbenzyl)oxy]phenyl}-N-{3-[(S-methylsulfonimidoyl)methyl]-phenyl}-1,3,5-triazin-2-amine

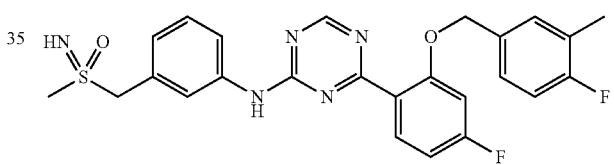

Example 96 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and (4-fluoro-3-methylphenyl)methanol (ABCR GmbH & CO. KG). The desired product was isolated by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 µm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.81 (s, 1H), 7.94 (m, 1H), 7.70 (m, 2H), 7.51 (br, 1H), 7.32 (m, 2H), 7.20 (m, 1H), 7.13 (m, 1H), 6.94 (m, 1H), 6.79 (m, 2H), 5.11 (s, 2H), 4.35 (d, 1H), 4.33 (d, 1H), 2.93 (s, 3H), 2.61 (s, 1H), 2.23 (s, 3H).

Example 97

(rac)-4-{2-[(3-Chloro-4-fluorobenzyl)oxy]-4-fluoro-phenyl}-N-{3-[(S-methylsulfonimidoyl)methyl]-phenyl}-1,3,5-triazin-2-amine

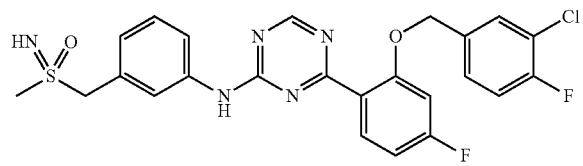 [SMILES: CS(=N)(=O)Cc1cccc(Nc2ncnc(-c3ccc(F)cc3OCc3ccc(F)c(Cl)c3)n2)c1]

Example 97 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and (3-chloro-4-fluorophenyl)methanol (ABCR GmbH & CO. KG). The desired product was isolated by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl₃, 300K) δ=8.84 (s, 1H), 8.00 (m, 1H), 7.76 (br, 1H), 7.69 (m, 2H), 7.48 (br, 1H), 7.36 (m, 1H), 7.27 (m, 1H), 7.11 (m, 2H), 6.79 (m, 2H), 5.12 (s, 2H), 4.37 (d, 1H), 4.24 (d, 1H), 2.95 (s, 3H), 2.71 (br, 1H).

Example 98

(rac)-3-({5-Fluoro-2-[4-({3-[(S-methylsulfonimidoyl)methyl]phenyl}amino)-1,3,5-triazin-2-yl]-phenoxy}methyl)benzonitrile

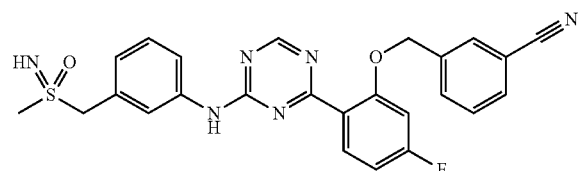

Example 98 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and 3-(hydroxymethyl)benzonitrile (ABCR GmbH & CO. KG). The desired product was isolated by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 μm 100 × 30 mm |
| Solvent: | A = H₂O + 0.2% NH₃ |
| | B = Acetonitrile |
| Gradient: | 0-8 min 30-70% B |
| Flow: | 50 mL/min |
| Temperature: | RT |
| Solution: | 473 mg/4.5 mL DMSO |
| Injektion: | 9 × 0.5 mL |
| Detection: | DAD scan range 210-400 nm |
| | MS ESI+, ESI−, scan range 160-1000 m/z |
| | ELSD |
| Retention: | 4.7-4.9 min |

$^1$H NMR (400 MHz, dc-DMSO, 300K) δ=10.35 (s, 1H), 8.83 (s, 1H), 7.85 (m, 6H), 7.53 (br, 1H), 7.28 (br, 1H), 7.16 (m, 1H), 7.11 (br, 1H), 6.95 (m, 1H), 5.32 (s, 2H), 4.32 (br, 2H), 3.55 (s, 1H), 2.79 (s, 3H).

Example 99

(rac)-4-{4-Fluoro-2-[(2-methylprop-2-en-1-yl)oxy]phenyl}-N-{3-[(S-methylsulfonimidoyl)methyl]-phenyl}-1,3,5-triazin-2-amine

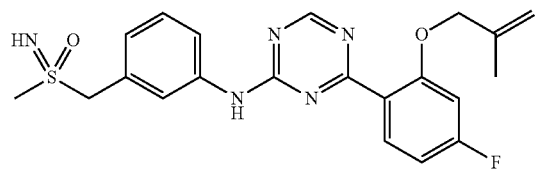 [SMILES: C=C(C)COc1cc(F)ccc1-c1ncnc(Nc2cccc(CS(C)(=N)=O)c2)n1]

Example 99 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and 2-methylprop-2-en-1-ol (Aldrich Chemical Company Inc). The desired product was isolated by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl₃, 300K) δ=8.83 (s, 1H), 7.94 (m, 1H), 7.76 (m, 2H), 7.55 (br, 1H), 7.42 (m, 1H), 7.18 (m, 1H), 6.78 (m, 2H), 5.18 (br, 1H), 5.01 (br, 1H), 4.55 (s, 2H), 4.41 (d, 1H), 4.28 (d, 1H), 2.97 (s, 3H), 2.70 (br, 1H), 1.82 (s, 3H).

Example 100

(rac)-4-[4-F-Fluoro-2-(4,4,4-trifluorobutoxy)phenyl]-N-{3-[(S-methylsulfonimidoyl)methyl]phenyl}-1,3,5-triazin-2-amine

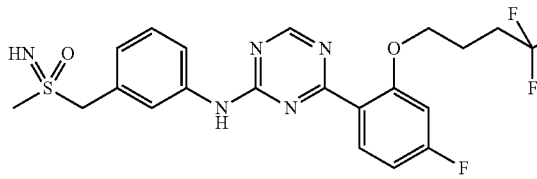

Example 100 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and 4,4,4-trifluorobutan-1-ol (ABCR GmbH & CO. KG). The desired product was isolated by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.82 (s, 1H), 7.95 (m, 1H), 7.80 (br, 1H), 7.70 (m, 1H), 7.46 (m, 2H), 7.19 (m, 1H), 6.82 (m, 1H), 6.73 (m, 1H), 4.42 (d, 1H), 4.29 (d, 1H), 4.12 (tr, 2H), 2.98 (s, 3H), 2.74 (br, 1H), 2.38 (m, 2H), 2.07 (m, 2H).

Example 101

(rac)-4-{4-Fluoro-2-[(2,3,5-trifluorobenzyl)oxy]phenyl}-N-{3-[(S-methylsulfonimidoyl)methyl]phenyl}-1,3,5-triazin-2-amine

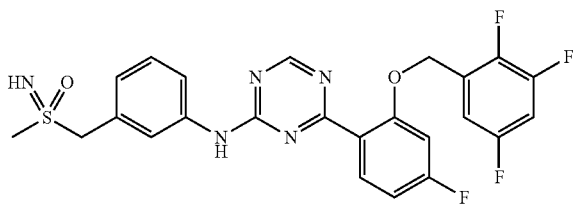 [SMILES: CS(=N)(=O)Cc1cccc(Nc2ncnc(-c3ccc(F)cc3OCc3cc(F)cc(F)c3F)n2)c1]

Example 101 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and (2,3,5-trifluorophenyl)methanol (ABCR GmbH & CO. KG). The desired product was isolated by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.87 (s, 1H), 8.07 (m, 1H), 7.80 (s, 1H), 7.72 (m, 1H), 7.40 (m, 3H), 7.18 (m, 1H), 6.89 (m, 3H), 5.26 (s, 2H), 4.42 (d, 1H), 4.28 (d, 1H), 2.98 (s, 3H), 2.71 (br, 1H).

Example 102

(rac)-4-{2-[(2Z)-But-2-en-1-yloxy]-4-fluorophenyl}-N-{3-[(S-methylsulfonimidoyl)methyl]phenyl}-1,3,5-triazin-2-amine

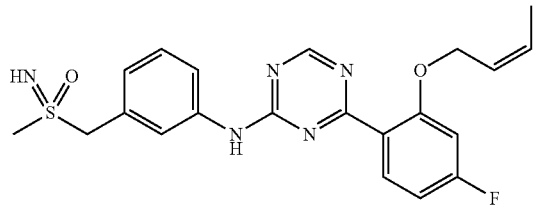

Example 102 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and (2Z)-but-2-en-1-ol (ChemSampCo, Inc.). The desired product was isolated by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.80 (s, 1H), 7.89 (m, 1H), 7.76 (m, 2H), 7.57 (br, 1H), 7.39 (m, 1H), 7.15 (m, 1H), 6.75 (m, 2H), 5.70 (m, 2H), 4.72 (m, 2H), 4.39 (d, 1H), 4.26 (d, 1H), 2.95 (s, 3H), 2.71 (br, 1H), 1.73 (d, 3H).

Example 103

(rac)-4-{4-Fluoro-2-[(2,4,5-trifluorobenzyl)oxy]phenyl}-N-{3-[(S-methylsulfonimidoyl)methyl]phenyl}-1,3,5-triazin-2-amine

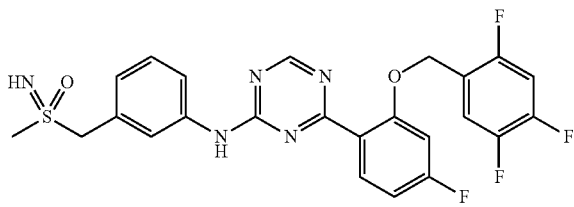 [SMILES: CS(=N)(=O)Cc1cccc(Nc2ncnc(-c3ccc(F)cc3OCc3cc(F)c(F)cc3F)n2)c1]

Example 103 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and (2,4,5-trifluorophenyl)methanol (ABCR GmbH & CO. KG). The desired product was isolated by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H₂O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI−, scan range 160-1000 m/z |

$^1$H NMR (400 MHz, CDCl₃, 300K) δ=8.84 (s, 1H), 8.03 (m, 1H), 7.77 (br, 1H), 7.65 (m, 2H), 7.48 (br, 1H), 7.39 (m, 1H), 7.15 (m, 1H), 6.94 (m, 1H), 6.83 (m, 2H), 5.17 (s, 2H), 4.39 (d, 1H), 4.25 (d, 1H), 2.96 (s, 3H), 2.70 (br, 1H).

Example 104

(rac)-4-{4-Fluoro-2-[(3,4,5-trifluorobenzyl)oxy]phenyl}-N-{3-[(S-methylsulfonimidoyl)methyl]phenyl}-1,3,5-triazin-2-amine

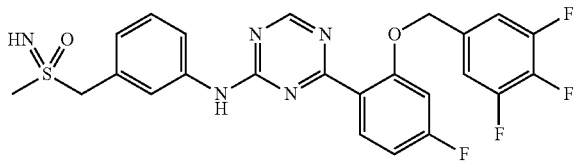 [SMILES: CS(=N)(=O)Cc1cccc(Nc2ncnc(-c3ccc(F)cc3OCc3cc(F)c(F)c(F)c3)n2)c1]

Example 104 was prepared under similar conditions as described in the preparation of Example 65 using (rac)-ethyl [(3-{[4-(2,4-difluorophenyl)-1,3,5-triazin-2-yl]amino}benzyl)(methyl)oxido-$\lambda^6$-sulfanylidene]carbamate and (3,4,5-trifluorophenyl)methanol (ABCR GmbH & CO. KG). The desired product was isolated by preparative HPLC.

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H₂O + 0.1% HCOOH<br>B = Acetonirile |
| Gradient: | 0-8 min 30-70% B |
| Flow: | 50 mL/min |
| Temperature: | RT |
| Solution: | 431 mg/4 mL DMSO |
| Injektion: | 8 × 0.5 mL |
| Detection: | DAD scan range 210-400 nm<br>MS ESI+, ESI−, scan range 160-1000 m/z<br>ELSD |
| Retention: | 5.6-6.0 min |

$^1$H NMR (400 MHz, CDCl₃, 300K) δ=8.84 (s, 1H), 8.02 (m, 1H), 7.77 (br, 1H), 7.69 (m, 1H), 7.39 (m, 2H), 7.17 (m, 3H), 6.85 (m, 1H), 6.74 (m, 1H), 5.10 (s, 2H), 4.39 (d, 1H), 4.25 (d, 1H), 2.95 (s, 3H), 2.69 (br, 1H).

Example 105

(rac)-[(2,3-Difluoro-{[4-(4-fluoro-2-methoxyphenyl)-1,3,5-triazin-2-yl]amino}benzyl)(methyl)oxido-$\lambda^6$-sulfanylidene]cyanamide

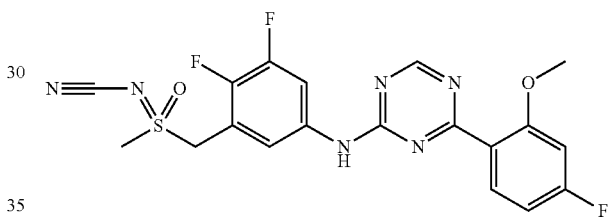

Preparation of Intermediate 105.1

(2,3-Difluoro-5-nitrophenyl)methanol

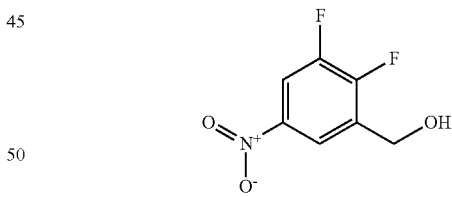

Borane-tetrahydrofuran complex (1.0 M solution in THF; 177 mL) was added under stirring to an ice-cold solution of 2,3-difluoro-5-nitrobenzoic acid (9.0 g; 44.3 mmol; Butt Park Ltd.) in THF (85 mL). The ice bath was removed and the batch was stirred for 18 hours at room temperature. The batch was cautiously diluted with methanol under stirring at 0° C. Ethyl acetate was added and the batch was washed with aqueous 1 M solution of sodium hydroxide and half-concentrated aqueous sodium chloride solution. The organic phase was dried (Na₂SO₄), filtered and concentrated. The residue was purified by chromatography (hexane/ethyl acetate 1:1) to give the desired product (8.2 g; 43.3 mmol).

$^1$H NMR (400 MHz, CDCl₃, 300K) δ=8.26 (m, 1H), 8.03 (m, 1H), 4.89 (s, 2H), 2.13 (br, 1H).

Preparation of Intermediate 105.2

(5-Amino-2,3-difluorophenyl)methanol

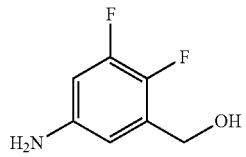 [SMILES: Nc1cc(F)c(F)c(CO)c1]

Intermediate 105.2 was prepared under similar conditions as described in the preparation of Intermediate 1.6 using (2,3-difluoro-5-nitrophenyl)methanol.

$^1$H NMR (400 MHz, CDCl$_3$, 300K) δ=6.46 (m, 1H), 6.39 (m, 1H), 4.67 (s, 2H), 3.02 (br, 3H).

Preparation of Intermediate 105.3

3-(Chloromethyl)-4,5-difluoroaniline

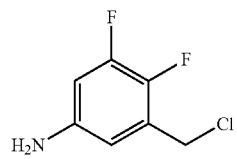 [SMILES: Nc1cc(F)c(F)c(CCl)c1]

Thionylchloride (7.7 g; 64.9 mmol) was added dropwise under stirring to a water-cooled solution of (5-amino-2,3-difluorophenyl)methanol (4.1 g; 26.0 mmol) in DCM (78 ml) and 1-methylpyrrolidin-2-one (11 ml). The batch was stirred at room temperature for 18 hours before it was diluted with ice-water, aqueous sodium bicarbonate solution and brine. The batch was stirred for 2 hours at room temperature and finally it was extracted with ethyl acetate (2×). The combined organic phases were filtered using a Whatman filter and concentrated to give the crude product (6.5 g) that was used without further purification.

Preparation of Intermediate 105.4

3,4-Difluoro-5-[(methylsulfanyl)methyl]aniline

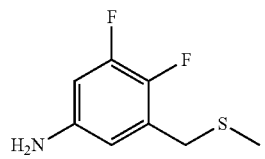

Intermediate 105.4 was prepared under similar conditions as described in the preparation of Intermediate 1.1 using crude 3-(chloromethyl)-4,5-difluoroaniline. The batch was purified by chromatography (hexane/ethyl acetate 1:1).

$^1$H NMR (400 MHz, CDCl$_3$, 300K) δ=6.35 (m, 2H), 3.62 (br, 4H), 2.99 (s, 3H).

Preparation of Intermediate 105.5

4-Chloro-N-{3,4-difluoro-5-[(methylsulfanyl)methyl]phenyl}-1,3,5-triazin-2-amine

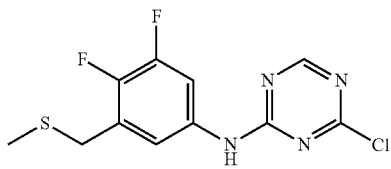 [SMILES: CSCc1cc(Nc2ncnc(Cl)n2)cc(F)c1F]

Intermediate 105.5 was prepared under similar conditions as described in the preparation of Intermediate 1.7 using 3,4-difluoro-5-[(methylsulfanyl)methyl]aniline.

| System: | Waters Acquity UPLC-MS: Binary Solvent Manager, Sample Manager/Organizer, Column Manager, PDA, ELSD, SQD |
|---|---|
| Column: | Acquity UPLC BEH C18 1.7 50 × 2.1 mm |
| Solvent: | A1 = H2O + 0.1% Vol. HCOOH (99%) |
| | A2 = H2O + 0.2% Vol. NH3 (32%) |
| | B1 = Acetonitril |
| Gradient: | 0-1.6 min 1-99% B, 1.6-2.0 min 99% B |
| Flow: | 0.8 mL/min |
| Temperatuer: | 60° C. |
| Injektion: | 2.0 µl |
| Detection: | DAD scan range 210-400 nm -> Peaktable ELSD |
| Method: | MS ESI+, ESI− Switch |
| | A2 + B1 = C:\MassLynx\NH3_Mass_100_1000.olp |
| Retention | 1.19 min |
| MS(ES−): | m/z = 303 [M + H] |

Preparation of Intermediate 105.6

N-{3,4-Difluoro-5-[(methylsulfanyl)methyl]phenyl}-4-(4-fluoro-2-methoxyphenyl)-1,3,5-triazin-2-amine

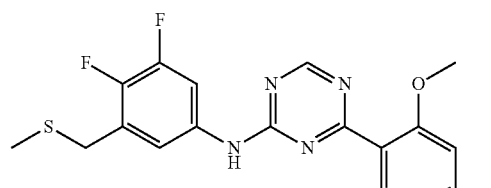

Intermediate 105.6 was prepared under similar conditions as described in the preparation of Example 42 using crude 4-chloro-N-{3,4-difluoro-5-[(methylsulfanyl)methyl]phenyl}-1,3,5-triazin-2-amine and (4-fluoro-2-methoxyphenyl) boronic acid (Aldrich Chemical Company Inc). The batch was purified by chromatography (hexane/ethyl acetate 1:1) to give the desired product.

$^1$H NMR (400 MHz, CDCl$_3$, 300K) δ=8.80 (s, 1H), 8.15 (br, 2H), 7.35 (m, 1H), 7.08 (br, 1H), 6.78 (m, 2H), 3.98 (s, 3H), 3.73 (s, 2H), 2.08 (s, 3H).

Preparation of Intermediate 105.7

(rac)-[(2,3-Difluoro-5-[{4-(4-fluoro-2-methoxyphenyl)-1,3,5-triazin-2-yl]amino}benzyl)(methyl)-$\lambda^4$-sulfanylidene]cyanamide

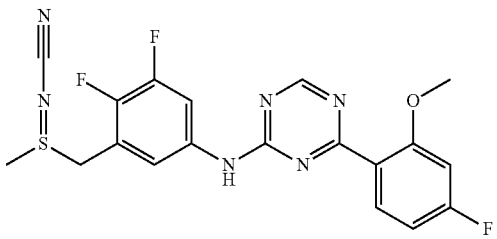 [SMILES: COc1cc(F)ccc1-c1ncnc(Nc2cc(F)c(F)c(CS(C)=NC#N)c2)n1]

Bis(acetyloxy)(phenyl)-$\lambda^3$-iodane (469 mg; 1.46 mmol) was added to a stirred solution of N-{3,4-difluoro-5-[(methylsulfanyl)methyl]phenyl}-4-(4-fluoro-2-methoxyphenyl)-1,3,5-triazin-2-amine (520 mg; 1.33 mmol) and cyanamide (111 mg; 2.65 mmol) in DCM (7.5 ml) at 0° C. The batch was stirred at this temperature for 4 hours. The batch was concentrated and the residue was purified by chromatography (DCM/EtOH 8:2) to give the desired product (300 mg; 0.69 mmol).

$^1$H NMR (400 MHz, CDCl$_3$, 300K) δ=8.81 (s, 1H), 8.49 (br, 1H), 8.06 (br, 1H), 7.87 (br, 1H), 7.22 (br, 1H), 6.79 (m, 2H), 4.34 (m, 2H), 3.96 (s, 3H), 2.86 (s, 3H).

Preparation of End Product:

Potassium permanganate (217 mg; 1.37 mmol) was added under stirring to a solution of (rac)-[(2,3-difluoro-5-{[4-(4-fluoro-2-methoxyphenyl)-1,3,5-triazin-2-yl]amino}benzyl)(methyl)-$\lambda^4$-sulfanylidene]-cyanamide (297 mg; 0.69 mmol) in acetone (6.9 mL) at room temperature. The batch was stirred at 50° C. for 1 hour. The batch was concentrated and the residue was purified by chromatography (DCM/EtOH 9:1) to give the desired product (153 mg; 0.34 mmol).

$^1$H NMR (400 MHz, d$_6$-DMSO, 300K) δ=10.62 (s, 1H), 8.81 (s, 1H), 8.55 (br, 1H), 7.96 (br, 1H), 7.43 (br, 1H), 7.08 (m, 1H), 6.89 (m, 1H), 5.06 (m, 2H), 3.87 (s, 3H), 3.50 (s, 3H).

Example 106

(rac)-N-{3,4-Difluoro-5-[(S-methylsulfonimidoyl)methyl]phenyl}-4-(4-fluoro-2-methoxyphenyl)-1,3,5-triazin-2-amine

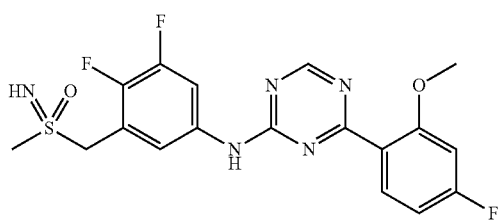 [SMILES: COc1cc(F)ccc1-c1ncnc(Nc2cc(F)c(F)c(CS(C)(=N)=O)c2)n1]

Trifluoroacetic anhydride (0.32 mL; 0.90 mmol) was added under stirring to an ice-cooled suspension of (rac)-[(2,3-difluoro-5-{[4-(4-fluoro-2-methoxyphenyl)-1,3,5-triazin-2-yl]amino}benzyl)(methyl)oxido-$\lambda^6$-sulfanylidene]cyanamide (134 mg; 0.30 mmol) in DCM (13 mL). The batch was stirred for 2 hours at room temperature before it was concentrated in vacuo. The residue was taken up in methanol (2.1 mL) and potassium carbonate (206 mg; 1.49 mmol) was added under stirring at room temperature. After 2 hours the batch was diluted with ethyl acetate and THF. The batch was washed with aqueous sodium chloride solution. The organic phase was filtered using a Whatman filter and concentrated in vacuo. The residue was purified by chromatography (DCM/EtOH 9:1) to give the desired product (68 mg; 0.16 mmol).

$^1$H NMR (400 MHz, CDCl$_3$, 300K) δ=8.78 (s, 1H), 8.49 (br, 1H), 8.08 (br, 1H), 7.69 (br, 1H), 7.18 (br, 1H), 6.78 (m, 2H), 4.46 (d, 1H), 4.38 (d, 1H), 3.94 (s, 3H), 3.03 (s, 3H).

Example 107

(rac)-[Ethyl(3-{[4-(4-(4-fluoro-2-methoxyphenyl)-1,3,5-triazin-2-yl]amino}benzyl)oxido-$\lambda^6$-sulfanylidene]cyanamide

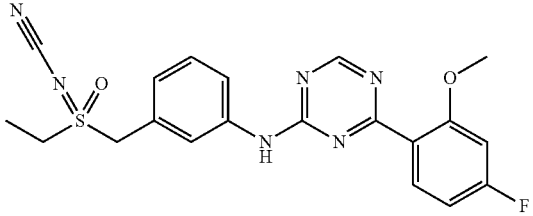 [SMILES: CCS(=O)(Cc1cccc(Nc2ncnc(-c3ccc(F)cc3OC)n2)c1)=NC#N]

Preparation of Intermediate 107.1

1-[(Ethylsulfanyl)methyl]-3-nitrobenzene

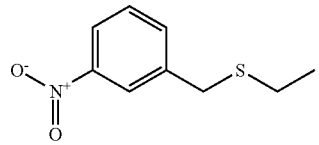

Intermediate 107.1 was prepared under similar conditions as described in the preparation of Intermediate 1.1 using 1-(chloromethyl)-3-nitrobenzene and sodium ethanethiolate.

$^1$H NMR (400 MHz, CDCl$_3$, 300K) δ=8.19 (m, 1H), 8.11 (m, 1H), 7.67 (m, 1H), 7.49 (m, 1H), 3.80 (s, 2H), 2.45 (q, 2H), 1.25 (tr, 3H).

Preparation of Intermediate 107.2

3-[(Ethylsulfanyl)methyl]aniline

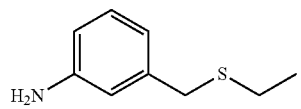

Intermediate 107.2 was prepared under similar conditions as described in the preparation of Intermediate 1.6 using 1-[(ethylsulfanyl)methyl]-3-nitrobenzene.

¹H NMR (400 MHz, CDCl₃, 300K) δ=7.09 (m, 1H), 6.68 (m, 2H), 6.57 (m, 1H), 3.63 (s, 2H), 3.42 (br, 2H), 2.45 (q, 2H), 1.23 (tr, 3H).

Preparation of Intermediate 107.3

4-Chloro-N-{3-[(ethylsulfanyl)methyl]phenyl}-1,3,5-triazin-2-amine

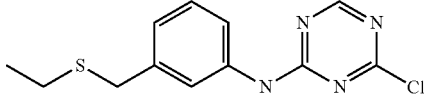 [SMILES: CCSCc1cccc(Nc2ncnc(Cl)n2)c1]

Intermediate 107.3 was prepared under similar conditions as described in the preparation of Intermediate 1.7 using 3-[(ethylsulfanyl)methyl]aniline.

| | |
|---|---|
| System: | Waters Acquity UPLC-MS: Binary Solvent Manager, Sample Manager/Organizer, Column Manager, PDA, ELSD, SQD |
| Column: | Acquity UPLC BEH C18 1.7 50 × 2.1 mm |
| Solvent: | A1 = H₂O + 0.1% Vol. HCOOH (99%) |
| | A2 = H₂O + 0.2% Vol. NH₃ (32%) |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 µl |
| Detection: | DAD scan range 210-400 nm -> Peaktable ELSD |
| Method: | MS ESI+, ESI– Switch |
| | A2 + B1 = C:\MassLynx\NH3_Mass_100_1000.olp |
| Retention | 1.22 min |
| MS(ES–): | m/z = 281 [M + H] |

Preparation of Intermediate 107.4

N-{3-[(Ethylsulfanyl)methyl]phenyl}-4-(4-fluoro-2-methoxyphenyl)-1,3,5-triazin-2-amine

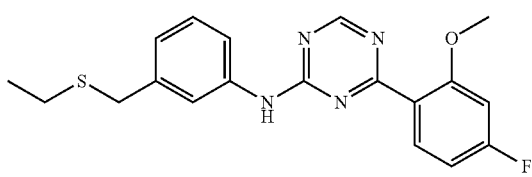 [SMILES: CCSCc1cccc(Nc2ncnc(-c3ccc(F)cc3OC)n2)c1]

Intermediate 107.4 was prepared under similar conditions as described in the preparation of Example 42 using crude 4-chloro-N-{3-[(ethylsulfanyl)methyl]phenyl}-1,3,5-triazin-2-amine and (4-fluoro-2-methoxyphenyl)boronic acid (Aldrich Chemical Company Inc.). The batch was purified by column chromatography (hexane/ethyl acetate 1:1) to give the desired product.

¹H NMR (400 MHz, CDCl₃, 300K) δ=8.80 (s, 1H), 7.98 (br, 1H), 7.62 (m, 2H), 7.46 (br, 1H), 7.31 (m, 1H), 7.08 (m, 1H), 6.76 (m, 2H), 3.93 (s, 3H), 3.73 (s, 2H), 2.46 (q, 2H), 1.23 (tr, 3H).

Preparation of Intermediate 107.5

(rac)-[Ethyl(3-{[4-(4-fluoro-2-methoxyphenyl)-1,3,5-triazin-2-yl]amino}benzyl-λ⁴-sulfanylidene]-cyanamide

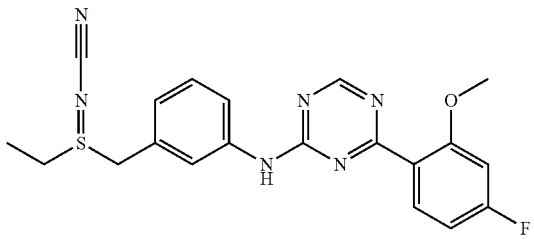 [SMILES: CCS(Cc1cccc(Nc2ncnc(-c3ccc(F)cc3OC)n2)c1)=NC#N]

Intermediate 107.5 was prepared under similar conditions as described in the preparation of Intermediate 105.7 using N-{3-[(ethylsulfanyl)methyl]phenyl}-4-(4-fluoro-2-methoxyphenyl)-1,3,5-triazin-2-amine.

¹H NMR (400 MHz, CDCl₃, 300K) δ=8.63 (s, 1H), 7.95 (m, 1H), 7.75 (m, 3H), 7.42 (m, 1H), 7.10 (m, 1H), 6.79 (m, 2H), 4.37 (d, 1H), 4.18 (d, 1H), 3.94 (s, 3H), 3.11 (m, 1H), 2.89 (m, 1H), 1.43 (tr, 3H).

Preparation of End Product:

Example 107 was prepared under similar conditions as described in the preparation of Example 105 using (rac)-[ethyl(3-{[4-(4-fluoro-2-methoxyphenyl)-1,3,5-triazin-2-yl]amino}benzyl-λ⁴-sulfanylidene]-cyanamide.

¹H NMR (400 MHz, CDCl₃, 300K) δ=8.85 (s, 1H), 7.95 (m, 2H), 7.75 (br, 1H), 7.66 (m, 1H), 7.45 (m, 1H), 7.18 (m, 1H), 6.79 (m, 2H), 4.60 (m, 2H), 3.94 (s, 3H), 3.16 (q, 2H), 1.44 (tr, 3H).

Example 108

(rac)-N-{3-[(S-ethylsulfonimidoyl)methyl]phenyl}-4-(4-fluoro-2-methoxyphenyl)-1,3,5-triazin-2-amine

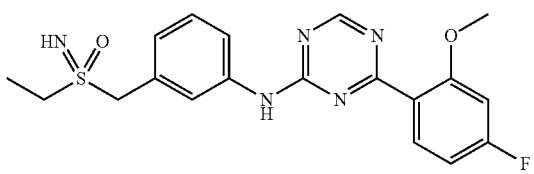 [SMILES: CCS(=N)(=O)Cc1cccc(Nc2ncnc(-c3ccc(F)cc3OC)n2)c1]

Example 108 was prepared under similar conditions as described in the preparation of Example 106 using (rac)-[ethyl(3-{[4-(4-fluoro-2-methoxyphenyl)-1,3,5-triazin-2-yl]amino}benzyl)oxido-λ⁶-sulfanylidene]cyanamide.

¹H NMR (400 MHz, CDCl₃, 300K) δ=8.81 (s, 1H), 7.96 (m, 1H), 7.78 (m, 2H), 7.41 (m, 2H), 7.16 (m, 1H), 6.78 (m, 2H), 4.33 (d, 1H), 4.18 (d, 1H), 3.94 (s, 3H), 3.04 (q, 2H), 1.43 (tr, 3H).

Example 109 and 110

Enantiomers of N-{3-[(S-ethylsulfonimidoyl)methyl]phenyl}-4-(4-fluoro-2-methoxyphenyl)-1,3,5-triazin-2-amine (rac)-N-{3-[(S-ethylsulfonimidoyl)methyl]phenyl}-4-(4-fluoro-2-methoxyphenyl)-1,3,5-triazin-2-amine was separated into the enantiomers by preparative HPLC:

| System: | Dionex: Pump P 580, Gilson: Liquid Handler 215, Knauer: UV-Detektor K-2501 |
|---|---|
| Column: | Chiralpak IC 5 µm 250 × 30 mm |
| Solvent: | Hexane/ethanol 70:30 (v/v) |
| Flow: | 50 mL/min |
| Temperature: | RT |
| Solution: | 205 mg/4.9 mL DCM/MeOH |
| Injektion: | 7 × 0.7 mL |
| Detection: | UV 280 nm |

| | Retention time in min | purity in % |
|---|---|---|
| Example 109 Enantiomer 1 | 17.8-19.2 | >99.9 |
| Example 110 Enantiomer 2 | 19.2-21.6 | 96.5 |

Enantiomer 1: $^1$H NMR (400 MHz, CDCl$_3$, 300K) δ=8.81 (s, 1H), 7.96 (m, 1H), 7.78 (m, 2H), 7.41 (m, 2H), 7.16 (m, 1H), 6.78 (m, 2H), 4.33 (d, 1H), 4.18 (d, 1H), 3.94 (s, 3H), 3.04 (q, 2H), 1.43 (tr, 3H).

Enantiomer 2: $^1$H NMR (400 MHz, CDCl$_3$, 300K) δ=8.81 (s, 1H), 7.96 (m, 1H), 7.78 (m, 2H), 7.41 (m, 2H), 7.16 (m, 1H), 6.78 (m, 2H), 4.33 (d, 1H), 4.18 (d, 1H), 3.94 (s, 3H), 3.04 (q, 2H), 1.43 (tr, 3H).

Example 111

(rac)-[(3-{[4-(4-Fluoro-2-methoxyphenyl)-1,3,5-triazin-2-yl]amino}-5-methylbenzyl)(methyl)oxido-λ$^6$-sulfanylidene]cyanamide

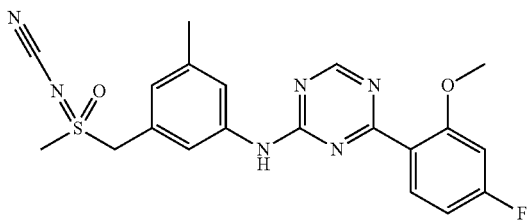 [SMILES: COc1cc(F)ccc1-c1ncnc(Nc2cc(C)cc(CS(C)(=O)=NC#N)c2)n1]

Preparation of Intermediate 111.1

3-(Chloromethyl)-5-methylaniline

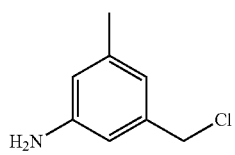

Thionylchloride (15.3 g; 128.5 mmol) was added dropwise under stirring to an ice-cooled solution of (3-amino-5-methylphenyl)methanol (6.3 g; 42.8 mmol; GLSyntech, LLC) in DCM (140 ml). The batch was stirred at room temperature for 18 hours before it was concentrated in vacuo. The residue was taken up in DCM and concentrated once more in vacuo to give the crude product that was used without further purification.

Preparation of Intermediate 111.2

3-Methyl-5-[(methylsulfanyl)methyl]aniline

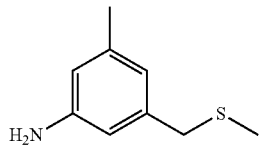

Intermediate 111.2 was prepared under similar conditions as described in the preparation of Intermediate 1.1 using crude 3-(chloromethyl)-5-methylaniline. The batch was purified by chromatography (hexane/ethyl acetate 6:4).

$^1$H NMR (400 MHz, d$_6$-DMSO, 300K) δ=6.26 (m, 1H), 6.21 (m, 2H), 3.43 (s, 2H), 2.07 (s, 3H), 1.89 (s, 3H).

Preparation of Intermediate 111.3

4-Chloro-N-{3-methyl-5-[(methylsulfanyl)methyl]phenyl}-1,3,5-triazin-2-amine

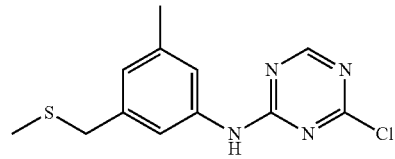 [SMILES: CSCc1cc(C)cc(Nc2ncnc(Cl)n2)c1]

Intermediate 111.3 was prepared under similar conditions as described in the preparation of Intermediate 1.7 using 3-methyl-5-[(methylsulfanyl)methyl]aniline. The crude product was purified by chromatography (hexane/ethylacetate 2:1) to give the desired product.

$^1$H NMR (400 MHz, d$_6$-DMSO, 300K) δ=10.63 (s, 1H), 8.59 (br, 1H), 7.37 (br, 1H), 7.30 (m, 1H), 6.87 (br, 1H), 3.60 (s, 2H), 2.25 (s, 3H), 1.95 (s, 3H).

Preparation of Intermediate 111.4

4-(4-Fluoro-2-methoxyphenyl)-N-{3-methyl-5-[(methylsulfanyl)methyl]phenyl}-1,3,5-triazin-2-amine

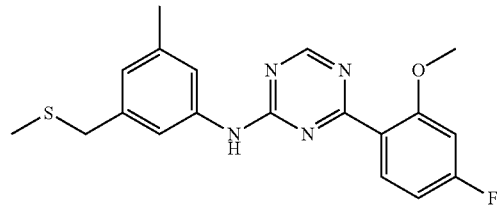 [SMILES: COc1cc(F)ccc1-c1ncnc(Nc2cc(C)cc(CSC)c2)n1]

Intermediate 111.4 was prepared under similar conditions as described in the preparation of Example 42 using 4-chloro-N-{3-methyl-5-[(methylsulfanyl)methyl]phenyl}-1,3,5-triazin-2-amine and (4-fluoro-2-methoxyphenyl)boronic acid (Aldrich Chemical Company Inc). The batch was purified by chromatography (hexane/ethyl acetate 1:1) to give the desired product.

$^1$H NMR (400 MHz, d$_6$-DMSO, 300K) δ=10.17 (s, 1H), 8.75 (s, 1H), 7.78 (br, 1H), 7.52 (m, 2H), 7.05 (m, 1H), 6.87 (m, 1H), 6.79 (m, 1H), 3.84 (s, 3H), 3.59 (s, 2H), 2.25 (s, 3H), 1.93 (s, 3H).

Preparation of Intermediate 111.5

(rac)-[(3-{[4-(4-Fluoro-2-methoxyphenyl)-1,3,5-triazin-2-yl]amino}-5-methylbenzyl)(methyl)-λ$^4$-sulfanylidene]cyanamide

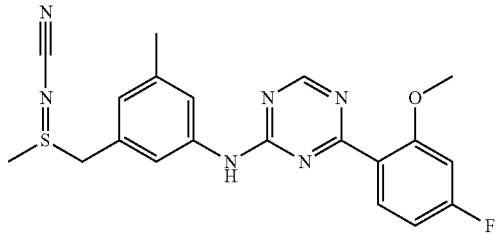 [SMILES: COc1cc(F)ccc1-c1ncnc(Nc2cc(C)cc(CS(C)=NC#N)c2)n1]

Intermediate 111.5 was prepared under similar conditions as described in the preparation of Example 105.7 using 4-(4-fluoro-2-methoxyphenyl)-N-{3-methyl-5-[(methylsulfanyl)methyl]phenyl}-1,3,5-triazin-2-amine. The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, d$_6$-DMSO, 300K) δ=10.32 (s, 1H), 8.77 (s, 1H), 7.68 (m, 3H), 7.07 (m, 1H), 6.87 (m, 2H), 4.39 (d, 1H), 4.20 (d, 1H), 3.84 (s, 3H), 2.81 (s, 3H), 2.29 (s, 3H).

Preparation of End Product:

Example 111 was prepared under similar conditions as described in the preparation of Example 105 using (rac)-[(3-{[4-(4-fluoro-2-methoxyphenyl)-1,3,5-triazin-2-yl]amino}-5-methylbenzyl)(methyl)-λ$^4$-sulfanylidene]cyanamide The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, d$_6$-DMSO, 300K) δ=10.34 (s, 1H), 8.77 (s, 1H), 7.76 (br, 2H), 7.62 (m, 1H), 7.07 (m, 1H), 6.96 (m, 1H), 6.87 (m, 1H), 4.89 (m, 2H), 3.83 (s, 3H), 3.34 (s, 3H), 2.30 (s, 3H).

Example 112

(rac)-2-({5-Fluoro-2-[4-({3-[(S-methylsulfonimidoyl)methyl]phenyl}amino)-1,3,5-triazin-2-yl]phenoxy}methyl)prop-2-en-1-ol

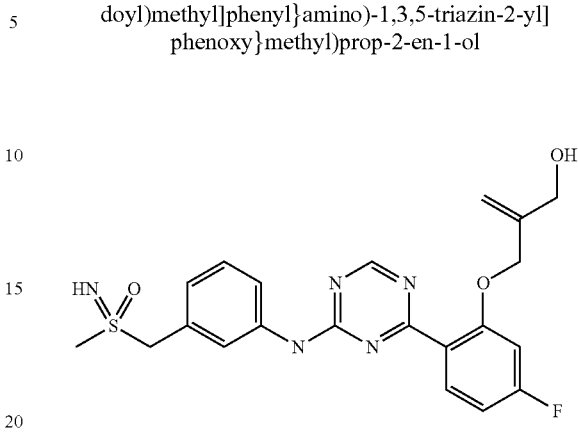

Example 112 was prepared under similar conditions as described in the preparation of Example 65 using (rac)-ethyl [(3-{[4-(2,4-difluorophenyl)-1,3,5-triazin-2-yl]amino})benzyl)(methyl)oxido-λ$^6$-sulfanylidene]carbamate and 2-methylidenepropane-1,3-diol (Aldrich Chemical Company Inc.).

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H$_2$O + 0.2% Vol. NH$_3$ (32%) |
| | B = Acetonitrile |
| Gradient: | 0-8 min 20-30% B |
| Flow: | 50 mL/min |
| Temperature: | RT |
| Solution: | 40 mg/1.5 mL DMSO/MeOH 1:1 |
| Injektion: | 3 × 0.5 mL |
| Detection: | DAD scan range 210-400 nm |
| | MS ESI+, ESI−, scan range 160-1000 m/z |
| | ELSD |
| Retention: | 7.2-7.8 min |

$^1$H NMR (400 MHz, CDCl$_3$, 300K) δ=8.77 (s, 1H), 8.53 (br, 1H), 8.36 (br, 1H), 7.81 (s, 1H), 7.64 (m, 1H), 7.42 (m, 1H), 7.18 (m, 1H), 6.83 (m, 1H), 6.76 (m, 1H), 5.29 (m, 2H), 4.78 (s, 2H), 4.40 (m, 3H), 4.28 (m, 1H), 2.97 (s, 3H).

Example 113

(rac)-[Cyclopropyl(3-{[4-(4-fluoro-2-methoxyphenyl)-1,3,5-triazin-2-yl]amino}benzyl)oxido-λ$^6$-sulfanylidene]cyanamide

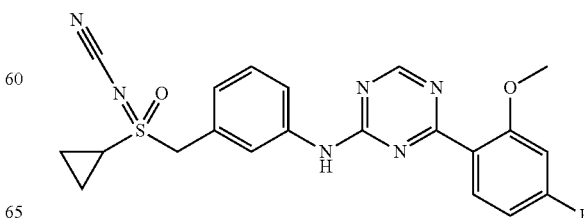

Preparation of Intermediate 113.1

1-[(Cyclopropylsulfanyl)methyl]-3-nitrobenzene

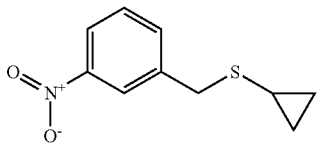 [SMILES: O=[N+]([O-])c1cccc(CSC2CC2)c1]

Sulfur (3.63 g; 25.0 mmol) was added portions wise to a stirred 0.5 M solution of bromo(cyclopropyl)magnesium in THF (50.0 ml; 25.0 mmol). The batch was stirred at 50° C. for 1 hour and then cooled to 0° C. Lithium tetrahydridoaluminate(1−) (522 mg; 13.8 mmol) was cautiously added under stirring. The batch was stirred for 30 minutes at 50° C. and cooled to 0° C. again. Water (2 ml) was cautiously added under stirring. Finally, sulfuric acid (5%; 100 ml) was cautiously added and the batch was stirred for 10 minutes. The organic phase was separated and the aqueous phase was extracted with diethyl ether (2×). The combined organic phases were washed with saturated aqueous ammonium chloride solution (2×), aqueous sodium bicarbonate solution (5%, 2×), water (2×) and saturated aqueous sodium chloride solution (2×). The organic phase was dried ($Na_2SO_4$) and filtered before it was slowly added to a stirred batch of 1-(chloromethyl)-3-nitrobenzene (2.15 g; 12.5 mmol) and potassium carbonate (2.59 g; 18.8 mmol) in DMF (40 ml). The batch was stirred at 85° C. over night. After cooling, the batch was filtered over celite and concentrated in vacuo. The residue was taken up in ethyl acetate and washed with water (2×) and saturated aqueous sodium chloride solution (2×). The organic phase was dried ($Na_2SO_4$), filtered and concentrated. The residue was purified by chromatography (hexane/ethyl acetate 8:2) to give the desired product (2.38 g; 11.4 mmol).

$^1$H NMR (400 MHz, $d_6$-DMSO, 300K) δ=8.16 (m, 1H), 8.06 (m, 1H), 7.75 (m, 1H), 7.56 (m, 1H), 3.90 (s, 2H), 1.72 (m, 1H), 0.77 (m, 2H), 0.39 (m, 2H).

Preparation of Intermediate 113.2

3-[(Cyclopropylsulfanyl)methyl]aniline

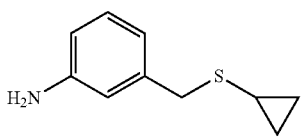 [SMILES: Nc1cccc(CSC2CC2)c1]

Intermediate 113.2 was prepared under similar conditions as described in the preparation of Intermediate 1.6 using 1-[(cyclopropylsulfanyl)methyl]-3-nitrobenzene. The batch was purified by chromatography.

$^1$H NMR (400 MHz, $d_6$-DMSO, 300K) δ=6.89 (m, 1H), 6.49 (m, 1H), 6.38 (m, 2H), 4.96 (s, 2H), 3.56 (s, 2H), 1.75 (m, 1H), 0.78 (m, 2H), 0.42 (m, 2H).

Preparation of Intermediate 113.3

4-Chloro-N-{3-[(cyclopropylsulfanyl)methyl]phenyl}-1,3,5-triazin-2-amine

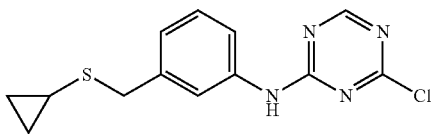 [SMILES: Clc1ncnc(Nc2cccc(CSC3CC3)c2)n1]

Intermediate 113.3 was prepared under similar conditions as described in the preparation of Intermediate 1.7 using 3-[(cyclopropylsulfanyl)methyl]aniline. The crude product was purified by chromatography (hexane/ethylacetate 4:1) to give the desired product.

$^1$H NMR (400 MHz, $d_6$-DMSO, 300K) δ=10.69 (s, 1H), 8.59 (br, 1H), 7.59 (br, 1H), 7.48 (m, 1H), 7.27 (m, 1H), 7.05 (m, 1H), 3.72 (s, 2H), 1.76 (m, 1H), 0.80 (m, 2H), 0.44 (m, 2H).

Preparation of Intermediate 113.4

N-{3-[(Cyclopropylsulfanyl)methyl]phenyl}-4-(4-fluoro-2-methoxyphenyl)-1,3,5-triazin-2-amine

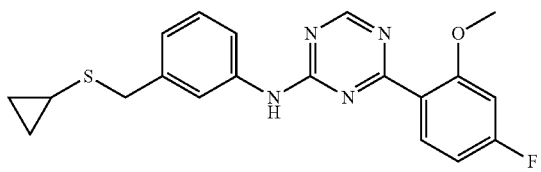 [SMILES: COc1cc(F)ccc1-c1ncnc(Nc2cccc(CSC3CC3)c2)n1]

Intermediate 113.4 was prepared under similar conditions as described in the preparation of Example 42 using 4-chloro-N-{3-[(cyclopropylsulfanyl)methyl]phenyl}-1,3,5-triazin-2-amine an d (4-fluoro-2-methoxyphenyl)boronic acid (Aldrich Chemical Company Inc). The batch was purified by chromatography (hexane/ethyl acetate 2:1) to give the desired product.

$^1$H NMR (400 MHz, $d_6$-DMSO, 300K) δ=10.24 (s, 1H), 8.75 (s, 1H), 7.75 (m, 3H), 7.25 (m, 1H), 7.07 (m, 1H), 6.99 (m, 1H), 6.86 (m, 1H), 3.84 (s, 3H), 3.72 (s, 2H), 1.74 (m, 1H), 0.75 (m, 2H), 0.42 (m, 2H).

Preparation of Intermediate 113.5

(rac)-[(3-{[4-(4-Fluoro-2-methoxyphenyl)-1,3,5-triazin-2-yl]amino}-5-methylbenzyl)(methyl)-$\lambda^4$-sulfanylidene]cyanamide

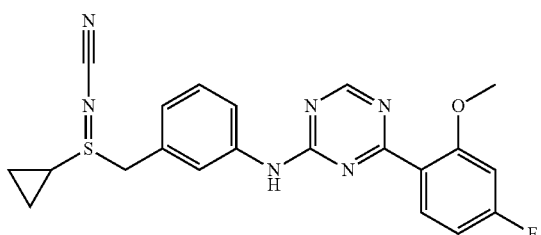

Intermediate 113.5 was prepared under similar conditions as described in the preparation of Example 105.7 using N-{3-[(cyclopropylsulfanyl)methyl]phenyl}-4-(4-fluoro-2-methoxyphenyl)-1,3,5-triazin-2-amine. The batch was purified by chromatography (ethyl acetate/methanol 9:1).

$^1$H NMR (400 MHz, d$_6$-DMSO, 300K) δ=10.38 (s, 1H), 8.78 (s, 11H), 7.63 (m, 3H), 7.37 (m, 1H), 7.14 (m, 1H), 7.06 (m 1H), 6.88 (m, 1H), 4.53 (d, 1H), 4.38 (d, 1H), 3.85 (s, 3H), 2.70 (m, 1H), 1.07 (m, 3H), 0.84 (m, 1H).

Preparation of End Product:

Example 113 was prepared under similar conditions as described in the preparation of Example 105 using (rac)-[(3-{[4-(4-fluoro-2-methoxyphenyl)-1,3,5-triazin-2-yl]amino}-5-methylbenzyl)(methyl)-?4-sulfanylidene]cyanamide The batch was purified by chromatography (gradient: ethyl acetate/hexanes 4:1→ethyl acetate).

$^1$H NMR (400 MHz, d$_6$-DMSO, 300K) δ=10.44 (s, 1H), 8.81 (s, 1H), 7.93 (m, 3H), 7.43 (m, 1H), 7.20 (m, 1H), 7.10 (m, 1H), 6.91 (m, 1H), 5.01 (m, 2H), 3.88 (br, 3H), 2.97 (m, 1H), 1.18 (m, 3H), 0.90 (m, 1H).

The following Table 1 provides an overview on the compounds of the invention:

TABLE 1

| Compound No. | Structure | Nomenclature |
|---|---|---|
| 1 | 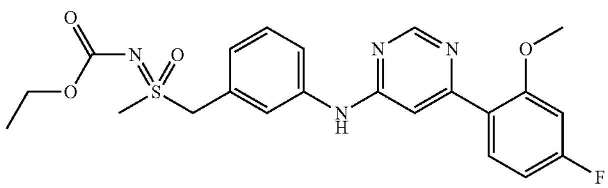 [SMILES: CCOC(=O)N=S(C)(=O)Cc1cccc(Nc2cc(-c3ccc(F)cc3OC)ncn2)c1] | (rac)-Ethyl [(3-{[4-(4-fluoro-2-methoxyphenyl)-1,3,5-triazin-2-yl]amino}benzyl)(methyl)oxido-λ$^6$-sulfanylidene]carbamate |
| 2 | 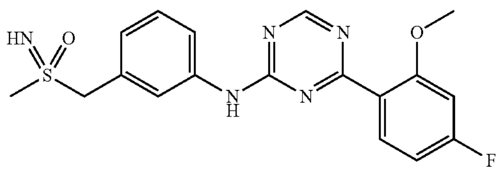 [SMILES: COc1cc(F)ccc1-c1ncnc(Nc2cccc(CS(C)(=N)=O)c2)n1] | (rac)-4-(4-Fluoro-2-methoxyphenyl)-N-{3-[(S-methylsulfonimidoyl)methyl]phenyl}-1,3,5-triazin-2-amine |
| 3 | 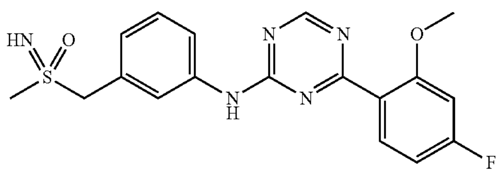 [SMILES: COc1cc(F)ccc1-c1ncnc(Nc2cccc(CS(C)(=N)=O)c2)n1] | (−)-4-(4-Fluoro-2-methoxyphenyl)-N-{3-[(S-methylsulfonimidoyl)methyl]phenyl}-1,3,5-triazin-2-amine; enantiomer 1 |
| 4 | 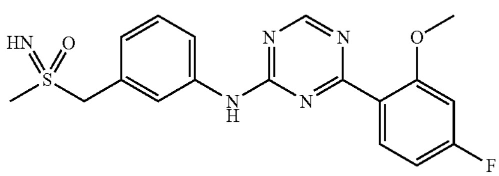 [SMILES: COc1cc(F)ccc1-c1ncnc(Nc2cccc(CS(C)(=N)=O)c2)n1] | (+)-4-(4-Fluoro-2-methoxyphenyl)-N-{3-[(S-methylsulfonimidoyl)methyl]phenyl}-1,3,5-triazin-2-amine; enantiomer 2 |
| 5 | 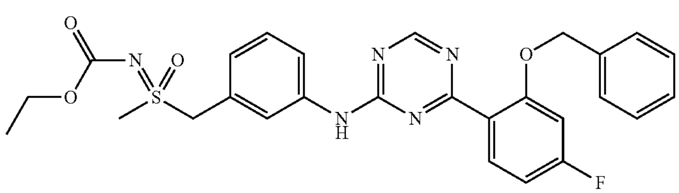 [SMILES: CCOC(=O)N=S(C)(=O)Cc1cccc(Nc2ncnc(-c3ccc(F)cc3OCc3ccccc3)n2)c1] | (rac)-Ethyl {[3-({4-[2-(benzyloxy)-4-fluorophenyl]-1,3,5-triazin-2-yl}amino)benzyl](methyl)oxido-λ$^6$-sulfanylidene}carbamate |
| 6 | 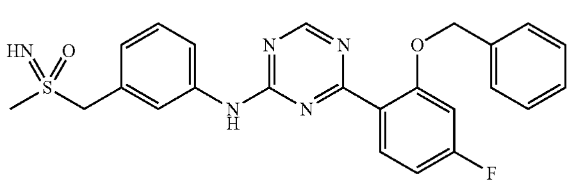 [SMILES: CS(=N)(=O)Cc1cccc(Nc2ncnc(-c3ccc(F)cc3OCc3ccccc3)n2)c1] | (rac)-4-[2-(Benzyloxy)-4-fluorophenyl]-N-{3-[(S-methylsulfonimidoyl)methyl]phenyl}-1,3,5-triazin-2-amine |
| 7 | 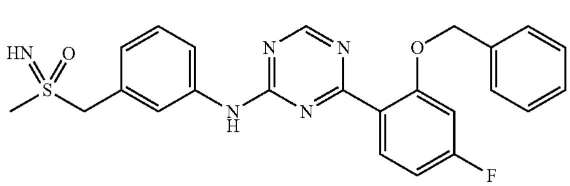 [SMILES: CS(=N)(=O)Cc1cccc(Nc2ncnc(-c3ccc(F)cc3OCc3ccccc3)n2)c1] | (−)-4-[2-(Benzyloxy)-4-fluorophenyl]-N-{3-[(S-methylsulfonimidoyl)methyl]phenyl}-1,3,5-triazin-2-amine; enantiomer 1 |

TABLE 1-continued

| Compound No. | Structure | Nomenclature |
|---|---|---|
| 8 | 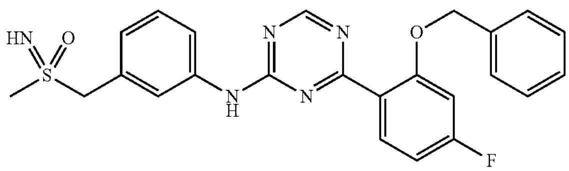 [SMILES: CS(=N)(=O)Cc1cccc(Nc2ncnc(-c3ccc(F)cc3OCc3ccccc3)n2)c1] | (+)-4-[2-(Benzyloxy)-4-fluorophenyl]-N-{3-[(S-methylsulfonimidoyl)methyl]phenyl}-1,3,5-triazin-2-amine; enantiomer 2 |
| 9 | 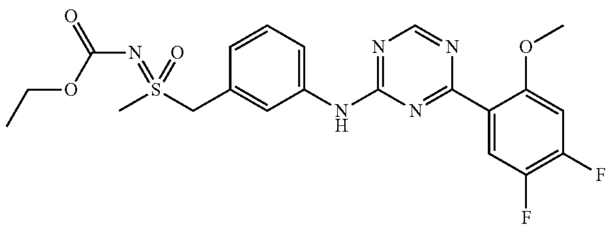 [SMILES: CCOC(=O)N=S(C)(=O)Cc1cccc(Nc2ncnc(-c3cc(F)c(F)cc3OC)n2)c1] | (rac)-Ethyl [(3-{[4-(4,5-difluoro-2-methoxyphenyl)-1,3,5-triazin-2-yl]amino}benzyl)(methyl)oxido-$\lambda^6$-sulfanylidene]carbamate |
| 10 | 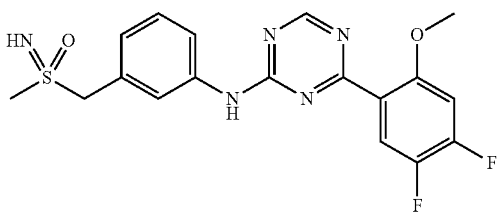 [SMILES: COc1cc(F)c(F)cc1-c1ncnc(Nc2cccc(CS(C)(=N)=O)c2)n1] | (rac)-4-(4,5-Difluoro-2-methoxyphenyl)-N-{3-[(S-methylsulfonimidoyl)methyl]phenyl}-1,3,5-triazin-2-amine |
| 11 | 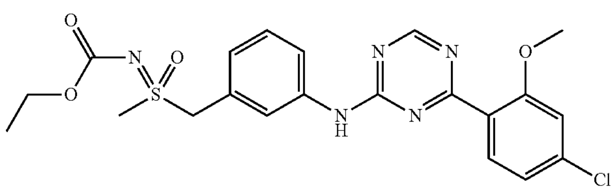 [SMILES: CCOC(=O)N=S(C)(=O)Cc1cccc(Nc2ncnc(-c3ccc(Cl)cc3OC)n2)c1] | (rac)-Ethyl [(3-{[4-(4-chloro-2-methoxyphenyl)-1,3,5-triazin-2-yl]amino}benzyl)(methyl)oxido-$\lambda^6$-sulfanylidene]carbamate |
| 12 | 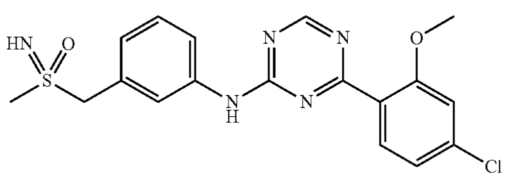 [SMILES: COc1cc(Cl)ccc1-c1ncnc(Nc2cccc(CS(C)(=N)=O)c2)n1] | (rac) 4-(4-Chloro-2-methoxyphenyl)-N-{3-[(S-methylsulfonimidoyl)methyl]phenyl}-1,3,5-triazin-2-amine |
| 13 | 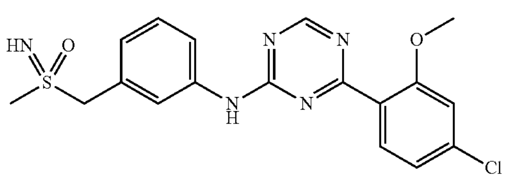 [SMILES: COc1cc(Cl)ccc1-c1ncnc(Nc2cccc(CS(C)(=N)=O)c2)n1] | 4-(4-Chloro-2-methoxyphenyl)-N-{3-[(S-methylsulfonimidoyl)methyl]phenyl}-1,3,5-triazin-2-amine; enantiomer 1 |
| 14 | 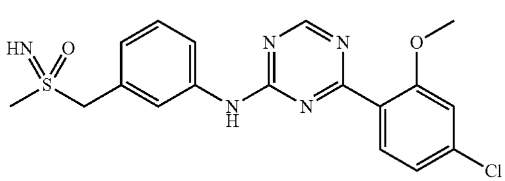 [SMILES: COc1cc(Cl)ccc1-c1ncnc(Nc2cccc(CS(C)(=N)=O)c2)n1] | 4-(4-Chloro-2-ethoxyphenyl)-N-{3-[(S-methylsulfonimidoyl)methyl]phenyl}-1,3,5-triazin-2-amine; enantiomer 2 |
| 15 | 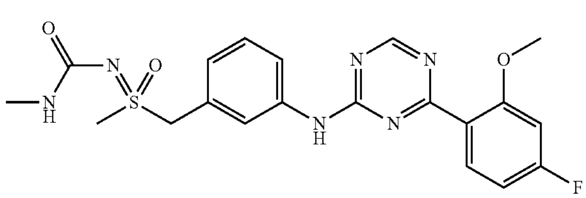 [SMILES: CNC(=O)N=S(C)(=O)Cc1cccc(Nc2ncnc(-c3ccc(F)cc3OC)n2)c1] | (rac)-1-[(3-{[4-(4-Fluoro-2-methoxyphenyl)-1,3,5-triazin-2-yl]amino}benzyl)(methyl)oxido-$\lambda 6$-sulfanylidene]-3-methylurea |

TABLE 1-continued

| Compound No. | Structure | Nomenclature |
|---|---|---|
| 16 | 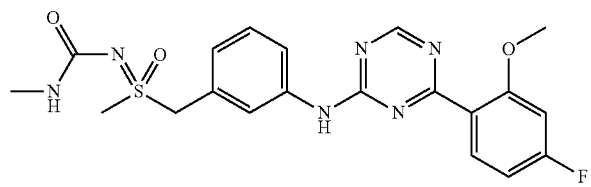 [SMILES: CNC(=O)N=S(C)(=O)Cc1cccc(Nc2ncnc(-c3ccc(F)cc3OC)n2)c1] | (−)-1-[(3-{[4-(4-Fluoro-2-methoxyphenyl)-1,3,5-triazin-2-yl]amino}benzyl)(methyl)oxido-λ6-sulfanylidene]-3-methylurea; enantiomer 1 |
| 17 | 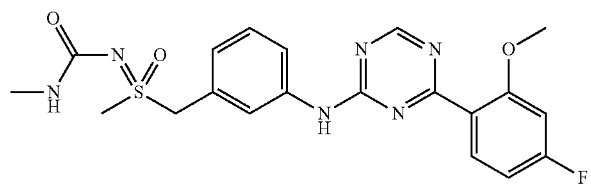 [SMILES: CNC(=O)N=S(C)(=O)Cc1cccc(Nc2ncnc(-c3ccc(F)cc3OC)n2)c1] | (+)-1-[(3-{[4-(4-Fluoro-2-methoxyphenyl)-1,3,5-triazin-2-yl]amino}benzyl)(methyl)oxido-λ6-sulfanylidene]-3-methylurea; enantiomer 2 |
| 18 | 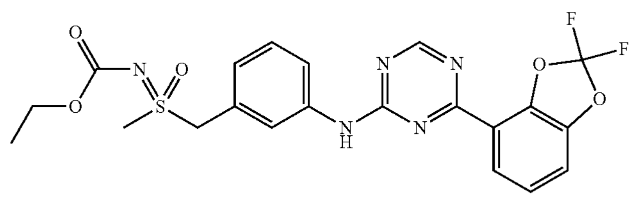 [SMILES: CCOC(=O)N=S(C)(=O)Cc1cccc(Nc2ncnc(-c3cccc4c3OC(F)(F)O4)n2)c1] | (rac)-Ethyl [(3-{[4-(2,2-difluoro-1,3-benzodioxol-4-yl)-1,3,5-triazin-2-yl]amino}benzyl)(methyl)oxido-λ$^6$-sulfanylidene]carbamate |
| 19 | 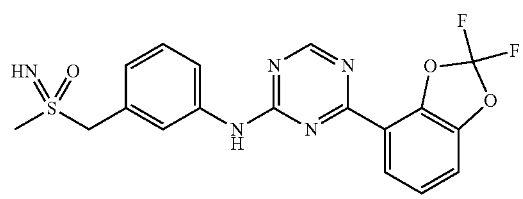 [SMILES: CS(=N)(=O)Cc1cccc(Nc2ncnc(-c3cccc4c3OC(F)(F)O4)n2)c1] | (rac)-4-(2,2-Difluoro-1,3-benzodioxol-4-yl)-N-{3-[(S-methylsulfonimidoyl)methyl]phenyl}-1,3,5-triazin-2-amine |
| 20 | 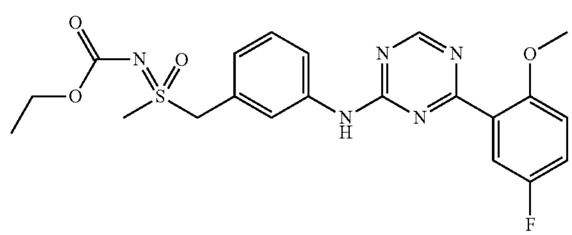 [SMILES: CCOC(=O)N=S(C)(=O)Cc1cccc(Nc2ncnc(-c3cc(F)ccc3OC)n2)c1] | (rac)-Ethyl [(3-{[4-(5-fluoro-2-methoxyphenyl)-1,3,5-triazin-2-yl]amino}benzyl)(methyl)oxido-λ$^6$-sulfanylidene]carbamate |
| 21 | 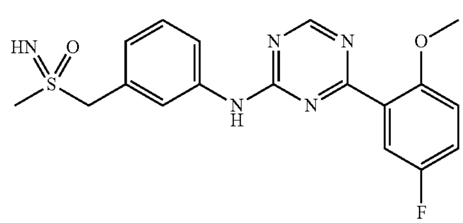 | (rac)-4-(5-Fluoro-2-methoxyphenyl)-N-{3-[(S-methylsulfonimidoyl)methyl]phenyl}-1,3,5-triazin-2-amine |
| 22 | 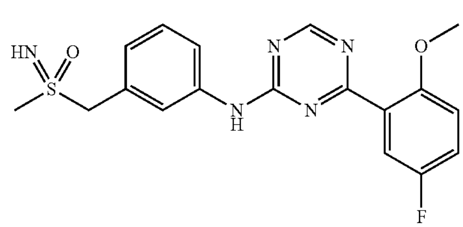 | 4-(5-Fluoro-2-methoxyphenyl)-N-{3-[(S-methylsulfonimidoyl)methyl]phenyl}-1,3,5-triazin-2-amine; enantiomer 1 |

TABLE 1-continued

| Compound No. | Structure | Nomenclature |
|---|---|---|
| 23 | 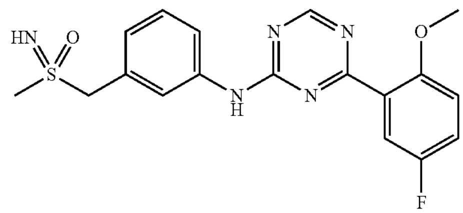 | 4-(5-Fluoro-2-methoxyphenyl)-N-{3-[(S-methylsulfonimidoyl)methyl]phenyl}-1,3,5-triazin-2-amine; enantiomer 2 |
| 24 | 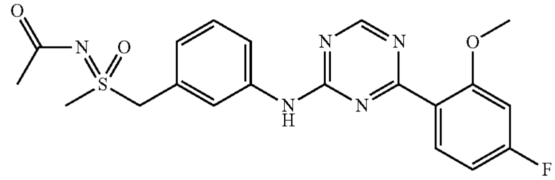 [SMILES: COc1cc(F)ccc1-c1ncnc(Nc2cccc(CS(C)(=O)=NC(C)=O)c2)n1] | (rac)-N-[(3-{[4-(4-fluoro-2-methoxyphenyl)-1,3,5-trazin-2-yl]amino}benzyl)(methyl)oxido-$\lambda^6$-sulfanylidene]acetamide |
| 25 | 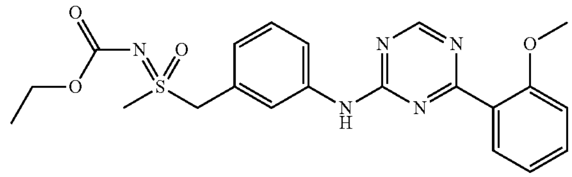 [SMILES: CCOC(=O)N=S(C)(=O)Cc1cccc(Nc2ncnc(-c3ccccc3OC)n2)c1] | (rac)-Ethyl [(3-{[4-(2-methoxyphenyl)-1,3,5-triazin-2-yl]amino}benzyl)(methyl)oxido-$\lambda^6$-sulfanylidene]carbamate |
| 26 | 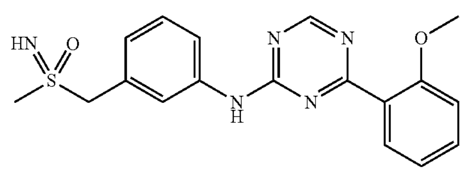 | (rac)-4-(2-Methoxyphenyl)-N-{3-[(S-methylsulfonimidoyl)methyl]phenyl}-1,3,5-triazin-2-amine |
| 27 | 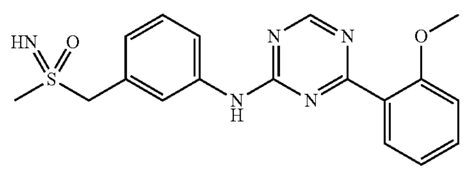 | 4-(2-Methoxyphenyl)-N-{3-[(S-methylsulfonimidoyl)methyl]phenyl}-1,3,5-triazin-2-amine; enantiomer 1 |
| 28 | 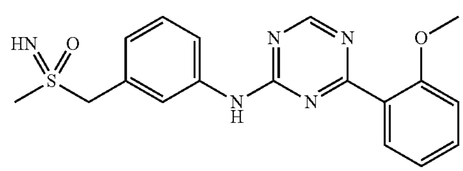 | 4-(2-Methoxyphenyl)-N-{3-[(S-methylsulfonimidoyl)methyl]phenyl}-1,3,5-triazin-2-amine; enantiomer 2 |
| 29 | 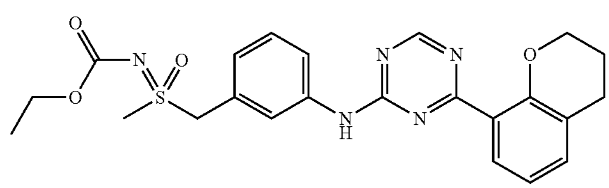 [SMILES: CCOC(=O)N=S(C)(=O)Cc1cccc(Nc2ncnc(-c3cccc4c3OCCC4)n2)c1] | (rac)-Ethyl [(3-{[4-(3,4-dihydro-2H-chromen-8-yl)-1,3,5-triazin-2-yl]amino}benzyl)(methyl)oxido-$\lambda^6$-sulfanylidene]carbamate |
| 30 | 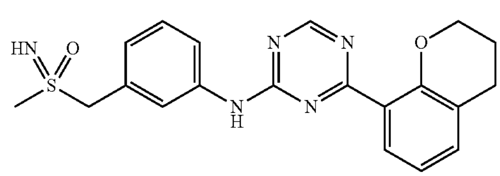 [SMILES: CS(=N)(=O)Cc1cccc(Nc2ncnc(-c3cccc4c3OCCC4)n2)c1] | (rac)-4-(3,4-Dihydro-2H-chromen-8-yl)-N-{3-[(S-methylsulfonimidoyl)methyl]phenyl}-1,3,5-triazin-2-amine |

TABLE 1-continued

| Compound No. | Structure | Nomenclature |
| --- | --- | --- |
| 31 | 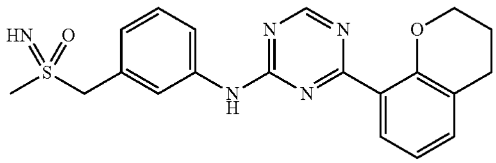 [SMILES: CS(=N)(=O)Cc1cccc(Nc2ncnc(-c3cccc4c3OCCC4)n2)c1] | 4-(3,4-Dihydro-2H-chromen-8-yl)-N-{3-[(S-methylsulfonimidoyl)methyl]phenyl}-1,3,5-triazin-2-amine; enantiomer 1 |
| 32 | 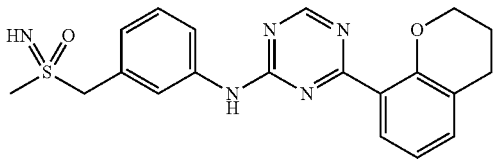 [SMILES: CS(=N)(=O)Cc1cccc(Nc2ncnc(-c3cccc4c3OCCC4)n2)c1] | 4-(3,4-Dihydro-2H-chromen-8-yl)-N-{3-[(S-methylsulfonimidoylmethyl]phenyl}-1,3,5-triazin-2-amine; enantiomer 2 |
| 33 | 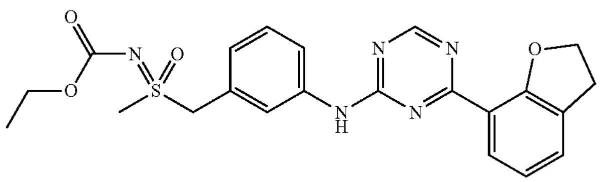 [SMILES: CCOC(=O)N=S(C)(=O)Cc1cccc(Nc2ncnc(-c3cccc4c3OCC4)n2)c1] | (rac)-Ethyl [(3-{[4-(2,3-dihydro-1-benzofuran-7-yl)-1,3,5-triazin-2-yl]amino}benzyl)(methyl)oxido-$\lambda^6$-sulfanylidene]carbamate |
| 34 | 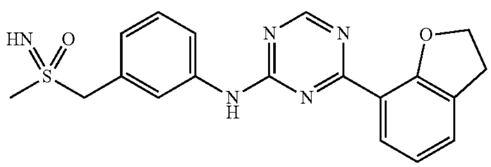 [SMILES: CS(=N)(=O)Cc1cccc(Nc2ncnc(-c3cccc4c3OCC4)n2)c1] | (rac)-4-(2,3-Dihydro-1-benzofuran-7-yl)-N-{3-[(S-methylsulfonimidoyl)methyl]phenyl}-1,3,5-triazin-2-amine |
| 35 | 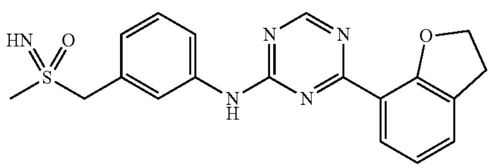 [SMILES: CS(=N)(=O)Cc1cccc(Nc2ncnc(-c3cccc4c3OCC4)n2)c1] | 4-(2,3-Dihydro-1-benzofuran-7-yl)-N-{3-[(S-methylsulfonimidoyl)methyl]phenyl}-1,3,5-triazin-2-amine; enantiomer 1 |
| 36 | 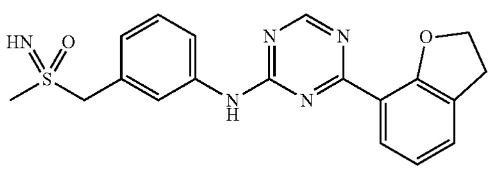 [SMILES: CS(=N)(=O)Cc1cccc(Nc2ncnc(-c3cccc4c3OCC4)n2)c1] | 4-(2,3-Dihydro-1-benzofuran-7-yl)-N-{3-[(S-methylsulfonimidoyl)methyl]phenyl}-1,3,5-triazin-2-amine; enantiomer 2 |
| 37 | 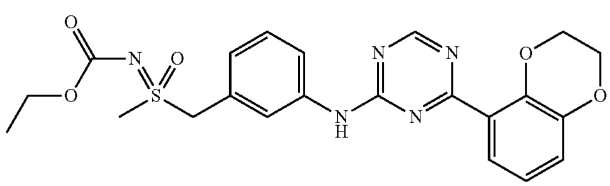 [SMILES: CCOC(=O)N=S(C)(=O)Cc1cccc(Nc2ncnc(-c3cccc4c3OCCO4)n2)c1] | (rac)-Ethyl [(3-{[4-(2,3-dihydro-1,4-benzodioxin-5-yl)-1,3,5-triazin-2-yl]amino}benzyl)(methyl)oxido-$\lambda^6$-sulfanylidene]carbamate |
| 38 | 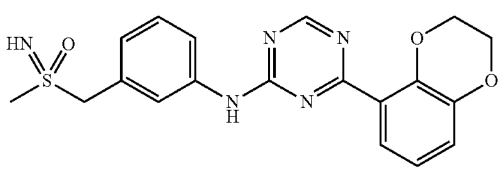 [SMILES: CS(=N)(=O)Cc1cccc(Nc2ncnc(-c3cccc4c3OCCO4)n2)c1] | (rac)-4-(2,3-Dihydro-1,4-benzodioxin-5-yl)-N-{3-[(S-methylsulfonimidoyl)methyl]phenyl}-1,3,5-triazin-2-amine |
| 39 | 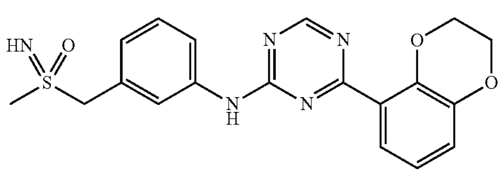 [SMILES: CS(=N)(=O)Cc1cccc(Nc2ncnc(-c3cccc4c3OCCO4)n2)c1] | 4-(2,3-Dihydro-1,4-benzodioxin-5-yl)-N-{3-[(S-methylsulfonimidoyl)methyl]phenyl}-1,3,5-triazin-2-amine; enantiomer 1 |

TABLE 1-continued

| Compound No. | Structure | Nomenclature |
|---|---|---|
| 40 | 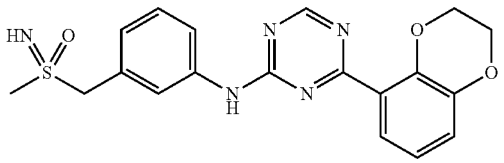 [SMILES: CS(=N)(=O)Cc1cccc(Nc2ncnc(-c3cccc4c3OCCO4)n2)c1] | 4-(2,3-Dihydro-1,4-benzodioxin-5-yl)-N-{3-[(S-methylsulfonimidoyl)methyl]phenyl}-1,3,5-triazin-2-amine; enantiomer 2 |
| 41 | 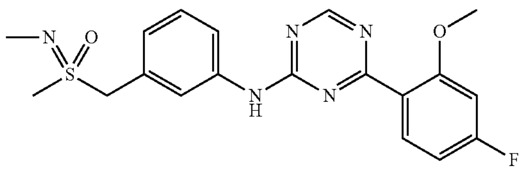 [SMILES: CN=S(C)(=O)Cc1cccc(Nc2ncnc(-c3ccc(F)cc3OC)n2)c1] | (rac)-N-{3-[(N,S-Dimethylsulfonimidoyl)methyl]phenyl}-4-(4-fluoro-2-methoxyphenyl)-1,3,5-triazin-2-amine |
| 42 | 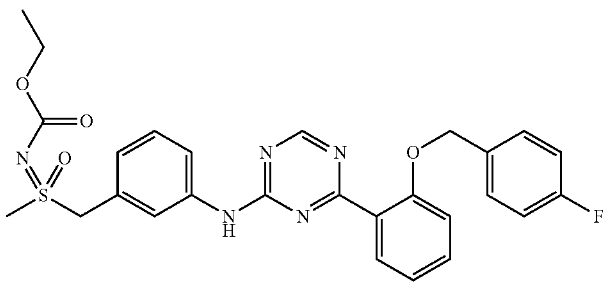 [SMILES: CCOC(=O)N=S(C)(=O)Cc1cccc(Nc2ncnc(-c3ccccc3OCc3ccc(F)cc3)n2)c1] | (rac)-Ethyl [{3-[(4-{2-[(4-fluorobenzyl)oxy]phenyl}-1,3,5-triazin-2-yl)amino]benzyl}(methyl)oxido-$\lambda^6$-sulfanylidene]carbamate |
| 43 | 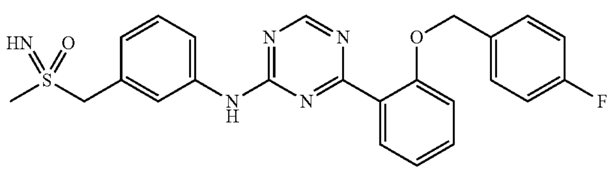 [SMILES: CS(=N)(=O)Cc1cccc(Nc2ncnc(-c3ccccc3OCc3ccc(F)cc3)n2)c1] | (rac)-4-{2-[(4-Fluorobenzyl)oxy]phenyl}-N-{3-[(S-methylsulfonimidoyl)methyl]phenyl}-1,3,5-triazin-2-amine |
| 44 | 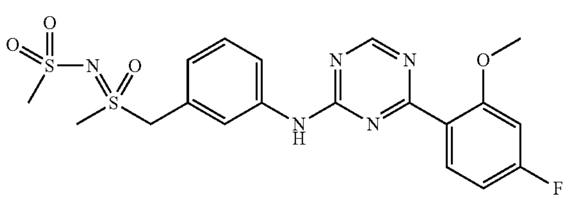 [SMILES: COc1cc(F)ccc1-c1ncnc(Nc2cccc(CS(C)(=O)=NS(C)(=O)=O)c2)n1] | (rac)-N-[(3-{[4-(4-Fluoro-2-methoxyphenyl)-1,3,5-triazin-2-yl]amino}benzyl)(methyl)oxido-$\lambda^6$-sulfanylidene]methanesulfonamide |
| 45 | 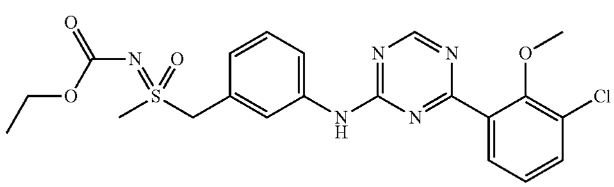 [SMILES: CCOC(=O)N=S(C)(=O)Cc1cccc(Nc2ncnc(-c3cccc(Cl)c3OC)n2)c1] | (rac)-Ethyl [(3-{[4-(3-chloro-2-methoxyphenyl)-1,3,5-triazin-2-yl]amino}benzyl)(methyl)oxido-$\lambda^6$-sulfanylidene]carbamate |
| 46 | 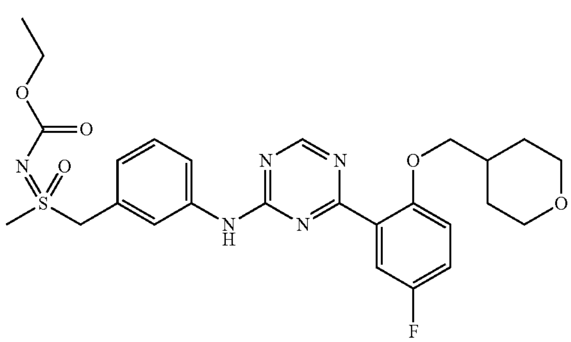 [SMILES: CCOC(=O)N=S(C)(=O)Cc1cccc(Nc2ncnc(-c3cc(F)ccc3OCC3CCOCC3)n2)c1] | (rac)-Ethyl {[3-({4-[5-fluoro-2-(tetrahydro-2H-pyran-4-ylmethoxy)phenyl]-1,3,5-triazin-2-yl}amino)benzyl](methyl)oxido-$\lambda^6$-sulfanylidene}carbamate |

TABLE 1-continued

| Compound No. | Structure | Nomenclature |
|---|---|---|
| 47 | 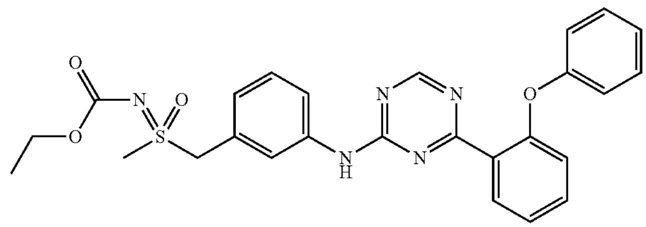 [SMILES: CCOC(=O)N=S(C)(=O)Cc1cccc(Nc2ncnc(-c3ccccc3Oc3ccccc3)n2)c1] | (rac)-Ethyl [methyl(oxido)(3-{[4-(2-phenoxyphenyl)-1,3,5-triazin-2-yl]amino}benzyl)-$\lambda^6$-sulfanylidene]carbamate |
| 48 | 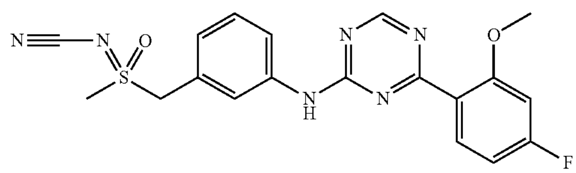 [SMILES: COc1cc(F)ccc1-c1ncnc(Nc2cccc(CS(C)(=O)=NC#N)c2)n1] | (rac)-[(3-{[4-(4-fluoro-2-methoxyphenyl)-1,3,5-triazin-2-yl]amino}benzyl)(methyl)oxido-$\lambda^6$-sulfanylidene]cyanamide |
| 49 | 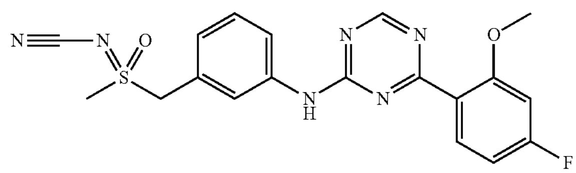 [SMILES: COc1cc(F)ccc1-c1ncnc(Nc2cccc(CS(C)(=O)=NC#N)c2)n1] | [(3-{[4-(4-fluoro-2-methoxyphenyl)-1,3,5-triazin-2-yl]amino}benzyl)(methyl)oxido-$\lambda^6$-sulfanylidene]cyanamide, enantiomer 1 |
| 50 | 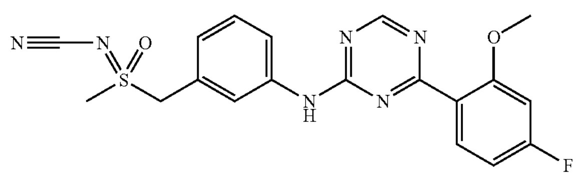 [SMILES: COc1cc(F)ccc1-c1ncnc(Nc2cccc(CS(C)(=O)=NC#N)c2)n1] | [(3-{[4-(4-fluoro-2-methoxyphenyl)-1,3,5-triazin-2-yl]amino}benzyl)(methyl)oxido-$\lambda^6$-sulfanylidene]cyanamide, enantiomer 2 |
| 51 | 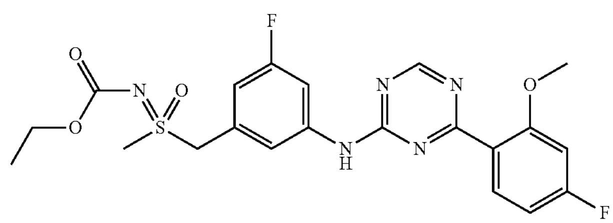 [SMILES: CCOC(=O)N=S(C)(=O)Cc1cc(F)cc(Nc2ncnc(-c3ccc(F)cc3OC)n2)c1] | (rac)-Ethyl [(3-fluoro-5-{[4-(4-fluoro-2-methoxyphenyl)-1,3,5-triazin-2-yl]amino}benzyl)(methyl)oxido-$\lambda^6$-sulfanylidene]carbamate |
| 52 | 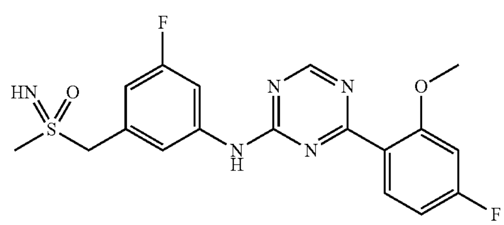 [SMILES: COc1cc(F)ccc1-c1ncnc(Nc2cc(F)cc(CS(C)(=N)=O)c2)n1] | (rac)-4-(4-Fluoro-2-methoxyphenyl)-N-{3-fluoro-5-[(S-methylsulfonimidoyl)methyl]phenyl}-1,3,5-triazin-2-amine |
| 53 | 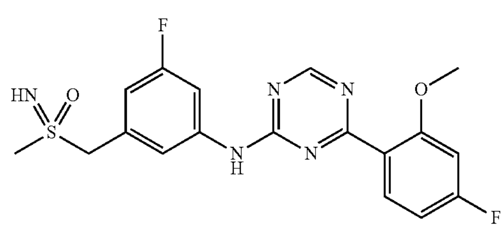 [SMILES: COc1cc(F)ccc1-c1ncnc(Nc2cc(F)cc(CS(C)(=N)=O)c2)n1] | 4-(4-Fluoro-2-methoxyphenyl)-N-{3-fluoro-5-[(S-methylsulfonimidoyl)methyl]phenyl}-1,3,5-triazin-2-amine; enantiomer 1 |

| Compound No. | Structure | Nomenclature |
|---|---|---|
| 54 | 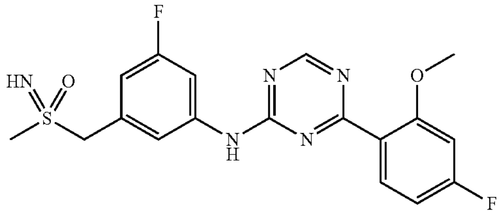 | 4-(4-Fluoro-2-methoxyphenyl)-N-{3-fluoro-5-[(S-methylsulfonimidoyl)methyl]phenyl}-1,3,5-triazin-2-amine; enantiomer 2 |
| 55 | 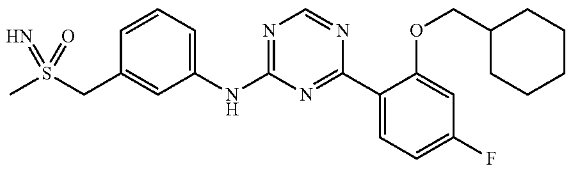 [SMILES: CS(=N)(=O)Cc1cccc(Nc2ncnc(-c3ccc(F)cc3OCC3CCCCC3)n2)c1] | (rac)-4-[2-(Cyclohexylmethoxy)-4-fluorophenyl]-N-{3-[(S-methylsulfonimidoyl)methyl]phenyl}-1,3,5-triazin-2-amine |
| 56 | 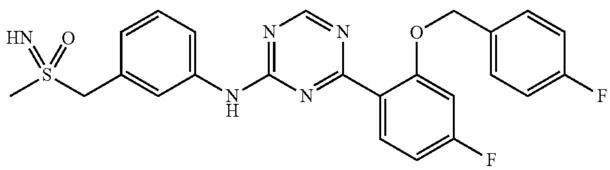 [SMILES: CS(=N)(=O)Cc1cccc(Nc2ncnc(-c3ccc(F)cc3OCc3ccc(F)cc3)n2)c1] | (rac)-4-{4-Fluoro-2-[(4-fluorobenzyl)oxy]phenyl}-N-{3-[(S-methylsulfonimidoyl)methyl]phenyl}-1,3,5-triazin-2-amine |
| 56.a | 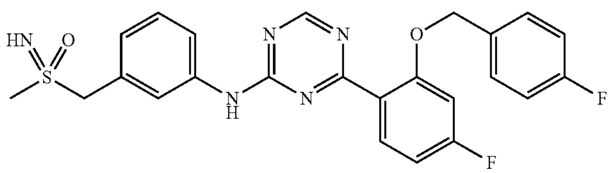 [SMILES: CS(=N)(=O)Cc1cccc(Nc2ncnc(-c3ccc(F)cc3OCc3ccc(F)cc3)n2)c1] | 4-{4-Fluoro-2-[(4-fluorobenzyl)oxy]phenyl}-N-{3-[(S-methylsulfonimidoyl)methyl]phenyl}-1,3,5-triazin-2-amine; enantiomer 1 |
| 56.b | 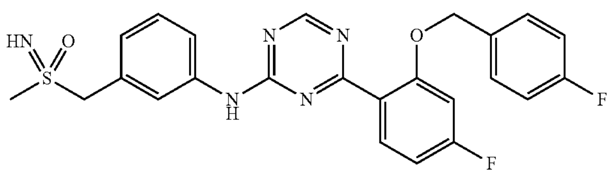 [SMILES: CS(=N)(=O)Cc1cccc(Nc2ncnc(-c3ccc(F)cc3OCc3ccc(F)cc3)n2)c1] | 4-{4-Fluoro-2-[(4-fluorobenzyl)oxy]phenyl}-N-{3-[(S-methylsulfonimidoyl)methyl]phenyl}-1,3,5-triazin-2-amine; enantiomer 2 |
| 57 | 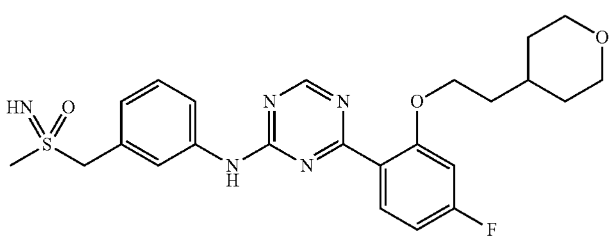 [SMILES: CS(=N)(=O)Cc1cccc(Nc2ncnc(-c3ccc(F)cc3OCCC3CCOCC3)n2)c1] | (rac)-4-{4-Fluoro-2-[2-(tetrahydro-2H-pyran-4-yl)ethoxy]phenyl}-N-{3-[(S-methylsulfonimidoyl)methyl]phenyl}-1,3,5-triazin-2-amine |
| 58 | 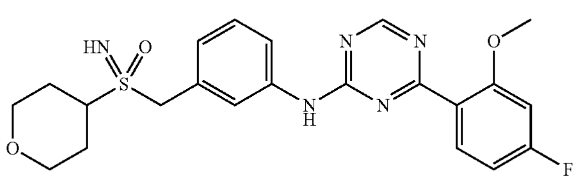 [SMILES: COc1cc(F)ccc1-c1ncnc(Nc2cccc(CS(=N)(=O)C3CCOCC3)c2)n1] | (rac)-4-(4-Fluoro-2-methoxyphenyl)-N-(3-{[S-(tetrahydro-2H-pyran-4-yl)sulfonimidoyl]methyl}phenyl)-1,3,5-triazin-2-amine |
| 59 | 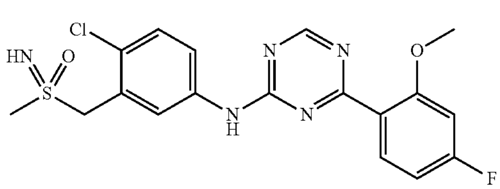 [SMILES: COc1cc(F)ccc1-c1ncnc(Nc2ccc(Cl)c(CS(C)(=N)=O)c2)n1] | (rac)-N-{4-Chloro-3-[(S-methylsulfonimidoyl)methyl]phenyl}-4-(4-fluoro-2-methoxyphenyl)-1,3,5-triazin-2-amine |

TABLE 1-continued

| Compound No. | Structure | Nomenclature |
| --- | --- | --- |
| 59.a | 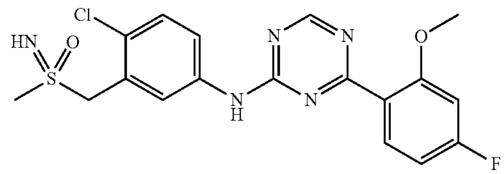 [SMILES: COc1cc(F)ccc1-c1ncnc(Nc2ccc(Cl)c(CS(C)(=N)=O)c2)n1] | N-{4-Chloro-3-[(S-methylsulfonimidoyl)methyl]phenyl}-4-(4-fluoro-2-methoxyphenyl)-1,3,5-triazin-2-amine; enantiomer 1 |
| 59.b | 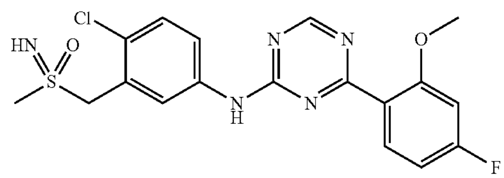 [SMILES: COc1cc(F)ccc1-c1ncnc(Nc2ccc(Cl)c(CS(C)(=N)=O)c2)n1] | N-{4-Chloro-3-[(S-methylsulfonimidoyl)methyl]phenyl}-4-(4-fluoro-2-methoxyphenyl)-1,3,5-triazin-2-amine; enantiomer 2 |
| 60 | 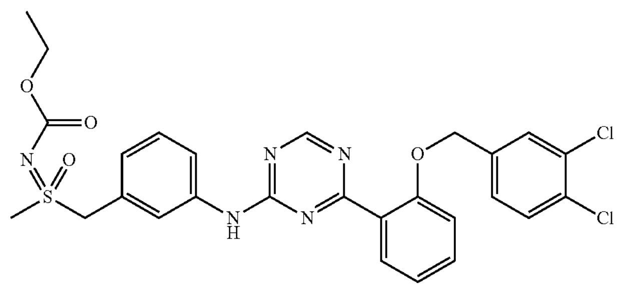 [SMILES: CCOC(=O)N=S(C)(=O)Cc1cccc(Nc2ncnc(-c3ccccc3OCc3ccc(Cl)c(Cl)c3)n2)c1] | (rac)-Ethyl [{3-[(4-{2-[(3,4-dichlorobenzyl)oxy]phenyl}-1,3,5-triazin-2-yl)amino]benzyl}(methyl)oxido-$\lambda^6$-sulfanylidene]carbamate |
| 61 | 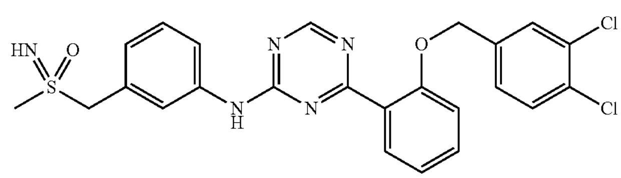 [SMILES: CS(=N)(=O)Cc1cccc(Nc2ncnc(-c3ccccc3OCc3ccc(Cl)c(Cl)c3)n2)c1] | (rac)-4-{2-[(3,4-Dichlorobenzyl)oxy]phenyl}-N-{3-[(S-methylsulfonimidoyl)methyl]phenyl}-1,3,5-triazin-2-amine |
| 62 | 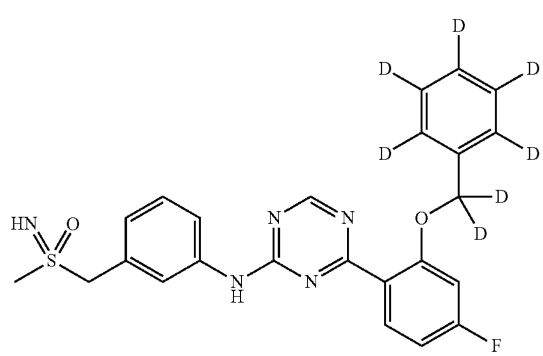 [SMILES: [2H]c1c([2H])c([2H])c(C([2H])([2H])Oc2cc(F)ccc2-c2ncnc(Nc3cccc(CS(C)(=N)=O)c3)n2)c([2H])c1[2H]] | (rac)-4-(4-Fluoro-2-{[($^2$H$_5$)phenyl($^2$H$_2$)methyl]oxy}phenyl)-N-{3-[(S-methylsulfonimidoyl)methyl]phenyl}-1,3,5-triazin-2-amine |
| 63 | 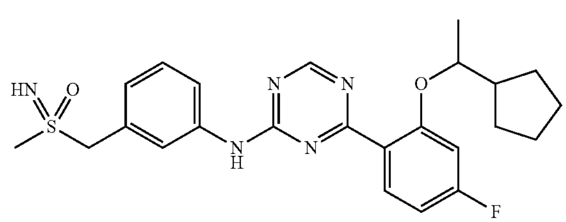 [SMILES: CC(Oc1cc(F)ccc1-c1ncnc(Nc2cccc(CS(C)(=N)=O)c2)n1)C1CCCC1] | 4-[2-(1-cyclopentylethoxy)-4-fluorophenyl]-N-{3-[(S-methylsulfonimidoyl)methyl]phenyl}-1,3,5-triazin-2-amine, mixture of all 4 stereoisomers |

TABLE 1-continued

| Compound No. | Structure | Nomenclature |
|---|---|---|
| 64 | 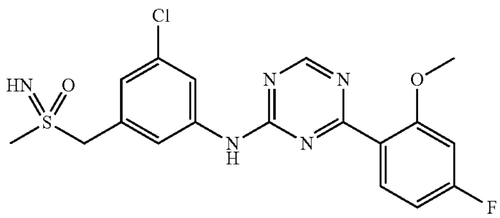 | (rac)-N-{3-Chloro-5-[(S-methylsulfonimidoyl)methyl]phenyl}-4-(4-fluoro-2-methoxyphenyl)-1,3,5-triazin-2-amine |
| 65 | 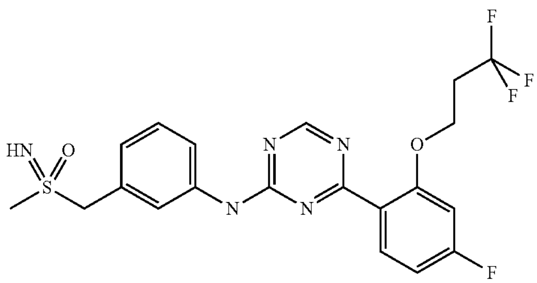 [SMILES: CS(=N)(=O)Cc1cccc(Nc2ncnc(-c3ccc(F)cc3OCCC(F)(F)F)n2)c1] | (rac)-4-[4-Fluoro-2-(3,3,3-trifluoropropoxy)phenyl]-N-{3-[(S-methylsulfonimidoyl)methyl]phenyl}-1,3,5-triazin-2-amine |
| 66 | 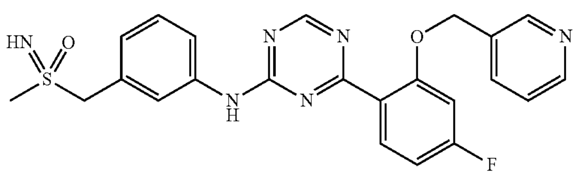 [SMILES: CS(=N)(=O)Cc1cccc(Nc2ncnc(-c3ccc(F)cc3OCc3cccnc3)n2)c1] | (rac)-4-[4-Fluoro-2-(pyridin-3-ylmethoxy)phenyl]-N-{3-[(S-methylsulfonimidoyl)methyl]phenyl}-1,3,5-triazin-2-amine |
| 67 | 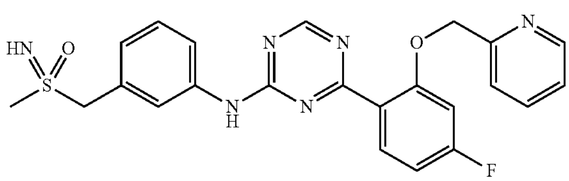 [SMILES: CS(=N)(=O)Cc1cccc(Nc2ncnc(-c3ccc(F)cc3OCc3ccccn3)n2)c1] | (rac)-4-[4-Fluoro-2-(pyridin-2-ylmethoxy)phenyl]-N-{3-[(S-methylsulfonimidoyl)methyl]phenyl}-1,3,5-triazin-2-amine |
| 68 | 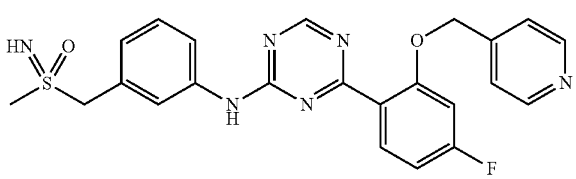 [SMILES: CS(=N)(=O)Cc1cccc(Nc2ncnc(-c3ccc(F)cc3OCc3ccncc3)n2)c1] | (rac)-4-[4-Fluoro-2-(pyridin-4-ylmethoxy)phenyl]-N-{3-[(S-methylsulfonimidoyl)methyl]phenyl}-1,3,5-triazin-2-amine |
| 69 | 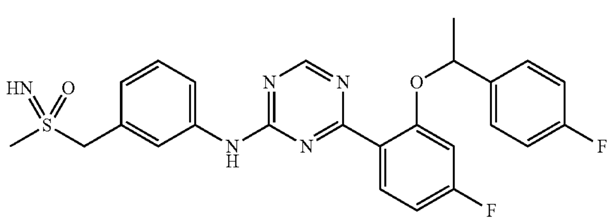 [SMILES: CC(Oc1cc(F)ccc1-c1ncnc(Nc2cccc(CS(C)(=N)=O)c2)n1)c1ccc(F)cc1] | 4-{4-Fluoro-2-[1-(4-fluorophenyl)ethoxy]phenyl}-N-{3-[(S-methylsulfonimidoyl)methyl]phenyl}-1,3,5-triazin-2-amine, mixture of 4 stereoisomers |
| 70 | 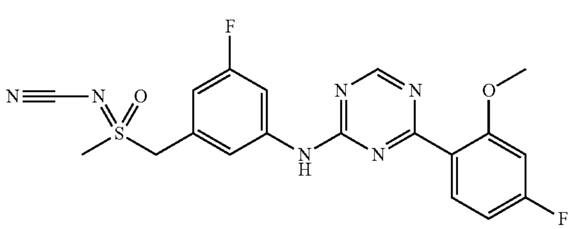 [SMILES: COc1cc(F)ccc1-c1ncnc(Nc2cc(F)cc(CS(C)(=O)=NC#N)c2)n1] | (rac)-[(3-Fluoro-5-{[4-(4-fluoro-2-methoxyphenyl)-1,3,5-triazin-2-yl]amino}benzyl)(methyl-$\lambda^6$-sulfanylidene]cyanamide |

TABLE 1-continued

| Compound No. | Structure | Nomenclature |
|---|---|---|
| 71 | 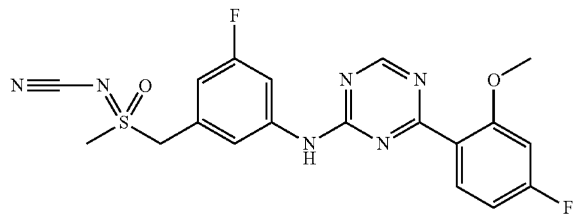 [SMILES: COc1cc(F)ccc1-c1ncnc(Nc2cc(F)cc(CS(C)(=O)=NC#N)c2)n1] | [(3-Fluoro-5-{[4-(4-fluoro-2-methoxyphenyl)-1,3,5-triazin-2-yl]amino}benzyl)(methyl-λ⁶-sulfanylidene]cyanamide; enantiomer 1 |
| 72 | 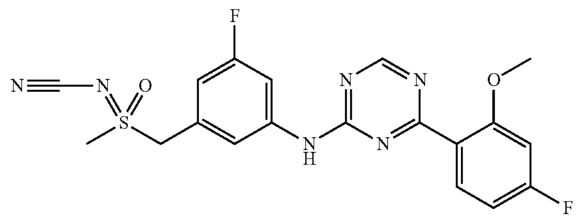 [SMILES: COc1cc(F)ccc1-c1ncnc(Nc2cc(F)cc(CS(C)(=O)=NC#N)c2)n1] | [(3-Fluoro-5-{[4-(4-fluoro-2-methoxyphenyl)-1,3,5-triazin-2-yl]amino}benzyl)(methyl-λ⁶-sulfanylidene]cyanamide; enantiomer 2 |
| 73 | 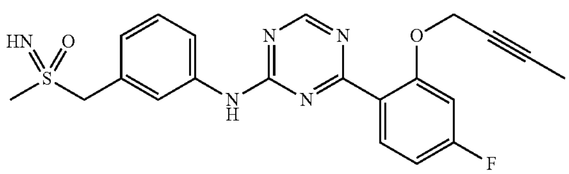 [SMILES: CC#CCOc1cc(F)ccc1-c1ncnc(Nc2cccc(CS(C)(=N)=O)c2)n1] | (rac)-4-[2-(But-2-yn-1-yloxy)-4-fluorophenyl]-N-{3-[(S-methylsulfonimidoyl)methyl]phenyl}-1,3,5-triazin-2-amine |
| 74 | 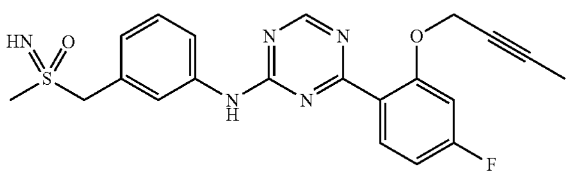 [SMILES: CC#CCOc1cc(F)ccc1-c1ncnc(Nc2cccc(CS(C)(=N)=O)c2)n1] | 4-[2-(But-2-yn-1-yloxy)-4-fluorophenyl]-N-{3-[(S-methylsulfonimidoyl)methyl]phenyl}-1,3,5-triazin-2-amine; enantiomer 1 |
| 75 | 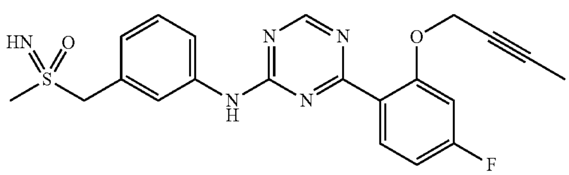 [SMILES: CC#CCOc1cc(F)ccc1-c1ncnc(Nc2cccc(CS(C)(=N)=O)c2)n1] | 4-[2-(But-2-yn-1-yloxy)-4-fluorophenyl]-N-{3-[(S-methylsulfonimidoyl)methyl]phenyl}-1,3,5-triazin-2-amine; enantiomer 2 |
| 76 | 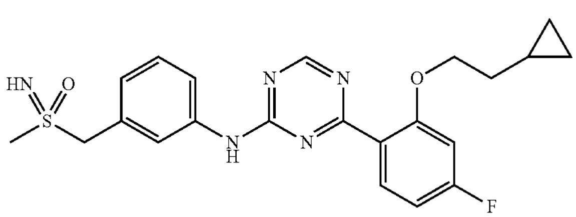 [SMILES: CS(=N)(=O)Cc1cccc(Nc2ncnc(-c3ccc(F)cc3OCCC3CC3)n2)c1] | (rac)-4-[2-(2-Cyclopropylethoxy)-4-fluorophenyl]-N-{3-[(S-methylsulfonimidoyl)methyl]phenyl}-1,3,5-triazin-2-amine |
| 77 | 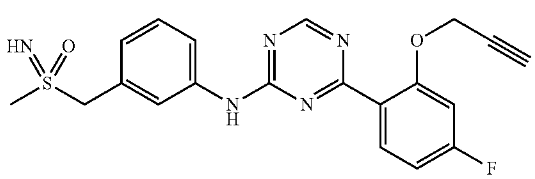 [SMILES: C#CCOc1cc(F)ccc1-c1ncnc(Nc2cccc(CS(C)(=N)=O)c2)n1] | (rac)-4-[4-Fluoro-2-(prop-2-yn-1-yloxy)phenyl]-N-{3-[(S-methylsulfonimidoyl)methyl]phenyl}-1,3,5-triazin-2-amine |
| 78 | 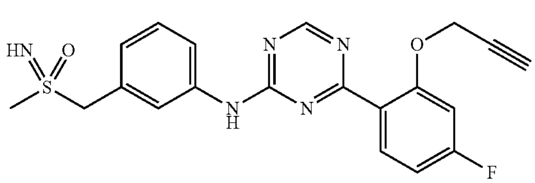 [SMILES: C#CCOc1cc(F)ccc1-c1ncnc(Nc2cccc(CS(C)(=N)=O)c2)n1] | 4-[4-Fluoro-2-(prop-2-yn-1-yloxy)phenyl]-N-{3-[(S-methylsulfonimidoyl)methyl]phenyl}-1,3,5-triazin-2-amine; enantiomer 1 |

TABLE 1-continued

| Compound No. | Structure | Nomenclature |
|---|---|---|
| 79 | 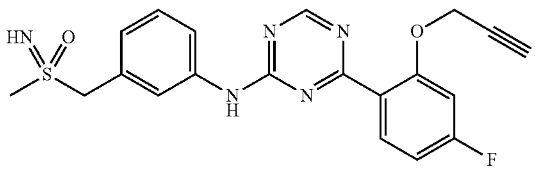 [SMILES: C#CCOc1cc(F)ccc1-c1ncnc(Nc2cccc(CS(C)(=N)=O)c2)n1] | 4-[4-Fluoro-2-(prop-2-yn-1-yloxy)phenyl]-N-{3-[(S-methylsulfonimidoyl)methyl]phenyl}-1,3,5-triazin-2-amine; enantiomer 2 |
| 80 | 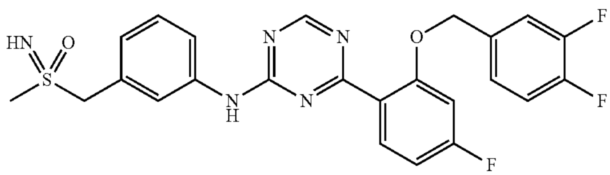 [SMILES: CS(=N)(=O)Cc1cccc(Nc2ncnc(-c3ccc(F)cc3OCc3ccc(F)c(F)c3)n2)c1] | (rac)-4-{2-[(3,4-Difluorobenzyl)oxy]-4-fluorophenyl}-N-{3-[(S-methylsulfonimidoyl)methyl]phenyl}-1,3,5-triazin-2-amine |
| 81 | 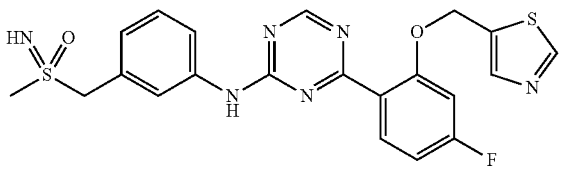 [SMILES: CS(=N)(=O)Cc1cccc(Nc2ncnc(-c3ccc(F)cc3OCc3cncs3)n2)c1] | (rac)-4-[4-Fluoro-2-(1,3-thiazol-5-ylmethoxy)phenyl]-N-{3-[(S-methylsulfonimidoyl)methyl]phenyl}-1,3,5-triazin-2-amine |
| 82 | 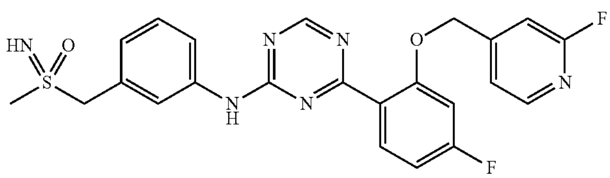 [SMILES: CS(=N)(=O)Cc1cccc(Nc2ncnc(-c3ccc(F)cc3OCc3ccnc(F)c3)n2)c1] | (rac)-4-{4-Fluoro-2-[(2-fluoropyridin-4-yl)methoxy]phenyl}-N-{3-[(S-methylsulfonimidoyl)methyl]phenyl}-1,3,5-triazin-2-amine |
| 83 | 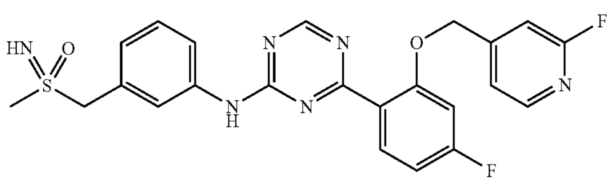 | 4-{4-Fluoro-2-[(2-fluoropyridin-4-yl)methoxy]phenyl}-N-{3-[(S-methylsulfonimidoyl)methyl]phenyl}-1,3,5-triazin-2-amine; enantiomer 1 |
| 84 | 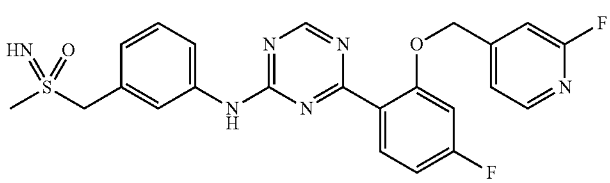 [SMILES: CS(=N)(=O)Cc1cccc(Nc2ncnc(-c3ccc(F)cc3OCc3ccnc(F)c3)n2)c1] | 4-{4-Fluoro-2-[(2-fluoropyridin-4-yl)methoxy]phenyl}-N-{3-[(S-methylsulfonimidoyl)methyl]phenyl}-1,3,5-triazin-2-amine; enantiomer 2 |
| 85 | 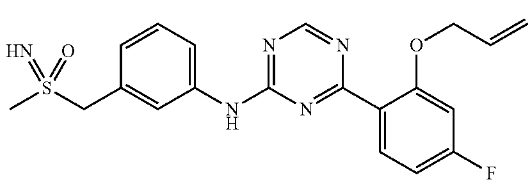 [SMILES: C=CCOc1cc(F)ccc1-c1ncnc(Nc2cccc(CS(C)(=N)=O)c2)n1] | (rac)-4-[4-Fluoro-2-(prop-2-en-1-yloxy)phenyl]-N-{3-[(S-methylsulfonimidoyl)methyl]phenyl}-1,3,5-triazin-2-amine |
| 86 | 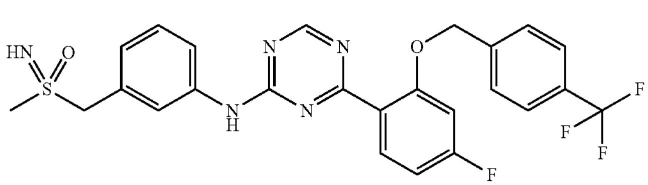 [SMILES: CS(=N)(=O)Cc1cccc(Nc2ncnc(-c3ccc(F)cc3OCc3ccc(C(F)(F)F)cc3)n2)c1] | (rac)-4-(4-Fluoro-2-{[4-(trifluoromethyl)benzyl]oxy}phenyl)-N-{3-[(S-methylsulfonimidoyl)methyl]phenyl}-1,3,5-triazin-2-amine |

TABLE 1-continued

| Compound No. | Structure | Nomenclature |
|---|---|---|
| 87 | 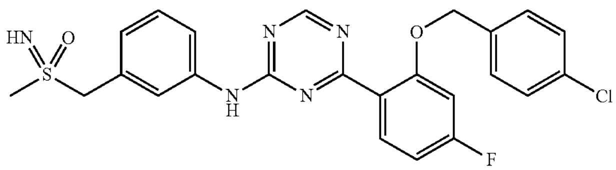 [SMILES: CS(=N)(=O)Cc1cccc(Nc2ncnc(-c3ccc(F)cc3OCc3ccc(Cl)cc3)n2)c1] | (rac)-4-{2-[(4-Chlorobenzyl)oxy]-4-fluorophenyl}-N-{3-[(S-methylsulfonimidoyl)methyl]phenyl}-1,3,5-triazin-2-amine |
| 88 | 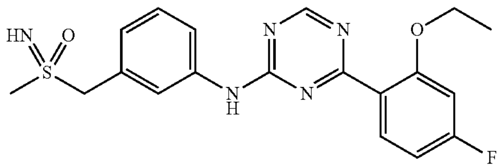 [SMILES: CCOc1cc(F)ccc1-c1ncnc(Nc2cccc(CS(C)(=N)=O)c2)n1] | (rac)-4-(2-Ethoxy-4-fluorophenyl)-N-{3-[(S-methylsulfonimidoyl)methyl]phenyl}-1,3,5-triazin-2-amine |
| 89 | 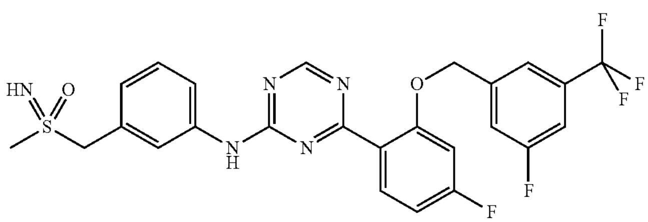 [SMILES: CS(=N)(=O)Cc1cccc(Nc2ncnc(-c3ccc(F)cc3OCc3cc(F)cc(C(F)(F)F)c3)n2)c1] | (rac)-4-(4-Fluoro 2-{[3-fluoro-5-(trifluoromethyl)benzyl]oxy}phenyl)-N-{3-[(S-methylsulfonimidoyl)methyl]phenyl}-1,3,5-triazin-2-amine |
| 90 | 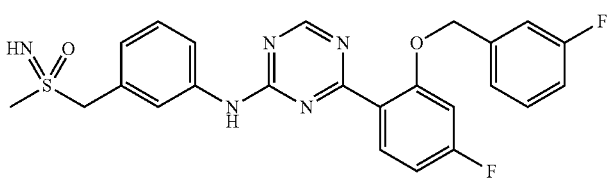 [SMILES: CS(=N)(=O)Cc1cccc(Nc2ncnc(-c3ccc(F)cc3OCc3cccc(F)c3)n2)c1] | (rac)-4-{4-Fluoro-2-[(3-fluorobenzyl)oxy]phenyl}-N-{3-[(S-methylsulfonimidoyl)methyl]phenyl}-1,3,5-triazin-2-amine |
| 91 | 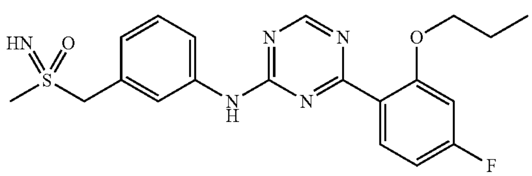 [SMILES: CCCOc1cc(F)ccc1-c1ncnc(Nc2cccc(CS(C)(=N)=O)c2)n1] | (rac)-4-(4-Fluoro-2-propoxyphenyl)-N-{3-[(S-methylsulfonimidoyl)methyl]phenyl}-1,3,5-triazin-2-amine |
| 92 | 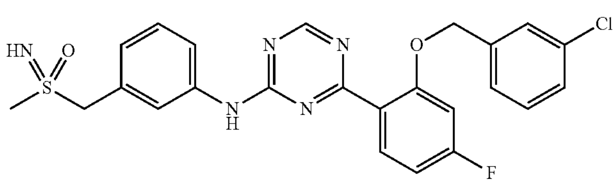 [SMILES: CS(=N)(=O)Cc1cccc(Nc2ncnc(-c3ccc(F)cc3OCc3cccc(Cl)c3)n2)c1] | (rac)-4-{2-[(3-Chlorobenzyl)oxy]-4-fluorophenyl}-N-{3-[(S-methylsulfonimidoyl)methyl]phenyl}-1,3,5-triazin-2-amine |
| 93 | 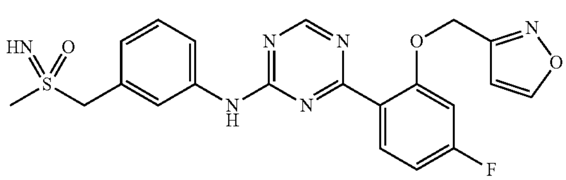 [SMILES: CS(=N)(=O)Cc1cccc(Nc2ncnc(-c3ccc(F)cc3OCc3ccon3)n2)c1] | (rac)-4-[4-Fluoro-2-(1,2-oxazol-3-ylmethoxy)phenyl]-N-{3-[(S-methylsulfonimidoyl)methyl]phenyl}-1,3,5-triazin-2-amine |
| 94 | 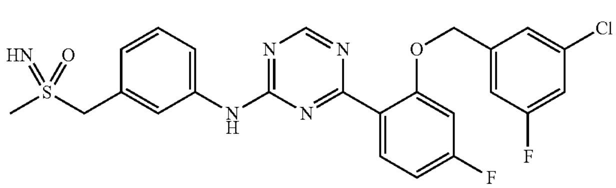 [SMILES: CS(=N)(=O)Cc1cccc(Nc2ncnc(-c3ccc(F)cc3OCc3cc(F)cc(Cl)c3)n2)c1] | (rac)-4-{2-[(3-Chloro-5-fluorobenzyl)oxy]-4-fluorophenyl}-N-{3-[(S-methylsulfonimidoyl)methyl]phenyl}-1,3,5-triazin-2-amine |

TABLE 1-continued

| Compound No. | Structure | Nomenclature |
|---|---|---|
| 95 | 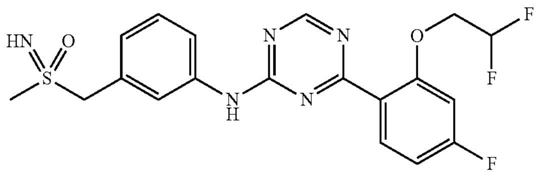 [SMILES: CS(=N)(=O)Cc1cccc(Nc2ncnc(-c3ccc(F)cc3OCC(F)F)n2)c1] | (rac)-4-[2-(2,2-Difluoroethoxy)-4-fluorophenyl]-N-{3-[(S-methylsulfonimidoyl)methyl]phenyl}-1,3,5-triazin-2-amine |
| 96 | 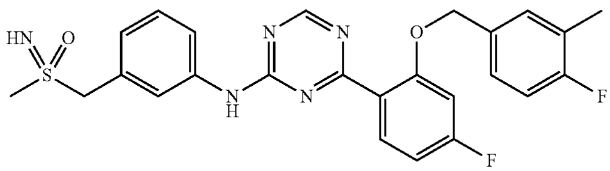 [SMILES: Cc1cc(COc2cc(F)ccc2-c2ncnc(Nc3cccc(CS(C)(=N)=O)c3)n2)ccc1F] | (rac)-4-{4-Fluoro-2-[(4-fluoro-3-methylbenzyl)oxy]phenyl}-N-{3-[(S-methylsulfonimidoyl)methyl]phenyl}-1,3,5-triazin-2-amine |
| 97 | 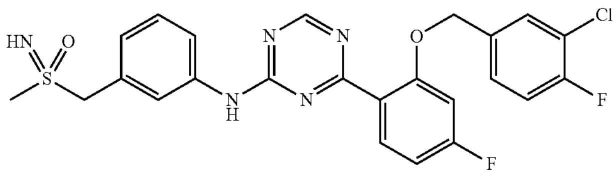 [SMILES: CS(=N)(=O)Cc1cccc(Nc2ncnc(-c3ccc(F)cc3OCc3ccc(F)c(Cl)c3)n2)c1] | (rac)-4-{2-[(3-Chloro-4-fluorobenzyl)oxy]-4-fluorophenyl}-N-{3-[(S-methylsulfonimidoyl)methyl]phenyl}-1,3,5-triazin-2-amine |
| 98 | 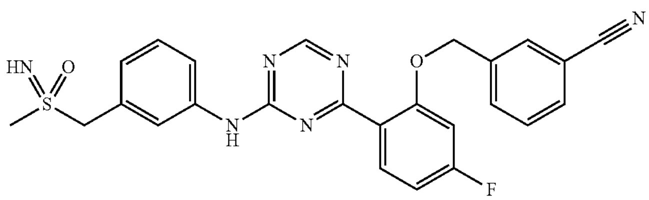 [SMILES: CS(=N)(=O)Cc1cccc(Nc2ncnc(-c3ccc(F)cc3OCc3cccc(C#N)c3)n2)c1] | (rac)-3-({5-Fluoro-2-[4-({3-[(S-methylsulfonimidoyl)methyl]phenyl}-amino)-1,3,5-triazin-2-yl]phenoxy}methyl)benzonitrile |
| 99 | 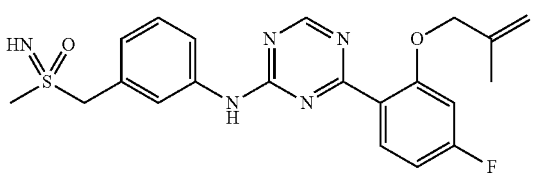 [SMILES: C=C(C)COc1cc(F)ccc1-c1ncnc(Nc2cccc(CS(C)(=N)=O)c2)n1] | (rac)-4-{4-Fluoro-2-[(2-methylprop-2-en-1-yl)oxy]phenyl}-N-{3-[(S-methylsulfonimidoyl)methyl]phenyl}-1,3,5-triazin-2-amine |
| 100 | 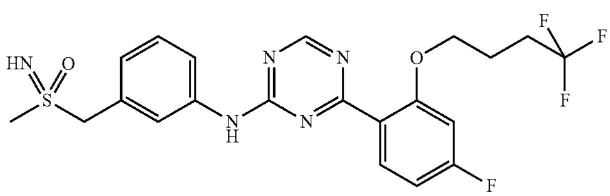 [SMILES: CS(=N)(=O)Cc1cccc(Nc2ncnc(-c3ccc(F)cc3OCCCC(F)(F)F)n2)c1] | (rac)-4-[4-Fluoro-2-(4,4,4-trifluorobutoxy)phenyl]-N-{3-[(S-methylsulfonimidoyl)methyl]phenyl}-1,3,5-triazin-2-amine |
| 101 | 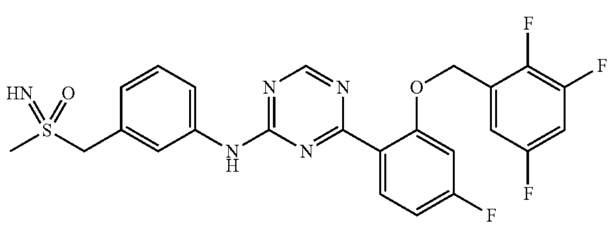 [SMILES: CS(=N)(=O)Cc1cccc(Nc2ncnc(-c3ccc(F)cc3OCc3cc(F)cc(F)c3F)n2)c1] | (rac)-4-{4-Fluoro-2-[(2,3,5-trifluorobenzyl)oxy]phenyl}-N-{3-[(S-methylsulfonimidoyl)methyl]phenyl}-1,3,5-triazin-2-amine |
| 102 | 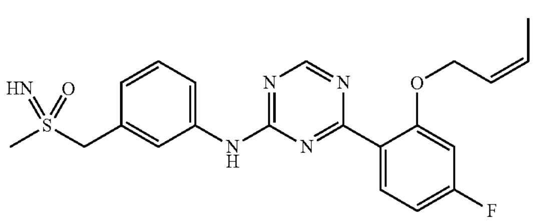 [SMILES: C/C=C\COc1cc(F)ccc1-c1ncnc(Nc2cccc(CS(C)(=N)=O)c2)n1] | (rac)-4-{2-[(2Z)-But-2-en-1-yloxy]-4-fluorophenyl}-N-{3-[(S-methylsulfonimidoyl)methyl]phenyl}-1,3,5-triazin-2-amine |

TABLE 1-continued

| Compound No. | Structure | Nomenclature |
|---|---|---|
| 103 | 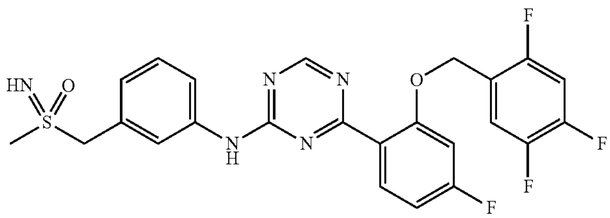 [SMILES: CS(=N)(=O)Cc1cccc(Nc2ncnc(-c3ccc(F)cc3OCc3cc(F)c(F)cc3F)n2)c1] | (rac)-4-{4-Fluoro-2-[(2,4,5-trifluorobenzyl)oxy]phenyl}-N-{3-[(S-methylsulfonimidoyl)methyl]phenyl}-1,3,5-triazin-2-amine |
| 104 | 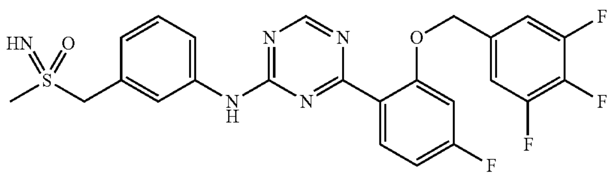 [SMILES: CS(=N)(=O)Cc1cccc(Nc2ncnc(-c3ccc(F)cc3OCc3cc(F)c(F)c(F)c3)n2)c1] | (rac)-4-{4-Fluoro-2-[(3,4,5-trifluorobenzyl)oxy]phenyl}-N-{3-[(S-methylsulfonimidoyl)methyl]phenyl}-1,3,5-triazin-2-amine |
| 105 | 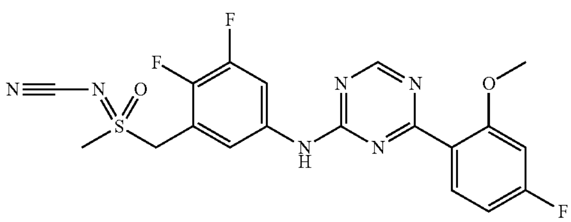 [SMILES: COc1cc(F)ccc1-c1ncnc(Nc2cc(F)c(F)c(CS(C)(=O)=NC#N)c2)n1] | (rac)-[(2,3-Difluoro-5-{[4-(4-fluoro-2-methoxyphenyl)-1,3,5-triazin-2-yl]amino}benzyl)(methyl)oxido-$\lambda^6$-sulfanylidene]cyanamide |
| 106 | 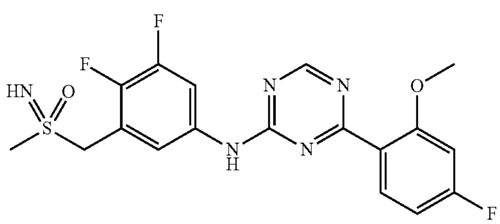 [SMILES: COc1cc(F)ccc1-c1ncnc(Nc2cc(F)c(F)c(CS(C)(=N)=O)c2)n1] | (rac)-N-{3,4-Difluoro-5-[(S-methylsulfonimidoyl)methyl]phenyl}-4-(4-fluoro-2-methoxyphenyl)-1,3,5-triazin-2-amine |
| 107 | 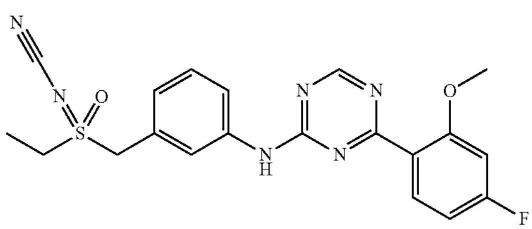 [SMILES: CCS(=O)(Cc1cccc(Nc2ncnc(-c3ccc(F)cc3OC)n2)c1)=NC#N] | (rac)-[Ethyl(3-{[4-(4-fluoro-2-methoxyphenyl)-1,3,5-triazin-2-yl]amino}benzyl)oxido-$\lambda^6$-sulfanylidene]cyanamide |
| 108 | 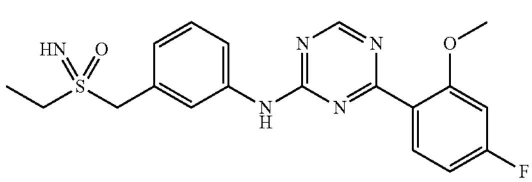 [SMILES: CCS(=N)(=O)Cc1cccc(Nc2ncnc(-c3ccc(F)cc3OC)n2)c1] | (rac)-N-{3-[(S-ethylsulfonimidoyl)methyl]phenyl}-4-(4-fluoro-2-methoxyphenyl)-1,3,5-triazin-2-amine |
| 109 | 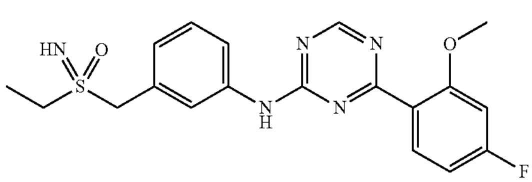 [SMILES: CCS(=N)(=O)Cc1cccc(Nc2ncnc(-c3ccc(F)cc3OC)n2)c1] | (rac)-N-{3-[(S-ethylsulfonimidoyl)methyl]phenyl}-4-(4-fluoro-2-methoxyphenyl)-1,3,5-triazin-2-amine; enantiomer 1 |

TABLE 1-continued

| Compound No. | Structure | Nomenclature |
|---|---|---|
| 110 | 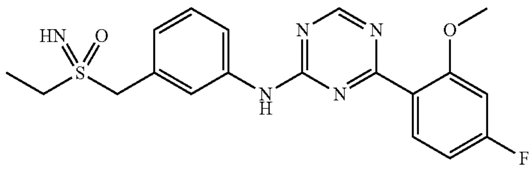 [SMILES: CCS(=N)(=O)Cc1cccc(Nc2ncnc(-c3ccc(F)cc3OC)n2)c1] | (rac)-N-{3-[(S-ethylsulfonimidoyl)methyl]phenyl}-4-(4-fluoro-2-methoxyphenyl)-1,3,5-triazin-2-amine; enantiomer 1 |
| 111 | 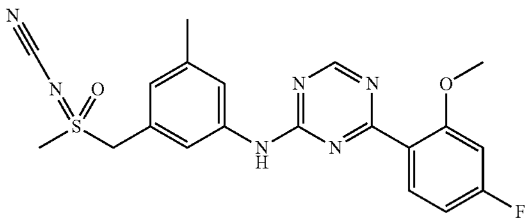 [SMILES: COc1cc(F)ccc1-c1ncnc(Nc2cc(C)cc(CS(C)(=O)=NC#N)c2)n1] | (rac)-[(3-{[4-(4-Fluoro-2-methoxyphenyl)-1,3,5-triazin-2-yl]amino}-5-methylbenzyl)(methyl)oxido-$\lambda^6$-sulfanylidene]cyanamide |
| 112 | 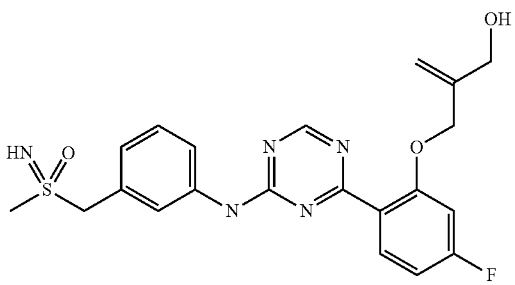 [SMILES: C=C(CO)COc1cc(F)ccc1-c1ncnc(Nc2cccc(CS(C)(=N)=O)c2)n1] | (rac)-2-({5-Fluoro-2-[4-({3-[(S-methylsulfonimidoyl)methyl]phenyl}amino)-1,3,5-triazin-2-yl]phenoxy}methyl)prop-2-en-1-ol |
| 113 | 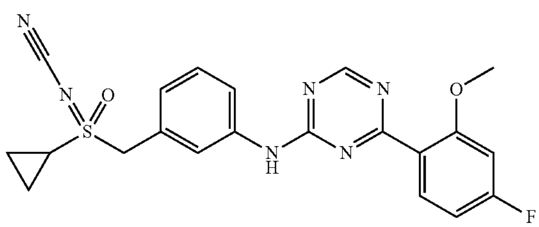 [SMILES: COc1cc(F)ccc1-c1ncnc(Nc2cccc(CS(=O)(=NC#N)C3CC3)c2)n1] | (rac)-[Cyclopropyl(3-{[4-(4-fluoro-2-methoxyphenyl)-1,3,5-triazin-2-yl]amino}benzyl)oxido-$\lambda^6$-sulfanylidene]cyanamide |

TABLE 2

Inhibition of CDK9 and CDK2 of compounds according to the present invention

| ① | Nomenclature | ② | ③ |
|---|---|---|---|
| 1 | (rac)-Ethyl [(3-{[4-(4-fluoro-2-methoxyphenyl)-1,3,5-triazin-2-yl]amino}benzyl)(methyl)oxido-$\lambda^6$-sulfanylidene]carbamate | 16 nM | 2200 nM |
| 2 | (rac)-4-(4-Fluoro-2-methoxyphenyl)-N-{3-[(S-methylsulfonimidoyl)methyl]phenyl}-1,3,5-triazin-2-amine | 25 nM | 2100 nM |
| 3 | (−)-4-(4-Fluoro-2-methoxyphenyl)-N-{3-[(S-methylsulfonimidoyl)methyl]phenyl}-1,3,5-triazin-2-amine; enantiomer 1 | 16 nM | 1700 nM |
| 4 | (+)-4-(4-Fluoro-2-methoxyphenyl)-N-{3-[(S-methylsulfonimidoyl)methyl]phenyl}-1,3,5-triazin-2-amine; enantiomer 2 | 13 nM | 1300 nM |
| 5 | Ethyl {[3-({4-[2-(benzyloxy)-4-fluorophenyl]-1,3,5-triazin-2-yl}amino)benzyl](methyl)oxido-$\lambda^6$-sulfanylidene}carbamate | 4 nM | 250 nM |
| 6 | 4-[2-(Benzyloxy)-4-fluorophenyl]-N-{3-[(S-methylsulfonimidoyl)methyl]phenyl}-1,3,5-triazin-2-amine | 3 nM | 220 nM |
| 9 | (rac)-Ethyl [(3-{[4-(4,5-difluoro-2-methoxyphenyl)-1,3,5-triazin-2-yl]amino}benzyl)(methyl)oxido-$\lambda^6$-sulfanylidene]carbamate | 8 nM | 690 nM |
| 10 | (rac)-4-(4,5-Difluoro-2-methoxyphenyl)-N-{3-[(S-methylsulfonimidoyl)methyl]phenyl}-1,3,5-triazin-2-amine | 28 nM | 1300 nM |
| 11 | (rac)-Ethyl [(3-{[4-(4-chloro-2-methoxyphenyl)-1,3,5-triazin-2-yl]amino}benzyl)(methyl)oxido-$\lambda^6$-sulfanylidene]carbamate | 23 nM | 5500 nM |
| 12 | (rac) 4-(4-Chloro-2-methoxyphenyl)-N-{3-[(S-methylsulfonimidoyl)methyl]phenyl}-1,3,5-triazin-2-amine | 74 nM | 6800 nM |

TABLE 2-continued

Inhibition of CDK9 and CDK2 of compounds according to the present invention

| ① | Nomenclature | ② | ③ |
|---|---|---|---|
| 13 | 4-(4-Chloro-2-methoxyphenyl)-N-{3-[(S-methylsulfonimidoyl)methyl]phenyl}-1,3,5-triazin-2-amine; enantiomer 1 | 93 nM | 9500 nM |
| 14 | 4-(4-Chloro-2-methoxyphenyl)-N-{3-[(S-methylsulfonimidoyl)methyl]phenyl}-1,3,5-triazin-2-amine; enantiomer 2 | 160 nM | 13000 nM |
| 15 | (rac)-1-[(3-{[4-(4-Fluoro-2-methoxyphenyl)-1,3,5-triazin-2-yl]amino}benzyl)(methyl)oxido-λ6-sulfanylidene]-3-methylurea | 7 nM | 930 nM |
| 16 | 1-[(3-{[4-(4-Fluoro-2-methoxyphenyl)-1,3,5-triazin-2-yl]amino}benzyl)(methyl)oxido-λ$^6$-sulfanylidene]-3-methylurea; enantiomer 1 | 19 nM | 1100 nM |
| 17 | 1-[(3-{[4-(4-Fluoro-2-methoxyphenyl)-1,3,5-triazin-2-yl]amino}benzyl)(methyl)oxido-λ$^6$-sulfanylidene]-3-methylurea; enantiomer 2 | 14 nM | 1200 nM |
| 18 | (rac)-Ethyl [(3-{[4-(2,2-difluoro-1,3-benzodioxol-4-yl)-1,3,5-triazin-2-yl]amino}benzyl)(methyl)oxido-λ$^6$-sulfanylidene]carbamate | 33 nM | 3900 nM |
| 19 | (rac)-4-(2,2-Difluoro-1,3-benzodioxol-4-yl)-N-{3-[(S-methylsulfonimidoyl)methyl]phenyl}-1,3,5-triazin-2-amine | 59 nM | 2100 nM |
| 20 | (rac)-Ethyl [(3-{[4-(5-fluoro-2-methoxyphenyl)-1,3,5-triazin-2-yl]amino}benzyl)(methyl)oxido-λ$^6$-sulfanylidene]carbamate | 22 nM | 2000 nM |
| 21 | (rac)-4-(5-Fluoro-2-methoxyphenyl)-N-{3-[(S-methylsulfonimidoyl)methyl]phenyl}-1,3,5-triazin-2-amine | 56 nM | 3500 nM |
| 22 | 4-(5-Fluoro-2-methoxyphenyl)-N-{3-[(S-methylsulfonimidoyl)methyl]phenyl}-1,3,5-triazin-2-amine; enantiomer 1 | 91 nM | 2800 nM |
| 23 | 4-(5-Fluoro-2-methoxyphenyl)-N-{3-[(S-methylsulfonimidoyl)methyl]phenyl}-1,3,5-triazin-2-amine; enantiomer 2 | 110 nM | 5600 nM |
| 24 | (rac)-N-[(3-{[4-(4-fluoro-2-methoxyphenyl)-1,3,5-triazin-2-yl]amino}benzyl)(methyl)oxido-λ$^6$-sulfanylidene]acetamide | 11 nM | 1800 nM |
| 25 | (rac)-Ethyl [(3-{[4-(2-methoxyphenyl)-1,3,5-triazin-2-yl]amino}benzyl)(methyl)oxido-λ$^6$-sulfanylidene]carbamate | 28 nM | 6300 nM |
| 26 | (rac)-4-(2-Methoxyphenyl)-N-{3-[(S-methylsulfonimidoyl)methyl]phenyl}-1,3,5-triazin-2-amine | 35 nM | 4600 nM |
| 27 | 4-(2-Methoxyphenyl)-N-{3-[(S-methylsulfonimidoyl)methyl]phenyl}-1,3,5-triazin-2-amine; enantiomer 1 | 100 nM | 7600 nM |
| 28 | 4-(2-Methoxyphenyl)-N-{3-[(S-methylsulfonimidoyl)methyl]phenyl}-1,3,5-triazin-2-amine; enantiomer 2 | 89 nM | 5900 nM |
| 29 | (rac)-Ethyl [(3-{[4-(3,4-dihydro-2H-chromen-8-yl)-1,3,5-triazin-2-yl]amino}benzyl)(methyl)oxido-λ$^6$-sulfanylidene]carbamate | 13 nM | 1200 nM |
| 30 | (rac)-4-(3,4-Dihydro-2H-chromen-8-yl)-N-{3-[(S-methylsulfonimidoyl)methyl]phenyl}-1,3,5-triazin-2-amine | 21 nM | 940 nM |
| 31 | 4-(3,4-Dihydro-2H-chromen-8-yl)-N-{3-[(S-methylsulfonimidoyl)methyl]phenyl}-1,3,5-triazin-2-amine; enantiomer 1 | 22 nM | 670 nM |
| 32 | 4-(3,4-Dihydro-2H-chromen-8-yl)-N-{3-[(S-methylsulfonimidoyl)methyl]phenyl}-1,3,5-triazin-2-amine; enantiomer 2 | 40 nM | 1600 nM |
| 33 | (rac)-Ethyl [(3-{[4-(2,3-dihydro-1-benzofuran-7-yl)-1,3,5-triazin-2-yl]amino}benzyl)(methyl)oxido-λ$^6$-sulfanylidene]carbamate | 21 nM | 3100 nM |
| 34 | (rac)-4-(2,3-Dihydro-1-benzofuran-7-yl)-N-{3-[(S-methylsulfonimidoyl)methyl]phenyl}-1,3,5-triazin-2-amine | 68 nM | 2200 nM |
| 35 | 4-(2,3-Dihydro-1-benzofuran-7-yl)-N-{3-[(S-methylsulfonimidoyl)methyl]phenyl}-1,3,5-triazin-2-amine; enantiomer 1 | 64 nM | 3100 nM |
| 36 | 4-(2,3-Dihydro-1-benzofuran-7-yl)-N-{3-[(S-methylsulfonimidoyl)methyl]phenyl}-1,3,5-triazin-2-amine; enantiomer 2 | 50 nM | 2900 nM |
| 37 | (rac)-Ethyl [(3-{[4-(2,3-dihydro-1,4-benzodioxin-5-yl)-1,3,5-triazin-2-yl]amino}benzyl)(methyl)oxido-λ$^6$-sulfanylidene]carbamate | 9 nM | 2300 nM |
| 38 | (rac)-4-(2,3-Dihydro-1,4-benzodioxin-5-yl)-N-{3-[(S-methylsulfonimidoyl)methyl]phenyl}-1,3,5-triazin-2-amine | 14 nM | 1600 nM |
| 39 | 4-(2,3-Dihydro-1,4-benzodioxin-5-yl)-N-{3-[(S-methylsulfonimidoyl)methyl]phenyl}-1,3,5-triazin-2-amine; enantiomer 1 | 29 nM | 1500 nM |
| 40 | 4-(2,3-Dihydro-1,4-benzodioxin-5-yl)-N-{3-[(S-methylsulfonimidoyl)methyl]phenyl}-1,3,5-triazin-2-amine; enantiomer 2 | 25 nM | 1800 nM |

TABLE 2-continued

Inhibition of CDK9 and CDK2 of compounds according to the present invention

| ① | Nomenclature | ② | ③ |
|---|---|---|---|
| 41 | (rac)-N-{3-[(N,S-Dimethylsulfonimidoyl)methyl]phenyl}-4-(4-fluoro-2-methoxyphenyl)-1,3,5-triazin-2-amine | 36 nM | 2600 nM |
| 42 | (rac)-Ethyl [{3-[(4-{2-[(4-fluorobenzyl)oxy]phenyl}-1,3,5-triazin-2-yl)amino]benzyl}(methyl)oxido-$\lambda^6$-sulfanylidene]carbamate | 5 nM | 1600 nM |
| 43 | (rac)-4-{2-[(4-Fluorobenzyl)oxy]phenyl}-N-{3-[(S-methylsulfonimidoyl)methyl]phenyl}-1,3,5-triazin-2-amine | 9 nM | 1900 nM |
| 44 | (rac)-N-[(3-{[4-(4-Fluoro-2-methoxyphenyl)-1,3,5-triazin-2-yl]amino}benzyl)(methyl)oxido-$\lambda^6$-sulfanylidene]methanesulfonamide | 20 nM | 1800 nM |
| 45 | (rac)-Ethyl [(3-{[4-(3-chloro-2-methoxyphenyl)-1,3,5-triazin-2-yl]amino}benzyl)(methyl)oxido-$\lambda^6$-sulfanylidene]carbamate | 820 nM | 9000 nM |
| 46 | (rac)-Ethyl {[3-({4-[5-fluoro-2-(tetrahydro-2H-pyran-4-ylmethoxy)phenyl]-1,3,5-triazin-2-yl}amino)benzyl](methyl)oxido-$\lambda^6$-sulfanylidene}carbamate | 120 nM | 11000 nM |
| 47 | (rac)-Ethyl [methyl(oxido(3-{[4-(2-phenoxyphenyl)-1,3,5-triazin-2-yl]amino}benzyl)-$\lambda^6$-sulfanylidene]carbamate | 35 nM | 6500 nM |
| 48 | (rac)-[(3-{[4-(4-fluoro-2-methoxyphenyl)-1,3,5-triazin-2-yl]amino}benzyl)(methyl)oxido-$\lambda^6$-sulfanylidene]cyanamide | 13 nM | 630 nM |
| 49 | [(3-{[4-(4-fluoro-2-methoxyphenyl)-1,3,5-triazin-2-yl]amino}benzyl)(methyl)oxido-$\lambda^6$-sulfanylidene]cyanamide; enantiomer 1 | 7 nM | 650 nM |
| 50 | [(3-{[4-(4-fluoro-2-methoxyphenyl)-1,3,5-triazin-2-yl]amino)benzyl)(methyl)oxido-$\lambda^6$-sulfanylidene]cyanamide; enantiomer 2 | 7 nM | 430 nM |
| 51 | (rac)-Ethyl [(3-fluoro-5-{[4-(4-fluoro-2-methoxyphenyl)-1,3,5-triazin-2-yl]amino}benzyl)(methyl)oxido-$\lambda^6$-sulfanylidene]carbamate | 10 nM | 430 nM |
| 52 | (rac)-4-(4-Fluoro-2-methoxyphenyl)-N-{3-fluoro-5-[(S-methylsulfonimidoyl)methyl]phenyl}-1,3,5-triazin-2-amine | 17 nM | 1000 nM |
| 53 | 4-(4-Fluoro-2-methoxyphenyl)-N-{3-fluoro-5-[(S-methylsulfonimidoyl)methyl]phenyl}-1,3,5-triazin-2-amine; enantiomer 1 | 16 nM | 540 nM |
| 54 | 4-(4-Fluoro-2-methoxyphenyl)-N-{3-fluoro-5-[(S-methylsulfonimidoyl)methyl]phenyl}-1,3,5-triazin-2-amine; enantiomer 2 | 16 nM | 850 nM |
| 55 | (rac)-4-[2-(Cyclohexylmethoxy)-4-fluorophenyl]-N-{3-[(S-methylsulfonimidoyl)methyl]phenyl}-1,3,5-triazin-2-amine | 10 nM | 2200 nM |
| 56 | (rac)-4-{4-Fluoro-2-[(4-fluorobenzyl)oxy]phenyl}-N-{3-[(S-methylsulfonimidoyl)methyl]phenyl}-1,3,5-triazin-2-amine | 6 nM | 410 nM |
| 56.a | 4-{4-Fluoro-2-[(4-fluorobenzyl)oxy]phenyl}-N-{3-[(S-methylsulfonimidoyl)methyl]phenyl}-1,3,5-triazin-2-amine; enantiomer 1 | 4 nM | 560 nM |
| 56.b | 4-{4-Fluoro-2-[(4-fluorobenzyl)oxy]phenyl}-N-{3-[(S-methylsulfonimidoyl)methyl]phenyl}-1,3,5-triazin-2-amine; enantiomer 2 | 5 nM | 560 nM |
| 57 | (rac)-4-{4-Fluoro-2-[2-(tetrahydro-2H-pyran-4-yl)ethoxy]phenyl}-N-{3-[(S-methylsulfonimidoyl)methyl]phenyl}-1,3,5-triazin-2-amine | 370 nM | 8300 nM |
| 58 | (rac)-4-(4-Fluoro-2-methoxyphenyl)-N-(3-{[S-(tetrahydro-2H-pyran-4-yl)sulfonimidoyl]methyl}phenyl)-1,3,5-triazin-2-amine | 89 nM | 5200 nM |
| 59 | (rac)-N-{4-Chloro-3-[(S-methylsulfonimidoyl)methyl]phenyl}-4-(4-fluoro-2-methoxyphenyl)-1,3,5-triazin-2-amine | 26 nM | 1400 nM |
| 59.a | N-{4-Chloro-3-[(S-methylsulfonimidoyl)methyl]phenyl}-4-(4-fluoro-2-methoxyphenyl)-1,3,5-triazin-2-amine; enantiomer 1 | 25 nM | 2900 nM |
| 59.b | N-{4-Chloro-3-[(S-methylsulfonimidoyl)methyl]phenyl}-4-(4-fluoro-2-methoxyphenyl)-1,3,5-triazin-2-amine; enantiomer 2 | 33 nM | 1800 nM |
| 60 | (rac)-Ethyl [{3-[(4-{2-[(3,4-dichlorobenzyl)oxy]phenyl}-1,3,5-triazin-2-yl)amino]benzyl}(methyl)oxido-$\lambda^6$-sulfanylidene]carbamate | 13 nM | 3300 nM |
| 61 | (rac)-4-{2-[(3,4-Dichlorobenzyl)oxy]phenyl}-N-{3-[(S-methylsulfonimidoyl)methyl]phenyl}-1,3,5-triazin-2-amine | 15 nM | 1200 nM |
| 62 | (rac)-4-(4-Fluoro-2-{[($^2H_5$)phenyl($^2H_2$)methyl]oxy}phenyl)-N-{3-[(S-methylsulfonimidoyl)methyl]phenyl}-1,3,5-triazin-2-amine | 7 nM | 220 nM |
| 63 | 4-[2-(1-cyclopentylethoxy)-4-fluorophenyl]-N-{3-[(S-methylsulfonimidoyl)methyl]phenyl}-1,3,5-triazin-2-amine, mixture of all 4 stereoisomers | 99 nM | n.t. |
| 64 | (rac)-N-{3-Chloro-5-[(S-methylsulfonimidoyl)methyl]phenyl}-4-(4-fluoro-2-methoxyphenyl)-1,3,5-triazin-2-amine | 15 nM | 250 nM |
| 65 | (rac)-4-[4-Fluoro-2-(3,3,3-trifluoropropoxy)phenyl]-N-{3-[(S-methylsulfonimidoyl)methyl]phenyl}-1,3,5-triazin-2-amme | 79 nM | 6000 nM |
| 66 | (rac)-4-[4-Fluoro-2-(pyridin-3-ylmethoxy)phenyl]-N-{3-[(S-methylsulfonimidoyl)methyl]phenyl}-1,3,5-triazin-2-amine | 24 nM | 1600 nM |

TABLE 2-continued

Inhibition of CDK9 and CDK2 of compounds according to the present invention

| ① | Nomenclature | ② | ③ |
|---|---|---|---|
| 67 | (rac)-4-[4-Fluoro-2-(pyridin-2-ylmethoxy)phenyl]-N-{3-[(S-methylsulfonimidoyl)methyl]phenyl}-1,3,5-triazin-2-amine | 97 nM | 6900 nM |
| 68 | (rac)-4-[4-Fluoro-2-(pyridin-4-ylmethoxy)phenyl]-N-{3-[(S-methylsulfonimidoyl)methyl]phenyl}-1,3,5-triazin-2-amine | 14 nM | 1500 nM |
| 69 | 4-{4-Fluoro-2-[1-(4-fluorophenyl)ethoxy]phenyl}-N-{3-[(S-methylsulfonimidoyl)methyl]phenyl}-1,3,5-triazin-2-amine, mixture of 4 stereoisomers | 22 nM | 3500 nM |
| 70 | (rac)-[(3-Fluoro-5-{[4-(4-fluoro-2-methoxyphenyl)-1,3,5-triazin-2-yl]amino}benzyl)(methyl)oxido-$\lambda^6$-sulfanylidene]cyanamide | 6 nM | 180 nM |
| 71 | [(3-Fluoro-5-{[4-(4-fluoro-2-methoxyphenyl)-1,3,5-triazin-2-yl]amino}benzyl)(methyl)oxido-$\lambda^6$-sulfanylidene]cyanamide; enantiomer 1 | 6 nM | 230 nM |
| 72 | [(3-Fluoro-5-{[4-(4-fluoro-2-methoxyphenyl)-1,3,5-triazin-2-yl]amino}benzyl)(methyl)oxido-$\lambda^6$-sulfanylidene]cyanamide; enantiomer 2 | 5 nM | 240 nM |
| 73 | (rac)-4-[2-(But-2-yn-1-yloxy)-4-fluorophenyl]-N-{3-[(S-methylsulfonimidoyl)methyl]phenyl}-1,3,5-triazin-amine | 8 nM | 820 nM |
| 74 | 4-[2-(But-2-yn-1-yloxy)-4-fluorophenyl]-N-{3-[(S-methylsulfonimidoyl)methyl]phenyl}-1,3,5-triazin-2-amine; enantiomer 1 | 3 nM | 590 nM |
| 75 | 4-[2-(But-2-yn-1-yloxy)-4-fluorophenyl]-N-{3-[(S-methylsulfonimidoyl)methyl]phenyl}-1,3,5-triazin-2-amine; enantiomer 2 | 4 nM | 450 nM |
| 76 | (rac)-4-[2-(2-Cyclopropylethoxy)-4-fluorophenyl]-N-{3-[(S-methylsulfonimidoyl)methyl]phenyl}-1,3,5-triazin-2-amine | 30 nM | 3200 nM |
| 77 | (rac)-4-[4-Fluoro-2-(prop-2-yn-1-yloxy)phenyl]-N-{3-[(S-methylsulfonimidoyl)methyl]phenyl}-1,3,5-triazin-2-amine | 15 nM | 1600 nM |
| 78 | 4-[4-Fluoro-2-(prop-2-yn-1-yloxy)phenyl]-N-(3-[(S-methylsulfonimidoyl)methyl]phenyl}-1,3,5-triazin-2-amine; enantiomer 1 | 9 nM | 580 nM |
| 79 | 4-[4-Fluoro-2-(prop-2-yn-1-yloxy)phenyl]-N-{3-[(S-methylsulfonimidoyl)methyl]phenyl}-1,3,5-triazin-2-amine; enantiomer 2 | 5 nM | 440 nM |
| 80 | (rac)-4-{2-[(3,4-Difluorobenzyl)oxy]-4-fluorophenyl}-N-{3-[(S-methylsulfonimidoyl)methyl]phenyl}-1,3,5-triazin-2-amine | 13 nM | 1000 nM |
| 81 | (rac)-4-[4-Fluoro-2-(1,3-thiazol-5-ylmethoxy)phenyl]-N-{3-[(S-methylsulfonimidoyl)methyl]phenyl}-1,3,5-triazin-2-amine | 23 nM | 1500 nM |
| 82 | (rac)-4-{4-Fluoro-2-[(2-fluoropyridin-4-yl)methoxy]phenyl}-N-{3-[(S-methylsulfonimidoyl)methyl]phenyl}-1,3,5-triazin-2-amine | 7 nM | 360 nM |
| 83 | 4-{4-Fluoro-2-[(2-fluoropyridin-4-yl)methoxy]phenyl}-N-{3-[(S-methylsulfonimidoyl)methyl]phenyl}-1,3,5-triazin-2-amine; enantiomer 1 | 2 nM | 270 nM |
| 84 | 4-{4-Fluoro-2-[(2-fluoropyridin-4-yl)methoxy]phenyl}-N-{3-[(S-methylsulfonimidoyl)methyl]phenyl}-1,3,5-triazin-2-amine; enantiomer 2 | 3 nM | 220 nM |
| 85 | (rac)-4-[4-Fluoro-2-(prop-2-en-1-yloxy)phenyl]-N-{3-[(S-methylsulfonimidoyl)methyl]phenyl}-1,3,5-triazin-2-amine | 9 nM | 380 nM |
| 86 | (rac)-4-(4-Fluoro-2-{[4-(trifluoromethyl)benzyl]oxy}phenyl)-N-{3-[(S-methylsulfonimidoyl)methyl]phenyl}-1,3,5-triazin-2-amine | 8 nM | 1400 nM |
| 87 | (rac)-4-{2-[(4-Chlorobenzyl)oxy]-4-fluorophenyl}-N-{3-[(S-methylsulfonimidoyl)methyl]phenyl}-1,3,5-triazin-2-amine | 3 nM | 680 nM |
| 88 | (rac)-4-(2-Ethoxy-4-fluorophenyl)-N-{3-[(S-methylsulfonimidoyl)methyl]phenyl}-1,3,5-triazin-2-amine | 11 nM | 1300 nM |
| 89 | (rac)-4-(4-Fluoro-2-{[3-fluoro-5-(trifluoromethyl)benzyl]oxy}phenyl)-N-{3-[(S-methylsulfonimidoyl)methyl]phenyl}-1,3,5-triazin-2-amine | 4 nM | 280 nM |
| 90 | (rac)-4-{4-Fluoro-2-[(3-fluorobenzyl)oxy]phenyl}-N-{3-[(S-methylsulfonimidoyl)methyl]phenyl}-1,3,5-triazin-2-amine | 2 nM | 260 nM |
| 91 | (rac)-4-(4-Fluoro-2-propoxyphenyl)-N-{3-[(S-methylsulfonimidoyl)methyl]phenyl}-1,3,5-triazin-2-amine | 29 nM | 2300 nM |
| 92 | (rac)-4-{2-[(3-Chlorobenzyl)oxy]-4-fluorophenyl}-N-{3-[(S-methylsulfonimidoyl)methyl]phenyl}-1,3,5-triazin-2-amine | 4 nM | 250 nM |
| 93 | (rac)-4-[4-Fluoro-2-(1,2-oxazol-3-ylmethoxy)phenyl]-N-{3-[(S-methylsulfonimidoyl)methyl]phenyl}-1,3,5-triazin-2-amine | 7 nM | 2000 nM |
| 94 | (rac)-4-{2-[(3-Chloro-5-fluorobenzyl)oxy]-4-fluorophenyl}-N-{3-[(S-methylsulfonimidoyl)methyl]phenyl}-1,3,5-triazin-2-amine | 3 nM | 230 nM |
| 95 | (rac)-4-[2-(2,2-Difluoroethoxy)-4-fluorophenyl]-N-{3-[(S-methylsulfonimidoyl)methyl]phenyl}-1,3,5-triazin-2-amine | 21 nM | 1800 nM |
| 96 | (rac)-4-{4-Fluoro-2-[(4-fluoro-3-methylbenzyl)oxy]phenyl}-N-{3-[(S-methylsulfonimidoyl)methyl]phenyl}-1,3,5-triazin-2-amine | 3 nM | 350 nM |

TABLE 2-continued

Inhibition of CDK9 and CDK2 of compounds according to the present invention

| ① | Nomenclature | ② | ③ |
|---|---|---|---|
| 97 | (rac)-4-{2-[(3-Chloro-4-fluorobenzyl)oxy]-4-fluorophenyl}-N-{3-[(S-methylsulfonimidoyl)methyl]phenyl}-1,3,5-triazin-2-amine | 3 nM | 200 nM |
| 98 | (rac)-3-({5-Fluoro-2-[4-({3-[(S-methylsulfonimidoyl)methyl]phenyl}amino)-1,3,5-triazin-2-yl]phenoxy}methyl)benzonitrile | 3 nM | 180 nM |
| 99 | (rac)-4-{4-Fluoro-2-[(2-methylprop-2-en-1-yl)oxy]phenyl}-N-{3-[(S-methylsulfonimidoyl)methyl]phenyl}-1,3,5-triazin-2-amine | 2 nM | 250 nM |
| 100 | (rac)-4-[4-Fluoro-2-(4,4,4-trifluorobutoxy)phenyl]-N-{3-[(S-methylsulfonimidoyl)methyl]phenyl}-1,3,5-triazin-2-amine | 6 nM | 1300 nM |
| 101 | (rac)-4-{4-Fluoro-2-[(2,3,5-trifluorobenzyl)oxy]phenyl}-N-{3-[(S-methylsulfonimidoyl)methyl]phenyl}-1,3,5-triazin-2-amine | 4 nM | 500 nM |
| 102 | (rac)-4-{2-[(2Z)-But-2-en-1-yloxy]-4-fluorophenyl}-N-{3-[(S-methylsulfonimidoyl)methyl]phenyl}-1,3,5-txiazin-2-amine | 7 nM | 800 nM |
| 103 | (rac)-4-{4-Fluoro-2-[(2,4,5-trifluorobenzyl)oxy]phenyl}-N-{3-[(S-methylsulfonimidoyl)methyl]phenyl}-1,3,5-triazin-2-amine | 7 nM | 1200 nM |
| 104 | (rac)-4-{4-Fluoro-2-[(3,4,5-trifluorobenzyl)oxy]phenyl}-N-{3-[(S-methylsulfonimidoyl)methyl]phenyl}-1,3,5-triazin-2-amine | 2 nM | 54 nM |
| 105 | (rac)-[(2,3-Difluoro-5-{[4-(4-fluoro-2-methoxyphenyl)-1,3,5-triazin-2-yl]amino}benzyl)(methyl)oxido-$\lambda^6$-sulfanylidene]cyanamide | 3 nM | 140 nM |
| 106 | (rac)-N-{3,4-Difluoro-5-[(S-methylsulfonimidoyl)methyl]phenyl}-4-(4-fluoro-2-methoxyphenyl)-1,3,5-triazin-2-amine | 7 nM | 400 nM |
| 107 | (rac)-[Ethyl(3-{[4-(4-fluoro-2-methoxyphenyl)-1,3,5-triazin-2-yl]amino}benzyl)oxido-$\lambda^6$-sulfanylidene]cyanamide | 4 nM | 360 nM |
| 108 | (rac)-N-{3-[(S-ethylsulfonimidoyl)methyl]phenyl}-4-(4-fluoro-2-methoxyphenyl)-1,3,5-triazin-2-amine | 8 nM | 1000 nM |
| 109 | N-{3-[(S-ethylsulfonimidoyl)methyl]phenyl}-4-(4-fluoro-2-methoxyphenyl)-1,3,5-triazin-2-amine; enantiomer 1 | 24 | 780 |
| 110 | N-{3-[(S-ethylsulfonimidoyl)methyl]phenyl}-4-(4-fluoro-2-methoxyphenyl)-1,3,5-triazin-2-amine; enantiomer 2 | 9 | 1100 |
| 111 | (rac)-[(3-{[4-(4-Fluoro-2-methoxyphenyl)-1,3,5-triazin-2-yl]amino}-5-methylbenzyl)(methyl)oxido-$\lambda^6$-sulfanylidene]cyanamide | 3 nM | 250 nM |
| 112 | (rac)-2-({5-Fluoro-2-[4-({3-[(S-methylsulfonimidoyl)methyl]phenyl}amino)-1,3,5-triazin-2-yl]phenoxy}methyl)prop-2-en-1-ol | 4 nM | 730 nM |
| 113 | (rac)-[Cyclopropyl(3-{[4-(4-fluoro-2-methoxyphenyl)-1,3,5-triazin-2-yl]amino}benzyl)oxido-$\lambda^6$-sulfanylidene]cyanamide | 2 nM | 300 nM |

The IC$_{50}$ (inhibitory concentration at 50% of maximal effect) values are indicated in nM of μM,
"n.t." means that the compounds have not been tested in this assay.

①: Compound Number
②: CDK9 CDK9/CycT1 kinase assay as described under Method 1. of Materials and Methods
③: CDK2 CDK2/CycE kinase assay as described under Method 2. of Materials and Methods

TABLE 3

Inhibition of proliferation of HeLa, HeLa/MaTu/ADR, NCI-H460, DU145, Caco-2 and B16F10 cells by compounds according to the present invention. Determined as described above (Method 3. of Materials and Methods section).

| ① | Nomenclature | ② | ③ | ④ | ⑤ | ⑥ | ⑦ |
|---|---|---|---|---|---|---|---|
| 1 | (rac)-Ethyl [(3-{[4-(4-fluoro-2-methoxyphenyl)-1,3,5-triazin-2-yl]amino}benzyl)(methyl)oxido-$\lambda^6$-sulfanylidene]carbamate | 1000 | 380 | 360 | 390 | 390 | 360 |
| 2 | (rac)-4-(4-Fluoro-2-methoxyphenyl)-N-{3-[(S-methylsulfonimidoyl)methyl]phenyl}-1,3,5-triazin-2-amine | 1100 | n.t. | n.t. | n.t. | n.t. | n.t. |
| 3 | (−)-4-(4-Fluoro-2-methoxyphenyl)-N-{3-[(S-methylsulfonimidoyl)methyl]phenyl}-1,3,5-triazin-2-amine; enantiomer 1 | 1100 | 400 | 1300 | 740 | 1300 | 1000 |
| 4 | (+)-4-(4-Fluoro-2-methoxyphenyl)-N-{3-[(S-methylsulfonimidoyl)methyl]phenyl}-1,3,5-triazin-2-amine; enantiomer 2 | 970 | 440 | 1200 | 670 | 1300 | 1000 |
| 5 | Ethyl {[3-({4-[2-(benzyloxy)-4-fluorophenyl]-1,3,5-triazin-2-yl}amino)benzyl](methyl)oxido-$\lambda^6$-sulfanylidene}carbamate | 100 | 270 | 210 | 260 | 250 | 270 |
| 6 | 4-[2-(Benzyloxy)-4-fluorophenyl]-N-{3-[(S-methylsulfonimidoyl)methyl]phenyl}-1,3,5-triazin-2-amine | <100 | 200 | 160 | 180 | 270 | 250 |

TABLE 3-continued

Inhibition of proliferation of HeLa, HeLa/MaTu/ADR, NCI-H460, DU145, Caco-2 and B16F10 cells by compounds according to the present invention. Determined as described above (Method 3. of Materials and Methods section).

| ① | Nomenclature | ② | ③ | ④ | ⑤ | ⑥ | ⑦ |
|---|---|---|---|---|---|---|---|
| 9 | (rac)-Ethyl [(3-{[4-(4,5-difluoro-2-methoxyphenyl)-1,3,5-triazin-2-yl]amino}benzyl)(methyl)oxido-$\lambda^6$-sulfanylidene]carbamate | 400 | 960 | 980 | 900 | 800 | 1000 |
| 10 | (rac)-4-(4,5-Difluoro-2-methoxyphenyl)-N-{3-[(S-methylsulfonimidoyl)methyl]phenyl}-1,3,5-triazin-2-amine | 1100 | n.t. | n.t. | n.t. | n.t. | n.t. |
| 15 | (rac)-1-[(3-{[4-(4-Fluoro-2-methoxyphenyl)-1,3,5-triazin-2-yl]amino}benzyl)(methyl)oxido-$\lambda^6$-sulfanylidene]-3-methylurea | 390 | 940 | 1000 | 370 | 1000 | 620 |
| 16 | 1-[(3-{[4-(4-Fluoro-2-methoxyphenyl)-1,3,5-triazin-2-yl]amino}benzyl)(methyl)oxido-$\lambda^6$-sulfanylidene]-3-methylurea; enantiomer 1 | 950 | n.t. | n.t. | n.t. | n.t. | n.t. |
| 17 | 1-[(3-{[4-(4-Fluoro-2-methoxyphenyl)-1,3,5-triazin-2-yl]amino}benzyl)(methyl)oxido-$\lambda^6$-sulfanylidene]-3-methylurea; enantiomer 2 | 580 | 600 | 540 | 580 | 800 | 410 |
| 24 | (rac)-N-[(3-{[4-(4-fluoro-2-methoxyphenyl)-1,3,5-triazin-2-yl]amino}benzyl)(methyl)oxido-$\lambda^6$-sulfanylidene]acetamide | 490 | 520 | 760 | 680 | 710 | 940 |
| 25 | (rac)-Ethyl [(3-{[4-(2-methoxyphenyl)-1,3,5-triazin-2-yl]amino}benzyl)(methyl)oxido-$\lambda^6$-sulfanylidene]carbamate | 1100 | n.t. | n.t. | n.t. | n.t. | n.t. |
| 29 | (rac)-Ethyl [(3-{[4-(3,4-dihydro-2H-chromen-8-yl)-1,3,5-triazin-2-yl]amino}benzyl)(methyl)oxido-$\lambda^6$-sulfanylidene]carbamate | 510 | 760 | 720 | 540 | 760 | 960 |
| 30 | (rac)-4-(3,4-Dihydro-2H-chromen-8-yl)-N-{3-[(S-methylsulfonimidoyl)methyl]phenyl}-1,3,5-triazin-2-amine | 1200 | n.t. | n.t. | n.t. | n.t. | n.t. |
| 37 | (rac)-Ethyl [(3-{[4-(2,3-dihydro-1,4-benzodioxin-5-yl)-1,3,5-triazin-2-yl]amino}benzyl)(methyl)oxido-$\lambda^6$-sulfanylidene]carbamate | 630 | 750 | 920 | 500 | 810 | 720 |
| 39 | 4-(2,3-Dihydro-1,4-benzodioxin-5-yl)-N-{3-[(S-methylsulfonimidoyl)methyl]phenyl}-1,3,5-triazin-2-amine; enantiomer 1 | 1100 | n.t. | n.t. | n.t. | n.t. | n.t. |
| 40 | 4-(2,3-Dihydro-1,4-benzodioxin-5-yl)-N-{3-[(S-methylsulfonimidoyl)methyl]phenyl}-1,3,5-triazin-2-amine; enantiomer 2 | 1100 | n.t. | n.t. | n.t. | n.t. | n.t. |
| 42 | (rac)-Ethyl [{3-[(4-{2-[(4-fluorobenzyl)oxy]phenyl}-1,3,5-triazin-2-yl)amino]benzyl}(methyl)oxido-$\lambda^6$-sulfanylidene]carbamate | 610 | 520 | 370 | 590 | 680 | 680 |
| 43 | (rac)-4-{2-[(4-Fluorobenzyl)oxy]phenyl}-N-{3-[(S-methylsulfonimidoyl)methyl]phenyl}-1,3,5-triazin-2-amine | 590 | 1100 | 530 | 800 | 1100 | 800 |
| 44 | (rac)-N-[(3-{[4-(4-Fluoro-2-methoxyphenyl)-1,3,5-triazin-2-yl]amino}benzyl)(methyl)oxido-$\lambda^6$-sulfanylidene]methanesulfonamide | 1000 | n.t. | n.t. | n.t. | n.t. | n.t. |
| 48 | (rac)-[(3-{[4-(4-fluoro-2-methoxyphenyl)-1,3,5-triazin-2-yl]amino}benzyl)(methyl)oxido-$\lambda^6$-sulfanylidene]cyanamide | 330 | 400 | 410 | 280 | 420 | 320 |
| 50 | [(3-{[4-(4-fluoro-2-methoxyphenyl)-1,3,5-triazin-2-yl]amino}benzyl)(methyl)oxido-$\lambda^6$-sulfanylidene]cyanamide; enantiomer 2 | 260 | 190 | 310 | 140 | 350 | 250 |
| 51 | (rac)-Ethyl [(3-fluoro-5-{[4-(4-fluoro-2-methoxyphenyl)-1,3,5-triazin-2-yl]amino}benzyl)(methyl)oxido-$\lambda^6$-sulfanylidene]carbamate | 300 | 240 | 230 | 240 | 290 | 340 |
| 52 | (rac)-4-(4-Fluoro-2-methoxyphenyl)-N-{3-fluoro-5-[(S-methylsulfonimidoyl)methyl]phenyl}-1,3,5-triazin-2-amine | 410 | 140 | 650 | 340 | 690 | 550 |
| 55 | (rac)-4-[2-(Cyclohexylmethoxy)-4-fluorophenyl]-N-{3-[(S-methylsulfonimidoyl)methyl]phenyl}-1,3,5-triazin-2-amine | 1000 | 850 | 980 | 990 | 890 | n.t. |
| 56 | (rac)-4-{4-Fluoro-2-[(4-fluorobenzyl)oxy]phenyl}-N-{3-[(S-methylsulfonimidoyl)methyl]phenyl}-1,3,5-triazin-2-amine | 370 | 780 | 350 | 370 | 860 | 470 |
| 56.a | 4-{4-Fluoro-2-[(4-fluorobenzyl)oxy]phenyl}-N-{3-[(S-methylsulfonimidoyl)methyl]phenyl}-1,3,5-triazin-2-amine; enantiomer 1 | 350 | 270 | 340 | 340 | 430 | 340 |

TABLE 3-continued

Inhibition of proliferation of HeLa, HeLa/MaTu/ADR, NCI-H460, DU145, Caco-2 and B16F10 cells by compounds according to the present invention. Determined as described above (Method 3. of Materials and Methods section).

| ① | Nomenclature | ② | ③ | ④ | ⑤ | ⑥ | ⑦ |
|---|---|---|---|---|---|---|---|
| 56.b | 4-{4-Fluoro-2-[(4-fluorobenzyl)oxy]phenyl}-N-{3-[(S-methylsulfonimidoyl)methyl]phenyl}-1,3,5-triazin-2-amine; enantiomer 2 | 540 | 540 | 470 | 400 | 540 | 390 |
| 59 | (rac)-N-{4-Chloro-3-[(S-methylsulfonimidoyl)methyl]phenyl}-4-(4-fluoro-2-methoxyphenyl)-1,3,5-triazin-2-amine | 860 | n.t. | n.t. | n.t. | n.t. | n.t. |
| 59.a | N-{4-Chloro-3-[(S-methylsulfonimidoyl)methyl]phenyl}-4-(4-fluoro-2-methoxyphenyl)-1,3,5-triazin-2-amine; enantiomer 1 | 1100 | n.t. | n.t. | n.t. | n.t. | n.t. |
| 59.b | N-{4-Chloro-3-[(S-methylsulfonimidoyl)methyl]phenyl}-4-(4-fluoro-2-methoxyphenyl)-1,3,5-triazin-2-amine; enantiomer 2 | 1100 | n.t. | n.t. | n.t. | n.t. | n.t. |
| 64 | (rac)-N-{3-Chloro-5-[(S-methylsulfonimidoyl)methyl]phenyl}-4-(4-fluoro-2-methoxyphenyl)-1,3,5-triazin-2-amine | 400 | 280 | 360 | 290 | 350 | 320 |
| 66 | (rac)-4-[4-Fluoro-2-(pyridin-3-ylmethoxy)phenyl]-N-{3-[(S-methylsulfonimidoyl)methyl]phenyl}-1,3,5-triazin-2-amine | 1700 | n.t. | n.t. | n.t. | n.t. | n.t. |
| 68 | (rac)-4-[4-Fluoro-2-(pyridin-4-ylmethoxy)phenyl]-N-{3-[(S-methylsulfonimidoyl)methyl]phenyl}-1,3,5-triazin-2-amine | 410 | 3000 | 1100 | 460 | 1300 | 740 |
| 70 | (rac)-[(3-Fluoro-5-{[4-(4-fluoro-2-methoxyphenyl)-1,3,5-triazin-2-yl]amino}benzyl)(methyl-$\lambda^6$-sulfanylidene]cyanamide | 150 | 120 | 230 | 79 | 170 | 130 |
| 71 | [(3-Fluoro-5-{[4-(4-fluoro-2-methoxyphenyl)-1,3,5-triazin-2-yl]amino}benzyl)(methyl-$\lambda^6$-sulfanylidene]cyanamide; enantiomer 1 | 100 | 120 | 160 | 120 | 130 | 110 |
| 72 | [(3-Fluoro-5-{[4-(4-fluoro-2-methoxyphenyl)-1,3,5-triazin-2-yl]amino}benzyl)(methyl-$\lambda^6$-sulfanylidene]cyanamide; enantiomer 2 | 71 | 120 | 160 | 110 | 190 | 160 |
| 73 | (rac)-4-[2-(But-2-yn-1-yloxy)-4-fluorophenyl]-N-{3-[(S-methylsulfonimidoyl)methyl]phenyl}-1,3,5-triazin-2-amine | 240 | 280 | 260 | 200 | 300 | 150 |
| 74 | 4-[2-(But-2-yn-1-yloxy)-4-fluorophenyl]-N-{3-[(S-methylsulfonimidoyl)methyl]phenyl}-1,3,5-triazin-2-amine; enantiomer 1 | 310 | 340 | 330 | 360 | 390 | 340 |
| 75 | 4-[2-(But-2-yn-1-yloxy)-4-fluorophenyl]-N-{3-[(S-methylsulfonimidoyl)methyl]phenyl}-1,3,5-triazin-2-amine; enantiomer 2 | 260 | 210 | 220 | 170 | 310 | 240 |
| 76 | (rac)-4-[2-(2-Cyclopropylethoxy)-4-fluorophenyl]-N-{3-[(S-methylsulfonimidoyl)methyl]phenyl}-1,3,5-triazin-2-amine | 1100 | n.t. | n.t. | n.t. | n.t. | n.t. |
| 77 | (rac)-4-[4-Fluoro-2-(prop-2-yn-1-yloxy)phenyl]-N-{3-[(S-methylsulfonimidoyl)methyl]phenyl}-1,3,5-triazin-2-amine | 470 | 630 | 560 | 480 | 300 | 520 |
| 78 | 4-[4-Fluoro-2-(prop-2-yn-1-yloxy)phenyl]-N-{3-[(S-methylsulfonimidoyl)methyl]phenyl}-1,3,5-triazin-2-amine; enantiomer 1 | 650 | 260 | 390 | 370 | 760 | 500 |
| 79 | 4-[4-Fluoro-2-(prop-2-yn-1-yloxy)phenyl]-N-{3-[(S-methylsulfonimidoyl)methyl]phenyl}-1,3,5-triazin-2-amine; enantiomer 2 | 440 | 350 | 420 | 380 | 390 | 370 |
| 80 | (rac)-4-{2-[(3,4-Difluorobenzyl)oxy]-4-fluorophenyl}-N-{3-[(S-methylsulfonimidoyl)methyl]phenyl}-1,3,5-triazin-2-amine | 730 | n.t. | n.t. | n.t. | n.t. | n.t. |
| 81 | (rac)-4-[4-Fluoro-2-(1,3-thiazol-5-ylmethoxy)phenyl]-N-{3-[(S-methylsulfonimidoyl)methyl]phenyl}-1,3,5-triazin-2-amine | 860 | n.t. | n.t. | n.t. | n.t. | n.t. |
| 82 | (rac)-4-{4-Fluoro-2-[(2-fluoropyridin-4-yl)methoxy]phenyl}-N-{3-[(S-methylsulfonimidoyl)methyl]phenyl}-1,3,5-triazin-2-amine | 180 | 190 | 180 | 130 | 180 | 150 |
| 83 | 4-{4-Fluoro-2-[(2-fluoropyridin-4-yl)-methoxy]phenyl}-N-{3-[(S-methylsulfonimidoyl)methyl]phenyl}-1,3,5-triazin-2-amine; enantiomer 1 | 110 | 640 | 180 | 180 | 210 | 220 |

TABLE 3-continued

Inhibition of proliferation of HeLa, HeLa/MaTu/ADR, NCI-H460, DU145, Caco-2 and B16F10 cells by compounds according to the present invention. Determined as described above (Method 3. of Materials and Methods section).

| ① | Nomenclature | ② | ③ | ④ | ⑤ | ⑥ | ⑦ |
|---|---|---|---|---|---|---|---|
| 84 | 4-{4-Fluoro-2-[(2-fluoropyridin-4-yl)methoxy]phenyl}-N-{3-[(S-methylsulfonimidoyl)methyl]phenyl}-1,3,5-triazin-2-amine; enantiomer 2 | 120 | 340 | 180 | 180 | 180 | 210 |
| 85 | (rac)-4-[4-Fluoro-2-(prop-2-en-1-yloxy)phenyl]-N-{3-[(S-methylsulfonimidoyl)methyl]phenyl}-1,3,5-triazin-2-amine | 330 | 560 | 230 | 190 | 51 | 280 |
| 86 | (rac)-4-(4-Fluoro-2-{[4-(trifluoromethyl)benzyl]oxy}phenyl)-N-{3-[(S-methylsulfonimidoyl)methyl]phenyl}-1,3,5-triazin-2-amine | 1100 | n.t. | n.t. | n.t. | n.t. | n.t. |
| 87 | (rac)-4-{2-[(4-Chlorobenzyl)oxy]-4-fluorophenyl}-N-{3-[(S-methylsulfonimidoyl)methyl]phenyl}-1,3,5-triazin-2-amine | 560 | 450 | 570 | 610 | 800 | 590 |
| 88 | (rac)-4-(2-Ethoxy-4-fluorophenyl)-N-{3-[(S-methylsulfonimidoyl)methyl]phenyl}-1,3,5-triazin-2-amine | 380 | 700 | 890 | 730 | 780 | 810 |
| 89 | (rac)-4-(4-Fluoro-2-{[3-fluoro-5-(trifluoromethyl)benzyl]oxy}phenyl)-N-{3-[(S-methylsulfonimidoyl)methyl]phenyl}-1,3,5-triazin-2-amine | 470 | 450 | 370 | 420 | 520 | 470 |
| 90 | (rac)-4-{4-Fluoro-2-[(3-fluorobenzyl)oxy]phenyl}-N-{3-[(S-methylsulfonimidoyl)methyl]phenyl}-1,3,5-triazin-2-amine | 170 | 100 | 110 | 110 | 80 | 100 |
| 91 | (rac)-4-(4-Fluoro-2-propoxyphenyl)-N-{3-[(S-methylsulfonimidoyl)methyl]phenyl}-1,3,5-triazin-2-amine | 1100 | n.t. | n.t. | n.t. | n.t. | n.t. |
| 92 | (rac)-4-{2-[(3-Chlorobenzyl)oxy]-4-fluorophenyl}-N-{3-[(S-methylsulfonimidoyl)methyl]phenyl}-1,3,5-triazin-2-amine | 470 | 360 | 170 | 380 | 430 | 390 |
| 93 | (rac)-4-[4-Fluoro-2-(1,2-oxazol-3-ylmethoxy)phenyl]-N-{3-[(S-methylsulfonimidoyl)methyl]phenyl}-1,3,5-triazin-2-amine | 680 | n.t. | n.t. | n.t. | n.t. | n.t. |
| 94 | (rac)-4-{2-[(3-Chloro-5-fluorobenzyl)oxy]-4-fluorophenyl}-N-{3-[(S-methylsulfonimidoyl)methyl]phenyl}-1,3,5-triazin-2-amine | 110 | 190 | 200 | 140 | 220 | 180 |
| 95 | (rac)-4-[2-(2,2-Difluoroethoxy)-4-fluorophenyl]-N-{3-[(S-methylsulfonimidoyl)methyl]phenyl}-1,3,5-triazin-2-amine | 1100 | n.t. | n.t. | n.t. | n.t. | n.t. |
| 96 | (rac)-4-{4-Fluoro-2-[(4-fluoro-3-methylbenzyl)oxy]phenyl}-N-{3-[(S-methylsulfonimidoyl)methyl]phenyl}-1,3,5-triazin-2-amine | 1000 | n.t. | n.t. | n.t. | n.t. | n.t. |
| 97 | (rac)-4-{2-[(3-Chloro-4-fluorobenzyl)oxy]-4-fluorophenyl}-N-{3-[(S-methylsulfonimidoyl)methyl]phenyl}-1,3,5-triazin-2-amine | 940 | n.t. | n.t. | n.t. | n.t. | n.t. |
| 98 | (rac)-3-({5-Fluoro-2-[4-({3-[(S-methylsulfonimidoyl)methyl]phenyl}amino)-1,3,5-triazin-2-yl]phenoxy}methyl)benzonitrile | 140 | 260 | 120 | 120 | 150 | 130 |
| 99 | (rac)-4-{4-Fluoro-2-[(2-methylprop-2-en-1-yl)oxy]phenyl}-N-{3-[(S-methylsulfonimidoyl)methyl]phenyl}-1,3,5-triazin-2-amine | 120 | 180 | 150 | 120 | 230 | 200 |
| 100 | (rac)-4-[4-Fluoro-2-(4,4,4-trifluorobutoxy)phenyl]-N-{3-[(S-methylsulfonimidoyl)methyl]phenyl}-1,3,5-triazin-2-amine | 920 | n.t. | n.t. | n.t. | n.t. | n.t. |
| 101 | (rac)-4-{4-Fluoro-2-[(2,3,5-trifluorobenzyl)oxy]phenyl}-N-{3-[(S-methylsulfonimidoyl)methyl]phenyl}-1,3,5-triazin-2-amine | 330 | 350 | 360 | 340 | 240 | 340 |
| 102 | (rac)-4-{2-[(2Z)-But-2-en-1-yloxy]-4-fluorophenyl}-N-{3-[(S-methylsulfonimidoyl)methyl]phenyl}-1,3,5-triazin-2-amine | 340 | 140 | 150 | 95 | 160 | 140 |

TABLE 3-continued

Inhibition of proliferation of HeLa, HeLa/MaTu/ADR, NCI-H460, DU145, Caco-2 and B16F10 cells by compounds according to the present invention. Determined as described above (Method 3. of Materials and Methods section).

| ① | Nomenclature | ② | ③ | ④ | ⑤ | ⑥ | ⑦ |
|---|---|---|---|---|---|---|---|
| 103 | (rac)-4-{4-Fluoro-2-[(2,4,5-trifluorobenzyl)oxy]phenyl}-N-{3-[(S-methylsulfonimidoyl)methyl]phenyl}-1,3,5-triazin-2-amine | 1100 | n.t. | n.t. | n.t. | n.t. | n.t. |
| 104 | (rac)-4-{4-Fluoro-2-[(3,4,5-trifluorobenzyl)oxy]phenyl}-N-{3-[(S-methylsulfonimidoyl)methyl]phenyl}-1,3,5-triazin-2-amine | 110 | 240 | 110 | 120 | 150 | 120 |
| 105 | (rac)-[(2,3-Difluoro-5-{[4-(4-fluoro-2-methoxyphenyl)-1,3,5-triazin-2-yl]amino}benzyl)(methyl)oxido-$\lambda^6$-sulfanylidene]cyanamide | 110 | 71 | 130 | 120 | 81 | 140 |
| 107 | (rac)-[Ethyl(3-{[4-(4-fluoro-2-methoxyphenyl)-1,3,5-triazin-2-yl]amino}benzyl)oxido-$\lambda^6$-sulfanylidene]cyanamide | 230 | 340 | 450 | 280 | 500 | 300 |
| 108 | (rac)-N-{3-[(S-ethylsulfonimidoyl)methyl]phenyl}-4-(4-fluoro-2-methoxyphenyl)-1,3,5-triazin-2-amine | 1000 | n.t. | n.t. | n.t. | n.t. | n.t. |
| 111 | (rac)-[(3-{[4-(4-Fluoro-2-methoxyphenyl)-1,3,5-triazin-2-yl]amino}-5-methylbenzyl)(methyl)oxido-$\lambda^6$-sulfanylidene]cyanamide | 100 | 170 | 270 | 110 | 220 | 130 |
| 112 | (rac)-2-({5-Fluoro-2-[4-({3-[(S-methylsulfonimidoyl)methyl]phenyl}amino)-1,3,5-triazin-2-yl]phenoxy}methyl)prop-2-en-1-ol | 330 | 390 | 320 | 300 | 350 | 320 |

All IC$_{50}$ (inhibitory concentration at 50% of maximal effect) values are indicated in nM, "n.t." means that the compounds have not been tested in this assay.
① Compound Number
② Inhibition of HeLa cell proliferation
③ Inhibition of HeLa/MaTu/ADR cell proliferation
④ Inhibition of NCI-H460 cell proliferation
⑤ Inhibition of DU145 cell proliferation
⑥ Inhibition of Caco-2 cell proliferation
⑦ Inhibition of B16F10 cell proliferation

TABLE 4

Thermodynamic solubility of compounds according to the present invention in water at pH 6.5 as determined by the equilibrium shake flask method described under Method 4. of Materials and Methods.

| ① | Nomenclature | ② |
|---|---|---|
| 3 | (−)-4-(4-Fluoro-2-methoxyphenyl)-N-{3-[(S-methylsulfonimidoyl)methyl]phenyl}-1,3,5-triazin-2-amine; enantiomer 1 | 601 |
| 4 | (+)-4-(4-Fluoro-2-methoxyphenyl)-N-{3-[(S-methylsulfonimidoyl)methyl]phenyl}-1,3,5-triazin-2-amine; enantiomer 2 | 479 |
| 10 | (rac)-4-(4,5-Difluoro-2-methoxyphenyl)-N-{3-[(S-methylsulfonimidoyl)methyl]phenyl}-1,3,5-triazin-2-amine | 130 |
| 16 | 1-[(3-{[4-(4-Fluoro-2-methoxyphenyl)-1,3,5-triazin-2-yl]amino}benzyl)(methyl)oxido-$\lambda^6$-sulfanylidene]-3-methylurea; enantiomer 1 | 323 |
| 17 | 1-[(3-{[4-(4-Fluoro-2-methoxyphenyl)-1,3,5-triazin-2-yl]amino}benzyl)(methyl)oxido-$\lambda^6$-sulfanylidene]-3-methylurea; enantiomer 2 | 429 |
| 22 | 4-(5-Fluoro-2-methoxyphenyl)-N-{3-[(S-methylsulfonimidoyl)methyl]phenyl}-1,3,5-triazin-2-amine; enantiomer 1 | 787 |
| 23 | 4-(5-Fluoro-2-methoxyphenyl)-N-{3-[(S-methylsulfonimidoyl)methyl]phenyl}-1,3,5-triazin-2-amine; enantiomer 2 | 888 |
| 31 | 4-(3,4-Dihydro-2H-chromen-8-yl)-N-{3-[(S-methylsulfonimidoyl)methyl]phenyl}-1,3,5-triazin-2-amine; enantiomer 1 | 1000 |
| 32 | 4-(3,4-Dihydro-2H-chromen-8-yl)-N-{3-[(S-methylsulfonimidoyl)methyl]phenyl}-1,3,5-triazin-2-amine; enantiomer 2 | 1000 |
| 39 | 4-(2,3-Dihydro-1,4-benzodioxin-5-yl)-N-{3-[(S-methylsulfonimidoyl)methyl]phenyl}-1,3,5-triazin-2-amine; enantiomer 1 | 819 |
| 40 | 4-(2,3-Dihydro-1,4-benzodioxin-5-yl)-N-{3-[(S-methylsulfonimidoyl)methyl]phenyl}-1,3,5-triazin-2-amine; enantiomer 2 | 865 |
| 49 | [(3-{[4-(4-fluoro-2-methoxyphenyl)-1,3,5-triazin-2-yl]amino}benzyl)(methyl)oxido-$\lambda^6$-sulfanylidene]cyanamide; enantiomer 1 | 88 |
| 50 | [(3-{[4-(4-fluoro-2-methoxyphenyl)-1,3,5-triazin-2-yl]amino}benzyl)(methyl)oxido-$\lambda^6$-sulfanylidene]cyanamide; enantiomer 2 | 126 |

TABLE 4-continued

Thermodynamic solubility of compounds according to the present invention in water at pH 6.5 as determined by the equilibrium shake flask method described under Method 4. of Materials and Methods.

| ① | Nomenclature | ② |
|---|---|---|
| 54 | 4-(4-Fluoro-2-methoxyphenyl)-N-{3-fluoro-5-[(S-methylsulfonimidoyl)methyl]phenyl}-1,3,5-triazin-2-amine; enantiomer 2 | 120 |
| 73 | (rac)-4-[2-(But-2-yn-1-yloxy)-4-fluorophenyl]-N-{3-[(S-methylsulfonimidoyl)methyl]phenyl}-1,3,5-triazin-2-amine | 1220 |
| 77 | (rac)-4-[4-Fluoro-2-(prop-2-yn-1-yloxy)phenyl]-N-{3-[(S-methylsulfonimidoyl)methyl]phenyl}-1,3,5-triazin-2-amine | 256 |
| 88 | (rac)-4-(2-Ethoxy-4-fluorophenyl)-N-{3-[(S-methylsulfonimidoyl)methyl]phenyl}-1,3,5-triazin-2-amine | 884 |
| 91 | (rac)-4-(4-Fluoro-2-propoxyphenyl)-N-{3-[(S-methylsulfonimidoyl)methyl]phenyl}-1,3,5-triazin-2-amine | 104 |

①: Compound Number
②: Solubilty in mg/l.

TABLE 5

Inhibition of Carbonic anhydrase-1 and Carbonic anhydrase-2 as determined by the Carbonic anhydrase Assay described above

| ① Nomenclature | 2 | ③ |
|---|---|---|
| 3  4-(4-Fluoro-2-methoxyphenyl)-N-{3-[(S-methylsulfonimidoyl)methyl]phenyl}-1,3,5-triazin-2-amine; enantiomer 1 | >1.0E−05 | >1.0E−05 |
| 4  4-(4-Fluoro-2-methoxyphenyl)-N-{3-[(S-methylsulfonimidoyl)methyl]phenyl}-1,3,5-triazin-2-amine; enantiomer 2 | >1.0E−05 | >1.0E−05 |

①: Compound Number
②: Inhibition of Carbonic anhydrase-1: the $IC_{50}$ (inhibitory concentration at 50% of maximal effect) values are indicated in (mol/l)
③: Inhibition of Carbonic anhydrase-2: the $IC_{50}$ (inhibitory concentration at 50% of maximal effect) values are indicated in (mol/l)

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Biotinylated peptide (C-terminus in amide form)

<400> SEQUENCE: 1

Tyr Ile Ser Pro Leu Lys Ser Pro Tyr Lys Ile Ser Glu Gly
1               5                   10 wherein:

$R^1$ is a group selected from $C_1$-$C_6$-alkyl-, $C_3$-$C_7$-cycloalkyl-, heterocyclyl-, phenyl, heteroaryl, phenyl-$C_1$-$C_3$-alkyl-, and heteroaryl-$C_1$-$C_3$-alkyl-, wherein said group is optionally substituted with one or two or three substituents, identically or differently, selected from the group consisting of hydroxy, cyano, halogen, halo-$C_1$-$C_3$-alkyl-, $C_1$-$C_6$-alkoxy-, $C_1$-$C_3$-fluoroalkoxy-, amino, alkylamino-, dialkylamino-, acetylamino-, N-methyl-N-acetylamino-, and cyclic amines;

The invention claimed is:
1. A compound of formula (I)

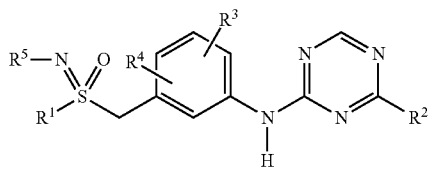

(I)

$R^2$ is a group selected from

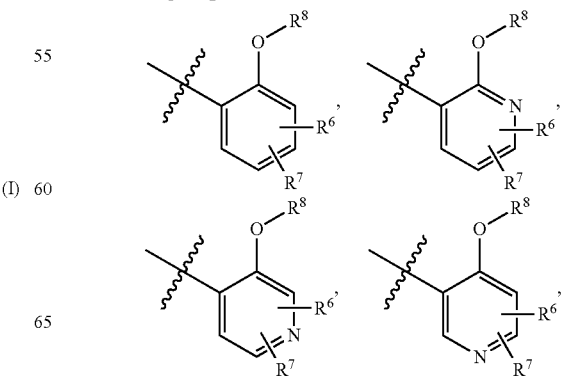

-continued

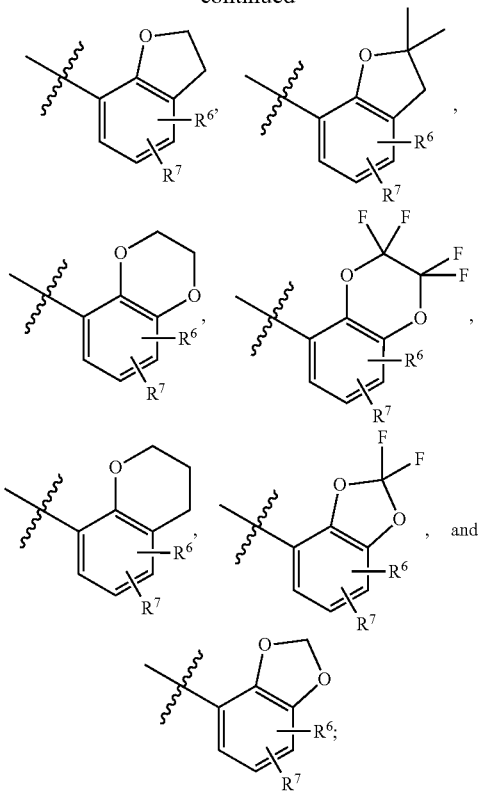

R³ and R⁴ are independently a group selected from a hydrogen atom, fluoro atom, chloro atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

R⁵ is a group selected from a hydrogen atom, cyano, —C(O)R⁹, —C(O)OR⁹, —S(O)₂R⁹, —C(O)NR¹⁰R¹¹, $C_1$-$C_6$-alkyl-, $C_3$-$C_7$-cycloalkyl-, heterocyclyl-, phenyl, and heteroaryl,
  wherein said $C_1$-$C_6$-alkyl-, $C_3$-$C_7$-cycloalkyl-, heterocyclyl-, phenyl or heteroaryl group is optionally substituted with one, two or three substituents, identically or differently, selected from halogen, cyano, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

R⁶ and R⁷ are independently a group selected from a hydrogen atom, fluoro atom, chloro atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

R⁸ is a group selected from
  a) a $C_1$-$C_{10}$-alkyl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, and heteroaryl,
    wherein said $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;
  b) a $C_3$-$C_7$-cycloalkyl- group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, and $C_2$-$C_3$-alkynyl-;
  c) a heterocyclyl- group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, and $C_2$-$C_3$-alkynyl-;
  d) a phenyl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;
  e) a heteroaryl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;
  f) a phenyl-$C_1$-$C_3$-alkyl- group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-; and
  g) a heteroaryl-$C_1$-$C_3$-alkyl- group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;

R⁹ is a group selected from $C_1$-$C_6$-alkyl-, $C_3$-$C_7$-cycloalkyl-, heterocyclyl-, phenyl, benzyl and heteroaryl, wherein said group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-; and R¹⁰ and R¹¹ are independently a group selected from hydrogen, $C_1$-$C_6$-alkyl-, $C_3$-$C_7$-cycloalkyl-, heterocyclyl-, phenyl and heteroaryl, wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-, or a salt or solvate thereof, or a salt of the solvate thereof.

2. The compound according to claim 1, wherein:

$R^1$ is a group selected from $C_1$-$C_6$-alkyl-, $C_3$-$C_7$-cycloalkyl- and heterocyclyl-;

$R^2$ is a group selected from

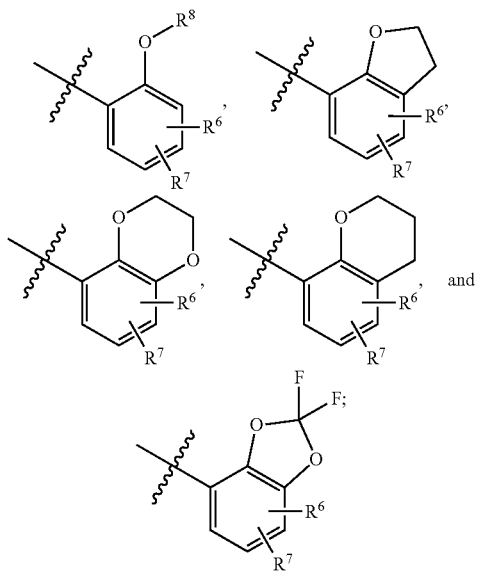

$R^3$ and $R^4$ are independently a group selected from a hydrogen atom, fluoro atom, chloro atom and $C_1$-$C_3$-alkyl-;

$R^5$ is a group selected from a hydrogen atom, cyano, —C(O)$R^9$, —C(O)O$R^9$, —S(O)$_2R^9$, —C(O)N$R^{10}R^{11}$, and $C_1$-$C_6$-alkyl-;

$R^6$ and $R^7$ are independently a group selected from a hydrogen atom, fluoro atom, and chloro atom;

$R^8$ is a group selected from a) a $C_1$-$C_{10}$-alkyl group, which is optionally substituted with one or two or three substituents, selected from the group consisting of halogen, hydroxy, $C_2$-$C_3$-alkenyl-, $C_2$-$C_3$-alkynyl-, $C_3$-$C_7$-cycloalkyl-, heterocyclyl-, phenyl, and heteroaryl,
wherein said $C_3$-$C_7$-cycloalkyl-, heterocyclyl-, phenyl or heteroaryl group is optionally substituted with one, two or three substituents, identically or differently, selected from halogen, cyano, $C_1$-$C_3$-alkyl-, and halo-$C_1$-$C_3$-alkyl-;

b) a phenyl group;

c) a phenyl-$C_1$-$C_3$-alkyl- group, the phenyl group of which is optionally substituted with one or two or three substituents, identically or differently, selected from the group consisting of halogen, cyano, $C_1$-$C_3$-alkyl-, and halo-$C_1$-$C_3$-alkyl-; and d) a heteroaryl-$C_1$-$C_3$-alkyl- group, the heteroaryl group of which is optionally substituted with one halogen;

$R^9$ is a $C_1$-$C_6$-alkyl group; and $R^{10}$ and $R^{11}$ are independently a group selected from hydrogen and $C_1$-$C_6$-alkyl-, or a salt or solvate thereof, or a salt of the solvate thereof.

3. The compound according to claim 1, which is of formula (Ia)

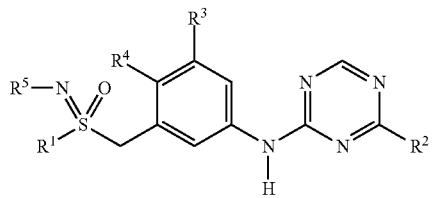

(Ia)

wherein:

$R^1$ is a $C_1$-$C_6$-alkyl- or $C_3$-$C_7$-cycloalkyl- group;

$R^2$ is a group selected from

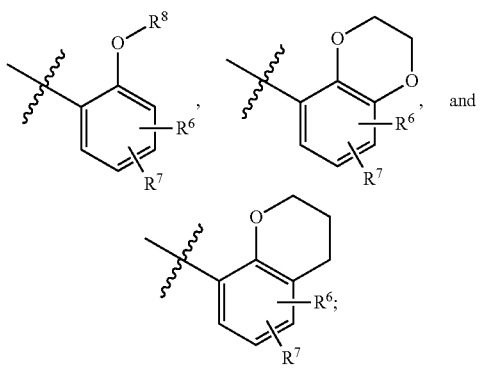

$R^3$ and $R^4$ are independently a group selected from a hydrogen atom, fluoro atom, chloro atom, and $C_1$-$C_3$-alkyl-;

$R^5$ is a group selected from a hydrogen atom, cyano, —C(O)$R^9$, —C(O)O$R^9$, and —C(O)N$R^{10}R^{11}$;

$R^6$ and $R^7$ are independently a hydrogen atom or fluoro atom;

$R^8$ is a group selected from a) a $C_1$-$C_{10}$-alkyl group, which is optionally substituted with one or two substituents, selected from the group consisting of hydroxy, $C_2$-$C_3$-alkenyl-, $C_2$-$C_3$-alkynyl-, $C_3$-$C_7$-cycloalkyl-, phenyl, and heteroaryl,
wherein said $C_3$-$C_7$-cycloalkyl-, phenyl or heteroaryl group is optionally substituted with one, two or three substituents, identically or differently, selected from halogen, cyano, and halo-$C_1$-$C_3$-alkyl-;

b) a phenyl-$C_1$-$C_3$-alkyl- group, the phenyl group of which is optionally substituted with one or two or three substituents, identically or differently, selected from the group consisting of halogen, cyano, and halo-$C_1$-$C_3$-alkyl-; and c) a heteroaryl-$C_1$-$C_3$-alkyl- group, the heteroaryl group of which is optionally substituted with one halogen;

$R^9$ is a $C_1$-$C_6$-alkyl group; and $R^{10}$ and $R^{11}$ are independently a group selected from hydrogen and $C_1$-$C_6$-alkyl-, or a salt or solvate thereof, or a salt of the solvate thereof.

4. The compound according to claim 1, which is of formula (Ia)

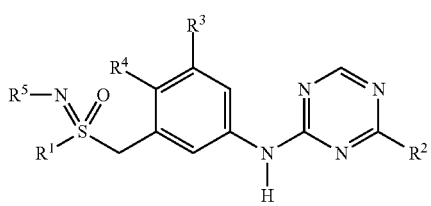

(Ia)

wherein:
$R^1$ is methyl;
$R^2$ is a group selected from 4-fluoro-2-methoxyphenyl-, 2-(benzyloxy)-4-fluorophenyl-, 4,5-difluoro-2-methoxyphenyl-, 2-[(4-fluorobenzyl)oxy]phenyl-, and 4-fluoro-2-[(4-fluorobenzyl)oxy]phenyl;
$R^3$ is a group selected from a hydrogen atom, fluoro atom, and chloro atom;
$R^4$ is a group selected from a hydrogen atom and chloro atom;
$R^5$ is a group selected from a hydrogen atom, —C(O)$R^9$, and —C(O)O$R^9$; and
$R^9$ is a group selected from methyl and ethyl,
or a salt or solvate thereof, or a salt of the solvate thereof.

5. The compound according to claim 1, which is of formula (Ia)

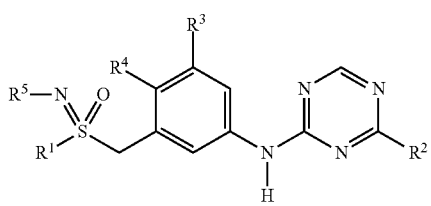

(Ia)

wherein:
$R^1$ is methyl;
$R^2$ is a group selected from 4-fluoro-2-methoxyphenyl- and 4,5-difluoro-2-methoxyphenyl-;
$R^3$ and $R^4$ are each a hydrogen atom; and
$R^5$ is a hydrogen atom,
or a salt or solvate thereof, or a salt of the solvate thereof.

6. The compound according to claim 1, wherein:
$R^1$ is a group selected from methyl, ethyl, cyclopropyl, and tetrahydro-2H-pyranyl-;
$R^2$ is a group selected from

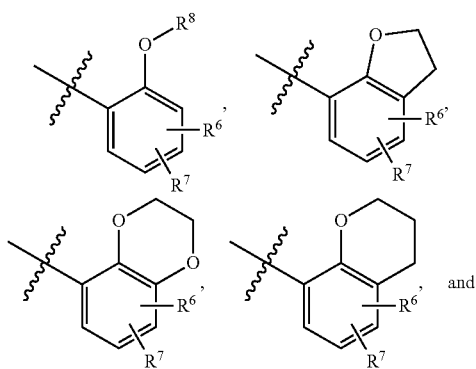

and

-continued

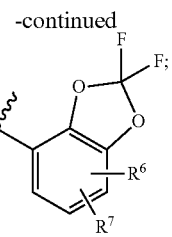

$R^3$ and $R^4$ are independently a group selected from a hydrogen atom, fluoro atom, chloro atom and methyl;
$R^5$ is a group selected from a hydrogen atom, cyano, —C(O)$R^9$, —C(O)O$R^9$, —S(O)$_2R^9$, —C(O)N$R^{10}R^{11}$, and $C_1$-$C_6$-alkyl-;
$R^6$ and $R^7$ are independently a group selected from a hydrogen atom, fluoro atom, and chloro atom;
$R^8$ is a group selected from
  a) a methyl, ethyl, propyl or butyl group, wherein said group is optionally substituted with one or two or three substituents, selected from the group consisting of halogen, hydroxy, ethenyl, propenyl, ethynyl-, propynyl-, cyclopentyl-, cyclohexyl, tetrahydro-2H-pyranyl-, phenyl, pyridinyl-, thiazolyl-, and oxazolyl,
    wherein said phenyl or pyridinyl- group is optionally substituted with one, two or three substituents, identically or differently, selected from a fluoro atom, chloro atom, cyano, methyl, and trifluoromethyl;
  b) a ($^2H_2$)methyl group substituted with a ($^2H_5$)phenyl group;
  c) a phenyl group;
  d) a benzyl group, the phenyl ring of which is optionally substituted with one or two or three substituents, identically or differently, selected from the group consisting of a fluoro atom, chloro atom, cyano, methyl and trifluoromethyl-;
  e) a pyridin-2-ylmethyl- group, wherein the pyridin-moiety is optionally substituted with one fluoro atom;
  f) a pyridin-3-ylmethyl- group, wherein the pyridin-moiety is optionally substituted with one fluoro atom;
  g) a pyridin-4-ylmethyl- group, wherein the pyridin-moiety is optionally substituted with one fluoro atom;
  h) a thiazolylmethyl- group; and
  i) an oxazolylmethyl- group;
$R^9$ is a methyl or ethyl group; and
$R^{10}$ and $R^{11}$ are independently from each other, a group selected from hydrogen and methyl,
or a salt or solvate thereof, or a salt of the solvate thereof.

7. The compound according to claim 1, wherein:
$R^1$ is a methyl, ethyl or cyclopropyl group;
$R^2$ is a group selected from

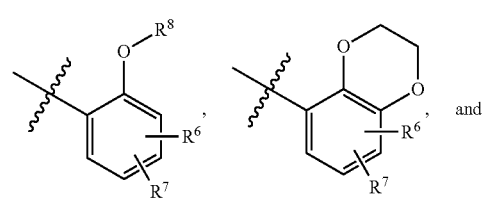

and

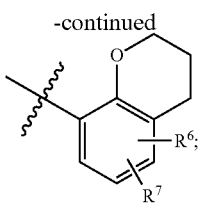

R³ is a group selected from a hydrogen atom, fluoro atom, chloro atom and methyl;
R⁴ is a group selected from a hydrogen atom and fluoro atom;
R⁵ is a group selected from a hydrogen atom, cyano, —C(O)R⁹, —C(O)OR⁹, and C(O)NR¹⁰R¹¹;
R⁶ and R⁷ are independently from each other, a group selected from a hydrogen atom and fluoro atom;
R⁸ is a group selected from
  methyl, ethyl, prop-2-en-1-yl-, 2-methylprop-2-en-1yl-, 2-(hydroxymethyl)prop-2-en-1-yl-, (2Z)-but-2-en-1-yl-, prop-2-yn-1yl-, but-2-yn-1yl-, cyclohexylmethyl-, benzyl-, 3-cyanobenzyl-, 3-fluorobenzyl-, 3-chlorobenzyl-, 4-fluorobenzyl-, 4-chlorobenzyl-, 3-fluoro-5-(trifluoromethyl)benzyl-, 3-chloro-5-fluorobenzyl-, pyridin-4-yl-, 2-fluoropyridin-4-yl-, 2,3,5-trifluorobenzyl-, and 3,4,5-trifluorobenzyl-;
R⁹ is a methyl or ethyl group; and
R¹⁰ and R¹¹ are independently from each other, a group selected from a hydrogen atom and C₁-C₆-alkyl-,
or a salt or solvate thereof, or a salt of the solvate thereof.

8. The compound according to claim 1, which is selected from the group consisting of:
(rac)-Ethyl [(3-{[4-(4-fluoro-2-methoxyphenyl)-1,3,5-triazin-2yl]amino}benzyl)(methyl)oxido-λ⁶-sulfanylidene]carbamate;
(rac)-Ethyl {[3-({4-[2-(benzyloxy)-4-fluorophenyl]-1,3,5-triazin-2-yl}amino)benzyl](methyl)oxido-λ⁶-sulfanylidene}carbamate;
(rac)-4-[2-(Benzyloxy)-4-fluorophenyl]-N-{3-[(S-methylsulfonimidoyl)methyl]phenyl}-1,3,5-triazin-2-amine;
4-[2-(Benzyloxy)-4-fluorophenyl]-N-{3-[(S-methylsulfonimidoyl)methyl]phenyl}-1,3,5-triazin-2-amine, enantiomer 1;
4-[2-(Benzyloxy)-4-fluorophenyl]-N-{3-[(S-methylsulfonimidoyl)methyl]phenyl}-1,3,5-triazin-2-amine, enantiomer 2;
(rac)-Ethyl [(3-{[4-(4,5-difluoro-2-methoxyphenyl)-1,3,5-triazin-2-yl]amino}benzyl)(methyl)oxido-λ⁶-sulfanylidene]carbamate;
(rac)-4-(4,5-Difluoro-2-methoxyphenyl)-N-{3-[(S-methylsulfonimidoyl)methyl]phenyl}-1,3,5-triazin-2-amine;
(rac)-Ethyl [(3-{[4-(4-chloro-2-methoxyphenyl)-1,3,5-triazin-2-yl]amino}benzyl)(methyl)oxido-λ⁶-sulfanylidene]carbamate;
(rac) 4-(4-Chloro-2-methoxyphenyl)-N-{3-[(S-methylsulfonimidoyl)methyl]phenyl}-1,3,5-triazin-2-amine;
4-(4-Chloro-2-methoxyphenyl)-N-{3-[(S-methylsulfonimidoyl)methyl]phenyl}-1,3,5-triazin-2-amine, enantiomer 1;
4-(4-Chloro-2-methoxyphenyl)-N-{3-[(S-methylsulfonimidoyl)methyl]phenyl}-1,3,5-triazin-2-amine, enantiomer 2;
(rac)-1-[(3-{[4-(4-Fluoro-2-methoxyphenyl)-1,3,5-triazin-2-yl]amino}benzyl)(methyl)oxido-λ⁶-sulfanylidene]-3-methylurea;
1-[(3-{[4-(4-Fluoro-2-methoxyphenyl)-1,3,5-triazin-2-yl]amino}benzyl)(methyl)oxido-λ⁶-sulfanylidene]-3-methylurea, enantiomer 1;
1-[(3-{[4-(4-Fluoro-2-methoxyphenyl)-1,3,5-triazin-2-yl]amino}benzyl)(methyl)oxido-λ⁶-sulfanylidene]-3-methylurea, enantiomer 2;
(rac)-Ethyl [(3-{[4-(2,2-difluoro-1,3-benzodioxol-4-yl)-1,3,5-triazin-2-yl]amino}benzyl)(methyl)oxido-λ⁶-sulfanylidene]carbamate;
(rac)-4-(2,2-Difluoro-1,3-benzodioxol-4-yl)-N-{3-[(S-methylsulfonimidoyl)methyl]phenyl}-1,3,5-triazin-2-amine;
(rac)-Ethyl [(3-{[4-(5-fluoro-2-methoxyphenyl)-1,3,5-triazin-2-yl]amino}benzyl)(methyl)oxido-λ⁶-sulfanylidene]carbamate;
(rac)-4-(5-Fluoro-2-methoxyphenyl)-N-{3-[(S-methylsulfonimidoyl)methyl]phenyl}-1,3,5-triazin-2-amine;
4-(5-Fluoro-2-methoxyphenyl)-N-{3-[(S-methylsulfonimidoyl)methyl]phenyl}-1,3,5-triazin-2-amine, enantiomer 1;
4-(5-Fluoro-2-methoxyphenyl)-N-{3-[(S-methylsulfonimidoyl)methyl]phenyl}-1,3,5-triazin-2-amine, enantiomer 2;
(rac)-N-[(3-{[4-(4-fluoro-2-methoxyphenyl)-1,3,5-triazin-2-yl]amino}benzyl)(methyl)oxido-λ⁶-sulfanylidene]acetamide;
(rac)-Ethyl [(3-{[4-(2-methoxyphenyl)-1,3,5-triazin-2-yl]amino}benzyl)(methyl)oxido-λ⁶-sulfanylidene]carbamate;
(rac)-4-(2-Methoxyphenyl)-N-{3-[(S-methylsulfonimidoyl)methyl]phenyl}-1,3,5-triazin-2-amine;
4-(2-Methoxyphenyl)-N-{3-[(S-methylsulfonimidoyl)methyl]phenyl}-1,3,5-triazin-2-amine, enantiomer 1;
4-(2-Methoxyphenyl)-N-{3-[(S-methylsulfonimidoyl)methyl]phenyl}-1,3,5-triazin-2-amine, enantiomer 2;
(rac)-Ethyl [(3-{[4-(3,4-dihydro-2H-chromen-8-yl)-1,3,5-triazin-2-yl]amino}benzyl)(methyl)oxido-λ⁶-sulfanylidene]carbamate;
(rac)-4-(3,4-Dihydro-2H-chromen-8-yl)-N-{3-[(S-methylsulfonimidoyl)methyl]phenyl}-1,3,5-triazin-2-amine;
4-(3,4-Dihydro-2H-chromen-8-yl)-N-{3-[(S-methylsulfonimidoyl)methyl]phenyl}-1,3,5-triazin-2-amine, enantiomer 1;
4-(3,4-Dihydro-2H-chromen-8-yl)-N-{3-[(S-methylsulfonimidoyl)methyl]phenyl}-1,3,5-triazin-2-amine, enantiomer 2;
(rac)-Ethyl [(3-{[4-(2,3-dihydro-1-benzofuran-7-yl)-1,3,5-triazin-2-yl]amino}benzyl)(methyl)oxido-λ⁶-sulfanylidene]carbamate;
(rac)-4-(2,3-Dihydro-1-benzofuran-7-yl)-N-{3-[(S-methylsulfonimidoyl)methyl]phenyl}-1,3,5-triazin-2-amine;
4-(2,3-Dihydro-1-benzofuran-7-yl)-N-{3-[(S-methylsulfonimidoyl)methyl]phenyl}-1,3,5-triazin-2-amine, enantiomer 1;
4-(2,3-Dihydro-1-benzofuran-7-yl)-N-{3-[(S-methylsulfonimidoyl)methyl]phenyl}-1,3,5-triazin-2-amine, enantiomer 2;
(rac)-Ethyl [(3-{[4-(2,3-dihydro-1,4-benzodioxin-5-yl)-1,3,5-triazin-2-yl]amino}benzyl)(methyl)oxido-λ⁶-sulfanylidene]carbamate;
(rac)-4-(2,3-Dihydro-1,4-benzodioxin-5-yl)-N-{3-[(S-methylsulfonimidoyl)methyl]phenyl}-1,3,5-triazin-2-amine;

4-(2,3-Dihydro-1,4-benzodioxin-5-yl)-N-{3-[(S-methyl-sulfonimidoyl)methyl]phenyl}-1,3,5-triazin-2-amine, enantiomer 1;

4-(2,3-Dihydro-1,4-benzodioxin-5-yl)-N-{3-[(S-methyl-sulfonimidoyl)methyl]phenyl}-1,3,5-triazin-2-amine, enantiomer 2;

(rac)-N-{3-[(N,S-Dimethylsulfonimidoyl)methyl]phe-nyl}-4-(4-fluoro-2-methoxyphenyl)-1,3,5-triazin-2-amine;

(rac)-Ethyl [{3-[(4-{2-[(4-fluorobenzyl)oxy]phenyl}-1,3,5-triazin-2-yl)amino]benzyl}(methyl)oxido-$\lambda^6$-sulfa-nylidene]carbamate;

(rac)-4-{2-[(4-Fluorobenzyl)oxy]phenyl}-N-{3-[(S-methylsulfonimidoyl)methyl]phenyl}-1,3,5-triazin-2-amine;

(rac)-N-[(3-{[4-(4-Fluoro-2-methoxyphenyl)-1,3,5-tri-azin-2-yl]amino}benzyl)(methyl)oxido-$\lambda^6$-sulfa-nylidene]methanesulfonamide;

(rac)-Ethyl [(3-{[4-(3-chloro-2-methoxyphenyl)-1,3,5-triazin-2-yl]amino}benzyl)(methyl)oxido-$\lambda^6$-sulfa-nylidene]carbamate;

(rac)-Ethyl {[3-({4-[5-fluoro-2-(tetrahydro-2H-pyran-4-ylmethoxy)phenyl]-1,3,5-triazin-2-yl}amino)benzyl](methyl)oxido-$\lambda^6$-sulfanylidene}carbamate;

(rac)-Ethyl [methyl(oxido)(3-{[4-(2-phenoxyphenyl)-1,3,5-triazin-2-yl]amino}benzyl)-$\lambda^6$-sulfanylidene]car-bamate;

(rac)-[(3-{[4-(4-fluoro-2-methoxyphenyl)-1,3,5-triazin-2-yl]amino}benzyl)(methyl)oxido-$\lambda^6$-sulfanylidene]cyanamide;

[(3-{[4-(4-fluoro-2-methoxyphenyl)-1,3,5-triazin-2-yl]amino}benzyl)(methyl)oxido-$\lambda^6$-sulfanylidene]cyana-mide, enantiomer 1;

[(3-{[4-(4-fluoro-2-methoxyphenyl)-1,3,5-triazin-2-yl]amino}benzyl)(methyl)oxido-$\lambda^6$-sulfanylidene]cyana-mide, enantiomer 2;

(rac)-Ethyl [(3-fluoro-5-{[4-(4-fluoro-2-methoxyphenyl)-1,3,5-triazin-2-yl]amino}benzyl)(methyl)oxido-$\lambda^6$-sul-fanylidene]carbamate;

(rac)-4-(4-Fluoro-2-methoxyphenyl)-N-{3-fluoro-5-[(S-methylsulfonimidoyl)methyl]phenyl}-1,3,5-triazin-2-amine;

4-(4-Fluoro-2-methoxyphenyl)-N-{3-fluoro-5-[(S-meth-ylsulfonimidoyl)methyl]phenyl}-1,3,5-triazin-2-amine, enantiomer 1;

4-(4-Fluoro-2-methoxyphenyl)-N-{3-fluoro-5-[(S-meth-ylsulfonimidoyl)methyl]phenyl}-1,3,5-triazin-2-amine, enantiomer 2;

(rac)-4-[2-(Cyclohexylmethoxy)-4-fluorophenyl]-N-{3-[(S-methylsulfonimidoyl)methyl]phenyl}-1,3,5-tri-azin-2-amine;

(rac)-4-{4-Fluoro-2-[(4-fluorobenzyl)oxy]phenyl}-N-{3-[(S-methylsulfonimidoyl)methyl]phenyl}-1,3,5-tri-azin-2-amine;

(rac)-4-{4-Fluoro-2-[2-(tetrahydro-2H-pyran-4-yl)ethoxy]phenyl}-N-{3-[(S-methylsulfonimidoyl)methyl]phenyl}-1,3,5-triazin-2-amine;

(rac)-4-(4-Fluoro-2-methoxyphenyl)-N-(3-{[S-(tetra-hydro-2H-pyran-4-yl)sulfonimidoyl]methyl}phenyl)-1,3,5-triazin-2-amine;

(rac)-N-{4-Chloro-3-[(S-methylsulfonimidoyl)methyl]phenyl}-4-(4-fluoro-2-methoxyphenyl)-1,3,5-triazin-2-amine;

(rac)-Ethyl [{3-[(4-{2-[(3,4-dichlorobenzyl)oxy]phenyl}-1,3,5-triazin-2-yl)amino]benzyl}(methyl)oxido-$\lambda^6$-sul-fanylidene]carbamate;

(rac)-4-{2-[(3,4-Dichlorobenzyl)oxy]phenyl}-N-{3-[(S-methylsulfonimidoyl)methyl]phenyl}-1,3,5-triazin-2-amine;

(rac)-4-(4-Fluoro-2-{[($^2$H$_5$)phenyl($^2$H$_2$)methyl]oxy}phenyl)-N-{3-[(S-methylsulfonimidoyl)methyl]phenyl}-1,3,5-triazin-2-amine;

4-[2-(1-cyclopentylethoxy)-4-fluorophenyl]-N-{3-[(S-methylsulfonimidoyl)methyl]phenyl}-1,3,5-triazin-2-amine;

(rac)-N-{3-Chloro-5-[(S-methylsulfonimidoyl)methyl]phenyl}-4-(4-fluoro-2-methoxyphenyl)-1,3,5-triazin-2-amine;

(rac)-4-[4-Fluoro-2-(3,3,3-trifluoropropoxy)phenyl]-N-{3-[(S-methylsulfonimidoyl)methyl]phenyl}-1,3,5-tri-azin-2-amine;

(rac)-4-[4-Fluoro-2-(pyridin-3-ylmethoxy)phenyl]-N-{3-[(S-methylsulfonimidoyl)methyl]phenyl}-1,3,5-tri-azin-2-amine;

(rac)-4-[4-Fluoro-2-(pyridin-2-ylmethoxy)phenyl]-N-{3-[(S-methylsulfonimidoyl)methyl]phenyl}-1,3,5-tri-azin-2-amine;

(rac)-4-[4-Fluoro-2-(pyridin-4-ylmethoxy)phenyl]-N-{3-[(S-methylsulfonimidoyl)methyl]phenyl}-1,3,5-tri-azin-2-amine;

4-{4-Fluoro-2-[1-(4-fluorophenyl)ethoxy]phenyl}-N-{3-[(S-methylsulfonimidoyl)methyl]phenyl}-1,3,5-tri-azin-2-amine, mixture of 4 stereoisomers;

(rac)-[(3-Fluoro-5-{[4-(4-fluoro-2-methoxyphenyl)-1,3,5-triazin-2-yl]amino}benzyl)(methyl-$\lambda$6-sulfa-nylidene]cyanamide;

[(3-Fluoro-5-{[4-(4-fluoro-2-methoxyphenyl)-1,3,5-tri-azin-2-yl]amino}benzyl)(methyl-$\lambda$6-sulfanylidene]cy-anamide, enantiomer 1;

[(3-Fluoro-5-{[4-(4-fluoro-2-methoxyphenyl)-1,3,5-tri-azin-2-yl]amino}benzyl)(methyl-$\lambda$6-sulfanylidene]cy-anamide, enantiomer 2;

(rac)-4-[2-(But-2-yn-1-yloxy)-4-fluorophenyl]-N-{3-[(S-methylsulfonimidoyl)methyl]phenyl}-1,3,5-triazin-2-amine;

4-[2-(But-2-yn-1-yloxy)-4-fluorophenyl]-N-{3-[(S-meth-ylsulfonimidoyl)methyl]phenyl}-1,3,5-triazin-2-amine, enantiomer 1;

4-[2-(But-2-yn-1-yloxy)-4-fluorophenyl]-N-{3-[(S-meth-ylsulfonimidoyl)methyl]phenyl}-1,3,5-triazin-2-amine, enantiomer 2;

(rac)-4-[2-(2-Cyclopropylethoxy)-4-fluorophenyl]-N-{3-[(S-methylsulfonimidoyl)methyl]phenyl}-1,3,5-tri-azin-2-amine;

(rac)-4-[4-Fluoro-2-(prop-2-yn-1-yloxy)phenyl]-N-{3-[(S-methylsulfonimidoyl)methyl]phenyl}-1,3,5-tri-azin-2-amine;

4-[4-Fluoro-2-(prop-2-yn-1-yloxy)phenyl]-N-{3-[(S-methylsulfonimidoyl)methyl]phenyl}-1,3,5-triazin-2-amine, enantiomer 1;

4-[4-Fluoro-2-(prop-2-yn-1-yloxy)phenyl]-N-{3-[(S-methylsulfonimidoyl)methyl]phenyl}-1,3,5-triazin-2-amine, enantiomer 2;

(rac)-4-{2-[(3,4-Difluorobenzyl)oxy]-4-fluorophenyl}-N-{3-[(S-methylsulfonimidoyl)methyl]phenyl}-1,3,5-triazin-2-amine;

(rac)-4-[4-Fluoro-2-(1,3-thiazol-5-ylmethoxy)phenyl]-N-{3-[(S-methylsulfonimidoyl)methyl]phenyl}-1,3,5-tri-azin-2-amine;

(rac)-4-{4-Fluoro-2-[(2-fluoropyridin-4-yl)methoxy]phe-nyl}-N-{3-[(S-methylsulfonimidoyl)methyl]phenyl}-1,3,5-triazin-2-amine;

4-{4-Fluoro-2-[(2-fluoropyridin-4-yl)methoxy]phenyl}-N-{3-[(S-methylsulfonimidoyl)methyl]phenyl}-1,3,5-triazin-2-amine, enantiomer 1;

4-{4-Fluoro-2-[(2-fluoropyridin-4-yl)methoxy]phenyl}-N-{3-[(S-methylsulfonimidoyl)methyl]phenyl}-1,3,5-triazin-2-amine, enantiomer 2;

(rac)-4-[4-Fluoro-2-(prop-2-en-1-yloxy)phenyl]-N-{3-[(S-methylsulfonimidoyl)methyl]phenyl}-1,3,5-triazin-2-amine;

(rac)-4-(4-Fluoro-2-{[4-(trifluoromethyl)benzyl]oxy}phenyl)-N-{3-[(S-methylsulfonimidoyl)methyl]phenyl}-1,3,5-triazin-2-amine;

(rac)-4-{2-[(4-Chlorobenzyl)oxy]-4-fluorophenyl}-N-{3-[(S-methylsulfonimidoyl)methyl]phenyl}-1,3,5-triazin-2-amine;

(rac)-4-(2-Ethoxy-4-fluorophenyl)-N-{3-[(S-methylsulfonimidoyl)methyl]phenyl}-1,3,5-triazin-2-amine;

(rac)-4-(4-Fluoro-2-{[3-fluoro-5-(trifluoromethyl)benzyl]oxy}phenyl)-N-{3-[(S-methylsulfonimidoyl)methyl]phenyl}-1,3,5-triazin-2-amine;

(rac)-4-{4-Fluoro-2-[(3-fluorobenzyl)oxy]phenyl}-N-{3-[(S-methylsulfonimidoyl)methyl]phenyl}-1,3,5-triazin-2-amine;

(rac)-4-(4-Fluoro-2-propoxyphenyl)-N-{3-[(S-methylsulfonimidoyl)methyl]phenyl}-1,3,5-triazin-2-amine;

(rac)-4-{2-[(3-Chlorobenzyl)oxy]-4-fluorophenyl}-N-{3-[(S-methylsulfonimidoyl)methyl]phenyl}-1,3,5-triazin-2-amine;

(rac)-4-[4-Fluoro-2-(1,2-oxazol-3-ylmethoxy)phenyl]-N-{3-[(S-methylsulfonimidoyl)methyl]phenyl}-1,3,5-triazin-2-amine;

(rac)-4-{2-[(3-Chloro-5-fluorobenzyl)oxy]-4-fluorophenyl}-N-{3-[(S-methylsulfonimidoyl)methyl]phenyl}-1,3,5-triazin-2-amine;

(rac)-4-[2-(2,2-Difluoroethoxy)-4-fluorophenyl]-N-{3-[(S-methylsulfonimidoyl)methyl]phenyl}-1,3,5-triazin-2-amine;

(rac)-4-{4-Fluoro-2-[(4-fluoro-3-methylbenzyl)oxy]phenyl}-N-{3-[(S-methylsulfonimidoyl)methyl]phenyl}-1,3,5-triazin-2-amine;

(rac)-4-{2-[(3-Chloro-4-fluorobenzyl)oxy]-4-fluorophenyl}-N-{3-[(S-methylsulfonimidoyl)methyl]phenyl}-1,3,5-triazin-2-amine;

(rac)-3-({5-Fluoro-2-[4-({3-[(S-methylsulfonimidoyl)methyl]phenyl}amino)-1,3,5-triazin-2-yl]phenoxy}methyl)benzonitrile;

(rac)-4-{4-Fluoro-2-[(2-methylprop-2-en-1-yl)oxy]phenyl}-N-{3-[(S-methylsulfonimidoyl)methyl]phenyl}-1,3,5-triazin-2-amine;

(rac)-4-[4-Fluoro-2-(4,4,4-trifluorobutoxy)phenyl]-N-{3-[(S-methylsulfonimidoyl)methyl]phenyl}-1,3,5-triazin-2-amine;

(rac)-4-{4-Fluoro-2-[(2,3,5-trifluorobenzyl)oxy]phenyl}-N-{3-[(S-methylsulfonimidoyl)methyl]phenyl}-1,3,5-triazin-2-amine;

(rac)-4-{2-[(2Z)-But-2-en-1-yloxy]-4-fluorophenyl}-N-{3-[(S-methylsulfonimidoyl)methyl]phenyl}-1,3,5-triazin-2-amine;

(rac)-4-{4-Fluoro-2-[(2,4,5-trifluorobenzyl)oxy]phenyl}-N-{3-[(S-methylsulfonimidoyl)methyl]phenyl}-1,3,5-triazin-2-amine;

(rac)-4-{4-Fluoro-2-[(3,4,5-trifluorobenzyl)oxy]phenyl}-N-{3-[(S-methylsulfonimidoyl)methyl]phenyl}-1,3,5-triazin-2-amine;

(rac)-[(2,3-Difluoro-5-{[4-(4-fluoro-2-methoxyphenyl)-1,3,5-triazin-2-yl]amino}benzyl)(methyl)oxido-$\lambda^6$-sulfanylidene]cyanamide;

(rac)-N-{3,4-Difluoro-5-[(S-methylsulfonimidoyl)methyl]phenyl}-4-(4-fluoro-2-methoxyphenyl)-1,3,5-triazin-2-amine;

(rac)-[Ethyl(3-{[4-(4-fluoro-2-methoxyphenyl)-1,3,5-triazin-2-yl]amino}benzyl)oxido-$\lambda^6$-sulfanylidene]cyanamide;

(rac)-N-{3-[(S-ethylsulfonimidoyl)methyl]phenyl}-4-(4-fluoro-2-methoxyphenyl)-1,3,5-triazin-2-amine;

N-{3-[(S-ethylsulfonimidoyl)methyl]phenyl}-4-(4-fluoro-2-methoxyphenyl)-1,3,5-triazin-2-amine, enantiomer 1;

N-{3-[(S-ethylsulfonimidoyl)methyl]phenyl}-4-(4-fluoro-2-methoxyphenyl)-1,3,5-triazin-2-amine, enantiomer 2;

(rac)-[(3-{[4-(4-Fluoro-2-methoxyphenyl)-1,3,5-triazin-2-yl]amino}-5 methylbenzyl)(methyl)oxido-$\lambda^6$-sulfanylidene]cyanamide;

(rac)-2-({5-Fluoro-2-[4-({3-[(S-methylsulfonimidoyl)methyl]phenyl}amino)-1,3,5-triazin-2-yl]phenoxy}methyl)prop-2-en-1-ol; and (rac)-[Cyclopropyl(3-{[4-(4-fluoro-2-methoxyphenyl)-1,3,5-triazin-2-yl]amino}benzyl)oxido-$\lambda^6$-sulfanylidene]cyanamide, or a salt or solvate thereof, or a salt of the solvate thereof.

9. A method for treatment of non-small cell lung carcinoma, comprising administering to a patient in need thereof the compound according to claim 1, or a salt or solvate thereof, or a salt of the solvate thereof.

10. A pharmaceutical combination comprising the compound according claim 1, or a salt or solvate thereof, or a salt of the solvate thereof, in combination with at least one or more additional active ingredients.

11. A pharmaceutical composition comprising the compound according to claim 1, or a salt or solvate thereof, or a salt of the solvate thereof, in combination with an inert, nontoxic, pharmaceutically suitable adjuvant.

12. The compound according to claim 1 or a salt thereof.

13. The compound according to claim 8 or a salt thereof.

14. The pharmaceutical composition according to claim 11 comprising the compound of formula (I) or a salt thereof.

15. The method of claim 9, comprising administering the compound of formula (I) or a salt thereof.

* * * * *